(12) United States Patent
Hinkle et al.

(10) Patent No.: US 10,513,703 B2
(45) Date of Patent: Dec. 24, 2019

(54) HEPATITIS B VIRUS (HBV) IRNA COMPOSITIONS AND METHODS OF USE THEREOF

(71) Applicant: Alnylam Pharmaceuticals, Inc., Cambridge, MA (US)

(72) Inventors: Gregory Hinkle, Cambridge, MA (US); Laura Sepp-Lorenzino, Jenkintown, PA (US); Vasant Jadhav, Sharon, MA (US); Martin Maier, Belmont, MA (US); Stuart Milstein, Arlington, MA (US); Muthiah Manoharan, Weston, MA (US); Kallanthottathil G. Rajeev, Wayland, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/591,532

(22) Filed: May 10, 2017

(65) Prior Publication Data

US 2017/0349900 A1    Dec. 7, 2017

Related U.S. Application Data

(63) Continuation of application No. PCT/US2015/059916, filed on Nov. 10, 2015.

(60) Provisional application No. 62/137,464, filed on Mar. 24, 2015, provisional application No. 62/077,799, filed on Nov. 10, 2014, provisional application No. 62/077,672, filed on Nov. 10, 2014.

(51) Int. Cl.
   *C12N 15/113*   (2010.01)
   *A61K 31/713*   (2006.01)
   *A61K 45/06*    (2006.01)

(52) U.S. Cl.
   CPC ........ *C12N 15/1131* (2013.01); *A61K 31/713* (2013.01); *A61K 45/06* (2013.01); *C12N 2310/14* (2013.01); *C12N 2310/315* (2013.01); *C12N 2310/321* (2013.01); *C12N 2310/322* (2013.01); *C12N 2310/335* (2013.01); *C12N 2310/3515* (2013.01)

(58) Field of Classification Search
   None
   See application file for complete search history.

(56) References Cited

U.S. PATENT DOCUMENTS

| | | |
|---|---|---|
| 5,571,026 A | 11/1996 | Kahre |
| 5,610,050 A | 3/1997 | Blum et al. |
| 5,629,153 A | 5/1997 | Urdea |
| 5,843,770 A | 12/1998 | Ill et al. |
| 5,981,274 A | 11/1999 | Tyrrell et al. |
| 5,994,517 A | 11/1999 | Ts'o et al. |
| 5,998,203 A | 12/1999 | Matulic-Adamic et al. |
| 6,001,990 A | 12/1999 | Wands et al. |
| 6,057,153 A | 5/2000 | George et al. |
| 6,287,770 B1 | 9/2001 | Weston et al. |
| 6,503,533 B1 | 1/2003 | Korba et al. |
| 6,518,417 B1 | 2/2003 | Sczakiel et al. |
| 6,558,954 B1 | 5/2003 | Takle et al. |
| 6,573,048 B1 | 6/2003 | VanAtta et al. |
| 6,906,182 B2 | 6/2005 | Ts'o et al. |
| 7,109,165 B2 | 9/2006 | Matulic-Adamic et al. |
| 7,491,805 B2 | 2/2009 | Vargeese et al. |
| 7,829,691 B2 | 11/2010 | Anthony et al. |
| 7,985,581 B2 | 7/2011 | Pachuk et al. |
| 7,989,612 B2 | 8/2011 | McSwiggen et al. |
| 8,350,021 B2 | 1/2013 | Pachuk et al. |
| 8,450,467 B2 | 5/2013 | Manoharan et al. |
| 8,575,327 B2 | 11/2013 | Pachuk et al. |
| 8,618,277 B2 | 12/2013 | Beigelman et al. |
| 8,648,185 B2 | 2/2014 | McSwigen et al. |
| 8,809,293 B2 | 8/2014 | Chin et al. |
| 9,029,341 B2 | 5/2015 | Bartz et al. |
| 9,034,841 B2 | 5/2015 | Swayze et al. |
| 9,200,281 B2 | 12/2015 | Pachuk et al. |
| 9,352,048 B2 | 5/2016 | Manoharan et al. |
| 9,464,290 B2 | 10/2016 | Bartz et al. |
| 9,879,262 B2 | 1/2018 | Bartz et al. |
| 9,982,263 B2 | 5/2018 | Pachuk et al. |
| 2002/0086356 A1 | 7/2002 | Tuschl et al. |
| 2002/0155124 A1 | 10/2002 | Sallberg et al. |
| 2003/0083294 A1 | 5/2003 | Sullenger et al. |
| 2003/0087855 A1 | 5/2003 | Ward et al. |
| 2003/0143732 A1 | 7/2003 | Fosnaugh et al. |
| 2003/0148928 A1 | 8/2003 | Beigelman et al. |

(Continued)

FOREIGN PATENT DOCUMENTS

| | | |
|---|---|---|
| CN | 1793359 A | 6/2006 |
| CN | 101314047 A | 12/2008 |

(Continued)

OTHER PUBLICATIONS

Australian Search Report, dated Oct. 12, 2006, for Singaporean Application No. 200507781-3, 7 pages.
Australian Written Opinion, dated Oct. 12, 2006, for Singaporean Application No. 200507781-3, 6 pages.
Tuschl et al., "The siRNA user guide," Revised Aug. 26, 2001, URL=http://www.mpibpc.gwdg.de/abteilungen/100/105/sirna_u.html, download date Nov. 14, 2001, 5 pages.

(Continued)

*Primary Examiner* — Sean McGarry
(74) *Attorney, Agent, or Firm* — Seed Intellectual Property Law Group LLP

(57) ABSTRACT

The present invention relates to RNAi agents, e.g., double-stranded RNAi agents, targeting the hepatitis B virus (HBV) genome, and methods of using such RNAi agents to inhibit expression of one or more HBV genes and methods of treating subjects having an HBV infection and/or HBV-associated disorder, e.g., chronic hepatitis B infection.

24 Claims, 8 Drawing Sheets
Specification includes a Sequence Listing.

(56) References Cited

U.S. PATENT DOCUMENTS

| | | |
|---|---|---|
| 2003/0190659 A1 | 10/2003 | LaCasse et al. |
| 2003/0206887 A1 | 11/2003 | Morrissey et al. |
| 2004/0091457 A1 | 5/2004 | John et al. |
| 2004/0110296 A1 | 6/2004 | Vargeese et al. |
| 2004/0180351 A1 | 9/2004 | Giese et al. |
| 2004/0235775 A1 | 11/2004 | Kung et al. |
| 2004/0259247 A1 | 12/2004 | Tuschl et al. |
| 2005/0020521 A1 | 1/2005 | Rana |
| 2005/0080246 A1 | 4/2005 | Allerson et al. |
| 2006/0148740 A1 | 7/2006 | Platenburg |
| 2007/0027099 A1 | 2/2007 | Lin et al. |
| 2009/0325297 A1 | 12/2009 | Tian et al. |
| 2010/0145038 A1 | 6/2010 | McSwiggen et al. |
| 2013/0005793 A1 | 1/2013 | Chin et al. |
| 2015/0374844 A1* | 12/2015 | Degrado .............. C07K 14/00 514/21.3 |
| 2018/0008724 A1* | 1/2018 | Rajeev ................. A61K 48/00 |
| 2018/0037886 A1* | 2/2018 | Bettencourt ......... A61K 31/713 |
| 2018/0195071 A1 | 7/2018 | Bartz et al. |
| 2019/0100757 A1 | 4/2019 | Pachuk et al. |

FOREIGN PATENT DOCUMENTS

| | | |
|---|---|---|
| CN | 101322847 A | 12/2008 |
| CN | 101603042 A | 12/2009 |
| CN | 101948827 A | 1/2011 |
| CN | 102559657 A | 7/2012 |
| CN | 102762215 A | 10/2012 |
| CN | 103014045 A | 4/2013 |
| CN | 103275971 A | 9/2013 |
| CN | 103333890 A | 10/2013 |
| CN | 103582648 A | 2/2014 |
| DE | 197 25 803 C1 | 2/1999 |
| EP | 0 957 107 A1 | 11/1999 |
| EP | 1 591 524 A1 | 11/2005 |
| EP | 2 071 030 A2 | 6/2009 |
| JP | 5-507203 A | 10/1993 |
| JP | 7-303485 A | 11/1995 |
| JP | 2002-335968 A | 11/2002 |
| JP | 2003-515327 A | 5/2003 |
| JP | 2007-503474 A | 2/2007 |
| JP | 2008-510489 A | 4/2008 |
| JP | 2010-519203 A | 6/2010 |
| JP | 2011-224013 A | 11/2011 |
| WO | 90/12096 A1 | 10/1990 |
| WO | 95/27788 A1 | 10/1995 |
| WO | 97/33991 A1 | 9/1997 |
| WO | 98/28004 A1 | 7/1998 |
| WO | 98/58055 A2 | 12/1998 |
| WO | 99/13886 A1 | 3/1999 |
| WO | 99/52932 A1 | 10/1999 |
| WO | 99/65925 A1 | 12/1999 |
| WO | 00/44914 A1 | 8/2000 |
| WO | 01/38498 A2 | 5/2001 |
| WO | 01/75164 A2 | 10/2001 |
| WO | 02/072763 A2 | 9/2002 |
| WO | 02/085908 A1 | 10/2002 |
| WO | 02/094185 A2 | 11/2002 |
| WO | 03/006477 A1 | 1/2003 |
| WO | 03/033700 A1 | 4/2003 |
| WO | 03/050308 A1 | 6/2003 |
| WO | 03/070918 A2 | 8/2003 |
| WO | 03/074654 A2 | 9/2003 |
| WO | 2004/011624 A2 | 2/2004 |
| WO | 2004/024757 A2 | 3/2004 |
| WO | 2004/045543 A2 | 6/2004 |
| WO | 2004/048566 A1 | 6/2004 |
| WO | 2004/063375 A1 | 7/2004 |
| WO | 2004/078181 A1 | 9/2004 |
| WO | 2004/078974 A1 | 9/2004 |
| WO | 2004/080406 A2 | 9/2004 |
| WO | 2004/090108 A2 | 10/2004 |
| WO | 2004/094595 A2 | 11/2004 |
| WO | 2005/014806 A2 | 2/2005 |
| WO | 2006/020768 A2 | 2/2006 |
| WO | 2006/033756 A2 | 3/2006 |
| WO | 2006/069064 A2 | 6/2006 |
| WO | 2006/078278 A2 | 7/2006 |
| WO | 2007/022369 A2 | 2/2007 |
| WO | 2008/103276 A2 | 8/2008 |
| WO | 2010/080724 A1 | 7/2010 |
| WO | 2012/024170 A2 | 2/2012 |
| WO | 2012/145697 A1 | 10/2012 |
| WO | 2013/003520 A1 | 1/2013 |
| WO | WO-2013074974 A2 * | 5/2013 ........... C12N 15/113 |
| WO | WO-2013155204 A2 * | 10/2013 ........... A61K 31/713 |
| WO | 2017/027350 A2 | 2/2017 |
| WO | 2017/121791 A1 | 7/2017 |
| WO | 2018/195165 A1 | 10/2018 |

OTHER PUBLICATIONS

Tuschl et al., "The siRNA user guide," Revised May 6, 2004, URL=http://diyhpl.us/~bryan/irc/protocol-online/protocol-cache/sirna.html, download date Oct. 10, 2018, 7 pages.

Biessen et al., "Synthesis of Cluster Galactosides with High Affinity for the Hepatic Asialoglycoprotein Receptor," *J. Med. Chem.* 38(9):1538-1546, 1995.

Biessen et al., "The Cholesterol Derivative of a Triantennary Galactoside with High Affinity for the Hepatic Asialoglycoprotein Receptor: a Potent Cholesterol Lowering Agent," *J. Med. Chem.* 38(11):1846-1852, 1995.

Crossman Jr. et al., "Synthesis of some second-generation substrate analogues of early intermediates in the biosynthetic pathway of glycosylphosphatidylinositol membrane anchors," *Carbohydrate Research* 321(1-2):42-51, 1999.

Hamzavi et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers," *Bioconjugate Chem.* 14:941-954, 2003.

Ikeda et al., "Ligand-Targeted Delivery of Therapeutic siRNA," *Pharm. Res.* 23(8):1631-1640, 2006.

Karskela et al., "Synthesis and Cellular Uptake of Fluorescently Labeled Multivalent Hyaluronan Disaccharide Conjugates of Oligonucleotide Phosphorothioates," *Bioconjugate Chem.* 19(12):2549-2558, 2008.

Katajisto et al., "An Aminooxy-Functionalized Non-Nucleosidic Phosphoramidite for the Construction of Multiantennary Oligonucleotide Glycoconjugates on a Solid Support," *Current Protocols in Nucleic Acid Chemistry* 21(1):4.26.1-4.26.16, 2005.

Katajisto et al., "Solid-Phase Synthesis of Multiantennary Oligonucleotide Glycoconjugates Utilizing On-Support Oximation," *Bioconjugate Chem.* 15(4):890-896, 2004.

Katajisto et al., "Solid-Phase Synthesis of Oligonucleotide Glycoconjugates Bearing Three Different Glycosyl Groups: Orthogonally Protected Bis(hydroxymethyl)-N,N'-bis(3-hydroxypropyl)malondiamide Phosphoramidite as Key Building Block," *J. Org. Chem.* 69(22):7609-7615, 2004.

Krapcho et al., "Mono-Protected Diamines. N-tert-Butoxycarbonyl-α, ω-Alkanediamines From α, ω-Alkanediamines," *Synthetic Communications* 20(16):2559-2564, 1990.

Li et al., "Folate-Mediated Targeting of Antisense Oligodeoxynucleotides to Ovarian Cancer Cells," *Pharm. Res.* 15(10):1540-1545, 1998.

Li et al., "siRNA Combinations Mediate Greater Suppression of Hepatitis B virus Replication in Mice," *Cell Biochemistry and Biophysics* 69(3):641-647, 2014.

Liu et al., "Targeted Drug Delivery to Chemoresistant Cells: Folic Acid Derivatization of FdUMP[10] Enhances Cytotoxicity toward 5-FU-Resistant Human Colorectal Tumor Cells," *J. Org. Chem.* 66(17):5655-5663, 2001.

Mahato et al., "Physicochemical and Disposition Characteristics of Antisense Oligonucleotides Complexed with Glycosylated Poly(L-lysine)," *Biochem. Pharmacol.* 53:887-895, 1997.

Murata et al., "Design of quaternary chitosan conjugate having antennary galactose residues as a gene delivery tool," *Carbohydrate Polymers* 32(2):105-109, 1997.

(56) References Cited

OTHER PUBLICATIONS

Okamoto et al., "Full-Length Sequence of a Hepatitis C Virus Genome Having Poor Homology to Reported Isolates: Comparative Study of Four Distinct Genotypes," *Virology* 188(1):331-341, 1992.
Olie et al., "Analysis of ribosyl-modified, mixed backbone analogs of a bc1-2/bc1-xL antisense oligonucleotide," *Biochim. Biophys. Acta* 1576(1-2):101-109, 2002.
Rensen et al., "Design and Synthesis of Novel N-Acetylgalactosamine-Terminated Glycolipids for Targeting of Lipoproteins to the Hepatic Asialoglycoprotein Receptor," *J. Med. Chem.* 47(23):5798-5808, 2004.
Sioud, "On the delivery of small interfering RNAs into mammalian cells," *Expert Opin. Drug Deliv.* 2(4):639-651, 2005.
Six et al., "An Efficient and Stereoselective Synthesis of 1,2-0-Dialkyl-3-0-β-D-Glycosyl-sn-Glycerols," *Tetrahedron Lett.* 24(12):1229-1232, 1983.
Six et al., "Influence of Carbohydrate Moities on Monolayer Properties of Dialkylglyceryletherglycosides, Simple Model Compounds of the Glycolipids of Halophilic Bacteria," *J. Colloid Interface Sci.* 93(1):109-114, 1983.
Sliedregt et al., "Design and Synthesis of Novel Amphiphilic Dendritic Galactosides for Selective Targeting of Liposomes to the Hepatic Asialoglycoprotein Receptor," *J. Med. Chem.* 42(4):609-618, 1999.
Vaino et al., "Synthesis of a $_D$-lactosyl cluster-nucleoside conjugate," *Chem. Commun.* 19:1871-1872, 1997.
Wang et al., "Immunotherapeutic interventions in chronic hepatitis B virus infection: A review," *Journal of Immunological Methods* 407:1-8, 2014.
Wong et al., "Lipid, Sugar and Liposaccharide Based Delivery Systems," *Curr. Med. Chem.* 8(9):1123-1136, 2001.
Zatsepin et al., "Synthesis and Applications of Oligonucleotide-Carbohydrate Conjugates," *Chem. Biodivers.* 1(10):1401-1417, 2004.
"AASLD Abstracts, Poster Session 4: Hepatitis B Therapy, Hepatology 60: 1088A-1128A, 2014."
Amarzguioui et al., "Tolerance for mutations and chemical modifications in a siRNA" *Nucl. Acids. Res.* 31(2):589-595, 2003.
Andino, "RNAi puts a lid on virus replication," *Nature Biotechnology* 21(6):629-630, 2003.
Backes et al., "Protein-prime/modified vaccinia virus Ankara vector-boost vaccination overcomes tolerance in high-antigenemic HBV-transgenic mice," *Vaccine* 34(7):923-932, 2016.
Bertoletti et al., "Adaptive immunity in HBV infection," *Journal of Hepatology* 64(1):S71-S83, 2016.
Bertrand et al., "Comparison of antisense oligonucleotides and siRNAs in cell culture and in vivo," *BBRC* 296:1000-1004, 2002.
Braasch et al., "Novel antisense and peptide Nucleic Acid Strategies for Controlling Gene Expression," *Biochem.* 41(14):4503-4510, 2002.
Caplen et al., "Specific inhibition of gene expression by small double-stranded RNAs in invertebrate and vertebrate systems," *Proc. Natl. Acad. Sci.* 98(17):9742-9747, 2001.
Chen et al., "RNAI for treating Hepatitis B Viral Infection," *Pharmaceutical Research* 25(1):72-86, 2008.
Chiu et al., "RNAi in Human Cells: Basic Structural and Functional Features of Small Interfering RNA," *Mol. Cell* 10:549-561, 2002.
Choi et al., "Targeting Cancer Cells with Basic Structural and Functional Features of Small Interfering RNA," *Cell Cycle* 4(5):669-671, 2005.
Chouteau et al., "A short N-proximal region in the large envelope protein harbors a Determinant That Contributes to the Species Specificity of Human Hepatitis B Virus," *Journal of Virology* 75(23):11565-11572, 2001.
Connolly et al., "Binding and Endocytosis of Cluster Glycosides by Rabbit Hepatocytes," *J. Biol. Chem.* 257(2):939-945, 1982.
Couzin, "Mini RNA Molecules Shield Mouse Liver From Hepatitis," *Science* 299:995, 2003. (2 pages).
Di Bisceglie, "Hepatitis B and Hepatocellular Carcinoma," *Hepatology* 49(5 Suppl):S56-S60, 2009.

Dubber et al., "Solid-Phase Synthesis of Multivalent Glycoconjugates on a DNA Synthesizer," *Bioconjugate Chem.* 14(1):239-246, 2006.
Elbashir et al., "Duplexes of 21-nucleotide RNAs mediate RNA interference in cultured mammalian cells," *Nature* 411:494-498, 2011.
Elbashir et al., "Functional anatomy of siRNA for mediating efficient RNAi in *Drosophila melanogaster* embryo lysate," *EMBO J.* 20(23):6877-6888, 2001.
European Search Report, dated Jan. 14, 2008, for European Application No. 04776661.3-1212, 2 pages.
Feitelson et al., "New Animal Models of Hepatitis B and C," *ILAR Journal* 42(2):127-138, 2001.
Freier et al., "The ups and downs of nucleic acid duplex stability: structure-stability studies on chemically-modified DNA:RNA duplexes," *Nucl. Acids Res.* 25(22):4429-4443, 1997.
Galibert et al., "Nucleotide sequence of the hepatitis B virus genome (subtype ayw) cloned in *E. coli*," *Nature* 281:646-650, 1979.
Giladi et al., "Small Interfering RNA Inhibits Hepatitis B Virus Replication in Mice," *Mol. Ther.* 8(5):769-776, 2003.
Guo et al., "Construction of Folate-Conjugated pRNA of bacteriophage phi29 DNA packaging motor for delivery of chimeric siRNA to nasopharyngeal carcinoma cells," *Gene Ther.* 13(10):814-820, 2006.
Hamasaki et al., "Short interfering RNA-directed inhibition of hepatitis B virus replication," *FEBS Letters* 543(1-3):51-54, 2003.
Holen et al., "Positional effects of short interfering RNAs targeting the human coagulation trigger Tissue Factor," *Nucleic Acids Research* 30(8):1757-1766, 2002.
Holen T. et al., "Similar behavior of single-strand and double-strand siRNSs suggests they act through a common RNAi pathway," *Nucleic Acids Research* 31(9):2401-2407, 2003.
Hung et al., "Specific inhibition of gene expression and transactivation functions of hepatitis B virus X protein and c-myc by small interfering RNAs," *FEBS Letters* 560(1-3):210-214, 2004.
International Preliminary Report on Patentability, dated Jan. 7, 2007, for International Application No. PCT/US2004/019229, 6 pages.
International Search Report, dated Sep. 16, 2005, for International Application No. PCT/US2004/019229, 8 pages.
Kapadia et al., "Interference of hepatitis C virus RNA replication by short interfering RNAs," *Proceedings of the National Academy of Sciences of the USA* 100(4):2014-2018, 2003.
Kim et al., "Increased in vivo immunological potency of HB-110, a novel therapeutic HBV DNA vaccine, by electroporation," *Experimental and Molecular Medicine* 40(6):669-676, 2008.
Liang, "Hepatitis B: The Virus and Disease," *Hepatology* 49(Suppl 5):S13-S21, 2009. (17 pages).
Mahato et al., "Modulation of gene expression by antisense and antigene oligodeoxynucleotides and small interfering RNA," *Expert Opin. Drug Deliv.* 2(1):3-28, 2005.
Maier et al., "Synthesis of Antisense Oligonucleotides Conjugated to a Multivalent Carbohydrate Cluster for Cellular Targeting," *Bioconjugate Chem.* 14:18-29, 2003.
Manoharan, "GalNAc-siRNA with Enhanced Stabilization Chemistry: ESC-GalNAc-siRNA," TIDES: Oligonucleotide and Peptide Research, Technology and Product Development, May 14, 2014, URL=http://www.alnylam.com/web/assets/ALNY-ESC-Ga1NAc-siRNA-TIDES-May2014-Capella.pdf, download date Feb. 2, 2016, 28 pages.
McCaffrey et al., "Inhibition of hepatitis B virus in mice by RNA interference," *Nature Biotechnology* 21(6):639-644, 2003.
McCaffrey et al., "RNA interference in adult mice," *Nature* 418(6893):38-39, 2002.
Meyers, "RNAi Roundtable: Advances in Delivery of RNAi Therapeutics with Enhanced Stabilization Chemistry (ESC)-GalNAc-siRNA Conjugates," Jul. 22, 2014, URL=http://www.alnylam.com/web/assets/Roundtable_ESC-Ga1NAc-Conjugates_072214.pdf, download date Feb. 2, 2016, 40 pages.
Michler et al., "Combinatorial RNAi/vaccination therapy for chronic hepatitis B achieves long-term functional cure in preclinical mouse model," *Journal of Hepatology* 68(Supp 1):S16, 2018.

(56) References Cited

OTHER PUBLICATIONS

Michler et al., "Preclinical study of a combinatorial RNAi/vaccination therapy as a potential cure for chronic hepatitis B," *Journal of Hepatology* 66(1):S112, 2017.
Parrish et al., "Functional Anatomy of a dsRNA Trigger: Differential Requirement for the Two Trigger Strands in RNA interference," *Mol. Cell* 6:1077-1087, 2000.
Radhakrishnan et al., "RNA interference as a new strategy against viral hepatitis," *Virology* 323(2):173-181, 2004.
Randall et al., "Clearance of replicating hepatitis C virus replicon RNAs in cell culture by small interfering RNAs," *PNAS* 100(1):235-240, 2003.
Reid et al., "RNAi Roundtable: ALN-HBV in Development for the Treatment of Hepatitis B Virus (HBV) Infection," Jul. 29, 2014, URL=http://www.alnylam.com/web/assets/Roundtable_ALN-HBV_072914.pdf, download date Feb. 2, 2016, 56 pages.
Seo et al., "Small Interfering RNA-Mediated Inhibition of Hepatitis C Virus Replication in the Human Hepatoma Cell Line Huh-7," *J. Virol.* 77(1):810-812, 2003.
Shlomai et al., "Inhibition of Hepatitis B Virus Expression and Replication by RNA Interference," *Hepatology* 37(4):764-770, 2003.
Sui et al., "A DNA vector-based RNAi technology to suppress gene expression in mammalian calls," *PNAS* 99(8):5515-5520, 2002.
Vitral et al., "The use of non-human primates as animal models for the study of hepatitis viruses," *Brazilian Journal of Medical and Biological Research* 31(8):1035-1048, 1998.
Wilson et al., "RNA interference blocks gene expression and Rna synthesis from hepatitis C replicons propagated in human liver cells," *Proceedings of the National Academy of Sciences of the USA* 100(5):2783-2788, 2003.

Wolfrum et al., "Mechanisms and optimization of in vivo delivery of lipophilic siRNAs," *Nature Biotechnology* 25(10):1149-1157, 2007.
Yu et al., "The Role of Antiviral Therapy for HBV-Related Hepatocellular Carcinoma," *International Journal of Hepatology* 2011:416459, 2011. (9 pages).
Zheng et al., "Distribution and anti-HBV effects of antisense oligodeoxynu-cleotides conjugated to galactosylated poly-L-lysine," *World J. Gastroenterol.* 9(6):1251-1255, 2003.
Zimmermann et al., "RNAi-mediated gene silencing in non-human primates," *Nature* 441(7089):111-114, 2006.
McCafferey et al., "Inhibition of hepatitis B virus in mice by RNA interference," *Nature Biotechnology* 21(6):639-644, 2003 (Supplemental Online Data (1)), XP055535056, retrieved from the Internet: https://media.nature.com/original/nature-assets/nbt/journal/v21/n6/extref/nbt824-S1.pdf (1 page).
McCafferey et al., "Inhibition of hepatitis B virus in mice by RNA interference," *Nature Biotechnology* 21(6):639-644, 2003 (Supplemental Online Data (2)), XP055535057, retrieved from the Internet: https://media.nature.com/original/nature-assets/nbt/journal/v21/n6/extref/nbt824-S2.pdf (2 pages).
Putlitz et al., "Antisense RNA Complementary to Hepatitis B Virus Specifically Inhibits Viral Replication," *Gastroenterology* 115:702-713, 1998.
U.S. Appl. No. 15/844,793, filed Dec. 18, 2017, RNA Interference Mediated Inhibition of Hepatitis B Virus (HBV) Gene Expression Using Short Interfering Nucleic Acid (SINA).
U.S. Appl. No. 15/965,309, filed Apr. 27, 2018, Conserved HBV and HCV Sequences Useful for Gene Silencing.

* cited by examiner

HEPATITIS B VIRUS (HBV) IRNA COMPOSITIONS AND METHODS OF USE THEREOF

RELATED APPLICATIONS

This application is a 35 § U.S.C. 111(a) continuation application which claims the benefit of priority to PCT/US2015/059916, filed on Nov. 10, 2015, which claims priority to U.S. Provisional Application, 62/077,799, filed on Nov. 10, 2014, and U.S. Provisional Application, 62/137,464, filed on Mar. 24, 2015. The entire contents of each of the foregoing patent applications are incorporated herein by reference.

This application also claims priority to U.S. Provisional Application, 62/077,672, filed on Nov. 10, 2014, the entire contents of which are hereby incorporated herein by reference.

This application is related to International Patent Application, PCT/US2015/059958, entitled "Hepatitis D Virus (HDV) iRNA Compositions and Methods of Use Thereof," filed on Nov. 10, 2015, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 21, 2017, is named 121301_02303_SL.txt and is 385,912 bytes in size.

BACKGROUND OF THE INVENTION

Worldwide more than 400 million people are chronically infected with HBV and are, thus, at increased risk of developing serious liver disease, such as chronic hepatitis, cirrhosis, liver failure and hepatocellular carcinoma (HCC) resulting in an estimated 600,000 deaths each year.

The natural evolution of chronic HBV infection includes four consecutive phases: (1) early 'immunotolerant' phase, high levels of virus replication and minimal liver inflammation; (2) immune reactive phase, significant hepatic inflammation and elevated serum aminotransferases; with some patients progressing to (3) 'non-replicative' phase, seroconversion to anti-HBe; undetectable or low level of viremia (below 2000 IU/ml by PCR-based assays); resolution of hepatic inflammation; and (4) HBeAg-negative chronic hepatitis B, due to the emergence of specific viral mutations, which prevent the production of HBeAg but do not hamper virus replication. This form of chronic hepatitis B (CHB) is characterized by fluctuating serum HBV DNA and serum aminostransferases (ALT and AST) levels, and progressive liver disease. It is important to note that CHB may present either as HBeAg-positive or HBeAg-negative CHB. Longitudinal studies of patients with CHB indicate that the 5-year cumulative incidence of developing cirrhosis ranges from 8 to 20%. The 5-year cumulative incidence of hepatic decompensation is approximately 20%. The worldwide incidence of HCC has increased and presently constitutes the fifth most common cancer. The annual incidence of HBV-related HCC is high, ranging from 2-5% when cirrhosis is established.

The primary goal of treatment for HBV is to permanently suppress HBV replication and improve liver disease. Clinically important short-term goals are to achieve HBeAg-seroconversion, normalization of serum ALT and AST, resolution of liver inflammation and to prevent hepatic decompensation. The ultimate goal of treatment is to achieve durable response to prevent development of cirrhosis, liver cancer and prolong survival. HBV infection cannot be eradicated completely due to persistence of a particular form of viral covalently closed circular DNA (ccc HBV DNA) in the nuclei of infected hepatocytes. However, treatment-induced clearance of serum HBsAg is a marker of termination of chronic HBV infection and has been associated with the best long-term outcome.

The current standard methods of treatment for HBV include interferon or thymosin a1-based immunotherapies and the suppression of viral production by inhibition of the HBV polymerase. HBV polymerase inhibitors are effective in reducing viral production but have little to no effect in rapidly reducing HBsAg or can slowly reduce HBsAg with long term treatment in a limited number of patients (as is the case with tenofovir disoproxil fumarate). Interferon based immunotherapy can achieve a reduction of both viral production and early removal of HBsAg from the blood but only in a small percentage of treated subjects. The generally accepted role of HBsAg in the blood is to sequester anti-HBsAg antibodies and allow infectious viral particles to escape immune detection which is likely one of the reasons why HBV infection remains a chronic condition. In addition HBsAg, HBeAg and HBcAg all have immuno-inhibitory properties and the persistence of these viral proteins in the blood of patients following the administration of any of the currently available treatments for HBV is likely having a significant impact in preventing patients from achieving immunological control of their HBV infection.

Although the three primary HBV proteins (HBsAg, HBeAg and HBcAg) all have immunoinhibitory properties, HBsAg comprises the overwhelming majority of HBV protein in the circulation of HBV infected subjects. Additionally, while the removal (via seroconversion) of HBeAg or reductions in serum viremia are not correlated with the development of sustained control of HBV infection off treatment, the removal of serum HBsAg from the blood (and seroconversion) in HBV infection is a well-recognized prognostic indicator of antiviral response on treatment which will lead to control of HBV infection off treatment (although this only occurs in a small fraction of patients receiving immunotherapy). Thus, while reduction of all three major HBV proteins (HBsAg, HBeAg and HBcAg) may result in the optimal removal of inhibitory effect, the removal of HBsAg alone is likely sufficient in and of itself to remove the bulk of the viral inhibition of immune function in subjects with HBV infection.

Therefore, in the absence of any current treatment regimen which can restore immunological control of HBV in a large proportion of patients, there is a need for an effective treatment against HBV infection which can inhibit viral replication as well as restore immunological control in the majority of patients. Accordingly, there is a need in the art for alternative therapies and combination therapies for subjects infected with HBV and/or having an HBV-associated disease.

SUMMARY OF THE INVENTION

The present invention provides iRNA compositions which effect the RNA-induced silencing complex (RISC)-mediated cleavage of RNA transcripts of a Hepatitis B virus (HBV) gene. The HBV gene may be within a cell, e.g., a cell within a subject, such as a human.

The present invention also provides methods and therapies for treating a subject having a disorder that would benefit from inhibiting or reducing the expression of an HBV gene, e.g., an HBV infection and/or an HBV-associated disease, such as chronic Hepatitis B infection (CHB), cirrhosis, liver failure, and hepatocellular carcinoma (HCC), using iRNA compositions which effect the RNA-induced silencing complex (RISC)-mediated cleavage of RNA transcripts of an HBV gene for inhibiting the expression of an HBV gene.

The RNAi agents of the invention have been designed to target regions in the HBV genome that are conserved across all 8 serotypes of HBV. In addition, the RNAi agents of the invention have been designed to inhibit all steps of the HBV life cycle, e.g., replication, assembly, secretion of virus, and secretion of sub-viral antigens, by inhibiting expression of more than one HBV gene. In particular, since transcription of the HBV genome results in polycistronic, overlapping RNAs, an RNAi agent of the invention targeting a single HBV gene results in significant inhibition of expression of most or all HBV transcripts. For example, because the HBV genome is transcribed into a single mRNA, an RNAi agent of the invention targeting the S gene will result in inhibition of not only S gene expression but also the expression of the "downstream" reverse transcriptase gene. Furthermore, the RNAi agents of the invention have been designed to inhibit HBV viral replication by targeting HBV structural genes, and the HBV X gene thereby permitting a subject's immune system to detect and respond to the presence of HBsAg to produce anti-HBV antibodies to clear an HBV infection. Without intending to be limited by theory, it is believed that a combination or sub-combination of the foregoing properties and the specific target sites and/or the specific modifications in these RNAi agents confer to the RNAi agents of the invention improved efficacy, stability, safety, potency, and durability.

Accordingly, in one aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises at least 15 contiguous nucleotides differing by no more than 3 nucleotides from the nucleotide sequence of SEQ ID NO:1, and said antisense strand comprises at least 15 contiguous nucleotides differing by no more than 3 nucleotides from the nucleotide sequence of SEQ ID NO:2, wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker.

In one embodiment, the one or more of the 3 nucleotide differences in the nucleotide sequence of the antisense strand is a nucleotide mismatch in the antisense strand.

In another embodiment, the one or more of the 3 nucleotide differences in the nucleotide sequence of the antisense strand is a nucleotide mismatch in the sense strand.

In one embodiment, all of the nucleotides of said sense strand and all of the nucleotides of said antisense strand are modified nucleotides.

In one embodiment, the sense strand and the antisense strand comprise a region of complementarity which comprises at least 15 contiguous nucleotides differing by no more than 3 nucleotides from any one of the sequences listed in any one of Tables 3, 4, 6, 7, 12, 13, 22, 23, 25, and 26.

In one embodiment, the at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydro-hexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, the at least one strand comprises a 3' overhang of at least 1 nucleotide. In another embodiment, the at least one strand comprises a 3' overhang of at least 2 nucleotides.

In one embodiment, the double-stranded region is 15-30 nucleotide pairs in length. In another embodiment, the double-stranded region is 17-23 nucleotide pairs in length. In yet another embodiment, the double-stranded region is 17-25 nucleotide pairs in length. In one embodiment, the e double-stranded region is 23-27 nucleotide pairs in length. In another embodiment, the double-stranded region is 19-21 nucleotide pairs in length. In yet another embodiment, the double-stranded region is 21-23 nucleotide pairs in length.

In one embodiment, each strand has 15-30 nucleotides. In another embodiment, each strand has 19-30 nucleotides.

In one embodiment, the ligand is

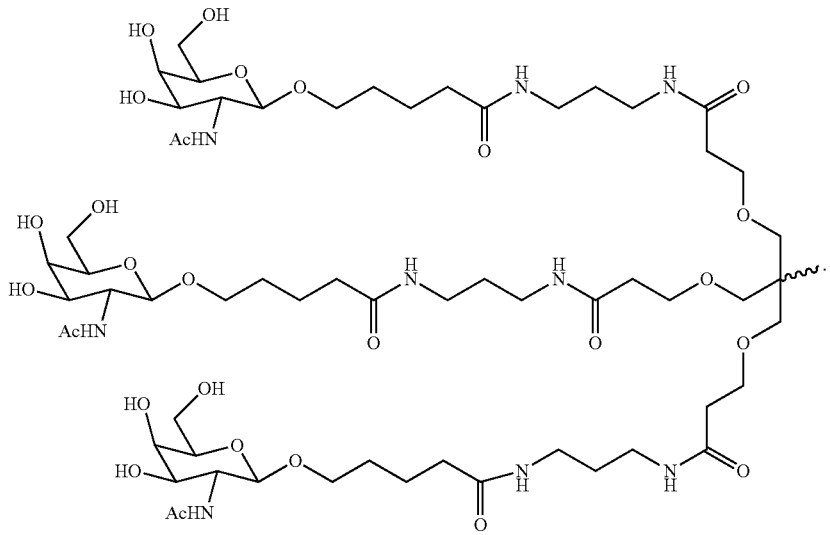 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand at the 3' end of the sense strand, as shown in the following structure:

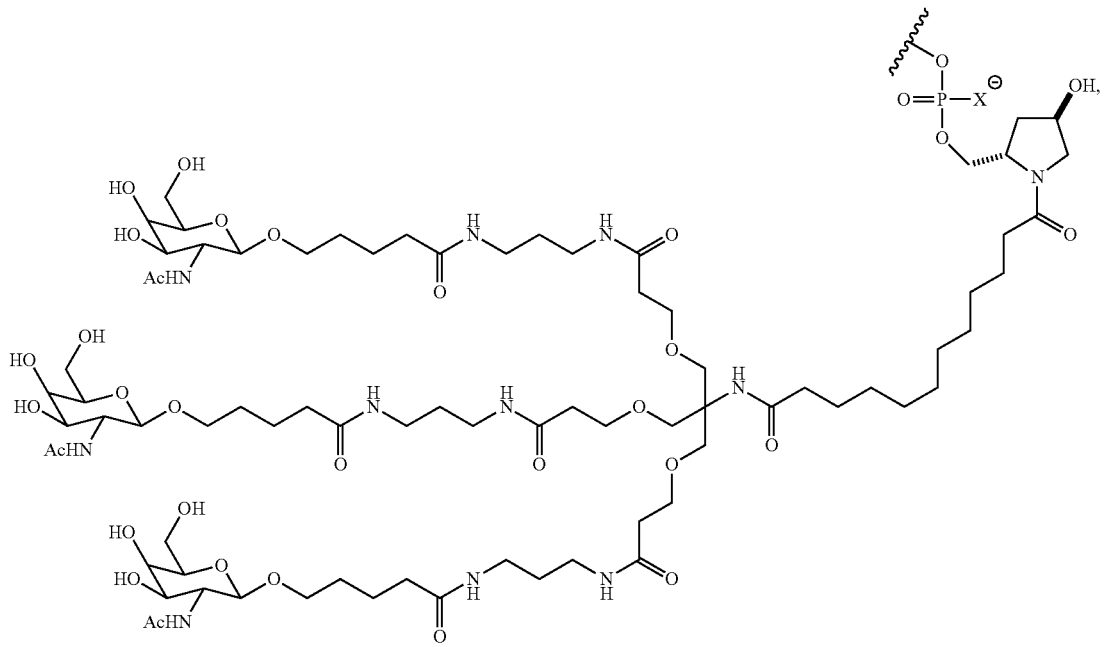

wherein X is O or S.

In one embodiment, the RNAi agent is selected from the group of RNAi agents listed in any one of Tables 3, 4, 6, 7, 12, 13, 22, 23, 25, and 26.

In one aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises 5'-UCGUGGUGGACUUCUCUCA-3' (SEQ ID NO:5), and said antisense strand comprises 5'-UGAGAGAAGUCCAC-CACGAUU-3' (SEQ ID NO:6), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker.

The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In another aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises 5'-GUGCACUUCGCUUCACCUCUA-3' (SEQ ID NO:7), and said antisense strand comprises 5'-UAGAG-GUGAAGCGAAGUGCACUU-3' (SEQ ID NO:8), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker. The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In another aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises 5'-CGUGGUGGACUUCUCUCAAUU-3' (SEQ ID NO:9), and said antisense strand comprises 5'-AAUUGAGAGAA-GUCCACCAGCAG-3' (SEQ ID NO:10), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker. The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In another aspect, the present invention provides double stranded RNAi agents for inhibiting expression of hepatitis B virus (HBV) in a cell. The double stranded RNAi agents include a sense strand and an antisense strand forming a double-stranded region, wherein the sense strand comprises 5'-CGUGGUGGUCUUCUCUAAAUU-3' (SEQ ID NO:37), and the antisense strand comprises 5'-AAUUGA-GAGAAGUCCACCAGCUU-3' (SEQ ID NO:38), wherein substantially all of the nucleotides of the sense strand and substantially all of the nucleotides of the antisense strand are modified nucleotides, wherein said sense strand is conjugated to a ligand attached at the 3'-terminus, and wherein the ligand is one or more GalNAc derivatives attached through a bivalent or trivalent branched linker. The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In another aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises 5'-GGUGGACUUCUCUCAAUUUUA-3' (SEQ ID NO:11), and said antisense strand comprises 5'-UAAAAUUGAGAGAAGUCCACCAC-3' (SEQ ID NO:12), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker. The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In another aspect, the present invention provides double stranded RNAi agents for inhibiting expression of hepatitis B virus (HBV) in a cell. The double stranded RNAi agents include a sense strand and an antisense strand forming a double-stranded region, wherein said sense strand comprises 5'-GUGUGCACUUCGCUUCACA-3' (SEQ ID NO:39), and said antisense strand comprises 5'-UGUGAAGC-GAAGUGCACACUU-3' (SEQ ID NO:40), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker. The present invention also provides RNAi agents comprising sense and antisense nucleotide sequences which are at least 90%, 91%, 92%, 93%, 94%, 95%, 96%, 97%, 98%, or 99% identical over their entire length to the foregoing sense and antisense nucleotide sequences.

In one embodiment, all of the nucleotides of said sense strand and all of the nucleotides of said antisense strand comprise a modification.

In one embodiment, at least one of said modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, the 5'-phosphate mimic is a 5'-vinyl phosphate (5'-VP).

In one embodiment, the sense strand comprises 5'-uscsguGfgUfGfGfacuucucuca-3' (SEQ ID NO:13) and the antisense strand comprises 5'-usGfsagaGfaAfGfuccaCfcAfcgasusu-3' (SEQ ID NO:14), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-uscsguGfgUfGfGfacuucucuca-3' (SEQ ID NO:15) and the antisense strand comprises 5'-PusGfsagaGfaAfGfuccaCfcAfcgasusu-3' (SEQ ID NO:16), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In one embodiment, the sense strand comprises 5'-gsusgcacUfuCfGfCfuucaccucua-3' (SEQ ID NO:17) and the antisense strand comprises 5'-usAfsgagGfugaagcgAfaGfugcacsusu-3' (SEQ ID NO:18), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-gsusgcacUfuCfGfCfuucaccucua-3' (SEQ ID NO:19) and the antisense strand comprises 5'-PusAfsgagGfugaagcgAfaGfugcacsusu-3' (SEQ ID NO:20), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In one embodiment, the sense strand comprises 5'-csgsugguGfgAfCfUfucucUfCfaauu-3' (SEQ ID NO:21) and the antisense strand comprises 5'-asAfsuugAfgAfgAfaguCfcAfccagcsasg-3' (SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-csgsugguGfgAfCfUfucucUfCfaauu-3' (SEQ ID NO:23) and the antisense strand comprises 5'-PasAfsuugAfgAfgAfaguCfcAfccagcsasg-3' (SEQ ID NO:24), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In another embodiment, the sense strand comprises 5'-csgsuggudGgucdTucucuaaauu-3' (SEQ ID NO:35) and the antisense strand comprises 5'-asdAsuugagagdAagudCcaccagcsusu-3' (SEQ ID NO:36), wherein A, C, G, and U are ribose A, C, G or U; a, g, c and u are 2'-O-methyl (2'-OMe) A, U, C, or G; dA, dC, dG, and dT are deoxyribose A, C, G, and T; and s is a phosphorothioate linkage.

In one embodiment, the sense strand comprises 5'-gsgsuggaCfuUfCfUfcucaAfUfuuua-3' (SEQ ID NO:25) and the antisense strand comprises 5'-usAfsaaaUfuGfAfgagaAfgUfccaccsasc-3' (SEQ ID NO:26), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-gsgsuggaCfuUfCfUfcucaAfUfuuua-3' (SEQ ID NO:27) and the antisense strand comprises 5'-PusAfsaaaUfuGfAfgagaAfgUfccaccsasc-3' (SEQ ID NO:28), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In another embodiment, the sense strand comprises 5'-gsusguGfcAfCfUfucgcuucaca-3' (SEQ ID NO:41) and the antisense strand comprises 5'-usGfsugaAfgCfGfaaguGfcAfcacsusu-3' (SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In one embodiment, the ligand is

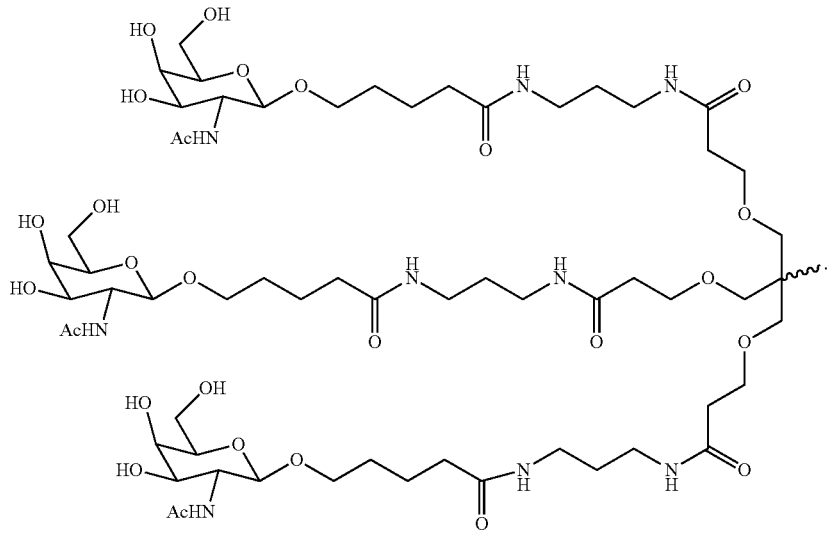 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand at the 3' end of the sense strand, as shown in the following structure:

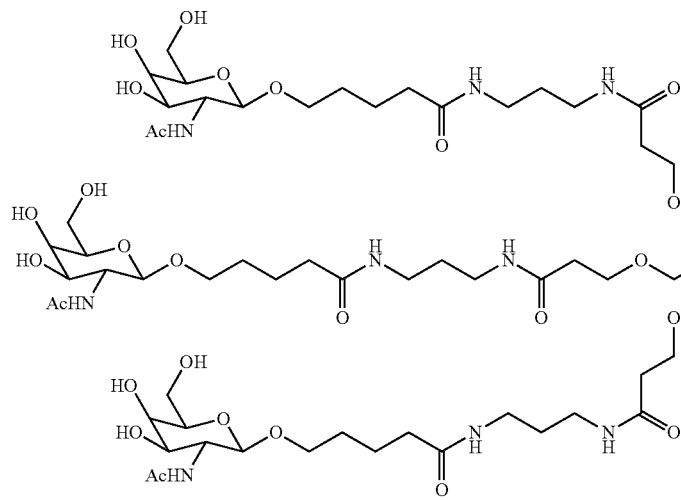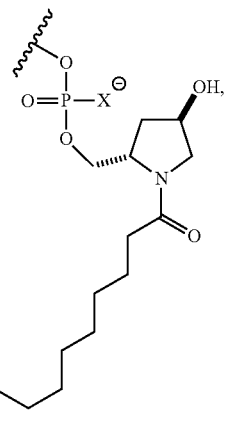

wherein X is O or S.

In one embodiment, the P is a 5'-phosphate mimic. In one embodiment, the 5'-phosphate mimic is a 5'-vinyl phosphate (5'-VP).

In another aspect, the present invention provides compositions comprising two or more double stranded RNAi agents for inhibiting expression of hepatitis B virus (HBV) in a cell, wherein each double stranded RNAi agent independently comprises a sense strand and an antisense strand forming a double-stranded region, wherein each of said sense strands independently comprises at least 15 contiguous nucleotides differing by no more than 3 nucleotides from the nucleotide sequence of SEQ ID NO:1, and each of said antisense strands independently comprises at least 15 contiguous nucleotides differing by no more than 3 nucleotides from the nucleotide sequence of SEQ ID NO:2, wherein substantially all of the nucleotides of each of said sense strands and substantially all of the nucleotides of each of said antisense strands are independently modified nucleotides, wherein each of said sense strands are independently conjugated to a ligand attached at the 3'-terminus, and wherein the ligand is one or more GalNAc derivatives attached through a bivalent or trivalent branched linker.

In one embodiment, the one or more of the 3 nucleotide differences in the nucleotide sequence of the antisense strand is a nucleotide mismatch in the antisense strand. In another embodiment, the one or more of the 3 nucleotide differences in the nucleotide sequence of the antisense strand is a nucleotide mismatch in the sense strand.

In one embodiment, all of the nucleotides of said sense strand and all of the nucleotides of said antisense strand are modified nucleotides.

In one embodiment, the sense strand and said antisense strand comprise a region of complementarity which comprises at least 15 contiguous nucleotides differing by no more than 3 nucleotides from any one of the sequences listed in any one of Tables 3, 4, 6, 7, 12, 13, 22, 23, 25, and 26.

In one embodiment, the at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In another aspect, the present invention provides compositions for inhibiting expression of hepatitis B virus (HBV) in a cell, the composition comprising (a) a first double-stranded RNAi agent comprising a first sense strand and a first antisense strand forming a double-stranded region, wherein substantially all of the nucleotides of said first sense strand and substantially all of the nucleotides of the first antisense strand are modified nucleotides, wherein said first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of said second sense strand and substantially all of the nucleotides of said second antisense strand are modified nucleotides, wherein said second sense strand is conjugated to a ligand attached at the 3'-terminus, and wherein the ligand is one or more GalNAc derivatives attached through a bivalent or trivalent branched linker; wherein the first and second sense strands each independently comprise a sequence selected from the group consisting of
5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9),
5'-CGUGGUGGUCUUCUCUAAAUU-3'(SEQ ID NO:37),
5'-GGUGGACUUCUCUCAAUUUUA-3'(SEQ ID NO:11), and
5'-GUGUGCACUUCGCUUCACA-3'(SEQ ID NO:39) (or a nucleotide sequence which is at least 90%, 91%, 92%, 93%, 94%, 95%, 96%, 97%, 98%, or 99% identical over its entire length to the foregoing nucleotide sequences), and wherein the first and second antisense strands each independently comprise a sequence selected from the group consisting of
5'-UGAGAGAAGUCCACCACGAUU-3'(SEQ ID NO:6),
5'-UAGAGGUGAAGCGAAGUGCACUU-3'(SEQ ID NO:8),
5'-AAUUGAGAGAAGUCCACCAGCAG-3'(SEQ ID NO:10),
5'-AAUUGAGAGAAGUCCACCAGCUU-3'(SEQ ID NO:38),
5'-UAAAAUUGAGAGAAGUCCACCAC-3'(SEQ ID NO:12), and
5'-UGUGAAGCGAAGUGCACACUU-3'(SEQ ID NO:40) (or a nucleotide sequence which is at least 90%, 91%, 92%, 93%, 94%, 95%, 96%, 97%, 98%, or 99% identical over its entire length to the foregoing nucleotide sequences).

In one embodiment, the first and second sense strand and/or all of the nucleotides of the first and second antisense strand comprise a modification.

In one embodiment, the at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, the first and second RNAi agents are selected from the group consisting of:
5'-uscsguGfgUfGfGfacuucucuca-3'(SEQ ID NO:13)
5'-usGfsagaGfaAfGfuccaCfcAfcgasusu-3'(SEQ ID NO:14);
5'-uscsguGfgUfGfGfacuucucuca-3'(SEQ ID NO:15)
5'-PusGfsagaGfaAfGfuccaCfcAfcgasusu-3'(SEQ ID NO:16);
5'-gsusgcacUfuCfGfCfuucaccucua-3'(SEQ ID NO:17)
5'-usAfsgagGfugaagcgAfaGfugcacsusu-3'(SEQ ID NO:18);
5'-gsusgcacUfuCfGfCfuucaccucua-3'(SEQ ID NO:19)
5'-PusAfsgagGfugaagcgAfaGfugcacsusu-3'(SEQ ID NO:20);
5'-csgsugguGfgAfCfUfucucUfCfaauu-3'(SEQ ID NO:21)
5'-asAfsuugAfgAfgAfaguCfcAfccagcsasg-3'(SEQ ID NO:22);
5'-csgsugguGfgAfCfUfucucUfCfaauu-3'(SEQ ID NO:23)
5'-PasAfsuugAfgAfgAfaguCfcAfccagcsasg-3'(SEQ ID NO:24);
5'-csgsuggudGgucdTucucuaaauu-3'(SEQ ID NO:35)
5'-asdAsuugagagdAagudCcaccagcsusu-3'(SEQ ID NO:36);
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26);
5'-gsgsuggaCfuUfCfUfcucaAfUfuuua-3'(SEQ ID NO:27)
5'-PusAfsaaaUfuGfAfgagaAfgUfccaccsasc-3'(SEQ ID NO:28); and
5'-gsusguGfcAfCfUfucgcuucaca-3'(SEQ ID NO:41)
5'-usGfsugaAfgCfGfaaguGfcAfcacsusu-3'(SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; dA, dC, dG, and dT are deoxyribose A, C, G, and T; s is a phosphorothioate linkage; and P is a 5'-phosphate or 5'phosphate mimic.

In one embodiment, the first and second RNAi agents are
5'-uscsguGfgUfGfGfacuucucuca-3'(SEQ ID NO:15)
5'-PusGfsagaGfaAfGfuccaCfcAfcgasusu-3'(SEQ ID NO:16)
5'-csgsugguGfgAfCfUfucucUfCfaauu-3'(SEQ ID NO:21)
5'-asAfsuugAfgAfgAfaguCfcAfccagcsasg-3'(SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic.

In another embodiment, the first and second RNAi agents are
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26); and
5'-gsusguGfcAfCfUfucgcuucaca-3'(SEQ ID NO:41)
5'-usGfsugaAfgCfGfaaguGfcAfcacsusu-3'(SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic.

In one aspect, the present invention provides a double stranded RNAi agent comprising the RNAi agents listed in any one of Tables 3, 4, 6, 7, 12, 13, 22, 23, 25, and 26.

The present invention also provides vectors and cells comprising the double stranded RNAi agent of the invention.

In another aspect, the present invention provides pharmaceutical compositions comprising the double stranded RNAi agents of the invention, or the compositions of the invention, or the vectors of the invention.

In one embodiment, the double stranded RNAi agent is administered in an unbuffered solution. In one embodiment, the unbuffered solution is saline or water.

In another embodiment, the double stranded RNAi agent is administered with a buffer solution. In one embodiment, the buffer solution comprises acetate, citrate, prolamine, carbonate, or phosphate or any combination thereof. In another embodiment, the buffer solution is phosphate buffered saline (PBS).

In one aspect, the present invention provides methods of inhibiting Hepatitis B virus (HBV) gene expression in a cell. The methods include contacting the cell with the double stranded RNAi agent of the invention, or the composition of the invention, or the vector of the invention, or the pharmaceutical composition of the invention; and maintaining the cell produced for a time sufficient to obtain degradation of the mRNA transcript of an HBV gene, thereby inhibiting expression of the HBV gene in the cell.

In one embodiment, the HBV gene is selected from the group consisting of C, X, P, S, and a combination thereof.

In one aspect, the present invention provides methods of inhibiting replication of a Hepatitis B virus (HBV) in a cell. The methods include contacting the cell with the double stranded RNAi agent of the invention, or the composition of the invention, or the vector of the invention, or the pharmaceutical composition of the invention; and maintaining the cell produced for a time sufficient to obtain degradation of the mRNA transcript of an HBV gene, thereby inhibiting replication of the HBV in the cell.

In one embodiment, the cell is within a subject. In one embodiment, the subject is a human.

In one embodiment, the subject suffers from an HBV-associated disease.

In one embodiment, HBV gene expression is inhibited by at least about 30%, about 40%, about 50%, about 60%, about 70%, about 80%, about 90%, about 95%, about 98% or about 100%.

In one embodiment, replication of HBV in the cell is inhibited by at least about 30%, about 40%, about 50%, about 60%, about 70%, about 80%, about 90%, about 95%, about 98% or about 100%.

In one aspect, the present invention provides methods of reducing the level of Hepatitis B virus (HBV) DNA in a subject infected with HBV. The methods include administering to the subject a therapeutically effective amount of the double stranded RNAi agent of the invention, or the composition of the invention, or the vector of the invention, or the pharmaceutical composition of the invention, thereby reducing the level of HBV ccc DNA in the subject.

In another aspect, the present invention provides methods of reducing the level of a Hepatitis B virus (HBV) antigen in a subject infected with HBV. The methods include administering to the subject a therapeutically effective amount of the double stranded RNAi agent of the invention, or the composition of the invention, or the vector of the invention, or the pharmaceutical composition of the invention, thereby reducing the level of the HBV antigen in the subject.

In one embodiment, the HBV antigen is HBsAg. In another embodiment, the HBV antigen is HBeAg.

In another aspect, the present invention provides methods of reducing the viral load of Hepatitis B virus (HBV) in a subject infected with HBV. The methods include administering to the subject a therapeutically effective amount of the double stranded RNAi agent of the invention, or the composition of the invention, or the vector of the invention, or the pharmaceutical composition of the invention, thereby reducing the viral load of HBV in the subject.

In yet another aspect, the present invention provides methods of reducing the level of alanine aminotransferase (ALT) in a subject infected with HBV. The methods include administering to the subject a therapeutically effective amount of the double stranded RNAi agent of the invention, or the composition of the invention, or the vector of the invention, or the pharmaceutical composition of the invention, thereby reducing the level of ALT in the subject.

In another aspect, the present invention provides methods of reducing the level of aspartate aminotransferase (AST) in a subject infected with HBV. The methods include administering to the subject a therapeutically effective amount of the double stranded RNAi agent of the invention, or the composition of the invention, or the vector of the invention, or the pharmaceutical composition of the invention, thereby reducing the level of AST in the subject.

In another aspect, the present invention provides methods of increasing the level of anti-Hepatitis B virus (HBV) antibodies in a subject infected with HBV. The methods include administering to the subject a therapeutically effective amount of the double stranded RNAi agent of the invention, or the composition of the invention, or the vector of the invention, or the pharmaceutical composition of the invention, thereby increasing the level of anti-HBV antibodies in the subject.

In one aspect, the present invention provides methods of treating a subject having a Hepatitis B virus (HBV) infection. The methods include administering to the subject a therapeutically effective amount of the double stranded RNAi agent of the invention, or the composition of the invention, or the vector of the invention, or the pharmaceutical composition of the invention, thereby treating said subject.

In another aspect, the present invention provides methods of treating a subject having a Hepatitis B virus (HBV)-associated disorder. The methods include administering to the subject a therapeutically effective amount of the double stranded RNAi agent of the invention, or the composition of the invention, or the vector of the invention, or the pharmaceutical composition of the invention, thereby treating said subject.

In one embodiment, the HBV-associated disorder is selected from the group consisting of hepatitis D virus infection, delta hepatitis, acute hepatitis B; acute fulminant hepatitis B; chronic hepatitis B; liver fibrosis; end-stage liver disease; hepatocellular carcinoma.

In one embodiment, the HBV-associated disorder is chronic hepatitis and the subject is HBeAg positive. In another embodiment, the HBV-associated disorder is chronic hepatitis and the subject is HBeAg negative.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein said sense strand comprises 5'-UCGUGGUGGACUUCUCUCA-3' (SEQ ID NO:5) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UGAGAGAAGUCCAC-CACGAUU-3' (SEQ ID NO:6) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein said double stranded RNAi agent comprises a sense strand and an antisense strand forming a double-stranded region, wherein said sense strand comprises 5'-UCGUGGUGGACUUCUCUCA-3' (SEQ ID NO:5) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UGAGAGAAGUC-CACCACGAUU-3' (SEQ ID NO:6) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein said sense strand comprises 5'-GUGCACUUCGCUUCACCUCUA-3' (SEQ ID NO:7) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UAGAGGUGAAGC-GAAGUGCACUU-3' (SEQ ID NO:8) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein said double stranded RNAi agent comprises a sense strand and an antisense strand forming a double-stranded region, wherein said sense strand comprises 5'-GUGCACUUCGCUUCACCUCUA-3' (SEQ ID NO:7) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UAGAG-GUGAAGCGAAGUGCACUU-3' (SEQ ID NO:8) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein said sense strand comprises 5'-CGUGGUGGACUUCUCUCAAUU-3' (SEQ ID NO:9) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-AAUUGAGAGAAGUC-CACCAGCAG-3' (SEQ ID NO:10) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein said double stranded RNAi agent comprises a sense strand and an antisense strand forming a double-stranded region, wherein said sense strand comprises 5'-CGUGGUGGACUUCUCUCAAUU-3' (SEQ ID NO:9) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-AAUUGAGAGAAGUCCACCAGCAG-3' (SEQ ID NO:10) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein the sense strand comprises 5'-CGUGGUGGUCUUCUCUAAAUU-3' (SEQ ID NO:37), (or a nucleotide sequence which is at least 90%, 91%, 92%, 93%, 94%, 95%, 96%, 97%, 98%, or 99% identical over its entire length to the foregoing nucleotide sequence), and the antisense strand comprises 5'-AAUUGA-GAGAAGUCCACCAGCUU-3' (SEQ ID NO:38) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein the double stranded RNAi agent comprises a sense strand and an antisense strand forming a double-stranded region, wherein the sense strand comprises 5'-CGUGGUGGUCUUCUCUAAAUU-3' (SEQ ID NO:37) (or a nucleotide sequence which is at least 90%, 91%, 92%, 93%, 94%, 95%, 96%, 97%, 98%, or 99% identical over its entire length to the foregoing nucleotide sequence), and the antisense strand comprises 5'-AAUUGA-GAGAAGUCCACCAGCUU-3' (SEQ ID NO:38) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of the sense strand and substantially all of the nucleotides of the antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein said sense strand comprises 5'-GGUGGACUUCUCUCAAUUUUA-3' (SEQ ID NO:11) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UAAAAUUGAGAGAAGU-CCACCAC-3' (SEQ ID NO:12) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein said double stranded RNAi agent comprises a sense strand and an antisense strand forming a double-stranded region, wherein said sense strand comprises 5'-GGUGGACUUCUCUCAAUUUUA-3' (SEQ ID NO:11) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UAAAAUUGAGAGAAGUCCACCAC-3' (SEQ ID NO:12) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one aspect, the present invention provides methods of treating a subject having a Hepatitis B virus (HBV) infection. The methods include administering to the subject a therapeutically effective amount of a double stranded RNAi agent, wherein said double stranded RNAi agent comprises a sense strand and an antisense strand forming a double-stranded region, wherein said sense strand comprises 5'-GUGCACUUCGCUUCACA-3' (SEQ ID NO:39) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UGUGAAGCGAAGUGCA-CACUU-3' (SEQ ID NO:40) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In another aspect, the present invention provides methods of treating a subject having a Hepatitis B virus (HBV)-associated disorder. The methods include administering to the subject a therapeutically effective amount of a double stranded RNAi agent, wherein said double stranded RNAi agent comprises a sense strand and an antisense strand forming a double-stranded region, wherein said sense strand comprises 5'-GUGUGCACUUCGCUUCACA-3' (SEQ ID NO:39) (or a nucleotide sequence which is at least 90%, 91%, 92%, 93%, 94%, 95%, 96%, 97%, 98%, or 99% identical over its entire length to the foregoing nucleotide sequence), and said antisense strand comprises 5'-UGUGAAGCGAAGUGCACACUU-3' (SEQ ID NO:40) (or a nucleotide sequence which is at least 90%, 91%, 92%, 93%, 94%, 95%, 96%, 97%, 98%, or 99% identical over its entire length to the foregoing nucleotide sequence), wherein substantially all of the nucleotides of said sense strand and substantially all of the nucleotides of said antisense strand are modified nucleotides, wherein said sense strand is conjugated to a ligand attached at the 3'-terminus, and wherein the ligand is one or more GalNAc derivatives attached through a bivalent or trivalent branched linker, thereby treating the subject.

In one embodiment, all of the nucleotides of said sense strand and all of the nucleotides of said antisense strand comprise a modification.

In one embodiment, the at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, the 5'-phosphate mimic is a 5'-vinyl phosphate (5'-VP).

In one embodiment, the sense strand comprises 5'-usc-sguGfgUfGfGfacuucucuca-3' (SEQ ID NO:13) and the antisense strand comprises 5'-usGfsagaGfaAfGfuccaCfcAfcga-susu-3' (SEQ ID NO:14), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-uscsguGfgUfGfGfacuucucuca-3' (SEQ ID NO:15) and the antisense strand comprises 5'-PusGfsagaGfaAfGfuccaCfcAfcgasusu-3' (SEQ ID NO:16), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In one embodiment, the sense strand comprises 5'-gsusgcacUfuCfGfCfuucaccucua-3' (SEQ ID NO:17) and the antisense strand comprises 5'-usAfsgagGfugaagcgAfaGfugcacsusu-3' (SEQ ID NO:18), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-gsusgcacUfuCfGfCfuucaccucua-3' (SEQ ID NO:19) and the antisense strand comprises 5'-PusAfsgagGfugaagcgAfaGfugcacsusu-3' (SEQ ID NO:20), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In one embodiment, the sense strand comprises 5'-csgsugguGfgAfCfUfucucUfCfaauu-3' (SEQ ID NO:21) and the antisense strand comprises 5'-asAfsuugAfgAfgAfaguCfcAfccagcsasg-3' (SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-csgsugguGfgAfCfUfucucUfCfaauu-3' (SEQ ID NO:23) and the antisense strand comprises 5'-PasAfsuugAfgAfgAfaguCfcAfccagcsasg-3' (SEQ ID NO:24), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In another embodiment, the sense strand comprises 5'-csgsuggudGgucdTucucuaaauu-3' (SEQ ID NO:35) and the antisense strand comprises 5'-asdAsuugagagdAagudCcaccagcsusu-3' (SEQ ID NO:36), wherein A, C, G, and U are ribose A, C, G or U; a, g, c and u are 2'-O-methyl (2'-OMe) A, U, C, or G; dA, dC, dG, and dT are deoxyribose A, C, G, and T; and s is a phosphorothioate linkage.

In one embodiment, the sense strand comprises 5'-gsgsuggaCfuUfCfUfcucaAfUfuuua-3' (SEQ ID NO:25) and the antisense strand comprises 5'-usAfsaaaUfuGfAfgagaAfgUfccaccsasc-3' (SEQ ID NO:26), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In another embodiment, the sense strand comprises 5'-gsgsuggaCfuUfCfUfcucaAfUfuuua-3' (SEQ ID NO:27) and the antisense strand comprises 5'-PusAfsaaaUfuGfAfgagaAfgUfccaccsasc-3' (SEQ ID NO:28), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic.

In another embodiment, the sense strand comprises 5'-gsusguGfcAfCfUfucgcuucaca-3' (SEQ ID NO:41) and the antisense strand comprises 5'-usGfsugaAfgCfGfaaguGfcAfcacsusu-3' (SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In one embodiment, the ligand is

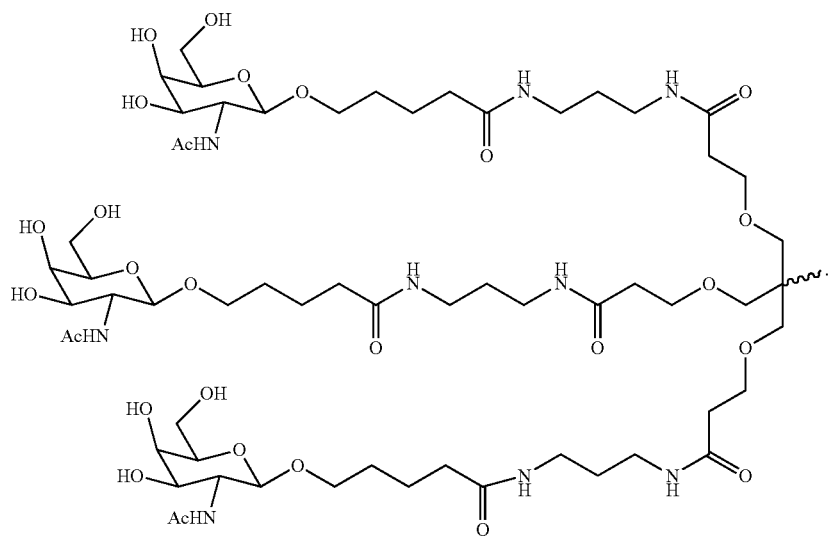 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the RNAi agent is conjugated to the ligand at the 3' end of the sense strand, as shown in the following structure:

5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9),

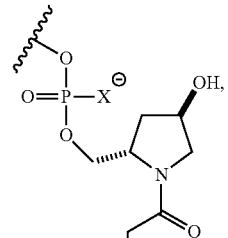

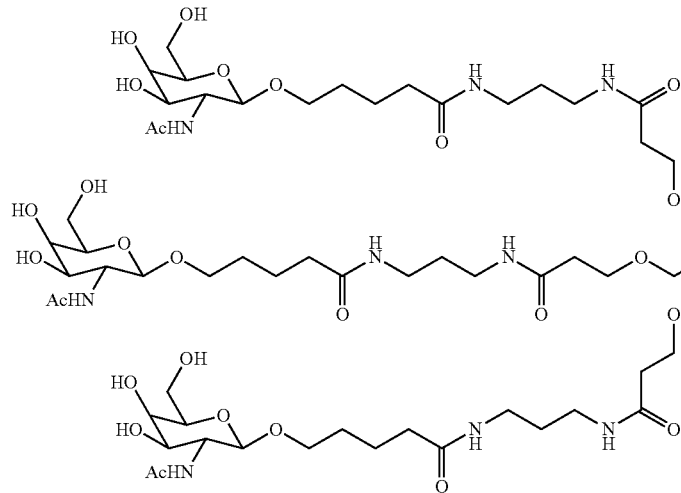

wherein X is O or S.

In one embodiment, the HBV-associated disorder is selected from the group consisting of hepatitis D virus infection, delta hepatitis, acute hepatitis B; acute fulminant hepatitis B; chronic hepatitis B; liver fibrosis; end-stage liver disease; hepatocellular carcinoma.

In one embodiment, the HBV-associated disorder is chronic hepatitis and the subject is HBeAg positive. In another embodiment, the HBV-associated disorder is chronic hepatitis and the subject is HBeAg negative.

In one aspect, the present invention provides methods of treating a subject having a Hepatitis B virus (HBV) infection. The methods include administering to the subject a therapeutically effective amount of a composition for inhibiting expression of hepatitis B virus (HBV) in a cell. The composition includes: (a) a first double-stranded RNAi agent comprising a first sense strand and a first antisense strand forming a double-stranded region, wherein substantially all of the nucleotides of said first sense strand and substantially all of the nucleotides of said first antisense strand are modified nucleotides, wherein said first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of said second sense strand and substantially all of the nucleotides of said second antisense strand are modified nucleotides, wherein said second sense strand is conjugated to a ligand attached at the 3'-terminus, and wherein the ligand is one or more GalNAc derivatives attached through a bivalent or trivalent branched linker; wherein the first and second sense strands each independently comprise a sequence selected from the group consisting of 5'-CGUGGUGGUCUUCUCUAAAUU-3'(SEQ ID NO:37),
5'-GGUGGACUUCUCUCAAUUUUA-3'(SEQ ID NO:11), and
5'-GUGUGCACUUCGCUUCACA-3'(SEQ ID NO:39) (or a nucleotide sequence which is at least 90%, 91%, 92%, 93%, 94%, 95%, 96%, 97%, 98%, or 99% identical over its entire length to any of the foregoing nucleotide sequences), and wherein the first and second antisense strands each independently comprise a sequence selected from the group consisting of
5'-UGAGAGAAGUCCACCACGAUU-3'(SEQ ID NO:6);
5'-UAGAGGUGAAGCGAAGUGCACUU-3'(SEQ ID NO:8);
5'-AAUUGAGAGAAGUCCACCAGCAG-3'(SEQ ID NO:10);
5'-AAUUGAGAGAAGUCCACCAGCUU-3'(SEQ ID NO:38),
5'-UAAAAUUGAGAGAAGUCCACCAC-3'(SEQ ID NO:12), and
5'-UGUGAAGCGAAGUGCACACUU-3'(SEQ ID NO:40) (or a nucleotide sequence which is at least 90%, 91%, 92%, 93%, 94%, 95%, 96%, 97%, 98%, or 99% identical over its entire length to any of the foregoing nucleotide sequences), thereby treating the subject.

In another aspect, the present invention provides methods of treating a subject having a Hepatitis B virus (HBV)-associated disorder. The methods include administering to the subject a therapeutically effective amount of a composition for inhibiting expression of hepatitis B virus (HBV) in a cell. The composition includes: (a) a first double-stranded RNAi agent comprising a first sense strand and a first antisense strand forming a double-stranded region, wherein substantially all of the nucleotides of said first sense strand and substantially all of the nucleotides of said first antisense strand are modified nucleotides, wherein said first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of said second sense strand and substantially all of the nucleotides of said second antisense strand are modified nucleotides, wherein said second sense strand is conjugated to a ligand attached at the 3'-terminus, and wherein the ligand is one or more GalNAc derivatives attached through a bivalent or trivalent branched linker; wherein the first and second sense strands each independently comprise a sequence selected from the group consisting of
5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9),
5'-CGUGGUGGUCUUCUCUAAAUU-3'(SEQ ID NO:37),
5'-GGUGGACUUCUCUCAAUUUUA-3'(SEQ ID NO:11), and
5'-GUGUGCACUUCGCUUCACA-3'(SEQ ID NO:39) (or a nucleotide sequence which is at least 90%, 91%, 92%, 93%, 94%, 95%, 96%, 97%, 98%, or 99% identical over its entire length to any of the foregoing nucleotide sequences), and wherein the first and second antisense strands each independently comprise a sequence selected from the group consisting of
5'-UGAGAGAAGUCCACCACGAUU-3'(SEQ ID NO:6);
5'-UAGAGGUGAAGCGAAGUGCACUU-3'(SEQ ID NO:8);
5'-AAUUGAGAGAAGUCCACCAGCAG-3'(SEQ ID NO:10);
5'-AAUUGAGAGAAGUCCACCAGCUU-3'(SEQ ID NO:38),
5'-UAAAAUUGAGAGAAGUCCACCAC-3'(SEQ ID NO:12), and
5'-UGUGAAGCGAAGUGCACACUU-3'(SEQ ID NO:40) (or a nucleotide sequence which is at least 90%, 91%, 92%, 93%, 94%, 95%, 96%, 97%, 98%, or 99% identical over its entire length to any of the foregoing nucleotide sequences), thereby treating the subject.

In one embodiment, all of the nucleotides of the first and second sense strand and all of the nucleotides of the first and second antisense strand comprise a modification.

In one embodiment, the at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In one embodiment, the first and second RNAi agent are selected from the group consisting of:
5'-uscsguGfgUfGfGfacuucucuca-3'(SEQ ID NO:13)
5'-usGfsagaGfaAfGfuccaCfcAfcgasusu-3'(SEQ ID NO:14);
5'-uscsguGfgUfGfGfacuucucuca-3'(SEQ ID NO:15)
5'-PusGfsagaGfaAfGfuccaCfcAfcgasusu-3'(SEQ ID NO:16);
5'-gsusgcacUfuCfGfCfuucaccucua-3'(SEQ ID NO:17)
5'-usAfsgagGfugaagcgAfaGfugcacsusu-3'(SEQ ID NO:18);
5'-gsusgcacUfuCfGfCfuucaccucua-3'(SEQ ID NO:19)
5'-PusAfsgagGfugaagcgAfaGfugcacsusu-3'(SEQ ID NO:20);
5'-csgsugguGfgAfCfUfucucUfCfaauu-3'(SEQ ID NO:21)
5'-asAfsuugAfgAfgAfaguCfcAfccagcsasg-3'(SEQ ID NO:22);
5'-csgsugguGfgAfCfUfucucUfCfaauu-3'(SEQ ID NO:23)
5'-PasAfsuugAfgAfgAfaguCfcAfccagcsasg-3'(SEQ ID NO:24);
5'-csgsuggudGgucdTucucuaaauu-3'(SEQ ID NO:35)
5'-asdAsuugagagdAagudCcaccagcsusu-3'(SEQ ID NO:36);
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26);
5'-gsgsuggaCfuUfCfUfcucaAfUfuuua-3'(SEQ ID NO:27)
5'-PusAfsaaaUfuGfAfgagaAfgUfccaccsasc-3'(SEQ ID NO:28); and
5'-gsusguGfcAfCfUfucgcuucaca-3'(SEQ ID NO:41)
5'-usGfsugaAfgCfGfaaguGfcAfcacsusu-3'(SEQ ID NO:42),
wherein A, C, G, and U are ribose A, C, G or U; a, g, c and u are 2'-O-methyl (2'-OMe) A, U, C, or G; Af, Cf, Gf or Uf are 2'-fluoro A, G, C or U; dA, dC, dG, and dT are deoxyribose A, C, G, and T; s is a phosphorothioate linkage; and P is a 5'-phosphate or 5'phosphate mimic.

In one embodiment, the first and second RNAi agents are
5'-uscsguGfgUfGfGfacuucucuca-3'(SEQ ID NO:15)
5'-PusGfsagaGfaAfGfuccaCfcAfcgasusu-3'(SEQ ID NO:16); and
5'-csgsugguGfgAfCfUfucucUfCfaauu-3'(SEQ ID NO:21)
5'-asAfsuugAfgAfgAfaguCfcAfccagcsasg-3'(SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic.

In another embodiment, the first and second RNAi agents are
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26); and
5'-gsusguGfcAfCfUfucgcuucaca-3'(SEQ ID NO:41)
5'-usGfsugaAfgCfGfaaguGfcAfcacsusu-3'(SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic.

In one embodiment, the ligand is

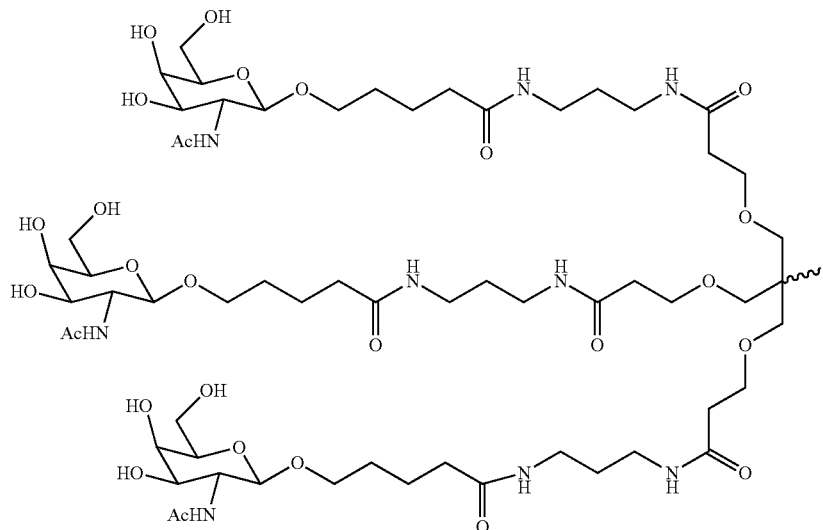

In one embodiment, the RNAi agent is conjugated to the ligand as shown in the following schematic In one embodiment, the RNAi agent is conjugated to the ligand at the 3' end of the sense strand, as shown in the following structure:

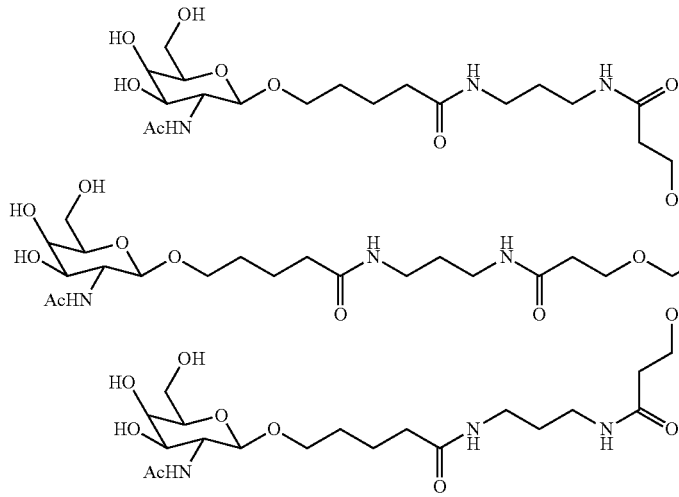 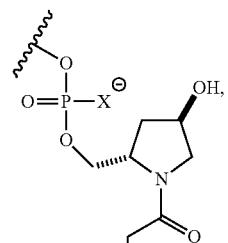

wherein X is O or S.

In one embodiment, the subject is a human.

In one embodiment, the HBV-associated disorder is selected from the group consisting of hepatitis D virus infection, delta hepatitis, acute hepatitis B; acute fulminant hepatitis B; chronic hepatitis B; liver fibrosis; end-stage liver disease; hepatocellular carcinoma.

In one embodiment, the HBV-associated disorder is chronic hepatitis and the subject is HBeAg positive. In another embodiment, the HBV-associated disorder is chronic hepatitis and the subject is HBeAg negative.

In one embodiment, the double stranded RNAi agent is administered at a dose of about 0.01 mg/kg to about 10 mg/kg or about 0.5 mg/kg to about 50 mg/kg.

In one embodiment, the double stranded RNAi agent is administered at a dose of about 10 mg/kg to about 30 mg/kg.

In another embodiment, the double stranded RNAi agent is administered at a dose of about 3 mg/kg. In one embodiment, the double stranded RNAi agent is administered at a dose of about 10 mg/kg.

In one embodiment, the double stranded RNAi agent is administered at a dose of about 0.5 mg/kg twice per week.

In one embodiment, the double stranded RNAi agent is administered at a fixed dose of about 50 mg to 200 mg.

In one embodiment, the double stranded RNAi agent is administered subcutaneously. In another embodiment, the double stranded RNAi agent is administered intravenously.

In one embodiment, the RNAi agent is administered in two or more doses.

In one embodiment, the RNAi agent is administered at intervals selected from the group consisting of once every about 12 hours, once every about 24 hours, once every about 48 hours, once every about 72 hours, and once every about 96 hours.

In one embodiment, the RNAi agent is administered twice per week. In another embodiment, the RNAi agent is administered every other week.

In one embodiment, the methods of the invention further include administering to the subject an additional therapeutic agent.

In one embodiment, the additional therapeutic agent is selected from the group consisting of an antiviral agent, a reverse transcriptase inhibitor, an immune stimulator, a therapeutic vaccine, a viral entry inhibitor, an oligonucleotide that inhibits the secretion or release of HbsAg, a capsid inhibitor, a cccDNA inhibitor, and a combination of any of the foregoing.

In another embodiment, the methods of the invention further include administering administering to the subject a reverse transcriptase inhibitor. In yet another embodiment, the methods of the invention further include administering to the subject a reverse transcriptase inhibitor and an immune stimulator.

In one embodiment, the reverse transcriptase inhibitor is selected from the group consisting of Tenofovir disoproxil fumarate (TDF), Tenofovir alafenamide, Lamivudine, Adefovir dipivoxil, Entecavir (ETV), Telbivudine, and AGX-1009.

In some embodiments, the methods of the invention further comprise treatment of hepatitis D virus (HDV) in the subject. Methods of treatment can include any methods of treatment known in the art. In certain embodiments, HDV is treated in the subject using one of more of the iRNA agents targeting HBV as described herein.

In some embodiments, the methods of the invention further include methods to modulate, e.g., decrease, the expression of PD-L1. Compositions and methods to reduce the expression of PD-L1 are provided, for example, in PCT publication no. WO2011/127180, the entire contents of which are hereby incorporated herein by reference.

In one embodiment, the immune stimulator is selected from the group consisting of pegylated interferon alfa 2a (PEG-IFN-α2a), Interferon alfa-2b, a recombinant human interleukin-7, and aToll-like receptor 7 (TLR7) agonist.

In a further aspect, the present invention provides a method of treating a subject having a Hepatitis B virus (HBV)-associated disorder, comprising administering to the subject a therapeutically effective amount of a double stranded RNAi agent, wherein the double stranded RNAi agent comprises a sense strand and an antisense strand forming a double-stranded region, wherein the sense strand comprises at least 15 contiguous nucleotides differing by no more than 3 nucleotides from the nucleotide sequence of SEQ ID NO:29, and said antisense strand comprises at least 15 contiguous nucleotides differing by no more than 3 nucleotides from the nucleotide sequence of SEQ ID NO:30, wherein substantially all of the nucleotides of the sense strand and substantially all of the nucleotides of the antisense strand are modified nucleotides, wherein the sense strand is conjugated to a ligand attached at the 3'-terminus, and wherein the ligand is one or more GalNAc derivatives attached through a bivalent or trivalent branched linker, thereby treating the subject.

In another aspect, the present invention also provides a method of treating a subject having a Hepatitis B virus (HBV) infection, comprising administering to the subject a therapeutically effective amount of a composition for inhibiting expression of hepatitis B virus (HBV) in a cell, said composition comprising (a) a first double-stranded RNAi agent comprising a first strand and a first antisense strand forming a double-stranded region, wherein substantially all of the nucleotides of the first sense strand and substantially all of the nucleotides of the first antisense strand are modified nucleotides, wherein said first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of the second sense strand and substantially all of the nucleotides of the second antisense strand are modified nucleotides, wherein the second sense strand is conjugated to a ligand attached at the 3'-terminus, and wherein the ligand is one or more GalNAc derivatives attached through a bivalent or trivalent branched linker; wherein the first sense strand comprises at least 15 contiguous nucleotides differing by no more than 3 nucleotides from the nucleotide sequence of SEQ ID NO:1, and said first antisense strand comprises at least 15 contiguous nucleotides differing by no more than 3 nucleotides from the nucleotide sequence of SEQ ID NO:2, wherein the sense second strand comprises at least 15 contiguous nucleotides differing by no more than 3 nucleotides from the nucleotide sequence of SEQ ID NO:29, and the second antisense strand comprises at least 15 contiguous nucleotides differing by no more than 3 nucleotides from the nucleotide sequence of SEQ ID NO:30, thereby treating the subject.

In some embodiments, the first sense strand comprises a sequence selected from the group consisting of
5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9),
5'-CGUGGUGGUCUUCUCUAAAUU-3'(SEQ ID NO:37)

5'-GGUGGACUUCUCUCAAUUUUA-3'(SEQ ID NO:11), and
5'-GUGUGCACUUCGCUUCACA-3'(SEQ ID NO:39), (or a nucleotide sequence which is at least 90%, 91%, 92%, 93%, 94%, 95%, 96%, 97%, 98%, or 99% identical over its entire length to the foregoing nucleotide sequences), and the second antisense strand comprises a sequence selected from the group consisting of
5'-UGAGAGAAGUCCACCACGAUU-3'(SEQ ID NO:6);
5'-UAGAGGUGAAGCGAAGUGCACUU-3'(SEQ ID NO:8);
5'-AAUUGAGAGAAGUCCACCAGCAG-3'(SEQ ID NO:10);
5'-AAUUGAGAGAAGUCCACCAGCUU-3'(SEQ ID NO:38);
5'-UAAAAUUGAGAGAAGUCCACCAC-3'(SEQ ID NO:12); and
5'-UGUGAAGCGAAGUGCACACUU-3'(SEQ ID NO:40) (or a nucleotide sequence which is at least 90%, 91%, 92%, 93%, 94%, 95%, 96%, 97%, 98%, or 99% identical over its entire length to the foregoing nucleotide sequences).

In some aspects, all of the nucleotides of the sense strand and all of the nucleotides of the antisense strand comprise a modification.

In certain embodiments, at least one of the modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydro-hexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In some embodiments, the ligand is

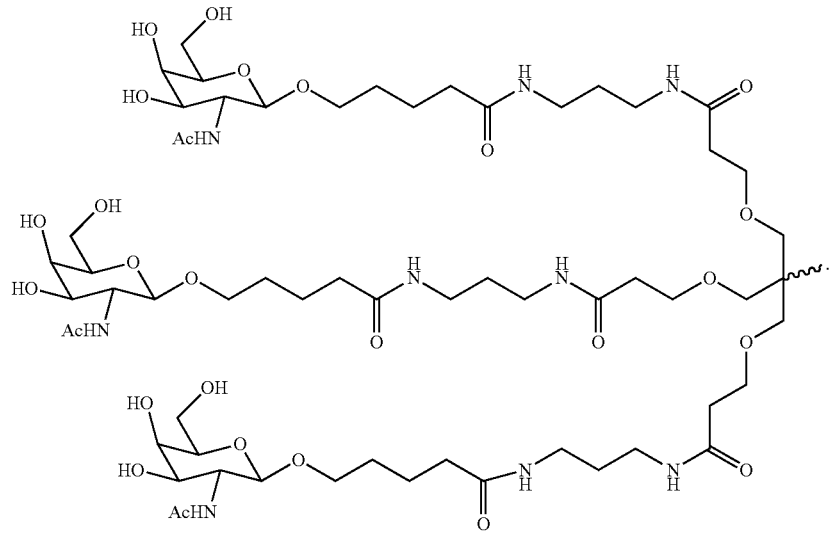 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In a specific embodiment, the RNAi agent is conjugated to the ligand at the 3' end of the sense strand, as shown in the following structure:

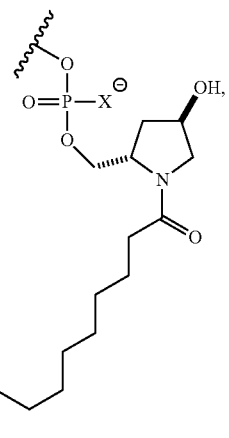
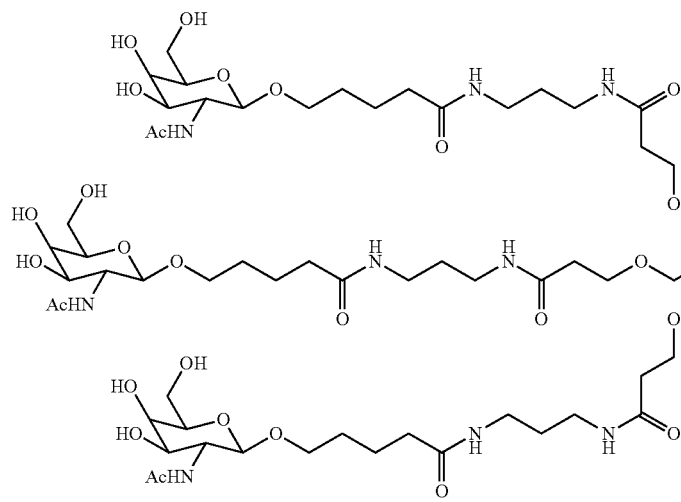

wherein X is O or S.

In certain embodiments, the double stranded RNAi agents and compositions provided herein are used for treatment of an HDV infection and/or an HDV-associated disorder.

Accordingly, the present invention provides methods of inhibiting replication of a Hepatitis D virus (HDV) in a cell. The methods include (a) contacting the cell with a double stranded RNAi agent, composition, vector, or the pharmaceutical composition provided herein; and (b) maintaining the cell produced in step (a) for a time sufficient to obtain degradation of the mRNA transcript of an HBV gene, thereby inhibiting replication of the HDV in the cell.

In certain embodiments, the cell is within a subject. In certain embodiments, the subject is a human The invention further provides methods of reducing the level of a Hepatitis D virus (HDV) antigen in a subject infected with HDV. The methods include administering to the subject a therapeutically effective amount of a double stranded RNAi agent, composition, vector, or the pharmaceutical composition provided herein, thereby reducing the level of the HDV antigen, e.g., S-HDAg or L-HDAg, in the subject.

The invention also provides methods of reducing the viral load of Hepatitis D virus (HDV) in a subject infected with HDV. The methods include administering to the subject a therapeutically effective amount of a double stranded RNAi agent, composition, vector, or pharmaceutical composition provided herein, thereby reducing the viral load of HDV in the subject.

The invention also provides methods of treating a subject having a Hepatitis D virus (HDV) infection, comprising administering to the subject a therapeutically effective amount of a double stranded RNAi agent, composition, vector, or pharmaceutical composition provided herein, thereby treating the subject.

In certain embodiments, the double stranded RNAi agent comprises a sense strand and an antisense strand forming a double-stranded region. Sense strand and antisense strands can be selected from the following RNAi agents wherein, the sense strand comprises 5'-UCGUGGUGGACUUCU-CUCA-3' (SEQ ID NO:5), and the antisense strand comprises 5'-UGAGAGAAGUCCACCACGAUU-3' (SEQ ID NO:6); the sense strand comprises 5'-GUGCACUUCGC-UUCACCUCUA-3' (SEQ ID NO:7), and the antisense strand comprises 5'-UAGAGGUGAAGCGAAGUGCA-CUU-3' (SEQ ID NO:8); the sense strand comprises 5'-CGUGGUGGACUUCUCUCAAUU-3' (SEQ ID NO:9), and the antisense strand comprises 5'-AAUUGAGAGAA-GUCCACCAGCAG-3' (SEQ ID NO:10); the sense strand comprises 5'-CGUGGUGGUCUUCUCUAAAUU-3' (SEQ ID NO:37), and the antisense strand comprises 5'-AAUUGAGAGAAGUCCACCAGCUU-3' (SEQ ID NO:38); the sense strand comprises 5'-GGUGGACUUCU-CUCAAUUUUA-3' (SEQ ID NO:11), and the antisense strand comprises 5'-UAAAAUUGAGAGAAGUCCAC-CAC-3' (SEQ ID NO:12); or the sense strand comprises 5'-GUGUGCACUUCGCUUCACA-3' (SEQ ID NO:39), and the antisense strand comprises 5'-UGUGAAGC-GAAGUGCACACUU-3' (SEQ ID NO:40), wherein substantially all of the nucleotides of the sense strand and substantially all of the nucleotides of the antisense strand are modified nucleotides, wherein the sense strand is conjugated to a ligand attached at the 3'-terminus, and wherein the ligand is one or more GalNAc derivatives attached through a bivalent or trivalent branched linker, thereby treating the subject.

In certain embodiments, all of the nucleotides of the sense strand and all of the nucleotides of the antisense strand comprise a modification. In certain embodiments, at least one of the modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic. In certain embodiments, the 5'-phosphate mimic is a 5'-vinyl phosphate (5'-VP).

In certain embodiments, the sense strand comprises 5'-uscsguGfgUfGfGfacuucucuca-3' (SEQ ID NO:13) and the antisense strand comprises 5'-usGfsagaGfaAfGfuccaCfcAfcgasusu-3' (SEQ ID NO:14), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In certain embodiments, the sense strand comprises 5'-uscsguGfgUfGfGfacuucucuca-3' (SEQ ID NO:15) and the antisense strand comprises 5'-PusGfsagaGfaAfGfuccaCfcAfcgasusu-3' (SEQ ID NO:16), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic In certain embodiments, the sense strand comprises 5'-gsusgcacUfuCfGfCfuucaccucua-3' (SEQ ID NO:17) and the antisense strand comprises 5'-usAfsgagGfugaagcgAfaGfugcacsusu-3' (SEQ ID NO:18), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In certain embodiments, the sense strand comprises 5'-gsusgcacUfuCfGfCfuucaccucua-3' (SEQ ID NO:19) and the antisense strand comprises 5'-PusAfsgagGfugaagcgAf-aGfugcacsusu-3' (SEQ ID NO:20), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic In certain embodiments, sense strand comprises 5'-csgsugguGfgAfCfUfucucUfCfaauu-3' (SEQ ID NO:21) and the antisense strand comprises 5'-AfsuugAfgAfgAfaguCfcAfccagcsasg-3' (SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In certain embodiments, the sense strand comprises 5'-csgsugguGfgAfCfUfucucUfCfaauu-3' (SEQ ID NO:23) and the antisense strand comprises 5'-PasAfsuugAfgAf-gAfaguCfcAfccagcsasg-3' (SEQ ID NO:24), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic In certain embodiments, the sense strand comprises 5'-csgsuggudGgucdTucucuaaauu-3' (SEQ ID NO:35) and the antisense strand comprises 5'-asdAsuugagagdAagudCcaccagcsusu-3' (SEQ ID NO:36), wherein A, C, G, and U are ribose A, C, G or U; a, g, c and u are 2'-O-methyl (2'-OMe) A, U, C, or G; dA, dC, dG, and dT are deoxyribose A, C, G, and T; and s is a phosphorothioate linkage.

In certain embodiments, the sense strand comprises 5'-gsgsuggaCfuUfCfUfcucaAfUfuuua-3' (SEQ ID NO:25) and the antisense strand comprises 5'-usAfsaaaUfuGfAfga-gaAfgUfccaccsasc-3' (SEQ ID NO:26), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In certain embodiments, the sense strand comprises 5'-gsgsuggaCfuUfCfUfcucaAfUfuuua-3' (SEQ ID NO:27) and the antisense strand comprises 5'-PusAfsaaaUfuGfAf-gagaAfgUfccaccsasc-3' (SEQ ID NO:28), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage; and P is a 5'-phosphate or 5'phosphate mimic In certain embodiments, sense strand comprises 5'-gsus-guGfcAfCfUfucgcuucaca-3' (SEQ ID NO:41) and the antisense strand comprises 5'-usGfsugaAfgCfGfaaguGfcAfcacsusu-3' (SEQ ID NO:42), wherein A, C, G, and U are ribose A, C, G or U; a, g, c and u are 2'-O-methyl (2'-OMe) A, U, C, or G; Af, Cf, Gf or Uf are 2'-fluoro A, G, C or U; and s is a phosphorothioate linkage.

In certain embodiments, the ligand is

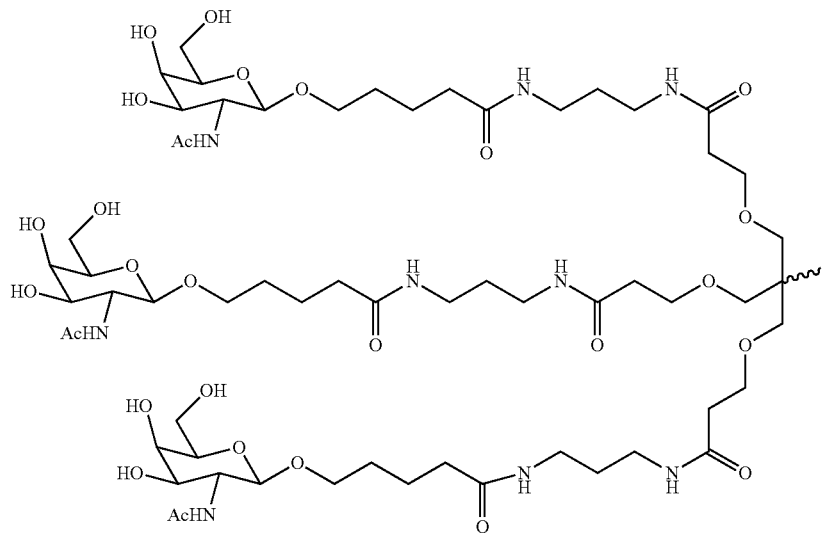

In certain embodiments, the RNAi agent is conjugated to the ligand at the 3' end of the sense strand, as shown in the following structure:

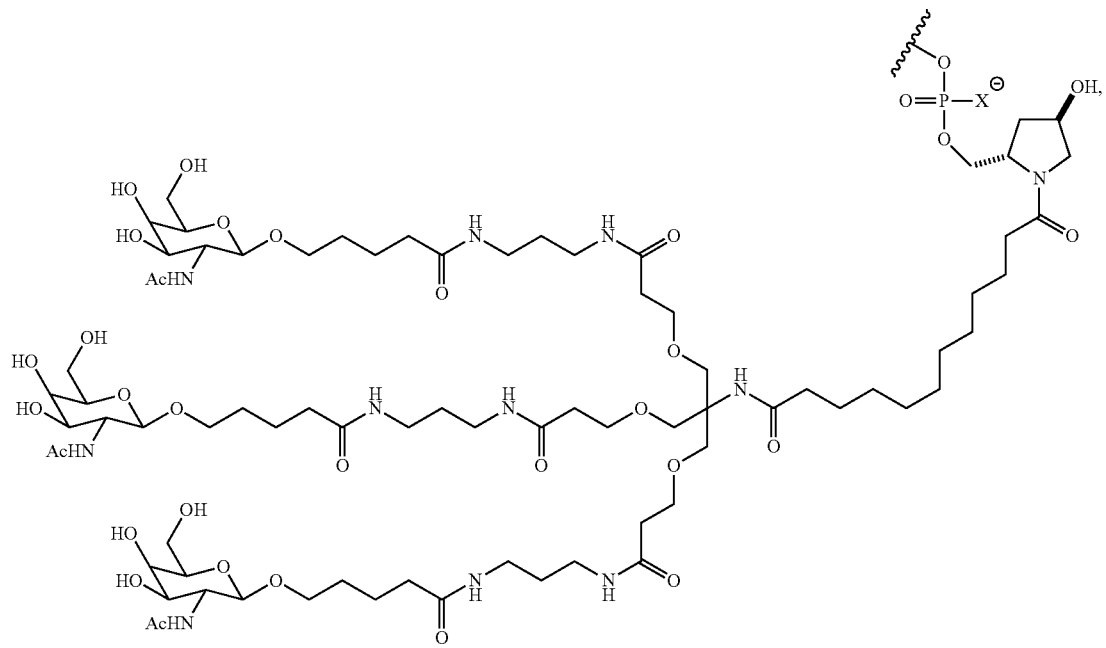

wherein X is O or S.

The invention provides methods of treating a subject having a Hepatitis D virus (HDV) infection. The methods include administering to the subject a therapeutically effective amount of a composition for inhibiting expression of hepatitis B virus (HBV) in a cell, the composition comprising (a) a first double-stranded RNAi agent comprising a first sense strand and a first antisense strand forming a double-stranded region, wherein substantially all of the nucleotides of the first sense strand and substantially all of the nucleotides of the first antisense strand are modified nucleotides, wherein the first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of the second sense strand and substantially all of the nucleotides of the second antisense strand are modified nucleotides, wherein the second sense strand is conjugated to a ligand attached at the 3'-terminus, and wherein the ligand is one or more GalNAc derivatives attached through a bivalent or trivalent branched linker; wherein the first and second sense strands each independently comprise a sequence selected from the group consisting of
5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9), 5'-CGUGGUGGUCUUCUCUAAAUU-3'(SEQ ID NO:37),
5'-GGUGGACUUCUCUCAAUUUUA-3'(SEQ ID NO:11), and
5'-GUGUGCACUUCGCUUCACA-3'(SEQ ID NO:39),
and wherein the first and second antisense strands each independently comprise a sequence selected from the group consisting of
5'-UGAGAGAAGUCCACCACGAUU-3'(SEQ ID NO:6);
5'-UAGAGGUGAAGCGAAGUGCACUU-3'(SEQ ID NO:8);
5'-AAUUGAGAGAAGUCCACCAGCAG-3'(SEQ ID NO:10);
5'-AAUUGAGAGAAGUCCACCAGCUU-3'(SEQ ID NO:38),
5'-UAAAAUUGAGAGAAGUCCACCAC-3'(SEQ ID NO:12), and
5'-UGUGAAGCGAAGUGCACACUU-3'(SEQ ID NO:40),
thereby treating the subject.

In certain embodiments, all of the nucleotides of the first and second sense strand and all of the nucleotides of the first and second antisense strand comprise a modification. In certain embodiments, at least one of the modified nucleotides is selected from the group consisting of a deoxynucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In certain embodiments, the first and second RNAi agent are selected from the group:
5'-uscsguGfgUfGfGfacuucucuca-3'(SEQ ID NO:13)
5'-usGfsagaGfaAfGfuccaCfcAfcgasusu-3'(SEQ ID NO:14);
5'-uscsguGfgUfGfGfacuucucuca-3'(SEQ ID NO:15)
5'-PusGfsagaGfaAfGfuccaCfcAfcgasusu-3'(SEQ ID NO:16);
5'-gsusgcacUfuCfGfCfuucaccucua-3'(SEQ ID NO:17)
5'-usAfsgagGfugaagcgAfaGfugcacsusu-3'(SEQ ID NO:18);
5'-gsusgcacUfuCfGfCfuucaccucua-3'(SEQ ID NO:19)
5'-PusAfsgagGfugaagcgAfaGfugcacsusu-3'(SEQ ID NO:20);
5'-csgsugguGfgAfCfUfucucUfCfaauu-3'(SEQ ID NO:21)
5'-asAfsuugAfgAfgAfaguCfcAfccagcsasg-3'(SEQ ID NO:22);
5'-csgsugguGfgAfCfUfucucUfCfaauu-3'(SEQ ID NO:23)
5'-PasAfsuugAfgAfgAfaguCfcAfccagcsasg-3'(SEQ ID NO:24);
5'-csgsuggudGgucdTucucuaaauu-3'(SEQ ID NO:35)
5'-asdAsuugagagdAagudCcaccagcsusu-3'(SEQ ID NO:36);
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26);
5'-gsgsuggaCfuUfCfUfcucaAfUfuuua-3'(SEQ ID NO:27)
5'-PusAfsaaaUfuGfAfgagaAfgUfccaccsasc-3'(SEQ ID NO:28); and
5'-gsusguGfcAfCfUfucgcuucaca-3'(SEQ ID NO:41)
5'-usGfsugaAfgCfGfaaguGfcAfcacsusu-3'(SEQ ID NO:42),
wherein A, C, G, and U are ribose A, C, G or U; a, g, c and u are 2'-O-methyl (2'-OMe) A, U, C, or G; Af, Cf, Gf or Uf are 2'-fluoro A, G, C or U; dA, dC, dG, and dT are deoxyribose A, C, G, and T; s is a phosphorothioate linkage; and P is a 5'-phosphate or 5'phosphate mimic In certain embodiments, the first and second RNAi agents are
5'-uscsguGfgUfGfGfacuucucuca-3'(SEQ ID NO:15)
5'-PusGfsagaGfaAfGfuccaCfcAfcgasusu-3'(SEQ ID NO:16); and
5'-csgsugguGfgAfCfUfucucUfCfaauu-3'(SEQ ID NO:21)
5'-asAfsuugAfgAfgAfaguCfcAfccagcsasg-3'(SEQ ID NO:22), wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic In certain embodiments, the first and second RNAi agents are
5'-gsgsuggaCfuUfCfUfcucaAfUfuuua-3'(SEQ ID NO:25)
5'-usAfsaaaUfuGfAfgagaAfgUfccaccsasc-3'(SEQ ID NO:26); and
5'-gsusguGfcAfCfUfucgcuucaca-3'(SEQ ID NO:41)
5'-usGfsugaAfgCfGfaaguGfcAfcacsusu-3'(SEQ ID NO:42),
wherein A, C, G, and U are ribose A, C, G or U; a, g, c and u are 2'-O-methyl (2'-OMe) A, U, C, or G; Af, Cf, Gf or Uf are 2'-fluoro A, G, C or U; s is a phosphorothioate linkage; and P is a 5'-phosphate or 5'phosphate mimic In certain embodiments, the ligand is

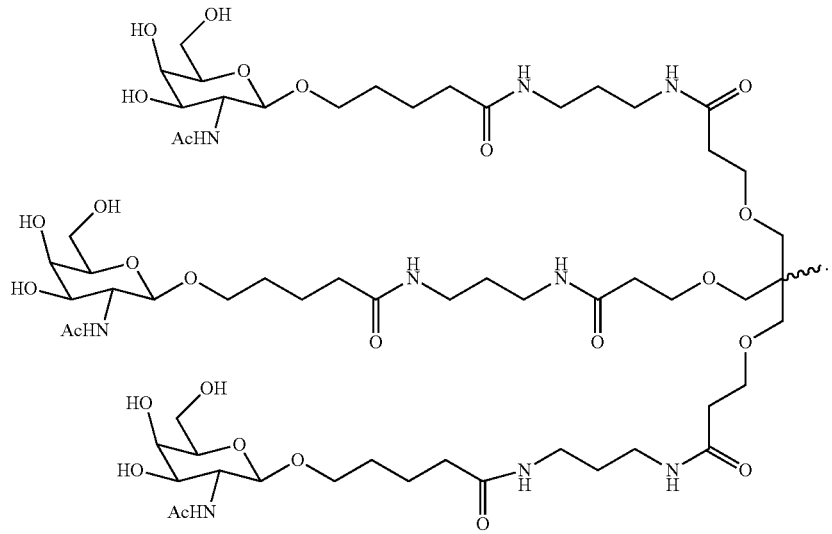 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the RNAi agent is conjugated to the ligand at the 3' end of the sense strand, as shown in the following structure:

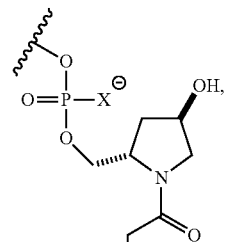
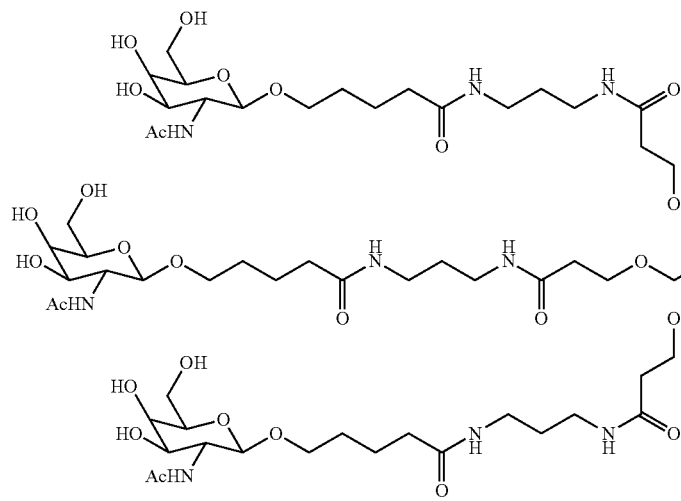

wherein X is O or S.

In certain embodiments, the subject is a human.

In certain embodiments, the double stranded RNAi agent is administered at a dose of about 0.01 mg/kg to about 10 mg/kg or about 0.5 mg/kg to about 50 mg/kg. In certain embodiments, the double stranded RNAi agent is administered at a dose of about 10 mg/kg to about 30 mg/kg. In certain embodiments, the double stranded RNAi agent is administered at a dose of about 3 mg/kg. In certain embodiments, the double stranded RNAi agent is administered at a dose of about 10 mg/kg. In certain embodiments, the double stranded RNAi agent is administered at a dose of about 0.5 mg/kg twice per week. In certain embodiments, the double stranded RNAi agent is administered at a fixed dose of about 50 mg to 200 mg.

In certain embodiments, the double stranded RNAi agent is administered subcutaneously.
In certain embodiments, the double stranded RNAi agent is administered intravenously.

In certain embodiments, the RNAi agent is administered in two or more doses. In certain embodiments, the RNAi agent is administered at intervals selected from the group consisting of once every about 12 hours, once every about 24 hours, once every about 48 hours, once every about 72 hours, and once every about 96 hours. In certain embodiments, the RNAi agent is administered twice per week. In certain embodiments, the RNAi agent is administered every other week. In certain embodiments, the RNAi agent is administered once per month. In certain embodiments, the RNAi agent is administered once every other month. In certain embodiments, the RNAi agent is administered once every three months.

In certain embodiments, the RNAi agent is administered to the subject with an additional therapeutic agent. Additional therapeutic agents include, for example, an antiviral agent, a reverse transcriptase inhibitor, an immune stimulator, a therapeutic vaccine, a viral entry inhibitor, an oligonucleotide that inhibits the secretion or release of HbsAg, a capsid inhibitor, a covalently closed circular (ccc) HBV DNA inhibitor, and a combination of any of the foregoing.

In certain embodiments, the additional agent is a reverse transcriptase inhibitor. In certain embodiments, the additional agent is a reverse transcriptase inhibitor and an immune stimulator. Exemplary reverse transcriptase inhibitors include Tenofovir disoproxil fumarate (TDF), Tenofovir alafenamide, Lamivudine, Adefovir dipivoxil, Entecavir (ETV), Telbivudine, and AGX-1009. Exemplary immune stimulators include pegylated interferon alfa 2a (PEG-IFN-α2a), Interferon alfa-2b, a recombinant human interleukin-7, and a Toll-like receptor 7 (TLR7) agonist.

The invention further provides methods of treating a subject having a Hepatitis D virus (HDV) infection, comprising administering to the subject a therapeutically effective amount of a composition for inhibiting expression of hepatitis B virus (HBV) in a cell, the composition comprising (a) a first double-stranded RNAi agent comprising a first strand and a first antisense strand forming a double-stranded region, wherein substantially all of the nucleotides of the first sense strand and substantially all of the nucleotides of the first antisense strand are modified nucleotides, wherein the first sense strand is conjugated to a ligand attached at the 3'-terminus, and wherein the ligand is one or more GalNAc derivatives attached through a bivalent or trivalent branched linker; and (b) a second double-stranded RNAi agent comprising a second sense strand and a second antisense strand forming a double-stranded region, wherein substantially all of the nucleotides of the second sense strand and substantially all of the nucleotides of the second antisense strand are modified nucleotides, wherein the second sense strand is conjugated to a ligand attached at the 3'-terminus, and wherein the ligand is one or more GalNAc derivatives attached through a bivalent or trivalent branched linker; wherein the first sense strand comprises at least 15 contiguous nucleotides differing by no more than 3 nucleotides from the nucleotide sequence of SEQ ID NO:1, and the first antisense strand comprises at least 15 contiguous nucleotides differing by no more than 3 nucleotides from the nucleotide sequence of SEQ ID NO:2, wherein the sense second strand comprises at least 15 contiguous nucleotides differing by no more than 3 nucleotides from the nucleotide sequence of SEQ ID NO:29, and the second antisense strand comprises at least 15 contiguous nucleotides differing by no more than 3 nucleotides from the nucleotide sequence of SEQ ID NO:30, thereby treating the subject.

In certain embodiments, the first sense strand comprises a sequence selected from the group consisting of

```
                              (SEQ ID NO: 5)
5'-UCGUGGUGGACUUCUCUCA-3', (SEQ ID NO: 7)
5'-GUGCACUUCGCUUCACCUCUA-3', (SEQ ID NO: 9)
5'-CGUGGUGGACUUCUCUCAAUU-3', (SEQ ID NO: 37)
5'-CGUGGUGGUCUUCUCUAAAUU-3', (SEQ ID NO: 11)
5'-GGUGGACUUCUCUCAAUUUUA-3',
and (SEQ ID NO: 39)
5'-GUGUGCACUUCGCUUCACA-3',
``` and the second antisense strand comprises a sequence selected from the group consisting of

```
                              (SEQ ID NO: 6)
5'-UGAGAGAAGUCCACCACGAUU-3';

(SEQ ID NO: 8)
5'-UAGAGGUGAAGCGAAGUGCACUU-3';

(SEQ ID NO: 10)
5'-AAUUGAGAGAAGUCCACCAGCAG-3';

(SEQ ID NO: 38)
5'-AAUUGAGAGAAGUCCACCAGCUU-3', (SEQ ID NO: 12)
5'-UAAAAUUGAGAGAAGUCCACCAC-3',
and (SEQ ID NO: 40)
5'-UGUGAAGCGAAGUGCACACUU-3'.
```

In certain embodiments, all of the nucleotides of the sense strand and all of the nucleotides of the antisense strand comprise a modification. In certain embodiments, the additional agent is at least one of the modified nucleotides is selected from the group consisting of a dexoy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In certain embodiments, the ligand is

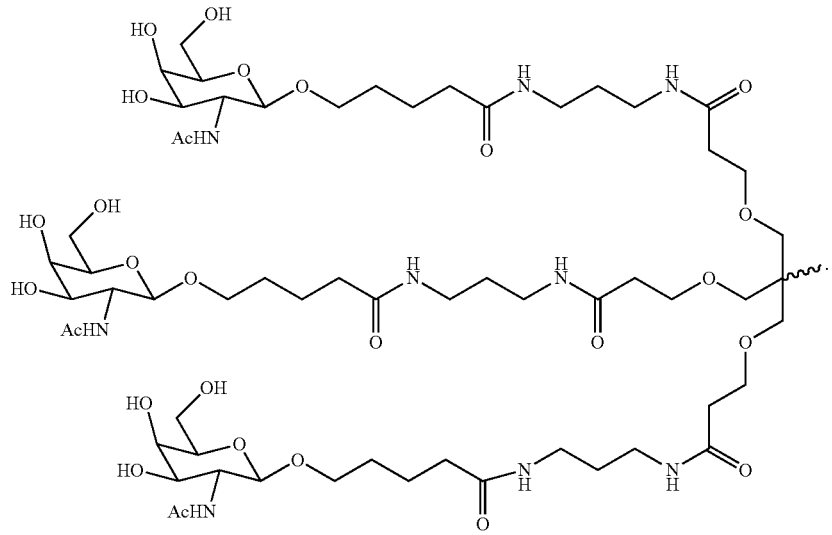 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the RNAi agent is conjugated to the ligand at the 3' end of the sense strand, as shown in the following structure:

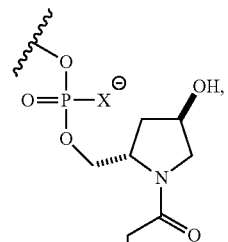
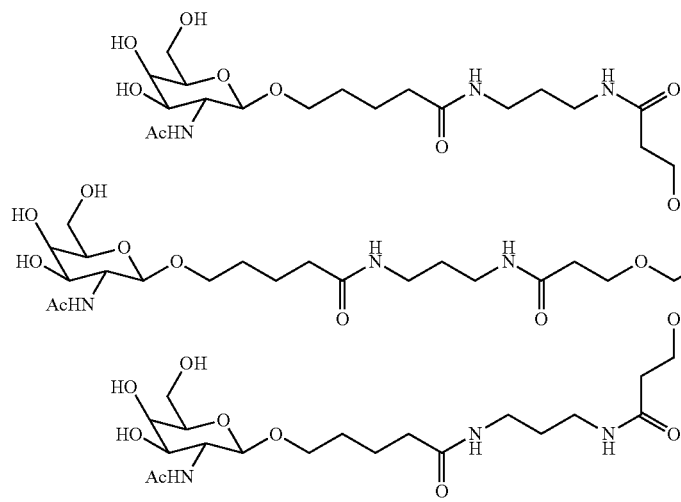

wherein X is O or S.

The present invention is further illustrated by the following detailed description and drawings.

BRIEF DESCRIPTION OF THE DRAWINGS

FIG. 4 also depicts the percent of HBsAG remaining at day 10 post-dose relative to the percent of HBsAG remaining at day 10 post-dose in an animal administered 3 mg/kg of a control dsRNA targeting mouse/rat transtherytin (mrTTR).

DETAILED DESCRIPTION OF THE INVENTION

Figure 1:
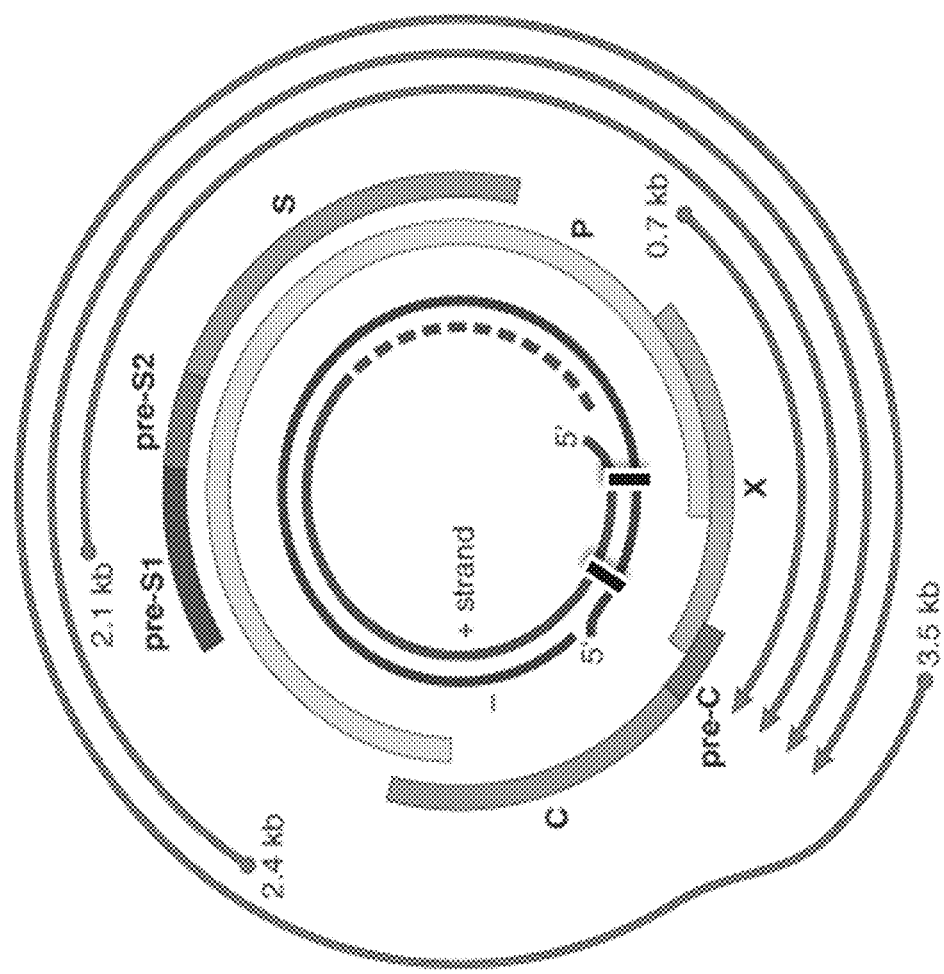
FIG. 1 schematically depicts the structure of the approximately 3.2 kb double-stranded HBV genome. Replication of the HBV genome occurs through an RNA intermediate and produces 4 overlapping viral transcripts (an about 3.5 kb transcript, an about 2.4 kb transcript, an about 2.1 kb transcript, and an about 0.7 kb transcript) encoding seven viral proteins (pre-S1, pre-S2, S, P, X, pre-C and C) translated across three reading frames.

The present invention provides iRNA compositions which effect the RNA-induced silencing complex (RISC)-mediated cleavage of RNA transcripts of a Hepatitis B virus (HBV) gene. The gene may be within a cell, e.g., a cell within a subject, such as a human. The use of these iRNAs enables the targeted degradation of mRNAs of the corresponding gene (HBV gene) in mammals.

The RNAi agents of the invention have been designed to target regions in the HBV genome that are conserved across all 8 serotypes of HBV. In addition, the RNAi agents of the invention have been designed to inhibit all steps of the HBV life cycle, e.g., replication, assembly, secretion of virus, and secretion of sub-viral antigens, by inhibiting expression of more than one HBV gene. In particular, since transcription of the HBV genome results in polycistronic, overlapping RNAs, an RNAi agent of the invention targeting a single HBV gene results in significant inhibition of expression of most or all HBV transcripts. For example, because the HBV genome is transcribed into a single mRNA, an RNAi agent of the invention targeting the S gene will result in inhibition of not only S gene expression but also the expression of the "downstream" polymerase gene. Furthermore, the RNAi agents of the invention have been designed to inhibit HBV viral replication by targeting HBV structural genes, and the HBV X gene thereby permitting a subject's immune system to detect and respond to the presence of HBsAg to produce anti-HBV antibodies to clear an HBV infection. Without intending to be limited by theory, it is believed that a combination or sub-combination of the foregoing properties and the specific target sites and/or the specific modifications in these RNAi agents confer to the RNAi agents of the invention improved efficacy, stability, safety, potency, and durability.

Using in vitro and in vivo assays, the present inventors have demonstrated that iRNAs targeting an HBV gene can potently mediate RNAi, resulting in significant inhibition of expression of more than one HBVgene. The present inventors have also demonstrated that the RNAi agents of the invention are exceptionally stable in the cytoplasm and lysosome. Thus, methods and compositions including these iRNAs are useful for treating a subject having an HBV infection and/or an HBV-associated disease, such as chronic hepatitis B (CHB).

Accordingly, the present invention also provides methods for treating a subject having a disorder that would benefit from inhibiting or reducing the expression of an HBV gene, e.g., an HBV-associated disease, such as chronic Hepatitis B virus infection (CHB), using iRNA compositions which effect the RNA-induced silencing complex (RISC)-mediated cleavage of RNA transcripts of an HBV gene.

Very low dosages of the iRNAs of the invention, in particular, can specifically and efficiently mediate RNA interference (RNAi), resulting in significant inhibition of expression of the corresponding gene (HBV gene).

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an HBV gene.

The following detailed description discloses how to make and use compositions containing iRNAs to inhibit the expression of an HBV gene as well as compositions, uses, and methods for treating subjects having diseases and disorders that would benefit from inhibition and/or reduction of the expression of an HBV gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Hepatitis B virus," used interchangeably with the term "HBV" refers to the well-known noncytopathic, liver-tropic DNA virus belonging to the Hepadnaviridae family.

The HBV genome is partially double-stranded, circular DNA with overlapping reading frames (see, e.g., FIG. 1).

There are four known genes encoded by the HBC genome, called C, X, P, and S. The core protein is coded for by gene C (HBcAg). Hepatitis B antigen (HBeAg) is produced by proteolytic processing of the pre-core (pre-C) protein. The DNA polymerase is encoded by gene P. Gene S is the gene that codes for the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the non-structural protein coded for by gene X is not fully understood but it is associated with the development of liver cancer and encodes a decoy protein which permits HBsAg in the blood to sequester anti-HBsAg antibodies and allow infectious viral particles to escape immune detection.

The proteins encoded by the HBV genome include: envelope proteins—i) small, Hepatitis B surface antigen (HBsAg); ii) middle—preS2 plus HBsAg; iii) large—preS1 plus preS2 plus HBsAg; nucleocapsid protein, hepatitis B core antigen (HBcAg). Hepatitis B e antigen (HBeAg) is a non-structural protein produced during the HBV replication which shares 90% amino acids with the nucleocapsid HBcAg; and the X protein is a nonstructural protein (HBx) which functions in the cytoplasm to activate various signaling pathways, many of which are controlled by modulation of cytosolic calcium and in the nucleus to regulate transcription through a direct interaction with different transcription factors and, in some cases, enhance their binding to specific transcription elements.

HBV is one of the few DNA viruses that utilize reverse transcriptase in the replication process which involves multiple stages including entry, uncoating and transport of the virus genome to the nucleus. Initially, replication of the HBV genome involves the generation of an RNA intermediate that is then reverse transcribed to produce the DNA viral genome.

Upon infection of a cell with HBV, the viral genomic relaxed circular DNA (rcDNA) is transported into the cell nucleus and converted into episomal covalently closed circular DNA (cccDNA), which serves as the transcription template for the viral mRNAs. After transcription and nuclear export, cytoplasmic viral pregenomic RNA (pgRNA) is assembled with HBV polymerase and capsid proteins to form the nucleocapsid, inside which polymerase-catalyzed reverse transcription yields minus-strand DNA, which is subsequently copied into plus-strand DNA to form the progeny rcDNA genome. The mature nucleocapsids are then either packaged with viral envelope proteins to egress as virion particles or shuttled to the nucleus to amplify the cccDNA reservoir through the intracellular cccDNA amplification pathway. cccDNA is an essential component of the HBV replication cycle and is responsible for the establishment of infection and viral persistence.

HBV infection results in the production of two different particles: 1) the HBV virus itself (or Dane particle) which includes a viral capsid assembled from the HBcAg and is covered by the HBsAg and is capable of reinfecting cells and 2) subviral particles (or SVPs) which are high density lipoprotein-like particles comprised of lipids, cholesterol, cholesterol esters and the small and medium forms of the hepatitis B surface antigen HBsAg which are non-infectious. For each viral particle produced, 1,000-10,000 SVPs are released into the blood. As such SVPs (and the HBsAg protein they carry) represent the overwhelming majority of viral protein in the blood. HBV infected cells also secrete a soluble proteolytic product of the pre-core protein called the HBV e-antigen (HBeAg).

Eight genotypes of HBV, designated A to H, have been determined, each having a distinct geographical distribution. The virus is non-cytopathic, with virus-specific cellular immunity being the main determinant for the outcome of exposure to HBV-acute infection with resolution of liver diseases with 6 months, or chronic HBV infection that is frequently associated with progressive liver injury.

The term "HBV" includes any of the eight genotypes of HBV (A to H). The amino acid and complete coding sequence of the reference sequence of the HBV genome may be found in for example, GenBank Accession Nos. GI:21326584 (SEQ ID NO:1) and GI:3582357 (SEQ ID NO:3).

Additional examples of HBV mRNA sequences are readily available using publicly available databases, e.g., GenBank, UniProt, and OMIM.

The term "HBV," as used herein, also refers to naturally occurring DNA sequence variations of the HBV genome.

As used herein, "Hepatitis D virus," used interchangeably with the term "HDV" refers to the well-known noncytopathic, liver-tropic DNA virus belonging to the Hepadnaviridae family. See, e.g., Ciancio and Rizzetto, Nat. Rev. 11:68-71, 2014; Le Gal et al., Emerg. Infect. Dis. 12:1447-1450, 2006; and Abbas and afzal, World J. Hep., 5:666-675, 2013, all of which are incorporated by reference. Unless otherwise indicated, HDV refers to all clades and variants of HDV.

HDV produces one protein, namely HDAg. It comes in two forms; a 27 kDa large-HDAg (also referred to herein as lHD, L-HDAg, and large HDV antigen), and a small-HDAg of 24 kDa (also referred to herein as sHD, S-HDAg, and small HDV antigen). The N-terminals of the two forms are identical, they differ by 19 amino acids in the C-terminal of the large HDAg. Both isoforms are produced from the same reading frame which contains an UAG stop codon at codon 196, which normally produces only the small-HDAg. However, editing by cellular enzyme adenosine deaminase-1 changes the stop codon to UCG, allowing the large-HDAg to be produced. Despite having 90% identical sequences, these two proteins play diverging roles during the course of an infection. HDAg-S is produced in the early stages of an infection and enters the nucleus and supports viral replication. HDAg-L, in contrast, is produced during the later stages of an infection, acts as an inhibitor of viral replication, and is required for assembly of viral particles.

Additional examples of HDV mRNA sequences are readily available using publicly available databases, e.g., GenBank, UniProt, and OMIM.

The term "HDV," as used herein, also refers to naturally occurring DNA sequence variations of the HDV genome.

As used herein, "target sequence" refers to a contiguous portion of the nucleotide sequence of an mRNA molecule formed during the transcription of an HBV gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an HBV gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of an HBV gene (e.g., one or more HBV genes) in a cell, e.g., a cell within a subject, such as a mammalian subject.

In one embodiment, an RNAi agent of the invention includes a single stranded RNA that interacts with a target RNA sequence, e.g., an HBV target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded siRNA (ssRNA) generated within a cell and which promotes the formation of a RISC complex to effect silencing of the target gene, i.e., an HBV gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an HBV gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, each strand of which comprises 24-30 nucleotides, that interacts with a target RNA sequence, e.g., an HBV target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107: 309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

"Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a HBV mRNA. As used herein, the term "region of complementarity" refers to the region on the antisense strand that is substantially complementary to a sequence, for example a target sequence, e.g., an HBV nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, 2, or 1 nucleotides of the 5'- and/or 3'-terminus of the iRNA. In one embodiment, a double-stranded RNAi agent of the invention includes a nucleotide mismatch in the antisense strand. In another embodiment, a double-stranded RNAi agent of the invention includes a nucleotide mismatch in the sense strand. In one embodiment, the nucleotide mismatch is, for example, within 5, 4, 3, 2, or 1 nucleotides from the 3'-terminus of the iRNA. In another embodiment, the nucleotide mismatch is, for example, in the 3'-terminal nucleotide of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding an HBV gene). For example, a polynucleotide is complementary to at least a part of an HBV mRNA if the sequence is substantially complementary to a non-interrupted portion of an mRNA encoding an HBV gene.

Accordingly, in some embodiments, the antisense strand polynucleotides disclosed herein are fully complementary to the target HBV sequence. In other embodiments, the antisense strand polynucleotides disclosed herein are substantially complementary to the target HBV sequence and comprise a contiguous nucleotide sequence which is at least about 80% complementary over its entire length to the equivalent region of the nucleotide sequence of SEQ ID NO:1, or a fragment of SEQ ID NO:1, such as about 85%, about 86%, about 87%, about 88%, about 89%, about 90%, about % 91%, about 92%, about 93%, about 94%, about 95%, about 96%, about 97%, about 98%, or about 99% complementary.

In one embodiment, an RNAi agent of the invention includes a sense strand that is substantially complementary to an antisense polynucleotide which, in turn, is complementary to a target HBV sequence, and wherein the sense strand polynucleotide comprises a contiguous nucleotide sequence which is at least about 80% complementary over its entire length to the equivalent region of the nucleotide sequence of any one of SEQ ID NOs:6, 8, 10, 12, 38, and 40, or a fragment of any one of SEQ ID NOs:6, 8, 10, 12, 38, and 40, such as about 85%, about 86%, about 87%, about 88%, about 89%, about 90%, about % 91%, about 92%, about 93%, about 94%, about 95%, about 96%, about 97%, about 98%, or about 99% complementary. In another embodiment, an RNAi agent of the invention includes an antisense strand that is substantially complementary to the target HBV sequence and comprise a contiguous nucleotide sequence which is at least about 80% complementary over its entire length to the equivalent region of the nucleotide sequence of any one of SEQ ID NOs:5, 7, 9, 11, 37, and 39, or a fragment of any one of SEQ ID NOs:5, 7, 9, 11, 37, and 39, such as about 85%, about 86%, about 87%, about 88%, about 89%, about 90%, about % 91%, about 92%, about 93%, about 94%, about 95%, about 96%, about 97%, about 98%, or about 99% complementary.

In some embodiments, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

In one aspect of the invention, an agent for use in the methods and compositions of the invention is a single-stranded antisense nucleic acid molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in HBV gene expression and/or replication; a human at risk for a disease, disorder or condition that would benefit from reduction in HBV gene expression and/or replication; a human having a disease, disorder or condition that would benefit from reduction in HBV gene expression and/or replication; and/or human being treated for a disease, disorder or condition that would benefit from reduction in HBV gene expression and/or replication, as described herein. In another embodiment, the subject has a hepatitis B virus (HBV) infection. In another embodiment, the subject has both a hepatitis B virus (HBV) infection and a hepatitis D virus (HDV) infection.

As used herein, the terms "treating" or "treatment" refer to a beneficial or desired result including, but not limited to, alleviation or amelioration of one or more symptoms associated with unwanted HBV gene expression and/or HBV replication, e.g., the presence of serum and/or liver HBV ccc DNA, the presence of serum and/or liver HBV antigen, e.g., HBsAg and/or HBeAg, elevated ALT, elevated AST, the absence or low level of anti-HBV antibodies, liver injury; cirrhosis; delta hepatitis, acute hepatitis B; acute fulminant hepatitis B; chronic hepatitis B; liver fibrosis; end-stage liver disease; hepatocellular carcinoma; serum sickness-like syndrome; anorexia; nausea; vomiting, low-grade fever; myalgia; fatigability; disordered gustatory acuity and smell sensations (aversion to food and cigarettes); and/or right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); high levels of alanine aminotransferase (ALT) and aspartate aminotransferase (AST), within a range of 1000-2000 IU/mL, although values 100 times above the upper limit of normal (ULN) can be also be identified; ALT levels higher than AST levels; elevated gamma-glutamyl transpeptidase (GGT) and alkaline phosphatase (ALP) levels (e.g., not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); the presence of serum and/or liverHBsAg, HBeAg, Hepatitis B core antibody (anti-HBc) immunoglobulin M (IgM); hepatitis B surface antibody (anti-HBs), hepatitis B e antibody (anti-HBe), and/or HBV DNA; elevation of the aminotransferases (≤5 times the ULN); ALT levels higher than the AST levels; increased bilirubin levels, prolonged prothrombin time (PT); hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); hyperbilirubinemia, prolonged PT, low platelet and white blood cell counts, AST levels higher than ALT levels; elevated alkaline phosphatase (ALP) and GGT levels; lobular, with degenerative and regenerative hepatocellular changes, and accompanying inflammation; predominantly centrilobular necrosis whether detectable or undetectable. "Treatment" can also mean prolonging survival as compared to expected survival in the absence of treatment.

The term "lower" in the context of the level of HBV gene expression and/or HBV replication in a subject or a disease marker or symptom refers to a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more and is preferably down to a level accepted as within the range of normal for an individual without such disorder. In certain embodiments, the expression of the target is normalized, i.e., decreased to a level accepted as within the range of normal for an individual without such disorder, e.g., the level of a disease marker, such as, ALT or AST, is decreased to a level accepted as within the range of normal for an individual without such disorder.

As used herein, "prevention" or "preventing," when used in reference to a disease, disorder or condition thereof, that would benefit from a reduction in expression of an HBV gene and/or replication, refers to a reduction in the likelihood that a subject will develop a symptom associated with such a disease, disorder, or condition, e.g., a symptom of unwanted HBV infection, such as the presence of serum and/or liver HBV ccc DNA, the presence of serum HBV DNA, the presence of serum and/or liver HBV antigen, e.g., HBsAg and/or HBeAg, elevated ALT, elevated AST, the absence or low level of anti-HBV antibodies, a liver injury; cirrhosis; delta hepatitis, acute hepatitis B; acute fulminant hepatitis B; chronic hepatitis B; liver fibrosis; end-stage liver disease; hepatocellular carcinoma; serum sickness-like syndrome; anorexia; nausea; vomiting, low-grade fever; myalgia; fatigability; disordered gustatory acuity and smell sensations (aversion to food and cigarettes); and/or right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); high levels of alanine aminotransferase (ALT) and aspartate aminotransferase (AST), within a range of 1000-2000 IU/mL, although values 100 times above the upper limit of normal (ULN) can be also be identified; ALT levels higher than AST levels; elevated gamma-glutamyl transpeptidase (GGT) and alkaline phosphatase (ALP) levels (e.g., not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); the presence of serum and/or liverHBsAg, HBeAg, Hepatitis B core antibody (anti-HBc) immunoglobulin M (IgM); hepatitis B surface antibody (anti-HBs), hepatitis B e antibody (anti-HBe), and/or HBV DNA; elevation of the aminotransferases (≤5 times the ULN); ALT levels higher than the AST levels; increased bilirubin levels, prolonged prothrombin time (PT); hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); hyperbilirubinemia, prolonged PT, low platelet and white blood cell counts, AST levels higher than ALT levels; elevated alkaline phosphatase (ALP) and GGT levels; lobular, with degenerative and regenerative hepatocellular changes, and accompanying inflammation; predominantly centrilobular necrosis, whether detectable or undetectable. The likelihood of developing, e.g., liver fibrosis, is reduced, for example, when an individual having one or more risk factors for liver fibrosis, e.g., chronic hepatitis B infection, either fails to develop liver fibrosis or develops liver fibrosis with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "Hepatitis B virus-associated disease" or "HBV-associated disease," is a disease or disorder that is caused by, or associated with HBV infection and/or replication. The term "HBV-associated disease" includes a disease, disorder or condition that would benefit from reduction in HBV gene expression and/or replication. Non-limiting examples of HBV-associated diseases include, for example, hepatitis D virus infection, delta hepatitis, acute hepatitis B; acute fulminant hepatitis B; chronic hepatitis B; liver fibrosis; end-stage liver disease; hepatocellular carcinoma.

In one embodiment, an HBV-associated disease is hepatitis D virus infection. Hepatitis D virus or hepatitis delta virus (HDV) is a human pathogen. However, the virus is defective and depends on obligatory helper functions provided by hepatitis B virus (HBV) for transmission; indeed, HDV requires an associated or pre-existing HBV infection to become infectious and thrive, in particular, the viral envelope containing the surface antigen of hepatitis B. HDV can lead to severe acute and chronic forms of liver disease in association with HBV. Hepatitis D infection and/or delta hepatitis is highly endemic to several African countries, the Amazonian region, and the Middle East, while its prevalence is low in industrialized countries, except in the Mediterranean.

Transmission of HDV can occur either via simultaneous infection with HBV (coinfection) or superimposed on chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest fatality rate of all the hepatitis infections, at 20%.

In one embodiment, an HBV-associated disease is acute hepatitis B. Acute hepatitis B includes inflammation of the liver that lasts less than six months. Typical symptoms of acute hepatitis B are fatigue, anorexia, nausea, and vomiting. Very high aminotransferase values (>1000 U/L) and hyperbilirubinemia are often observed. Severe cases of acute hepatitis B may progress rapidly to acute liver failure, marked by poor hepatic synthetic function. This is often defined as a prothrombin time (PT) of 16 seconds or an international normalized ratio (INR) of 1.5 in the absence of previous liver disease. Acute hepatitis B may evolve into chronic hepatitis B.

In one embodiment, an HBV-associated disease is chronic hepatitis. Chronic hepatitis B (CHB) includes inflammation of the liver that lasts more than six months. Subjects having chronic hepatitis B disease can be immune tolerant or have an inactive chronic infection without any evidence of active disease, and they are also asymptomatic. Patients with chronic active hepatitis, especially during the replicative state, may have symptoms similar to those of acute hepatitis. The persistence of HBV infection in CHB subjects is the result of ccc HBV DNA. In one embodiment, a subject having CHB is HBeAg positive. In another embodiment, a subject having CHB is HBeAg negative. Subjects having CHB have a level of serum HBV DNA of less than about $10^5$ and a persistent elevation in transaminases, for examples ALT, AST and gamma-glutamyl transferase. A subject having CHB may have a liver biopsy score of less than about 4 (e.g., a necroinflammatory score). In addition, a subject having CHB may have In one embodiment, an HBV-associated disease is acute fulminant hepatitis B. A subject having acute fulminant hepatitis B has symptoms of acute hepatitis and the additional symptoms of confusion or coma (due to the liver's failure to detoxify chemicals) and bruising or bleeding (due to a lack of blood clotting factors).

Subjects having an HBV infection, e.g., CHB, may develop liver fibrosis. Accordingly, in one embodiment, an HBV-associated disease is liver fibrosis. Liver fibrosis, or cirrhosis, is defined histologically as a diffuse hepatic process characterized by fibrosis (excess fibrous connective tissue) and the conversion of normal liver architecture into structurally abnormal nodules.

Subjects having an HBV infection, e.g., CHB, may develop end-stage liver disease. Accordingly, in one embodiment, an HBV-associated disease is end-stage liver disease. For example, liver fibrosis may progress to a point where the body may no longer be able to compensate for, e.g., reduced liver function, as a result of liver fibrosis, and result in, e.g., mental and neurological symptoms and liver failure.

Subjects having an HBV infection, e.g., CHB, may develop hepatocellular carcinoma (HCC), also referred to as malignant hepatoma. Accordingly, in one embodiment, an HBV-associated disease is HCC. HCC commonly develops in subjects having CHB and may be fibrolamellar, pseudoglandular (adenoid), pleomorphic (giant cell) or clear cell.

An "HDV-associated disorder" or a Hepatitis D-virus-associated disorder" is a disease or disorder associated with expression of an HDV. Exemplary HDV-associated disorders include, hepatitis B virus infection, acute hepatitis B, acute hepatitis D; acute fulminant hepatitis D; chronic hepatitis D; liver fibrosis; end-stage liver disease; and hepatocellular carcinoma.

"Therapeutically effective amount," as used herein, is intended to include the amount of an RNAi agent that, when administered to a patient for treating a subject having an HBV infection and/or HBV-associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by HBV gene expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of an HBV infection and/or HBV-associated disease, but who may be predisposed, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. RNAi agents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes), the retina or parts of the retina (e.g., retinal pigment epithelium), the central nervous system or parts of the central nervous system (e.g., ventricles or choroid plexus), or the pancreas or certain cells or parts of the pancreas. In some embodiments, a "sample derived from a subject" refers to cerebrospinal fluid obtained from the subject. In preferred embodiments, a "sample derived from a subject" refers to blood or plasma drawn from the subject. In further embodiments, a "sample derived from a subject" refers to liver tissue (or subcomponents thereof) or retinal tissue (or subcomponents thereof) derived from the subject.

II. iRNAs of the Invention

The present invention provides iRNAs which inhibit the expression of one or more HBV genes. In one embodiment, the iRNA agent includes double-stranded ribonucleic acid (dsRNA) molecules for inhibiting the expression of an HBV gene in a cell, such as a cell within a subject, e.g., a mammal, such as a human having an HBV-associated disease, e.g., chronic hepatitis B. The dsRNA includes an antisense strand having a region of complementarity which is complementary to at least a part of an mRNA formed in the expression of an HBV gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the HBV gene, the iRNA inhibits the expression of the HBV gene by at least about 10% as assayed by, for example, a PCR or branched DNA (bDNA)-based method, or by a protein-based method, such as by immunofluorescence analysis, using, for example, western blotting or flow cytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an HBV gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 20 nucleotides in length, or between about 25 and about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target HBV gene expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in any one of Tables 3, 4, 6, 7, 12, 13, 22, 23, 25, and 26, and the corresponding antisense strand of the sense strand is selected from the group of sequences of any one of Tables 3, 4, 6, 7, 12, 13, 22, 23, 25, and 26. In this aspect, one of the two sequences is complementary to the other of the two sequences, with one of the sequences being substantially complementary to a sequence of an mRNA generated in the expression of an HBV gene. As such, in this aspect, a dsRNA will include two oligonucleotides, where one oligonucleotide is described as the sense strand in any one of Tables 3, 4, 6, 7, 12, 13, 22, 23, 25, and 26, and the second oligonucleotide is described as the corresponding antisense strand of the sense strand in any one of Tables 3, 4, 6, 7, 12, 13, 22, 23, 25, and 26. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 3, 4, 6, 7, 12, 13, 22, 23, 25, and 26 are described as modified and/or conjugated sequences, the RNA of the iRNA of the invention e.g., a dsRNA of the invention, may comprise any one of the sequences set forth in Tables 3, 4, 6, 7, 12, 13, 22, 23, 25, and 26 that is un-modified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 3, 4, 6, 7, 12, 13, 22, 23, 25, and 26, dsRNAs described herein can include at least one strand of a length of minimally 21 nucleotides. It can be reasonably expected that shorter duplexes having one of the sequences of any one of Tables 3, 4, 6, 7, 12, 13, 22, 23, 25, and 26 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3, 4, 6, 7, 12, 13, 22, 23, 25, and 26, and differing in their ability to inhibit the expression of a HBV gene by not more than about 5, 10, 15, 20, 25, or 30% inhibition from a dsRNA comprising the full sequence, are contemplated to be within the scope of the present invention.

In addition, the RNAs provided in any one of Tables 3, 4, 6, 7, 12, 13, 22, 23, 25, and 26 identify a site(s) in a HBV transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 3, 4, 6, 7, 12, 13, 22, 23, 25, and 26 coupled to additional nucleotide sequences taken from the region contiguous to the selected sequence in a HBV gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 3, 4, 6, 7, 12, 13, 22, 23, 25, and 26 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 3, 4, 6, 7, 12, 13, 22, 23, 25, and 26, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of an HBV gene, generally does not contain any mismatch within the central 13 nucleotides. The methods described herein or methods known in the art can be used to determine whether an iRNA containing a mismatch to a target sequence is effective in inhibiting the expression of an HBV gene. Consideration of the efficacy of iRNAs with mismatches in inhibiting expression of an HBV gene is important, especially if the particular region of complementarity in an HBV gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science*, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_{.n}$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy (2'-$OCH_3$), 2'-aminopropoxy (2'-$OCH_2CH_2CH_2NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.,* 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-0-2' bridge. In one embodiment, a constrained ethyl nucleotide is in the S conformation referred to herein as "5-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification.

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT (idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

A. Modified iRNAs Comprising Motifs of the Invention

In certain aspects of the invention, the double-stranded RNAi agents of the invention include agents with chemical modifications as disclosed, for example, in WO 2013/075035, filed on Nov. 16, 2012, the entire contents of which are incorporated herein by reference. As shown herein and in PCT Publication No. WO 2013/075035, a superior result may be obtained by introducing one or more motifs of three identical modifications on three consecutive nucleotides into a sense strand and/or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are completely modified to have one or more motifs of three identical modifications on three consecutive nucleotides at or near the cleavage site of at least one strand of an RNAi agent, the gene silencing activity of the RNAi agent was superiorly enhanced.

Accordingly, the invention provides double-stranded RNAi agents capable of inhibiting the expression of a target gene (i.e., HBV gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB...," "AAB-BAABBAABB...," "AABAABAABAAB...," "AAABAAABAAAB...," "AAABBBAAABBB...," or "ABCABCABCABC...," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB...", "ACACAC..." "BDBDBD..." or "CDCDCD...," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisense strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYYN$_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5'end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

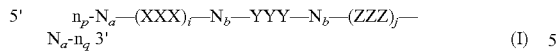 (I)

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12 or 11, 12, 13) of—the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

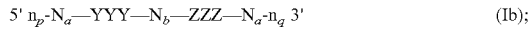 (Ib);

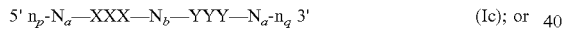 (Ic); or

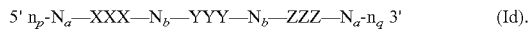 (Id).

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides. Each of X, Y and Z may be the same or different from each other.

In other embodiments, i is 0 and j is 0, and the sense strand may be represented by the formula:

 (Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

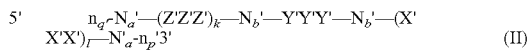 (II)

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

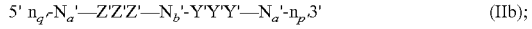 (IIb);

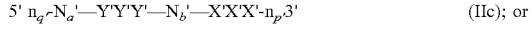 (IIc); or

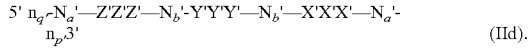 (IId).

When the antisense strand is represented by formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

 (Ia).

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other. Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

sense: 5' $n_p$-$N_a$—(XXX)$_i$-$N_b$—YYY—$N_b$—(ZZZ)$_j$-$N_a$-$n_q$ 3' antisense: 3' $n_p'$-$N_a'$—(X'X'X')$_k$-$N_b'$-Y'Y'Y'—$N_b'$—(Z'Z'Z')$_l$—$N_a'$-$n_q'$ 5'     (III)

wherein:

j, k, and l are each independently 0 or 1;

p, p', q, and q' are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and 1 is 0; or k is 1 and 1 is 0; k is 0 and 1 is 1; or both k and 1 are 0; or both k and 1 are 1.

Exemplary combinations of the sense strand and antisense strand forming a RNAi duplex include the formulas below:

5' $n_p$-$N_a$—YYY—$N_a$-$n_q$ 3'

3' $n_p'$-$N_a'$—Y'Y'Y'—$N_a'n_q'$ 5'     (IIIa)

5' $n_p$-$N_a$—YYY—$N_b$—ZZZ—$N_a$-$n_q$ 3'

3' $n_p'$-$N_a'$—Y'Y'Y'—$N_b'$—Z'Z'Z'—$N_a'n_q'$ 5'     (IIIb)

5' $n_p$-$N_a$—XXX—$N_b$—YYY—$N_a$-$n_q$ 3'

3' $n_p'$-$N_a'$—X'X'X'—$N_b'$—Y'Y'Y'—$N_a'$-$n_q'$ 5'     (IIIc)

5' $n_p$-$N_a$—XXX—$N_b$—YYY—$N_b$—ZZZ—$N_a$-$n_q$ 3'

3' $n_p'$-$N_a'$—X'X'X'—$N_b'$—Z'Z'Z'—$N_a'$-$n_q'$ 5'     (IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'$>0 and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

As described in more detail below, the RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is an agent selected from the group of agents listed in any one of Tables 3, 4, 6, 7, 12, 13, 22, 23, 25, and 26. These agents may further comprise a ligand.

IV. iRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acad. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 43). An RFGF analogue (e.g., amino acid sequence AALLPVLLAAP (SEQ ID NO: 44) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 45) and the *Drosophila* Antennapedia protein (RQIKIWFQNRRMKWKK (SEQ ID NO: 46) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include HBV and above (e.g., HBV, C6, C7, or C8) sugars; di- and trisaccharides include sugars having two or three monosaccharide units (e.g., HBV, C6, C7, or C8).

In one embodiment, a carbohydrate conjugate for use in the compositions and methods of the invention is a monosaccharide. In one embodiment, the monosaccharide is an N-acetylgalactosamine, such as

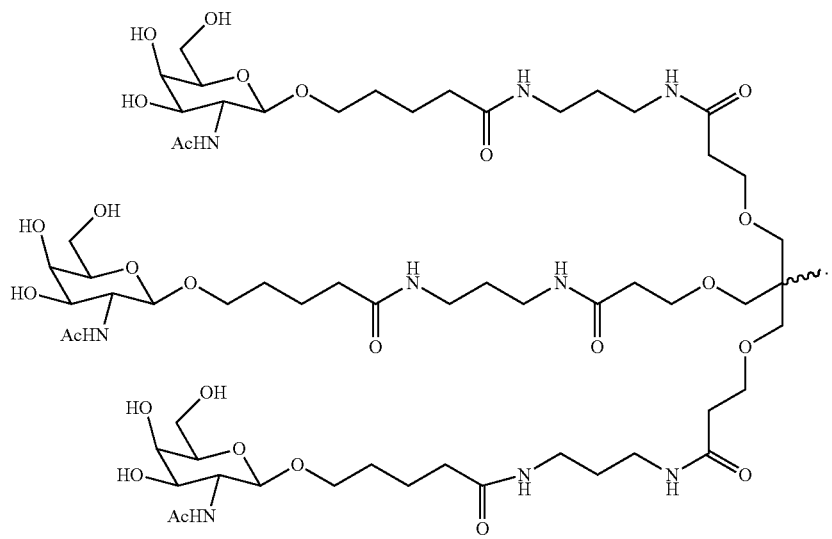 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Formula II

In another embodiment, a carbohydrate conjugate for use in the compositions and methods of the invention is selected from the grout) consisting of:

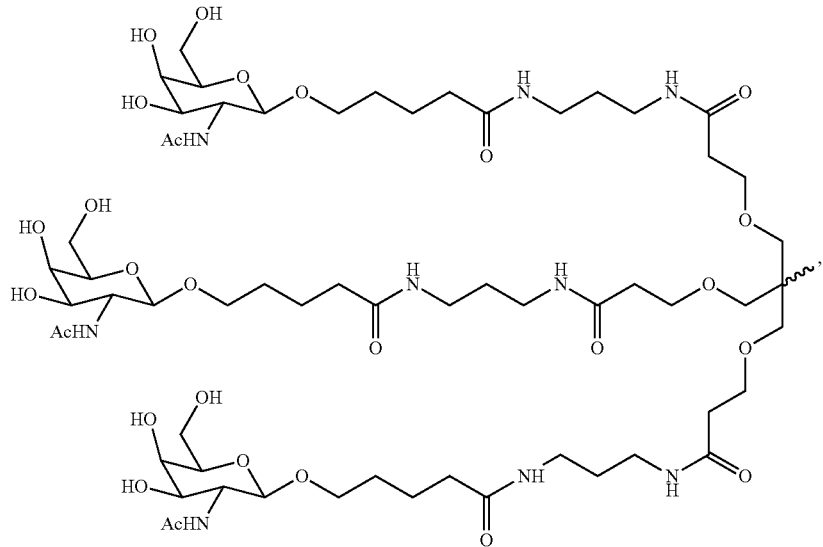

Formula II

-continued
Formula III
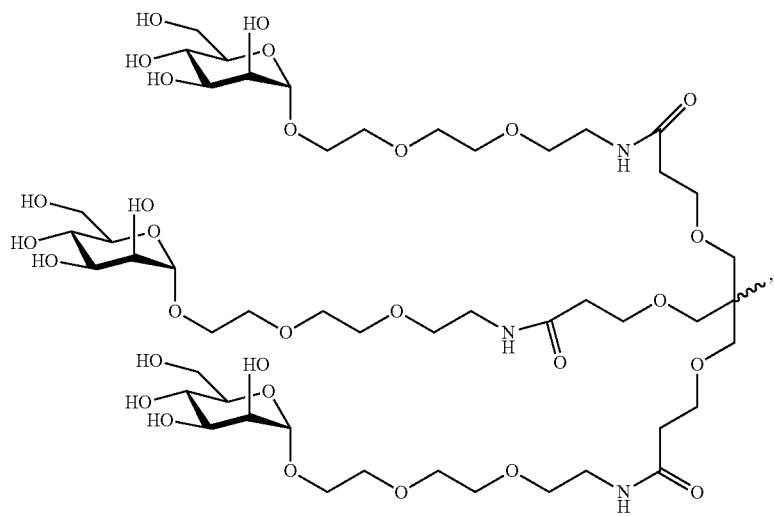
Formula IV
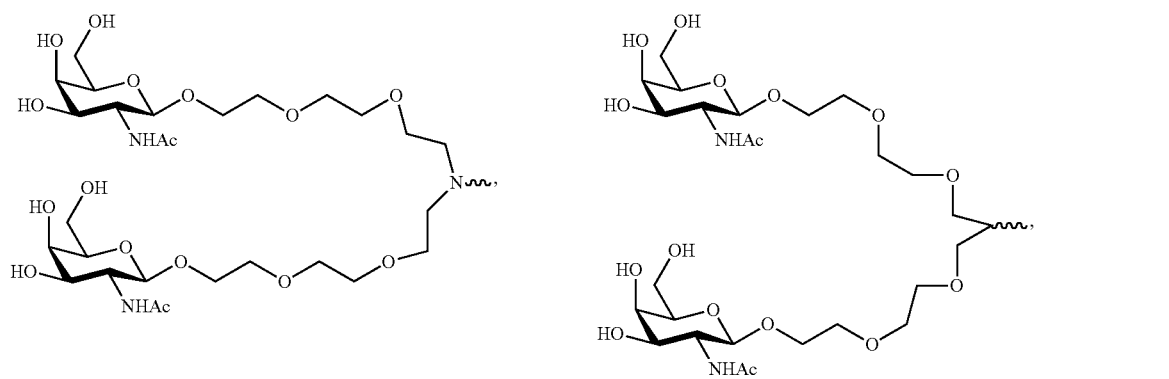
Formula V
Formula VI
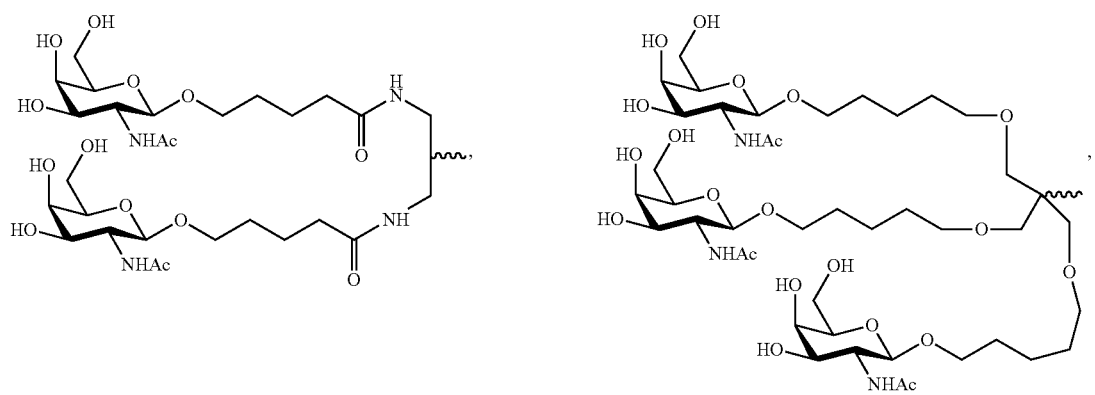
Formula VII
Formula VIII
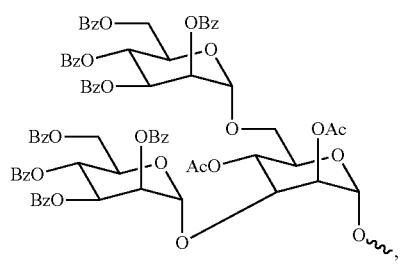

-continued
Formula IX
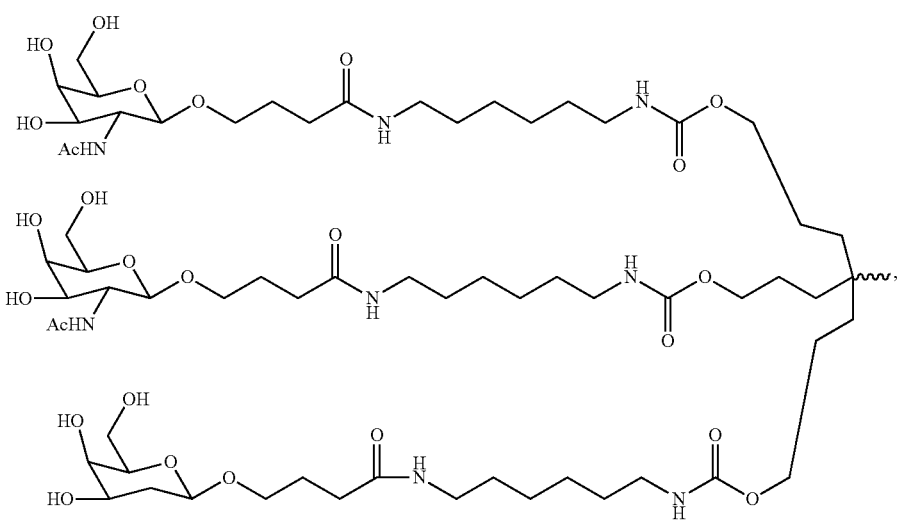
Formula X
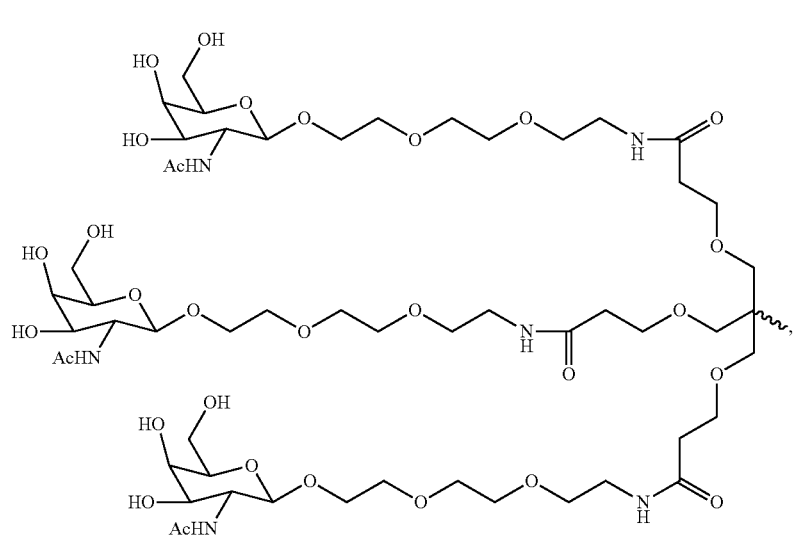
Formula XI
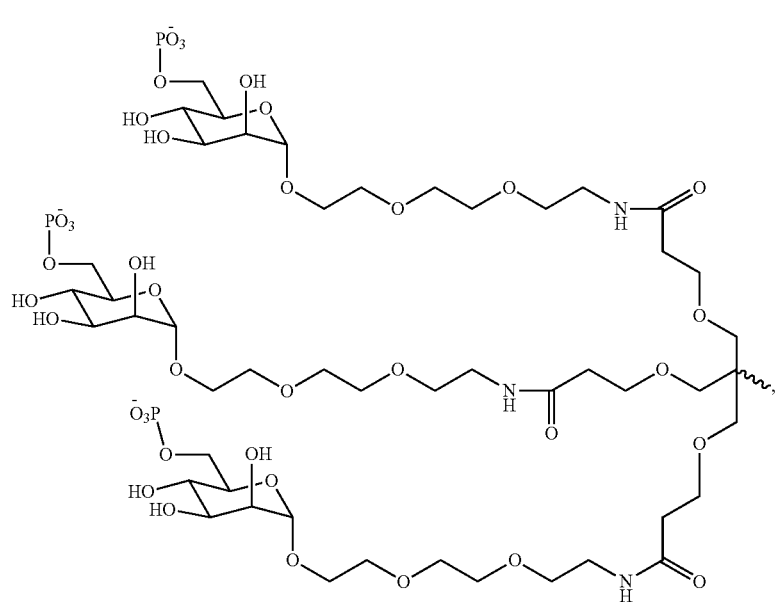

-continued
Formula XII
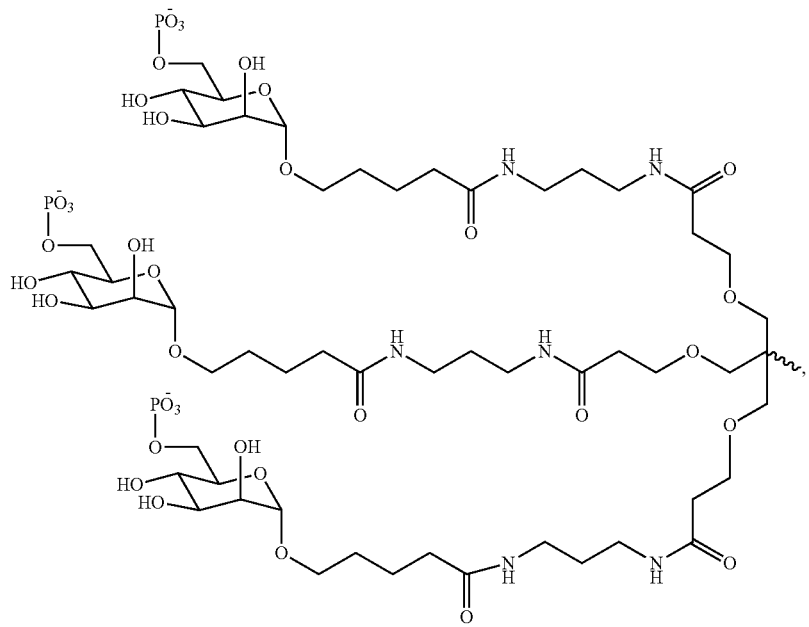
Formula XIII
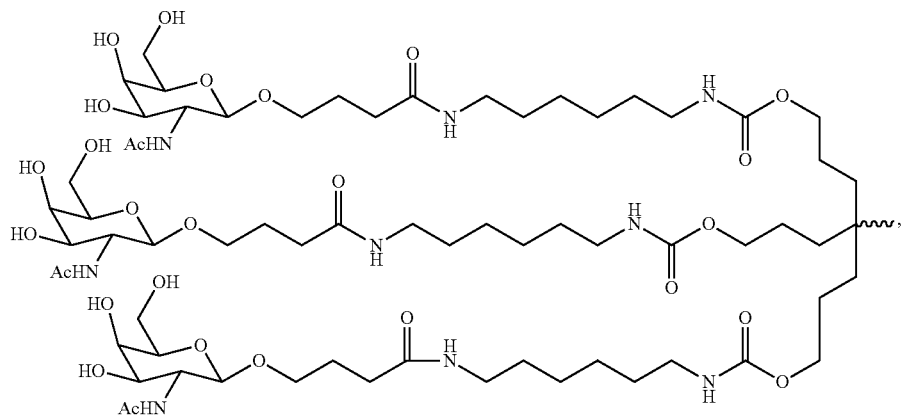
Formula XIV
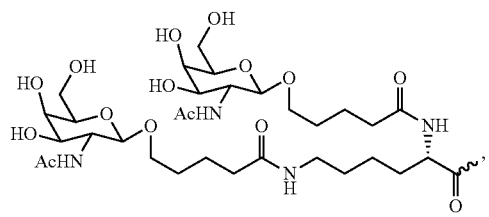
Formula XV
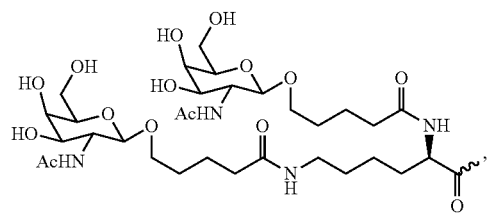
Formula XVI
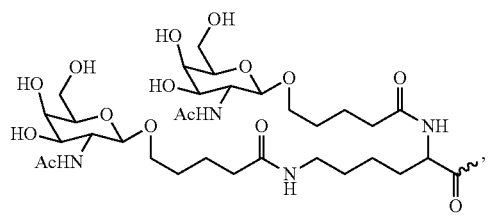
Formula XVII
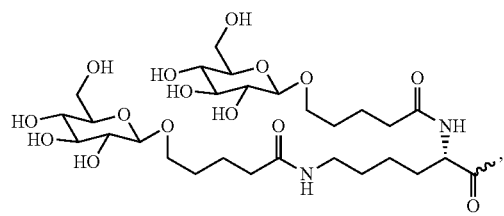

Formula XVIII 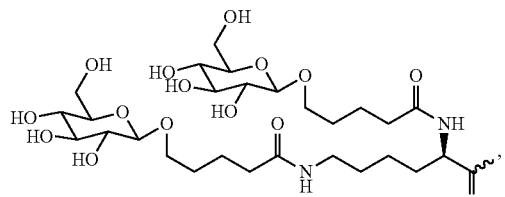 Formula XIX 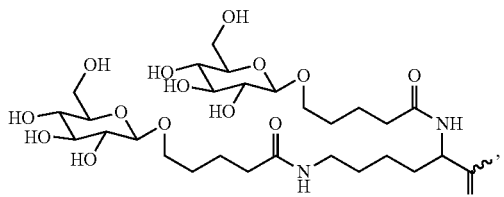
Formula XX Formula XXI
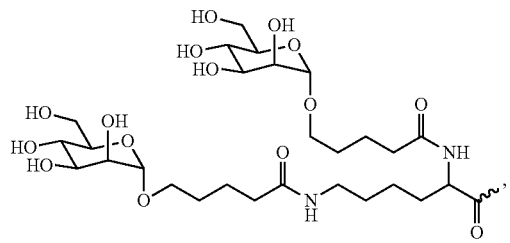
Formula XXII
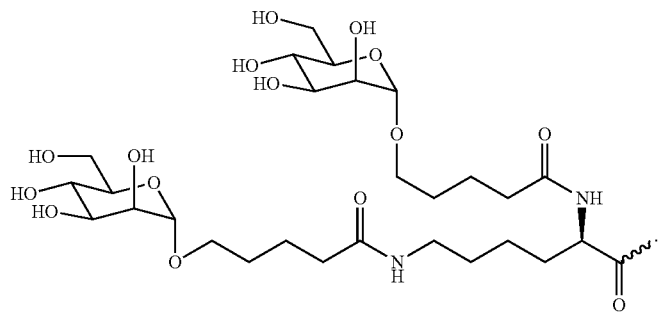
Another representative carbohydrate conjugate for use in the embodiments described herein includes, but is not limited to,
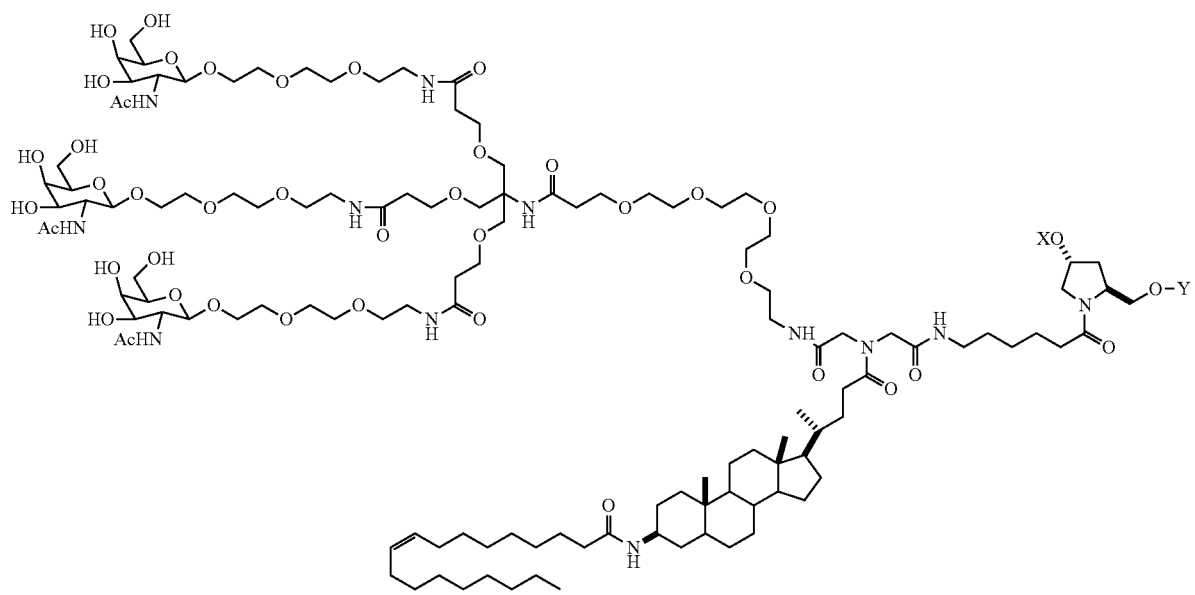
(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

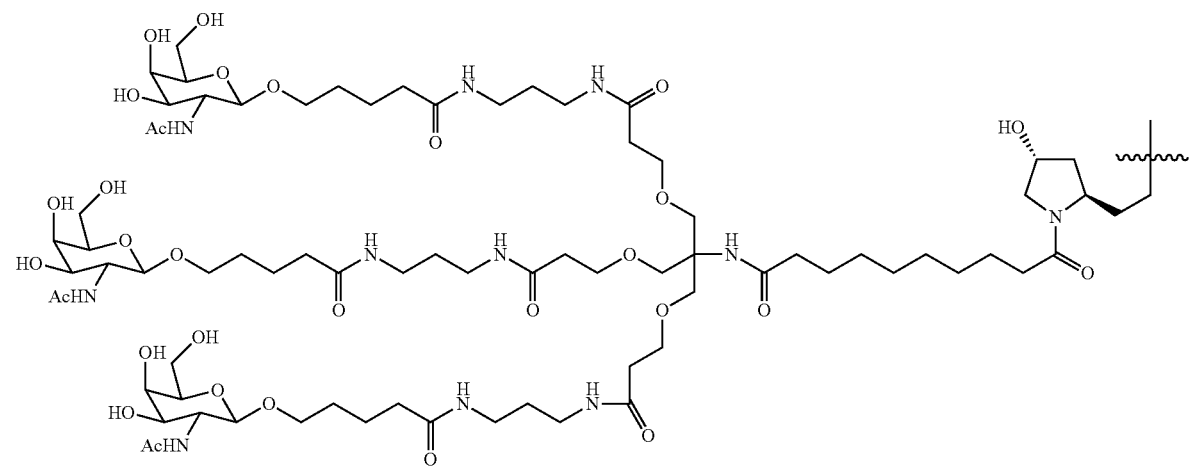

(Formula XXV)
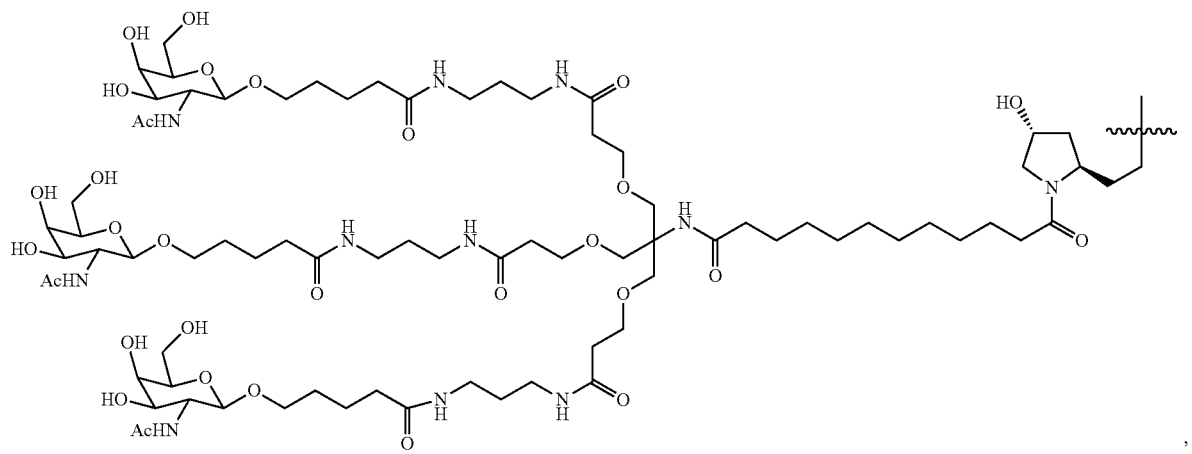
(Formula XXVI)
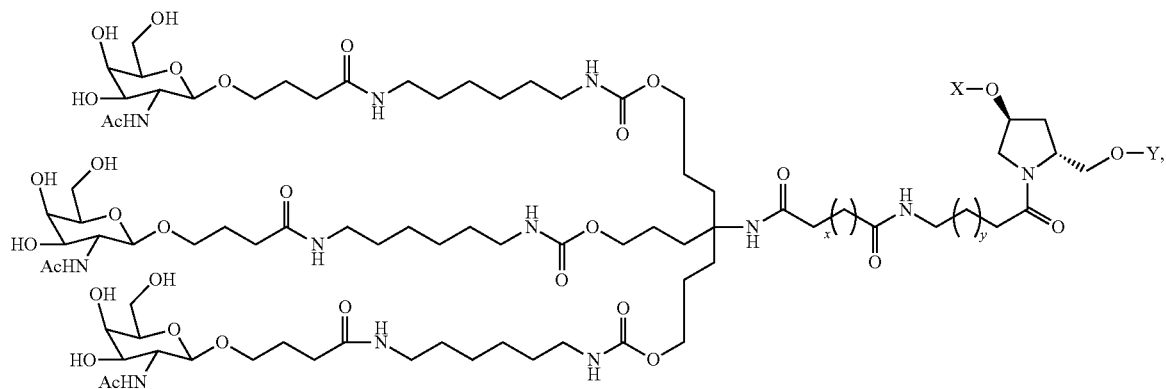
x = 1-30
y = 1-15
(Formula XXVII)
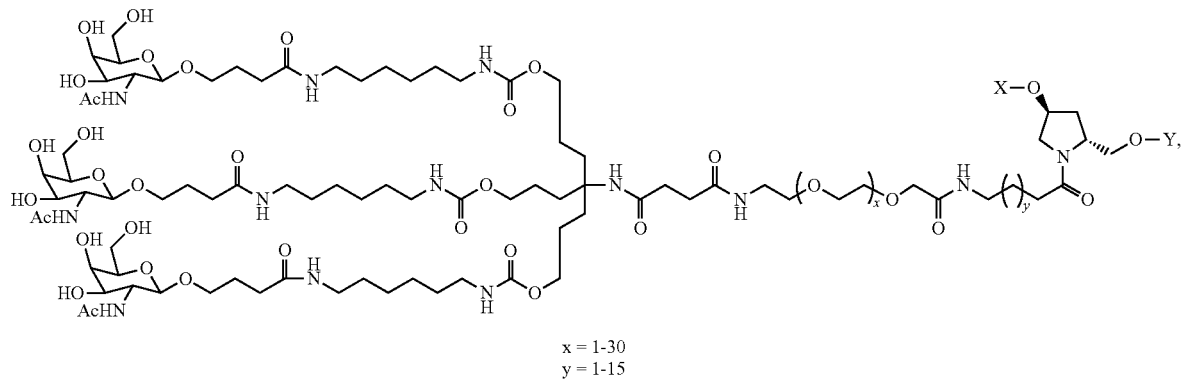
x = 1-30
y = 1-15

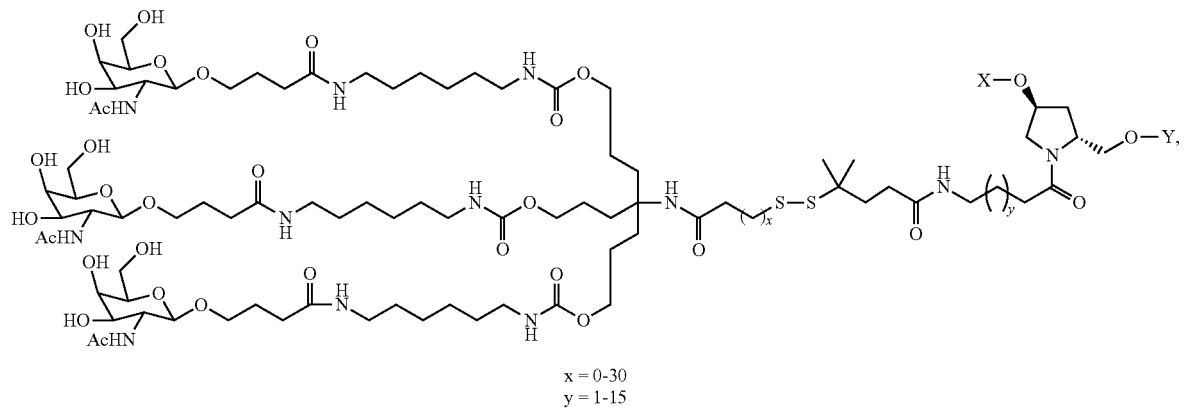
(Formula XXVIII)
x = 0-30
y = 1-15
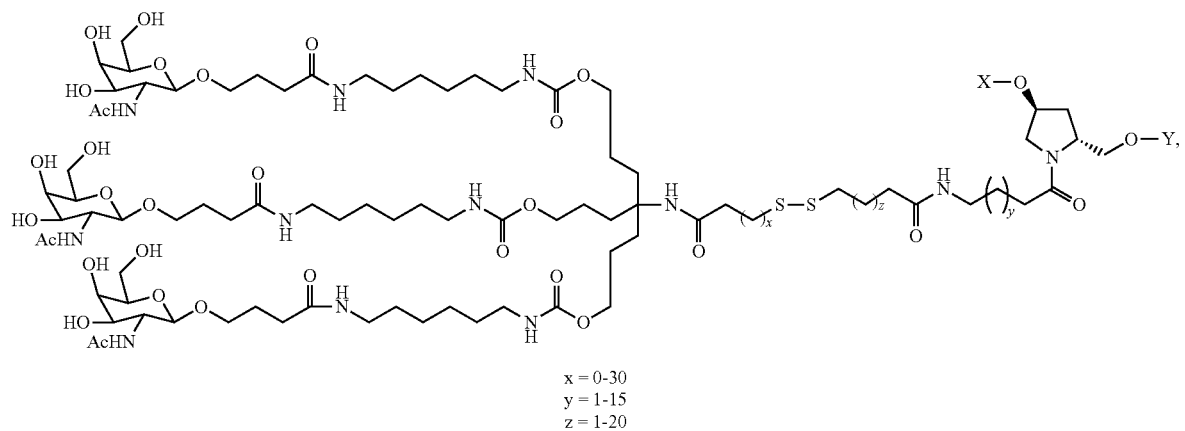
(Formula XXIX)
x = 0-30
y = 1-15
z = 1-20
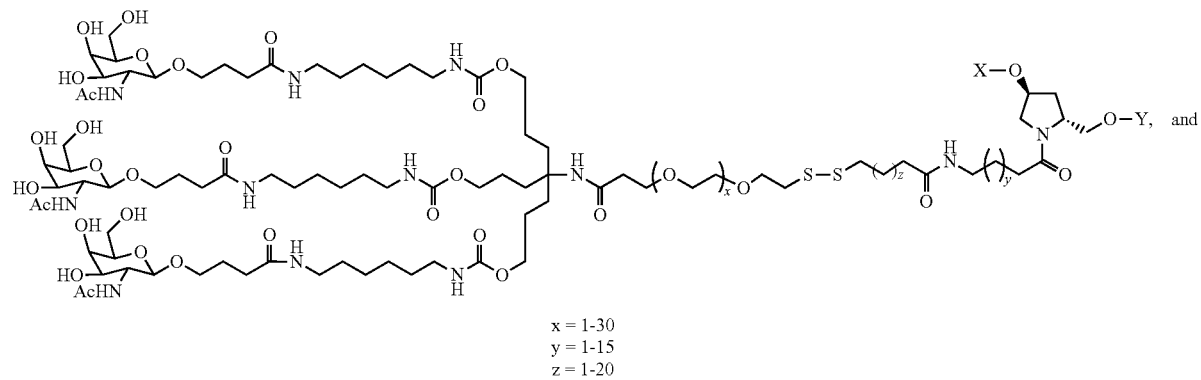
(Formula XXX) and
x = 1-30
y = 1-15
z = 1-20

-continued (Formula XXXI)

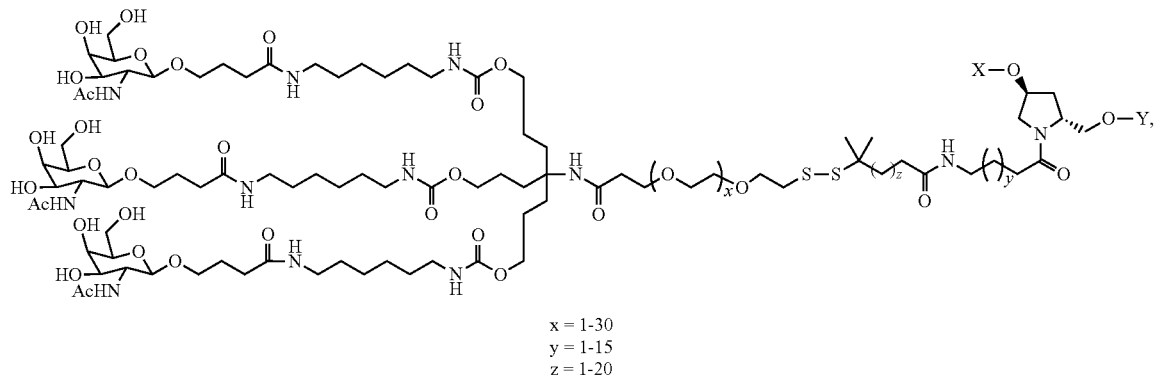

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

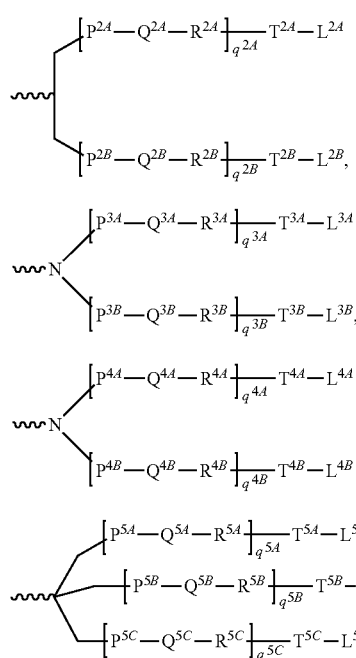

Formula XXXII

Formula XXXIII

Formula XXXIV

Formula XXXV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of 0, S, S(O), $SO_2$, $N(R^N)$, C(R')=C(R''), CC or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—$CH(R^a)$—NH—, CO, CH=N—

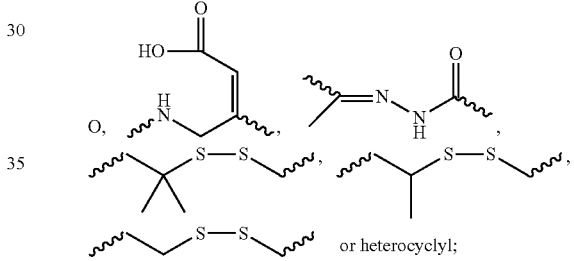

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXVI):

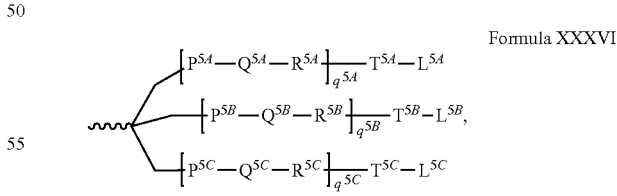

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941; 6,294,664; 6,320, 017; 6,576,752; 6,783,931; 6,900,297; 7,037,646; 8,106, 022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an iRNA of the Invention

The delivery of an iRNA of the invention to a cell e.g., a cell within a subject, such as a human subject (e.g., a subject in need thereof, such as a subject having a disease, disorder or condition associated with HBV infection) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the HBV gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436, 146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VI. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of an HBV gene. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of an HBV gene.

In one embodiment, an iRNA agent of the invention is administered to a subject as a weight-based dose. A "weight-based dose" (e.g., a dose in mg/kg) is a dose of the iRNA agent that will change depending on the subject's weight. In another embodiment, an iRNA agent is administered to a subject as a fixed dose. A "fixed dose" (e.g., a dose in mg) means that one dose of an iRNA agent is used for all subjects regardless of any specific subject-related factors, such as weight. In one particular embodiment, a fixed dose of an iRNA agent of the invention is based on a predetermined weight or age.

In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered, e.g., subcutaneously or intravenously, a single therapeutic amount of iRNA, such as about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In some embodiments, subjects are administered, e.g., subcutaneously or intravenously, multiple doses of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A multi-dose regimen may include administration of a therapeutic amount of iRNA daily, such as for two days, three days, four days, five days, six days, seven days, or longer.

In other embodiments, subjects are administered, e.g., subcutaneously or intravenously, a repeat dose of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A repeat-dose regimen may include administration of a therapeutic amount of iRNA on a regular basis, such as every other day, every third day, every fourth day, twice a week, once a week, every other week, or once a month.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In certain embodiments of the invention, for example, when a double-stranded RNAi agent includes a modification (e.g., one or more motifs of three identical modifications on three consecutive nucleotides), including one such motif at or near the cleavage site of the agent, six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/kg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

In some embodiments, the RNAi agent is administered as a fixed dose of between about 100 mg to about 900 mg, e.g., between about 100 mg to about 850 mg, between about 100 mg to about 800 mg, between about 100 mg to about 750 mg, between about 100 mg to about 700 mg, between about 100 mg to about 650 mg, between about 100 mg to about 600 mg, between about 100 mg to about 550 mg, between about 100 mg to about 500 mg, between about 200 mg to about 850 mg, between about 200 mg to about 800 mg, between about 200 mg to about 750 mg, between about 200 mg to about 700 mg, between about 200 mg to about 650 mg, between about 200 mg to about 600 mg, between about 200 mg to about 550 mg, between about 200 mg to about 500 mg, between about 300 mg to about 850 mg, between about 300 mg to about 800 mg, between about 300 mg to about 750 mg, between about 300 mg to about 700 mg, between about 300 mg to about 650 mg, between about 300 mg to about 600 mg, between about 300 mg to about 550 mg, between about 300 mg to about 500 mg, between about 400 mg to about 850 mg, between about 400 mg to about 800 mg, between about 400 mg to about 750 mg, between about 400 mg to about 700 mg, between about 400 mg to about 650 mg, between about 400 mg to about 600 mg, between about 400 mg to about 550 mg, or between about 400 mg to about 500 mg.

In some embodiments, the RNAi agent is administered as a fixed dose of about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly. In some embodiments of the invention, a single dose of the pharmaceutical compositions of the invention is administered once per month, once every other month, or once quarterly (i.e., every three months).

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate iRNA. In some cases the liposomes are also specifically targeted, e.g., to direct the iRNA to particular cell types.

A liposome containing an iRNA agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA agent preparation is then added to the micelles that include the lipid component. The cationic groups on the lipid interact with the iRNA agent and condense around the iRNA agent to form a liposome. After condensation, the detergent is removed, e.g., by dialysis, to yield a liposomal preparation of iRNA agent.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.,* 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNA agents to macrophages.

Further advantages of liposomes include: liposomes obtained from natural phospholipids are biocompatible and biodegradable; liposomes can incorporate a wide range of water and lipid soluble drugs; liposomes can protect encapsulated iRNA agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA agent (see, e.g., Feigner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA agent into the skin. In some implementations, liposomes are used for delivering iRNA agent to epidermal cells and also to enhance the penetration of iRNA agent into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2, 405-410 and du Plessis et al., *Antiviral Research,* 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA agent can be delivered, for example, subcutaneously by infection in order to deliver iRNA agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in, for example, PCT Publication No. WO 2008/042973, the entire contents of which are incorporated herein by reference.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98•4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

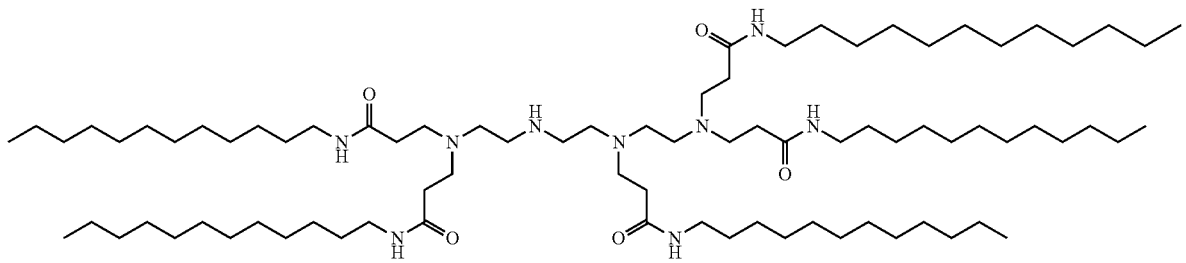

ND98 Isomer I

LNP01 formulations are described, e.g., in International Application Publication No. WO 2008/042973, which is hereby incorporated by reference.

Additional exemplary lipid-dsRNA formulations are described in Table 1.

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |

TABLE 1-continued

| | Ionizable/Cationic Lipid | cationic lipid/non-cationic lipid/cholesterol/PEG-lipid conjugate Lipid:siRNA ratio |
|---|---|---|
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000) SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.
XTC comprising formulations are described, e.g., in PCT Publication No. WO 2010/088537, the entire contents of which are incorporated herein by reference.
MC3 comprising formulations are described, e.g., in U.S. Publication No. 2010/0324120, filed Jun. 10, 2010, the entire contents of which are incorporated herein by reference.
ALNY-100 comprising formulations are described, e.g., PCT Publication No. WO 2010/054406, the entire contents of which are incorporated herein by reference.
C12-200 comprising formulations are described in PCT Publication No. WO 2010/129709, the entire contents of which are incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; poly-alkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An iRNA agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-20 alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, M A, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen;

Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), iRNAMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), Trans-Pass' D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-iRNA mechanism and which are useful in treating an HBV infection. Examples of such agents include, but are not limited to antiviral agents aimed at suppressing or destroying HBV by interfering with viral replication; and immune modulators aimed at helping the human immune system mount a defense against the virus. In contrast, immune modulators, such as corticosteroids, which induce an enhanced expression of virus and viral antigens, and a suppression of T-lymphocyte function, or adenine arabinoside, acyclovir, or dideoxyinosine, are not beneficial for the treatment of chronic hepatitis B. Suitable agents are discussed in more detail below.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by HBV expression. In any event, the administering physician can adjust the amount and timing of iRNA administration on the basis of results observed using standard measures of efficacy known in the art or described herein.

VII. Methods of the Invention

The present invention provides therapeutic and prophylactic methods which include administering to a subject having an HBV infection and/or HBV-associated disease, disorder, and/or condition, or prone to developing, an HBV-associated disease, disorder, and/or condition (e.g., CHB), compositions comprising an iRNA agent, or pharmaceutical compositions comprising an iRNA agent, or vectors comprising an iRNA of the invention.

The methods of the invention are useful for treating a subject having an HBV infection, e.g., a subject that would benefit from reduction in HBV gene expression and/or HBV replication. In one aspect, the present invention provides methods of reducing the level of Hepatitis B virus ccc DNA in a subject infected with HBV. In another aspect, the present invention provides methods of reducing the level of HBV antigen, e.g., HBsAg and/or HBeAg, in a subject infected with HBV. In another aspect, the present invention provides methods of reducing the viral load of HBV in a subject infected with HBV. The present invention also provides methods of reducing the level of alanine aminotransferase (ALT) and/or aspartate aminotransferase (AST) in a subject infected with HBV. In one aspect, the present invention provides methods for increasing the level of anti-HBV antibodies in a subject infected with HBV. In another aspect, the present invention provides methods of treating a subject having an HBV infection. In one aspect, the present invention provides methods of treating a subject having an HBV-associated disease, e.g., hepatitis D virus infection, delta hepatitis, acute hepatitis B; acute fulminant hepatitis B; chronic hepatitis B; liver fibrosis; end-stage liver disease; hepatocellular carcinoma. Furthermore, as HDV infection depends on obligatory helper functions provided by HBV for transmission, and subjects having an HBV infection may also have an HDV infection, the methods for treatment described herein are also useful for treating a subject having an HDV infection and/or an HDV-associated disorder, such as hepatitis B virus infection, chronic hepatitis B infection (CHB), chronic Hepatitis B infection (CHB), cirrhosis, liver failure, and hepatocellular carcinoma (HCC). The treatment methods (and uses) of the invention include administering to the subject, e.g., a human, a therapeutically effective amount of an iRNA agent of the invention targeting an HBV gene or a pharmaceutical composition comprising an iRNA agent of the invention targeting an HBV gene or a vector of the invention comprising an iRNA agent targeting an HBV gene.

In one aspect, the invention provides methods of preventing at least one symptom in a subject having an HBV infection, e.g., the presence of serum and/or liver HBV ccc DNA, the presence of serum HBV DNA the presence of serum and/or liver HBV antigen, e.g., HBsAg and/or HBeAg, elevated ALT, elevated AST, the absence or low level of anti-HBV antibodies, a liver injury; cirrhosis; hepatitis D virus infection, delta hepatitis, acute hepatitis B; acute fulminant hepatitis B; chronic hepatitis B; liver fibrosis; end-stage liver disease; hepatocellular carcinoma; serum sickness-like syndrome; anorexia; nausea; vomiting, low-grade fever; myalgia; fatigability; disordered gustatory acuity and smell sensations (aversion to food and cigarettes); and/or right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); high levels of alanine aminotransferase (ALT) and aspartate aminotransferase (AST), within a range of 1000-2000 IU/mL, although values 100 times above the upper limit of normal (ULN) can be also be identified; ALT levels higher than AST levels; elevated gamma-glutamyl transpeptidase (GGT) and alkaline phosphatase (ALP) levels (e.g., not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); the presence of serum and/or liverHBsAg, HBeAg, Hepatitis B core antibody (anti-HBc) immunoglobulin M (IgM); hepatitis B surface antibody (anti-HBs), hepatitis B e antibody (anti-HBe), and/or HBV DNA; elevation of the aminotransferases ($\leq 5$ times the ULN); ALT levels higher than the AST levels; increased bilirubin levels, prolonged prothrombin time (PT); hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); hyperbilirubinemia, prolonged PT, low platelet and white blood cell counts, AST levels higher than ALT levels; elevated alkaline phosphatase (ALP) and GGT levels; lobular, with degenerative and regenerative hepatocellular changes, and accompanying inflammation; predominantly centrilobular necrosis. The methods include administering to the subject a therapeutically effective amount of the iRNA agent, e.g., dsRNA, pharmaceutical compositions, or vectors of the invention, thereby preventing at least one symptom in the subject having a disorder that would benefit from reduction in HBV gene expression, such as a subject having an HBV infection or a subject having both an HBV and an HDV infection.

In another aspect, the present invention provides uses of a therapeutically effective amount of an iRNA agent of the invention for treating a subject, e.g., a subject that would benefit from a reduction and/or inhibition of HBV gene expression, such as a subject having an HBV infection or a subject having both an HBV and an HDV infection.

In a further aspect, the present invention provides uses of an iRNA agent, e.g., a dsRNA, of the invention targeting an HBV gene or pharmaceutical composition comprising an iRNA agent targeting an HBV gene in the manufacture of a medicament for treating a subject, e.g., a subject that would benefit from a reduction and/or inhibition of HBV gene expression and/or HBV replication, such as a subject having an HBV infection or a subject having both an HBV and an HDV infection, and a subject having a disorder that would benefit from reduction in HBV gene expression, e.g., a HBV-associated disease.

In another aspect, the invention provides uses of an iRNA, e.g., a dsRNA, of the invention for preventing at least one symptom in a subject suffering from a disorder that would benefit from a reduction and/or inhibition of HBV gene expression and/or HBV replication.

In a further aspect, the present invention provides uses of an iRNA agent of the invention in the manufacture of a medicament for preventing at least one symptom in a subject suffering from a disorder that would benefit from a reduction and/or inhibition of HBV gene expression and/or HBV replication, such as a HBV-associated disease.

In one embodiment, an iRNA agent targeting HBV is administered to a subject having an HBV infection or both and HBV and an HDV infection, and/or an HBV-associated disease such that the expression of one or more HBV genes, HBV ccc DNA levels, HBV antigen levels, HBV viral load levels, ALT, and/or AST, e.g., in a cell, tissue, blood or other tissue or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more when the dsRNA agent is administered to the subject.

In one embodiment, an iRNA agent targeting HBV is administered to a subject having an HBV infection or both and HBV and an HDV infection, and/or an HBV-associated disease such that the level of anti-HBV antibodies, e.g., in a cell, tissue, blood or other tissue or fluid of the subject are increased by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more when the dsRNA agent is administered to the subject.

The methods and uses of the invention include administering a composition described herein such that expression of the target HBV gene is decreased, such as for about 1, 2, 3, 4 5, 6, 7, 8, 12, 16, 18, 24, 28, 32, 36, 40, 44, 48, 52, 56, 60, 64, 68, 72, 76, or about 80 hours. In one embodiment, expression of the target HBV gene is decreased for an extended duration, e.g., at least about two, three, four, five, six, seven days or more, e.g., about one week, two weeks, three weeks, or about four weeks or longer.

Administration of the dsRNA according to the methods and uses of the invention may result in a reduction of the severity, signs, symptoms, and/or markers of such diseases or disorders in a patient with an HBV infection or both and HBV and an HDV infection, and/or HBV-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of CHB may be assessed, for example, by periodic monitoring of viral load and transaminase levels. Comparison of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting HBV or pharmaceutical composition thereof, "effective against" an HBV-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating HBV infection and/or an HBV-associated disease and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In certain embodiments of the invention, for example, when a double-stranded RNAi agent includes a modification (e.g., one or more motifs of three identical modifications on three consecutive nucleotides), including one such motif at or near the cleavage site of the agent, six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/kg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

In some embodiments, the RNAi agent is administered as a fixed dose of between about 100 mg to about 900 mg, e.g., between about 100 mg to about 850 mg, between about 100 mg to about 800 mg, between about 100 mg to about 750 mg, between about 100 mg to about 700 mg, between about 100 mg to about 650 mg, between about 100 mg to about 600 mg, between about 100 mg to about 550 mg, between about 100 mg to about 500 mg, between about 200 mg to about 850 mg, between about 200 mg to about 800 mg, between about 200 mg to about 750 mg, between about 200 mg to about 700 mg, between about 200 mg to about 650 mg, between about 200 mg to about 600 mg, between about 200 mg to about 550 mg, between about 200 mg to about 500 mg, between about 300 mg to about 850 mg, between about 300 mg to about 800 mg, between about 300 mg to about 750 mg, between about 300 mg to about 700 mg, between about 300 mg to about 650 mg, between about 300 mg to about 600 mg, between about 300 mg to about 550 mg, between about 300 mg to about 500 mg, between about 400 mg to about 850 mg, between about 400 mg to about 800 mg, between about 400 mg to about 750 mg, between about 400 mg to about 700 mg, between about 400 mg to about 650 mg, between about 400 mg to about 600 mg, between about 400 mg to about 550 mg, or between about 400 mg to about 500 mg.

In some embodiments, the RNAi agent is administered as a fixed dose of about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, or about 900 mg.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the iRNA can reduce the presence of serum and/or liver HBV ccc DNA, the presence of serum and/or liver HBV antigen, e.g., HBsAg and/or HBeAg, ALT levels, and/or AST levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more, e.g., to below the level of detection of the assay.

Administration of the iRNA can increase the presence of serum and/or liver anti-HBV antibodies, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the iRNA, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on HBV expression, a composition according to the invention or a pharmaceutical composition prepared therefrom can enhance the quality of life.

An iRNA of the invention may be administered in "naked" form, where the modified or unmodified iRNA agent is directly suspended in aqueous or suitable buffer solvent, as a "free iRNA." A free iRNA is administered in the absence of a pharmaceutical composition. The free iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of HBV gene expression are those having an HBV infection and/or an HBV-associated disease or disorder as described herein.

Treatment of a subject that would benefit from a reduction and/or inhibition of HBV gene expression includes therapeutic and prophylactic treatment.

The invention further provides methods and uses of an iRNA agent or a pharmaceutical composition thereof for treating a subject that would benefit from reduction and/or inhibition of HBV gene expression, e.g., a subject having a HBV-associated disease, in combination with other pharmaceuticals and/or other therapeutic methods, e.g., with known pharmaceuticals and/or known therapeutic methods, such as, for example, those which are currently employed for treating these disorders.

For example, in certain embodiments, an iRNA targeting one or more HBV genes is administered in combination with, e.g., an agent useful in treating an HBV-associated disease as described elsewhere herein. For example, additional therapeutics and therapeutic methods suitable for treating a subject that would benefit from reduction in HBV expression, e.g., a subject having a HBV-associated disease, include an iRNA agent targeting a different portion of the HBV genome, an antiviral agent, a reverse transcriptase inhibitor (e.g., Tenofovir disoproxil fumarate (TDF), Tenofovir alafenamide, Lamivudine, Adefovir dipivoxil, Entecavir (ETV), Telbivudine, and AGX-1009), an immune stimulator (e.g., pegylated interferon alfa 2a (PEG-IFN-α2a), Interferon alfa-2b, a recombinant human interleukin-7, and aToll-like receptor 7 (TLR7) agonist), a therapeutic vaccine (e.g., GS-4774, DV-601, and TG1050), a viral entry inhibitor (e.g., Myrcludex), an oligonucleotide that inhibits the secretion or release of HbsAg (e.g., REP 9AC), a capsid inhibitor (e.g., Bay41-4109 and NVR-1221), a cccDNA inhibitor (e.g., IHVR-25), or other therapeutic agents and/or procedures, e.g., liver transplant, chemotherapy, for treating a HBV-associated disease, a combination of any of the foregoing.

In certain embodiments, a first iRNA agent targeting one or more HBV genes is administered in combination with a second iRNA agent targeting a different portion of the HBV genome. For example, a first iRNA agent targeting one or more structural genes may be administered in combination with a second RNAi agent targeting the X gene. For example, the first RNAi agent comprises a first sense strand and a first antisense strand forming a double-stranded region, wherein substantially all of the nucleotides of said first sense strand and substantially all of the nucleotides of the first antisense strand are modified nucleotides, wherein said first sense strand is conjugated to a ligand attached at the 3'-terminus, and wherein the ligand is one or more GalNAc derivatives attached through a bivalent or trivalent branched linker; and the second RNAi agent comprises a second sense strand and a second antisense strand forming a double-stranded region, wherein substantially all of the nucleotides of the second sense strand and substantially all of the nucleotides of the second antisense strand are modified nucleotides, wherein the second sense strand is conjugated to a ligand attached at the 3'-terminus, and wherein the ligand is one or more GalNAc derivatives attached through a bivalent or trivalent branched linker; wherein the first sense strand comprises a sequences selected from the group consisting of 5'-UCGUGGUGGACUUCUCUCA-3'(SEQ ID NO:5),
5'-GUGCACUUCGCUUCACCUCUA-3'(SEQ ID NO:7),
5'-CGUGGUGGACUUCUCUCAAUU-3'(SEQ ID NO:9),
5'-CGUGGUGGUCUUCUCUAAAUU-3'(SEQ ID NO:37),
5'-GGUGGACUUCUCUCAAUUUUA-3'(SEQ ID NO:11), and
5'-GUGUGCACUUCGCUUCACA-3'(SEQ ID NO:39) (or a nucleotide sequence which is at least 90%, 91%, 92%, 93%, 94%, 95%, 96%, 97%, 98%, or 99% identical over its entire length to any of the foregoing nucleotide sequences), and wherein the first and second antisense strands each independently comprise a sequence selected from the group consisting of 5'-UGAGAGAAGUCCACCACGAUU-3'(SEQ ID NO:6);
5'-UAGAGGUGAAGCGAAGUGCACUU-3'(SEQ ID NO:8);

5'-AAUUGAGAGAAGUCCACCAGCAG-3' (SEQ ID NO:10);
5'-AAUUGAGAGAAGUCCACCAGCUU-3' (SEQ ID NO:38),
5'-UAAAAUUGAGAGAAGUCCACCAC-3' (SEQ ID NO:12), and
5'-UGUGAAGCGAAGUGCACACUU-3' (SEQ ID NO:40) (or a nucleotide sequence which is at least 90%, 91%, 92%, 93%, 94%, 95%, 96%, 97%, 98%, or 99% identical over its entire length to any of the foregoing nucleotide sequences), thereby treating the subject.

In one embodiment, all of the nucleotides of the first and second sense strand and/or all of the nucleotides of the first and second antisense strand comprise a modification.

In one embodiment, the at least one of the modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In certain embodiments, a first iRNA agent targeting one or more HBV genes is administered in combination with a second iRNA agent targeting a gene that is different from one or more HBV genes. For example, the iRNA agent targeting one or more HBV genes may be administered in combination with an iRNA agent targeting a CD274/PD-L1 gene. Examples of iRNA agents targeting a CD274/PD-L1 gene are described in WO 2011/127180, the entire contents of which are incorporated herein by reference. The first iRNA agent targeting one or more HBV genes and the second iRNA agent targeting a gene different from one or more HBV genes, e.g., a CD274/PD-L1 gene and/or an HDV gene, may be administered as parts of the same pharmaceutical composition. Alternatively, the first iRNA agent targeting one or more HBV genes and the second iRNA agent targeting a gene different from one or more HBV genes, e.g., a CD274/PD-L1 gene and/or an HDV gene, may be administered as parts of different pharmaceutical compositions.

CD274 or PD-L1 is a 290 amino acid type I transmembrane protein encoded by the CD274 gene on mouse chromosome 19 and human chromosome 9. CD274/PD-L1 expression is implicated in evasion of immune responses involved in chronic infection, e.g., by viruses (including, for example, HIV, HBV, HCV and HTLV, among others), by bacteria (including, for example, *Helicobacter pylori*, among others) and by parasites (including, for example, *Schistosoma mansoni*).

PD-L1 can influence immune responses by engaging PD-1 or B7-1 (CD80) and modifying TCR or BCR signaling, but can also deliver signals into PD-L1 expressing cells, i.e., reverse signaling through PD-L1. Surface plasmon resonance studies demonstrate specific and unique interaction between both PD-L1 and B7-1, with an affinity of 1.7 μM, and an affinity of 0.5 μM for the interaction between PD-L1 and PD-1. Chemical cross-linking studies indicate that PD-L1 and B7-1, like PD-L1 and PD-1, can also interact through their IgV-like domains. The PD-L1:B7-1 interface overlaps at least partially with the putative PD-L1:PD-1 interface. B7-1:PD-L1 interactions can induce an inhibitory signal into T cells. Ligation of PD-L1 on CD4 T cells by B7-1, or ligation of B7-1 on CD4 T cells by PD-L1, delivers a functionally significant, inhibitory signal. Because both PD-L1 and B7-1 are expressed on T cells, B cells, DCs, and macrophages, there is the potential for bidirectional interactions between B7-1 and PD-L1 on these cell types. In addition, PD-L1 on nonhematopoietic cells may interact with B7-1 as well as PD-1 on T cells to regulate cells (Keir M E et al., 2008. *Annu Rev Immunol.* 26:677-704).

In chronic viral infections in humans, several groups have shown that PD-1 expression is high on HIV-specific (Petrovas C et al., 2006, *J. Exp. Med.* 203:2281-92; Day C L et al., 2006, *Nature* 443:350-54; Trautmann L et al., 2006, *Nat. Med.* 12: 1198-202), HBV-specific (Boettler T et al., 2006, *J. Virol.* 80:3532-40; Boni C et al. 2007, *J. Virol.* 81:4215-25), and HCV-specific T cells (Urbani S et al., 2006, *J. Virol.* 80: 11398-403). PD-L1 is also upregulated on peripheral blood CD14+ monocytes and myeloid DCs in patients with chronic HBV infection (Chen L et al., 2007, *J. Immunol.* 178:6634-41; Ceng L et al., 2006, *J. Viral Hepat.* 13:725-33), and on CD14+ cells and T cells in HIV patients (Trabattoni D et al., 2003. *Blood* 101:2514-20). Blocking PD-LPD-L interactions in vitro reverses the exhaustion of HIV-specific, HBV-specific (Boni C et al. 2007, *J. Virol.* 81:4215-25), HCV-specific, and SIV-specific (Velu V et al., 2007, *J. Virol.* 81:5819-28) CD8 and CD4 T cells and restores proliferation and cytokine production (Petrovas C et al., 2006, *J. Exp. Med.* 203:2281-92; Day C L et al., 2006, *Nature* 443:350-54; Trautmann L et al., 2006, *Nat. Med.* 12: 1198-202; Urbani S et al., 2006, *J. Virol.* 80: 11398-403). Recent work shows that the HCV core, a nucleocapsid protein, can upregulate PD-1 and PD-L1 expression on healthy donor T cells and that upregulation of PD-1 is mediated by interaction of the HCV core with the complement receptor C1QBP (Yao Z Q et al., 2007, *Viral Immunol.* 20:276-87).

A subject administered a first RNAi agent or a first and second RNAi agent of the invention may further be administered with one or more other therapeutics which function by a non-iRNA mechanism and which are useful in treating an HBV infection. Exemplary therapeutics that may be used in a combination therapy of the invention include immune modulators which stimulate the immune system by, for example, enhancing T-cell helper activity, maturation of B lymphocytes, inhibiting T-cell suppressors, and enhancing HLA type I expression. Suitable immune modulators include interferons which have a variety of properties that include antiviral, immunomodulatory, and antiproliferative effects.

For example, the current treatment for chronic hepatitis B is interferon therapy, which is administered to subjects who have a documented HBV infection for at least six months, elevated liver enzymes (AST and ALT) and an actively dividing virus in their blood (HBeAg, and/or HBV DNA positive tests). Interferon-α therapy produces a long-term, sustained remission of the disease in about 35% of those with chronic hepatitis B, with normalization of liver enzymes and loss of the three markers for an active infection (HBeAg, HBV DNA, and HBsAg). Subjects with an acute HBV infection, end stage cirrhosis or other major medical problems are typically not treated with interferon.

In addition, interferon therapy for patients with HBV-related cirrhosis decreases significantly the hepatocellular carcinoma (HCC) rate, particularly in patients with a larger amount of serum HBV DNA. In patients with HBeAg-positive compensated cirrhosis, virological and biochemical remission following interferon therapy is associated with improved survival. In patients with chronic HBV infection, the clearance of HBeAg after treatment with interferon-α is associated with improved clinical outcomes.

The standard duration of therapy is considered 16 weeks. Patients who exhibit a low level of viral replication at the end of the standard regimen benefit most from prolonged treatment.

Other exemplary therapeutic agents which can be used in a combination therapy of the invention include, for example, an antiviral agent, a nucleotide analog, a nucleoside analog, a reverse transcriptase inhibitor (e.g., Tenofovir disoproxil fumarate (TDF), Tenofovir alafenamide, Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, and ganciclovir), an immune stimulator (e.g., pegylated interferon alfa 2a (PEG-IFN-α2a), Interferon alfa-2b, a recombinant human interleukin-7, and aToll-like receptor 7 (TLR7) agonist), a therapeutic vaccine (e.g., GS-4774, DV-601, and TG1050), a viral entry inhibitor (e.g., Myrcludex), an oligonucleotide that inhibits the secretion or release of HbsAg (e.g., REP 9AC), a capsid inhibitor (e.g., Bay41-4109 and NVR-1221), a cccDNA inhibitor (e.g., IHVR-25), or other therapeutic agents and/or procedures, e.g., liver transplant, chemotherapy, for treating a HBV-associated disease, a combination of any of the foregoing.

In one embodiment, the methods of the invention include administering to a subject having an HBV infection and/or HBV-associate disease a reverse transcriptase inhibitor. In another embodiment, the methods of the invention include administering to a subject having an HBV infection and/or HBV-associate disease a reverse transcriptase inhibitor and an immune stimulator.

The iRNA agent(s) and an additional therapeutic agent and/or treatment may be administered at the same time and/or in the same combination, e.g., parenterally, or the additional therapeutic agent can be administered as part of a separate composition or at separate times and/or by another method known in the art or described herein.

The present invention also provides methods of using an iRNA agent of the invention and/or a composition containing an iRNA agent of the invention to reduce and/or inhibit HBV expression in a cell. In other aspects, the present invention provides an iRNA of the invention and/or a composition comprising an iRNA of the invention for use in reducing and/or inhibiting HBV gene expression in a cell. In yet other aspects, use of an iRNA of the invention and/or a composition comprising an iRNA of the invention for the manufacture of a medicament for reducing and/or inhibiting HBV gene expression in a cell are provided. In still other aspect, the present invention provides an iRNA of the invention and/or a composition comprising an iRNA of the invention for use in reducing and/or inhibiting HBV replication in a cell. In yet other aspects, use of an iRNA of the invention and/or a composition comprising an iRNA of the invention for the manufacture of a medicament for reducing and/or inhibiting HBV replication in a cell are provided. The methods and uses include contacting the cell with an iRNA, e.g., a dsRNA, of the invention and maintaining the cell for a time sufficient to obtain degradation of the mRNA transcript of an HBV gene, thereby inhibiting expression of the HBV gene or inhibiting HBV replication in the cell.

Reduction in gene expression can be assessed by any methods known in the art. For example, a reduction in the expression of HBV may be determined by determining the mRNA expression level of HBV using methods routine to one of ordinary skill in the art, e.g., northern blotting, qRT-PCR, by determining the protein level of HBV using methods routine to one of ordinary skill in the art, such as western blotting, immunological techniques, flow cytometry methods, ELISA, and/or by determining a biological activity of HBV.

In the methods and uses of the invention the cell may be contacted in vitro or in vivo, i.e., the cell may be within a subject.

A cell suitable for treatment using the methods of the invention may be any cell that expresses an HBV gene, e.g., a cell infected with HBV or a cell comprising an expression vector comprising an HBV genome or portion of an HBV gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

HBV gene expression may be inhibited in the cell by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%, i.e., to below the level of detection of the assay.

HBV replication may be inhibited in the cell by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%, i.e., to below the level of detection of the assay.

The in vivo methods and uses of the invention may include administering to a subject a composition containing an iRNA, where the iRNA includes a nucleotide sequence that is complementary to at least a part of an RNA transcript of the HBV gene of the mammal to be treated. When the organism to be treated is a human, the composition can be administered by any means known in the art including, but not limited to subcutaneous, intravenous, oral, intraperitoneal, or parenteral routes, including intracranial (e.g., intraventricular, intraparenchymal and intrathecal), intramuscular, transdermal, airway (aerosol), nasal, rectal, and topical (including buccal and sublingual) administration. In certain embodiments, the compositions are administered by subcutaneous injection. In some embodiments, the compositions are administered by intravenous infusion or injection. In other embodiments, the compositions are administered by intramuscular injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of HBV, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of an HBV gene in a mammal, e g, a human. The present invention also provides a composition comprising an iRNA, e.g., a dsRNA, that targets an HBV gene in a cell of a mammal for use in inhibiting expression of the HBV gene in the mammal. In another aspect, the present invention provides use of an iRNA, e.g., a dsRNA, that targets an HBV gene in a cell of a mammal in the manufacture of a medicament for inhibiting expression of the HBV gene in the mammal.

The methods and uses include administering to the mammal, e.g., a human, a composition comprising an iRNA, e.g., a dsRNA, that targets an HBV gene in a cell of the mammal and maintaining the mammal for a time sufficient to obtain degradation of the mRNA transcript of the HBV gene, thereby inhibiting expression of the HBV gene in the mammal Reduction in gene expression can be assessed in peripheral blood sample of the iRNA-administered subject by any methods known it the art, e.g. qRT-PCR, described herein. Reduction in protein production can be assessed by any methods known it the art and by methods, e.g., ELISA or western blotting, described herein. In one embodiment, a puncture liver biopsy sample serves as the tissue material for monitoring the reduction in HBV gene and/or protein expression. In another embodiment, a blood sample serves as the tissue material for monitoring the reduction in HBV gene and/or protein expression.

In one embodiment, verification of RISC medicated cleavage of target in vivo following administration of iRNA agent is done by performing 5'-RACE or modifications of the protocol as known in the art (Lasham A et al., (2010) *Nucleic Acid Res.*, 38 (3) p-e19) (Zimmermann et al. (2006) *Nature* 441: 111-4).

This invention is further illustrated by the following examples which should not be construed as limiting. The entire contents of all references, patents and published patent applications cited throughout this application, as well as the Figures and the Sequence Listing, are hereby incorporated herein by reference.

Examples

Example 1. iRNA Synthesis

Source of Reagents

Where the source of a reagent is not specifically given herein, such reagent can be obtained from any supplier of reagents for molecular biology at a quality/purity standard for application in molecular biology.

Transcripts siRNA Design

The selection of siRNA designs targeting HBV was driven by two primary factors: a) potency and b), the desire to employ siRNA with near-perfect matches with greater than 90% fractional coverage of the large number of public HBV sequences of all known serotypes (A through H). The coordinates for the siRNA selection were determined relative to the NCBI HBV reference genome sequence NC_003977.1 (GenBank Accession No. GI:21326584 (SEQ ID NO:1). A first set of siRNAs containing structure-activity modifications, including various 2'-O-methyl and 2'-fluoro substitution patterns, centered on two adjacent regions of the HBV genome coding for surface antigen (HbSAg) and the HBV polymerase, were designed, synthesized and screened in-vitro. A second set of siRNAs were designed, synthesized and screened targeting additional target regions with particular attention to positions 1581-1599 of SEQ ID NO:1 that code, in addition to the HbSAg and polymerase, the X gene.

A detailed list of the unmodified HBV sense and antisense strand sequences is shown in Table 3.

A detailed list of the modified HBV sense and antisense strand sequences is shown in Table 4.

siRNA Synthesis

HBV siRNA sequences were synthesized at 1 µmol scale on Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, Wis.) and Hongene (China). 2'F 2'-O-Methyl, GNA (glycol nucleic acids), 5'phosphate and abasic modifications were introduced employing the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, Mass., USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 µL Aqueous Methylamine reagents at 60° C. for 20 minutes. At the end of cleavage and deprotection step, the synthesis plate was allowed to come to room temperature and was precipitated by addition of 1 mL of acetonitile: ethanol mixture (9:1). The plates were cooled at −80 C for 2 hrs, supernatant decanted carefully with the aid of a multi channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples by IEX chromatography to determine purity.

Annealing of HBV single strands was performed on a Tecan liquid handling robot. Equimolar mixture of sense and antisense single strands were combined and annealed in 96 well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 µM in 1×PBS.

Example 2. In Vitro Screening of siRNA Duplexes

Cell Culture and Transfections

Cos7 cells (ATCC, Manassas, Va.) were grown to near confluence at 37° C. in an atmosphere of 5% CO2 in DMEM (ATCC) supplemented with 10% FBS, before being released from the plate by trypsinization. Dual-Glo® Luciferase constructs generated in the psiCHECK2 plasmid containing approximately 1.1 kb of HBV genomic sequences were transfected into approximately $15 \times 10^4$ cells using Lipofectamine 2000 (Invitrogen, Carlsbad Calif. cat #11668-019). For each well of a 96 well plate, 0.2 µl of Lipofectamine was added to 10 ng of plasmid vector in 14.8 µl of Opti-MEM and allowed to complex at room temperature for 15 minutes. The mixture was then added to the cells which were resuspended in 80 µl of fresh complete media. After approximately 24 hours, the media were removed and the cells re-transfected with siRNA. Each siRNA was transfected into cells that had previously been transfected with the psiCHECK2-HBV vector that had a perfect match for the siRNA. siRNA transfection was carried out by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. The mixture was then added to the cells previously transfected with the psiCHECK2-HBV plasmid that had a perfect match to the siRNA sequence. Cells were incubated for 24 hours before luciferase was measured.

Single dose experiments were performed at 10 nM and 0.01 nM final duplex concentration.

Dual-Glo® Luciferase Assay

Twenty-four hours after the siRNAs were transfected, Firefly (transfection control) and *Renilla* (fused to HBV target sequence) luciferase were measured. First, media was removed from cells. Then Firefly luciferase activity was measured by adding 75 µl of Dual-Glo® Luciferase Reagent equal to the culture medium volume to each well and mix. The mixture was incubated at room temperature for 30 minutes before luminescence (500 nm) was measured on a Spectramax (Molecular Devices) to detect the Firefly luciferase signal. *Renilla* luciferase activity was measured by adding 75 µl of room temperature of Dual-Glo® Stop & Glo® Reagent was added to each well and the plates were incubated for 10-15 minutes before luminescence was again measured to determine the *Renilla* luciferase signal. The Dual-Glo® Stop & Glo® Reagent, quench the firefly luciferase signal and sustain luminescence for the *Renilla* luciferase reaction. siRNA activity was determined by normalizing the *Renilla* (HBV) signal to the Firefly (control) signal within each well. The magnitude of siRNA activity was then assessed relative to cells that were transfected with the same vector but were not treated with siRNA or were treated with a non-targeting siRNA. All transfections were done at n=2 or greater.

Table 5 shows the results of a single dose screen in Cos7 cells transfected with the indicated HBV iRNAs. Data are expressed as percent of mRNA remaining relative to negative control.

TABLE 2

Abbreviations of nucleotide monomers used in nucleic acid sequence representation. It will be understood that, unless otherwise indicated, these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| (dT) | 2'-deoxythymidine-3'-phosphate |
| Y34 | 2-hydroxymethyl-tetrahydrofurane-4-methoxy-3-phosphate (abasic 2'-OMe furanose) |
| Y44 | 2-hydroxymethyl-tetrahydrofurane-5-phosphate |
| (Agn) | Adenosine-glycol nucleic acid (GNA) |
| (Tgn) | Thymidine-glycol nucleic acid (GNA) S-Isomer |
| (Cgn) | Cytidine-glycol nucleic acid (GNA) |
| P | Phosphate |
| VP | Vinyl-phosphate |

TABLE 3

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-61522.2 | A-123463.2 | AGUAUAUGGAUGAUGUGGUA | 47 | A-123464.2 | UACCACAUCAUCCAUAUACUGA | 263 | 731_753 |
| AD-61547.2 | A-123487.2 | GGAUGUGUCUGCCGCGUUUUA | 48 | A-123488.2 | UAAAACGCCGCAGACACAUCCAG | 264 | 373_395 |
| AD-63938.2 | A-127896.1 | ACUCGUGGUGGACUUCUCUCA | 49 | A-127897.1 | UGAGAGAAGUCCACCACGAGUCU | 265 | 250_272 |
| AD-63939.2 | A-127909.1 | ACUCGUGGUGGACUUCUCUCA | 50 | A-127906.3 | UGAGAGAAGUCCACCACGAGUCU | 266 | 250_272 |
| AD-63940.2 | A-127917.1 | ACUCGUGGUGGACUUCUCUCA | 51 | A-127906.11 | UGAGAGAAGUCCACCACGAGUCU | 267 | 250_272 |
| AD-63941.2 | A-127905.8 | ACUCGUGGUGGACUUCUCUCA | 52 | A-127925.1 | UGAGAGAAGUCCACCACGAGUCU | 268 | 250_272 |
| AD-63942.2 | A-127933.1 | UCGUGGUGGACUUCUCUCA | 53 | A-127934.1 | UGAGAGAAGUCCACCACGAGU | 269 | 252_274 |
| AD-63943.2 | A-127944.2 | ACUCGUGGUGGACUUCUCUCA | 54 | A-127942.2 | UGAGAGAAGUCCACCACGAGUCU | 270 | 250_272 |
| AD-63945.2 | A-127910.1 | ACUCGUGGUGGACUUCUCUCA | 55 | A-127906.4 | UGAGAGAAGUCCACCACGAGUCU | 271 | 250_272 |
| AD-63946.2 | A-127918.1 | ACUCGUGGUGGACUUCUCUCA | 56 | A-127906.12 | UGAGAGAAGUCCACCACGAGUCU | 272 | 250_272 |
| AD-63947.2 | A-127905.9 | ACUCGUGGUGGACUUCUCUCA | 57 | A-127926.1 | UGAGAGAAGUCCACCACGAGUCU | 273 | 250_272 |
| AD-63948.2 | A-127935.1 | GUGGUGGACUUCUCUCA | 58 | A-127936.1 | UGAGAGAAGUCCACCACGA | 274 | 254_276 |
| AD-63949.2 | A-127944.3 | ACUCGUGGUGGACUUCUCUCA | 59 | A-127906.14 | UGAGAGAAGUCCACCACGAGUCU | 275 | 250_272 |
| AD-63950.2 | A-127900.1 | UCGUGGUGGACUUCUCUCAUU | 60 | A-127901.1 | UGAGAGAAGUCCACCACGAGAUU | 276 | 252_274 |
| AD-63951.2 | A-127911.1 | ACUCGUGGUGGACUUCUCUCA | 61 | A-127906.5 | UGAGAGAAGUCCACCACGAGUCU | 277 | 250_272 |
| AD-63952.2 | A-127905.2 | ACUCGUGGUGGACUUCUCUCA | 62 | A-127919.1 | UGAGAGAAGUCCACCACGAGUCU | 278 | 250_272 |
| AD-63953.2 | A-127905.10 | ACUCGUGGUGGACUUCUCUCA | 63 | A-127927.1 | UGAGAGAAGUCCACCACGAGUCU | 279 | 250_272 |
| AD-63955.2 | A-127945.1 | ACUCGUGGUGGACUUCUCUCA | 64 | A-127940.3 | UGAGAGAAGUCCACCACGAGUCU | 280 | 250_272 |
| AD-63956.2 | A-127902.1 | UCGUGGUGGACUUCUCUCA | 65 | A-127903.1 | UGAGAGAAGUCCACCACGAGAUU | 281 | 252_274 |
| AD-63957.2 | A-127912.1 | ACUCGUGGUGGACUUCUCUCA | 66 | A-127906.6 | UGAGAGAAGUCCACCACGAGUCU | 282 | 250_272 |
| AD-63958.2 | A-127905.3 | ACUCGUGGUGGACUUCUCUCA | 67 | A-127920.1 | UGAGAGAAGUCCACCACGAGUCU | 283 | 250_272 |
| AD-63959.2 | A-127905.11 | ACUCGUGGUGGACUUCUCUCA | 68 | A-127928.1 | UGAGAGAAGUCCACCACGAGUCU | 284 | 250_272 |
| AD-63960.2 | A-126619.2 | UAUUUCCUAGGGUACAA | 69 | A-127938.1 | UGAGAGAAGUCCACCACGA | 285 | 254_276 |

TABLE 3-continued

Unmodified Sense and Antisense Strand Sequences of HBV dsRNAs

| Duplex Name | Sense Oligo Name | SEQ ID NO | Sense Sequence (5' to 3') | Antisense Oligo Name | Antisense Sequence (5' to 3') | SEQ ID NO: | Position in NC_003977.1 |
|---|---|---|---|---|---|---|---|
| AD-63961.2 | A-127945.2 | 70 | ACUCGUGGUGGACUUCUCUCA | A-127942.3 | UGAGAGAAGUCCACCACGAGUCU | 286 | 250_272 |
| AD-63962.2 | A-127902.2 | 71 | UCUGUGGUGGACUUCUCUCA | A-127904.1 | UGAGAGAAGUCCACCACGAGAUU | 287 | 252_274 |
| AD-63963.2 | A-127913.1 | 72 | ACUCGUGGUGGACUUCUCUCA | A-127906.7 | UGAGAGAAGUCCACCACGAGUCU | 288 | 250_272 |
| AD-63964.2 | A-127905.4 | 73 | ACUCGUGGUGGACUUCUCUCA | A-127921.1 | UGAGAGAAGUCCACCACGAGUCU | 289 | 250_272 |
| AD-63965.2 | A-127905.12 | 74 | ACUCGUGGUGGACUUCUCUCA | A-127929.1 | UGAGAGAAGUCCACCACGAGUCU | 290 | 250_272 |
| AD-63966.2 | A-127939.1 | 75 | ACUCGUGGUGGACUUCUCUCA | A-127940.1 | UGAGAGAAGUCCACCACGAGUCU | 291 | 250_272 |
| AD-63967.2 | A-127945.3 | 76 | ACUCGUGGUGGACUUCUCUCA | A-127906.15 | UGAGAGAAGUCCACCACGAGUCU | 292 | 250_272 |
| AD-63968.2 | A-127905.1 | 77 | ACUCGUGGUGGACUUCUCUCA | A-127906.1 | UGAGAGAAGUCCACCACGAGUCU | 293 | 250_272 |
| AD-63968.4 | A-127905.15 | 78 | ACUCGUGGUGGACUUCUCUCA | A-127906.17 | UGAGAGAAGUCCACCACGAGUCU | 294 | 250_272 |
| AD-63968.5 | A-127905.17 | 79 | ACUCGUGGUGGACUUCUCUCA | A-127906.18 | UGAGAGAAGUCCACCACGAGUCU | 295 | 250_272 |
| AD-63969.2 | A-127914.1 | 80 | ACUCGUGGUGGACUUCUCUCA | A-127906.8 | UGAGAGAAGUCCACCACGAGUCU | 296 | 250_272 |
| AD-63970.2 | A-127905.5 | 81 | ACUCGUGGUGGACUUCUCUCA | A-127922.1 | UGAGAGAAGUCCACCACGAGUCU | 297 | 250_272 |
| AD-63971.2 | A-127905.13 | 82 | ACUCGUGGUGGACUUCUCUCA | A-127930.1 | UGAGAGAAGUCCACCACGAGUCU | 298 | 250_272 |
| AD-63972.2 | A-127941.1 | 83 | ACUCGUGGUGGACUUCUCUCA | A-127942.1 | UGAGAGAAGUCCACCACGAGUCU | 299 | 250_272 |
| AD-63973.2 | A-127946.1 | 84 | ACUCGUGGUGGACUUCUCUCA | A-127947.1 | UGAGAGAAGUCCACCACGAGUCU | 300 | 250_272 |
| AD-63975.2 | A-127915.1 | 85 | ACUCGUGGUGGACUUCUCUCA | A-127906.9 | UGAGAGAAGUCCACCACGAGUCU | 301 | 250_272 |
| AD-63976.2 | A-127905.6 | 86 | ACUCGUGGUGGACUUCUCUCA | A-127923.1 | UGAGAGAAGUCCACCACGAGUCU | 302 | 250_272 |
| AD-63977.2 | A-127917.2 | 87 | ACUCGUGGUGGACUUCUCUCA | A-127931.1 | UGAGAGAAGUCCACCACGAGUCU | 303 | 250_272 |
| AD-63978.2 | A-127943.1 | 88 | ACUCGUGGUGGACUUCUCUCA | A-127906.13 | UGAGAGAAGUCCACCACGAGUCU | 304 | 250_272 |
| AD-63979.2 | A-127908.1 | 89 | ACUCGUGGUGGACUUCUCUCA | A-127906.2 | UGAGAGAAGUCCACCACGAGUCU | 305 | 250_272 |
| AD-63980.2 | A-127916.1 | 90 | ACUCGUGGUGGACUUCUCUCA | A-127906.10 | UGAGAGAAGUCCACCACGAGUCU | 306 | 250_272 |
| AD-63981.2 | A-127905.7 | 91 | ACUCGUGGUGGACUUCUCUCA | A-127924.1 | UGAGAGAAGUCCACCACGAGUCU | 307 | 250_272 |
| AD-63982.2 | A-127917.3 | 92 | ACUCGUGGUGGACUUCUCUCA | A-127932.1 | UGAGAGAAGUCCACCACGAGUCU | 308 | 250_272 |
| AD-63983.2 | A-127944.1 | 93 | ACUCGUGGUGGACUUCUCUCA | A-127940.2 | UGAGAGAAGUCCACCACGAGUCU | 309 | 250_272 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-63985.2 | A-127961.1 | GUGGUGGACUUCUCUCAAUUU | 94 | A-127956.4 | AAAUUGAGAGAAGUCCACCACGA | 310 | 254_276 |
| AD-63986.2 | A-127969.1 | GUGGUGGACUUCUCUCAAUUU | 95 | A-127956.12 | AAAUUGAGAGAAGUCCACCACGA | 311 | 254_276 |
| AD-63987.2 | A-127955.9 | GGGGUGGACUUCUCUCAAUUU | 96 | A-127977.1 | AAAUUGAGAGAAGUCCACCACGA | 312 | 254_276 |
| AD-63988.2 | A-127986.1 | UGGACUUCUCUCAAUUU | 97 | A-127987.1 | AAAUUGAGAGAAGUCCACC | 313 | 258_280 |
| AD-63989.2 | A-127996.1 | GUGGUGGACUUCUCUCAAUUU | 98 | A-127992.2 | AAAUUGAGAGAAGUCCACCACGA | 314 | 254_276 |
| AD-63990.2 | A-127950.1 | GGGUGGACUUCUCUCAAUUUUU | 99 | A-127951.1 | AAAUUGAGAGAAGUCCACCACCUU | 315 | 256_278 |
| AD-63991.2 | A-127962.1 | GUGGUGGACUUCUCUCAAUUU | 100 | A-127956.5 | AAAUUGAGAGAAGUCCACCACGA | 316 | 254_276 |
| AD-63992.2 | A-127955.2 | GUGGUGGACUUCUCUCAAUUU | 101 | A-127970.1 | AAAUUGAGAGAAGUCCACCACGA | 317 | 254_276 |
| AD-63993.2 | A-127955.10 | GUGGUGGACUUCUCUCAAUUU | 102 | A-127978.1 | AAAUUGAGAGAAGUCCACCACGA | 318 | 254_276 |
| AD-63994.2 | A-127984.2 | GGUGGACUUCUCUCAAUUU | 103 | A-127988.1 | AAAUUGAGAGAAGUCCACCAC | 319 | 256_278 |
| AD-63995.2 | A-127996.2 | GUGGUGGACUUCUCUCAAUUU | 104 | A-127993.2 | AAAUUGAGAGAAGUCCACCACGA | 320 | 254_276 |
| AD-63996.2 | A-127952.1 | GGUGGACUUCUCUCAAUUU | 105 | A-127953.1 | AAAUUGAGAGAAGUCCACCACCUU | 321 | 256_278 |
| AD-63997.2 | A-127963.1 | GUGGUGGACUUCUCUCAAUUU | 106 | A-127956.6 | AAAUUGAGAGAAGUCCACCACGA | 322 | 254_276 |
| AD-63999.2 | A-127955.11 | GUGGUGGACUUCUCUCAAUUU | 107 | A-127979.1 | AAAUUGAGAGAAGUCCACCACGA | 323 | 254_276 |
| AD-64000.2 | A-127986.2 | UGGACUUCUCUCAAUUU | 108 | A-127989.1 | AAAUUGAGAGAAGUCCACC | 324 | 258_280 |
| AD-64001.2 | A-127996.3 | GUGGUGGACUUCUCUCAAUUU | 109 | A-127994.2 | AAAUUGAGAGAAGUCCACCACGA | 325 | 254_276 |
| AD-64002.2 | A-127952.2 | GGUGGACUUCUCUCAAUUU | 110 | A-127954.1 | AAAUUGAGAGAAGUCCACCACCUU | 326 | 256_278 |
| AD-64003.2 | A-127964.1 | GUGGUGGACUUCUCUCAAUUU | 111 | A-127956.7 | AAAUUGAGAGAAGUCCACCACGA | 327 | 254_276 |
| AD-64004.2 | A-127955.4 | GUGGUGGACUUCUCUCAAUUU | 112 | A-127972.1 | AAAUUGAGAGAAGUCCACCACGA | 328 | 254_276 |
| AD-64005.2 | A-127955.12 | GUGGUGGACUUCUCUCAAUUU | 113 | A-127980.1 | AAAUUGAGAGAAGUCCACCACGA | 329 | 254_276 |
| AD-64006.2 | A-127990.1 | GUGGUGGACUUCUCUCAAUUU | 114 | A-127991.1 | AAAUUGAGAGAAGUCCACCACGA | 330 | 254_276 |
| AD-64007.2 | A-127996.4 | GUGGUGGACUUCUCUCAAUUU | 115 | A-127995.2 | AAAUUGAGAGAAGUCCACCACGA | 331 | 254_276 |
| AD-64008.2 | A-127955.1 | GUGGUGGACUUCUCUCAAUUU | 116 | A-127956.1 | AAAUUGAGAGAAGUCCACCACGA | 332 | 254_276 |
| AD-64008.4 | A-127955.15 | GUGGUGGACUUCUCUCAAUUU | 117 | A-127956.14 | AAAUUGAGAGAAGUCCACCACGA | 333 | 254_276 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64009.2 | A-127965.1 | GUGGUGGACUUCUCUCAAUUU | 118 | A-127956.8 | AAAUUGAGAGAAGUCCACCACGA | 334 | 254_276 |
| AD-64010.2 | A-127955.5 | GUGGUGGACUUCUCUCAAUUU | 119 | A-127973.1 | AAAUUGAGAGAAGUCCACCACGA | 335 | 254_276 |
| AD-64011.2 | A-127955.13 | GUGGUGGACUUCUCUCAAUUU | 120 | A-127981.1 | AAAUUGAGAGAAGUCCACCACGA | 336 | 254_276 |
| AD-64012.2 | A-127990.2 | GUGGUGGACUUCUCUCAAUUU | 121 | A-127992.1 | AAAUUGAGAGAAGUCCACCACGA | 337 | 254_276 |
| AD-64013.2 | A-127997.1 | GUGGUGGACUUCUCUCAAUUU | 122 | A-127998.1 | AAAUUGAGAGAAGUCCACCACGA | 338 | 254_276 |
| AD-64014.2 | A-127957.1 | GUGGUGGACUUCUCUCAAUUU | 123 | A-127958.1 | AAAUUGAGAGAAGUCCACCACGA | 339 | 254_276 |
| AD-64015.2 | A-127966.1 | GUGGUGGACUUCUCUCAAUUU | 124 | A-127956.9 | AAAUUGAGAGAAGUCCACCACGA | 340 | 254_276 |
| AD-64016.2 | A-127955.6 | GUGGUGGACUUCUCUCAAUUU | 125 | A-127974.1 | AAAUUGAGAGAAGUCCACCACGA | 341 | 254_276 |
| AD-64017.2 | A-127968.2 | GUGGUGGACUUCUCUCAAUUU | 126 | A-127982.1 | AAAUUGAGAGAAGUCCACCACGA | 342 | 254_276 |
| AD-64018.2 | A-127990.3 | GUGGUGGACUUCUCUCAAUUU | 127 | A-127993.1 | AAAUUGAGAGAAGUCCACCACGA | 343 | 254_276 |
| AD-64019.2 | A-127959.1 | GUGGUGGACUUCUCUCAAUUU | 128 | A-127956.2 | AAAUUGAGAGAAGUCCACCACGA | 344 | 254_276 |
| AD-64020.2 | A-127967.1 | GUGGUGGACUUCUCUCAAUUU | 129 | A-127956.10 | AAAUUGAGAGAAGUCCACCACGA | 345 | 254_276 |
| AD-64021.2 | A-127955.7 | GUGGUGGACUUCUCUCAAUUU | 130 | A-127975.1 | AAAUUGAGAGAAGUCCACCACGA | 346 | 254_276 |
| AD-64022.2 | A-127968.3 | GUGGUGGACUUCUCUCAAUUU | 131 | A-127983.1 | AAAUUGAGAGAAGUCCACCACGA | 347 | 254_276 |
| AD-64023.2 | A-127990.4 | GUGGUGGACUUCUCUCAAUUU | 132 | A-127994.1 | AAAUUGAGAGAAGUCCACCACGA | 348 | 254_276 |
| AD-64024.2 | A-127960.1 | GUGGUGGACUUCUCUCAAUUU | 133 | A-127956.3 | AAAUUGAGAGAAGUCCACCACGA | 349 | 254_276 |
| AD-64025.2 | A-127968.1 | GUGGUGGACUUCUCUCACCUG | 134 | A-127956.11 | AAAUUGAGAGAAGUCCACCACGA | 350 | 254_276 |
| AD-64026.2 | A-127955.8 | GUGGUGGACUUCUCUCAAUUU | 135 | A-127976.1 | AAAUUGAGAGAAGUCCACCACGA | 351 | 254_276 |
| AD-64027.2 | A-127984.1 | GGUGGACUUCUCUCAAUUU | 136 | A-127985.1 | AAAUUGAGAGAAGUCCACCAC | 352 | 256_278 |
| AD-64028.2 | A-127990.5 | GUGGUGGACUUCUCUCAAUUU | 137 | A-127995.1 | AAAUUGAGAGAAGUCCACCACGA | 353 | 254_276 |
| AD-64272.2 | A-128001.2 | GUGCACUUCGCUUCACCUCUG | 138 | A-128002.2 | CAGAGGUGAAGCGAAGUGCACAC | 354 | 1577_1599 |
| AD-64274.1 | A-128363.1 | GUUGACAAAAAUCCUCACAAU | 139 | A-128364.1 | AUUGUGAGGAUUUUUGUCAACAA | 355 | 215_237 |
| AD-64275.1 | A-128377.1 | UGUUGACAAAAAUCCUCACAA | 140 | A-128378.1 | UUGUGAGGAUUUUUGUCAACAAG | 356 | 214_236 |
| AD-64276.1 | A-128393.1 | GGUGGACUUCUCUCAAUUUUA | 141 | A-128394.1 | UAAAAUUGAGAGAAGUCCACCAC | 357 | 256_278 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64277.1 | A-128407.1 | UCUUUUGGAGUGUGGAUUCGA | 142 | A-128408.1 | UCGAAUCCACACUCCAAAGACA | 358 | 2259_2281 |
| AD-64277.1 | A-128407.1 | UCUUUUGGAGUGUGGAUUCGA | 143 | A-128408.1 | UCGAAUCCACACUCCAAAGACA | 359 | 2259_2281 |
| AD-64278.1 | A-128423.1 | ACUGUUCAAGCCUCCAAGCUA | 144 | A-128424.1 | UAGCUUGGAGGCUUGAACAAGAC | 360 | 1857_1879 |
| AD-64279.1 | A-128435.1 | UCUGCCGAUCCAUACUGCGGA | 145 | A-128436.1 | UCCGCAGUAUGGAUCGGCAGAGG | 361 | 1255_1277 |
| AD-64280.1 | A-128379.1 | AUGUGUCUGCGGCGUUUUAUA | 146 | A-128380.1 | UAUAAAACGCCGCAGACACAUCC | 362 | 375_397 |
| AD-64281.1 | A-128395.1 | CCCGUCUGUGCCUUCUCAUA | 147 | A-128396.1 | UAUGAGAAGGCACAGACCGGGAG | 363 | 1545_1567 |
| AD-64282.1 | A-128409.1 | GCCUAAUCAUCUUUGUUCAU | 148 | A-128410.1 | AUGAACAAGAGAUGAUUAGCGAG | 364 | 1831_1853 |
| AD-64283.1 | A-128425.1 | UCUAGACUCGUGUGGACUUC | 149 | A-128426.1 | GAAGUCCACCACGAGUCUAGACU | 365 | 245_267 |
| AD-64284.1 | A-128437.1 | CUGCCGAUCCAUACUGCGGAA | 150 | A-128438.1 | UUCCGCAGUAUGGAUCGGCAGAG | 366 | 1256_1278 |
| AD-64285.1 | A-128365.1 | UUUUUCUUGACAAAAAUA | 151 | A-128366.1 | UAUUUUUGUCAAGAAAAACC | 367 | 207_229 |
| AD-64286.1 | A-128381.1 | AUCUUCUUGGUUGUUCUUCUA | 152 | A-128382.1 | UAGAAGAACCAACAAGAAGAUGA | 368 | 426_448 |
| AD-64289.1 | A-128367.1 | GUUUUCUUGACAAGAAAAAU | 153 | A-128368.1 | AUUUUGUCAAGAAAACCC | 369 | 206_228 |
| AD-64290.1 | A-128383.1 | CUGCCUAAUCAUCUCUUGUUA | 154 | A-128384.1 | UAACAAGAGAUGAUUAGGCAGAG | 370 | 1829_1851 |
| AD-64291.1 | A-128399.1 | UCCUCACAAUACCACAGAGUA | 155 | A-128400.1 | UACUCUGUGGUAUUGUGAGGAUU | 371 | 226_248 |
| AD-64292.1 | A-128413.1 | CUUGUUGACAAAAAUCCUCAA | 156 | A-128414.1 | UUGAGGAUUUUUGUCAACAAGAA | 372 | 212_234 |
| AD-64293.1 | A-128439.1 | GCAACUUUUCACCUCUGCCU | 157 | A-128440.1 | AGGCAGAGGUGAAAAGUUGCAU | 373 | 1814_1836 |
| AD-64294.1 | A-128369.1 | GGGAACAAGAGCUACAGCAUA | 158 | A-128370.1 | UAUGCUGUAGCUCUUGUUCCCAA | 374 | 2828_2850 |
| AD-64295.1 | A-128385.1 | CGUGGUGACUUCUCUCAAUU | 159 | A-128386.1 | AAUUGAGAAGUCCACCAGCAG | 375 | 253_275 |
| AD-64297.1 | A-128415.1 | CUGCUGCUAUGCCUCAUCUUA | 160 | A-128416.1 | UAAGAUGAGGCAUAGCAGCAGGA | 376 | 411_433 |
| AD-64298.1 | A-128427.1 | GUUGGAUGUGUCUGCGGCGUU | 161 | A-128428.1 | AACGCCGCAGACACAUCCAACGA | 377 | 370_392 |
| AD-64299.1 | A-128441.1 | UUCAUCCUGCUGCUAUGCCUA | 162 | A-128442.1 | UAGGCAUAGCAGCAGGAUGAAGA | 378 | 405_427 |
| AD-64300.1 | A-128371.1 | UUCUUGUUGACAAAAAUCCUA | 163 | A-128372.1 | UAGGAUUUUUGUCAACAAGAAAA | 379 | 210_232 |
| AD-64302.1 | A-128417.1 | UAUAUGGAUGUGGUAUUA | 164 | A-128418.1 | UAAUACCACAUCCAUAUAAC | 380 | 734_756 |
| AD-64303.1 | A-128429.1 | UUCAUCCUGCUGCUAUGCCUC | 165 | A-128430.1 | GAGGCAUAGCAGCAGGAUGAAGA | 381 | 405_427 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64304.1 | A-128443.1 | GUGCACUUCGCUUCACCUCUA | 166 | A-128444.1 | UAGAGGUGAAGCGAAGUGCACAC | 382 | 1577_1599 |
| AD-64305.1 | A-128373.1 | UUGACAAAAUCCUCACAAUA | 167 | A-128374.1 | UAUUGUGAGGAUUUUGUCAACA | 383 | 216_238 |
| AD-64307.1 | A-128403.1 | AAGCCUCCAAGCUGUGCCUUA | 168 | A-128404.1 | UAAGGCACAGCUUGGAGGCUUGA | 384 | 1864_1886 |
| AD-64308.1 | A-128419.1 | CCUCUUCAUCCUGCUGCUAUA | 169 | A-128420.1 | UAUAGCAGCAGGAUGAAGAGGAA | 385 | 401_423 |
| AD-64309.1 | A-128431.1 | CCUGCUGUAUGCCUCAUCUU | 170 | A-128432.1 | AAGAUGAGGCAUAGCAGCAGGAU | 386 | 410_432 |
| AD-64310.1 | A-128375.1 | CAUCUUCUUGUUGGUUCUCU | 171 | A-128376.1 | AGAAGAACCAACAAGAAGAUGAG | 387 | 425_447 |
| AD-64311.1 | A-128391.1 | CCGUCUGUGGCCUUCUCAUCUA | 172 | A-128392.1 | UAGAUGAGAAGGCACAGACGGGG | 388 | 1547_1569 |
| AD-64312.1 | A-128405.1 | CCUCAUCUUCUUGUUGGUUCU | 173 | A-128406.1 | AGAACCAACAAGAAGAUGAGGCA | 389 | 422_444 |
| AD-64313.1 | A-128421.1 | CCACCAAAUGCCCCUAUCUUA | 174 | A-128422.1 | UAAGAUAGGGGCAUUUGGUGGUC | 390 | 2298_2320 |
| AD-64314.1 | A-128433.1 | GCUCCUCUGCCGAUCCAUACU | 175 | A-128434.1 | AGUAUGGAUCGGCAGAGGAGCCA | 391 | 1250_1272 |
| AD-64315.1 | A-128363.2 | GUUGACAAAAAUCCUCACAAU | 176 | A-128445.1 | AUUGUGAGGAUUUUUGUCAACAA | 392 | 215_237 |
| AD-64316.1 | A-128377.2 | UGUUGACAAAAAUCCUCACAA | 177 | A-128453.1 | UUGUGAGGAUUUUUGUCAACAAG | 393 | 214_236 |
| AD-64317.1 | A-128393.2 | GGUGGACUUCUCUCAAUUUUA | 178 | A-128461.1 | UAAAAAUUGAGAGAAGUCCACCAC | 394 | 256_278 |
| AD-64318.1 | A-128407.2 | UCUUUUGGAGUGUGGAAUCGA | 179 | A-128469.1 | UCGAAUCCACACUCCAAAAGACA | 395 | 2259_2281 |
| AD-64319.1 | A-128407.2 | UCUUUUGGAGUGUGGAUUCGA | 180 | A-128469.1 | UCGAAUCCACACUCCAAAAGACA | 396 | 2259_2281 |
| AD-64320.1 | A-128423.2 | ACUGUUCAAGCCUCCAAGCUA | 181 | A-128477.1 | UAGCUUGGAGGCUUGAACAAGAC | 397 | 1857_1879 |
| AD-64321.1 | A-128435.2 | UCUGCCGAUCCAUACUGCGGA | 182 | A-128483.1 | UCCGCAGUAUGGAUCGGCAGAGG | 398 | 1255_1277 |
| AD-64322.1 | A-128463.3 | AGUAUAUGGAUGAUGUGGUA | 183 | A-128446.1 | UACCACAUCAUCCAUAUAACUGA | 399 | 731_753 |
| AD-64323.1 | A-128379.2 | AUGUGUCUGCGGCGUUUUAUA | 184 | A-128454.1 | UAUAAAACGCCGCAGACACAUCC | 400 | 375_397 |
| AD-64324.1 | A-128395.2 | CCCCGCUGUGCCUUCUCAUA | 185 | A-128462.1 | UAUGAGAAGGCACAGACGGGGAG | 401 | 1545_1567 |
| AD-64325.1 | A-128409.2 | GCCUAAUCACUCUUGUUCAU | 186 | A-128470.1 | AUGAACAAGAGAUUAGCGAG | 402 | 1831_1853 |
| AD-64326.1 | A-128425.2 | UCUAGACUCGUGGACUUC | 187 | A-128478.1 | GAAGUCCACCGAGUCUAGACU | 403 | 245_267 |
| AD-64327.1 | A-128437.2 | CUGCCGAUCCAUACUGCGGAA | 188 | A-128484.1 | UUCCGCAGUAUGGAUCGGCAGAG | 404 | 1256_1278 |
| AD-64328.1 | A-128381.2 | AUCUUCUUGUUGGUUCUCUA | 189 | A-128455.1 | UAGAAGAACCAACAAGAAGAUGA | 405 | 426_448 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64330.1 | A-128411.2 | UUCUCUCAAUUUUCUAGGGGA | 190 | A-128471.1 | UCCCCUAGAAAAUUGAGAGAAGU | 406 | 263_285 |
| AD-64331.1 | A-127905.16 | ACUCGUGUGGACUUCUCUCA | 191 | A-127907.2 | UGAGAGAAGUCCACCACGAGUCU | 407 | 250_272 |
| AD-64332.1 | A-128001.3 | GUGCACUUCGCUUCACCUCUG | 192 | A-128485.1 | CAGAGGUGAAGCGAAGUGCACAC | 408 | 1577_1599 |
| AD-64333.1 | A-128367.2 | GUUUUCUUGUUGACAAAAAU | 193 | A-128448.1 | AUUUUGUCAACAAGAAAAACCC | 409 | 206_228 |
| AD-64334.1 | A-128383.2 | CUGCCUAAUCAUCUCUUGUUA | 194 | A-128456.1 | UAACAAGAGAUGAUUAGGCAGAG | 410 | 1829_1851 |
| AD-64335.1 | A-128399.2 | UCCUCACAUACCACAGAGUA | 195 | A-128464.1 | UACUCUGUGGUAUUGUGAGGAUU | 411 | 226_248 |
| AD-64336.1 | A-128413.2 | CUUGUUGACAAAAAUCCUCAA | 196 | A-128472.1 | UUGAGGAUUUUUGUCAACAAGAA | 412 | 212_234 |
| AD-64337.1 | A-127955.16 | GUGGUGGACUUCUCUCAAUUU | 197 | A-127958.2 | AAAUUGAGAGAAGUCCACCACGA | 413 | 254_276 |
| AD-64338.1 | A-128439.2 | GCAACUUUUUCACCUCUGCCU | 198 | A-128486.1 | AGGCAGAGGUGAAAAAGUUGCAU | 414 | 1814_1836 |
| AD-64339.1 | A-128369.2 | GGGAACAAGACUACAGACAUA | 199 | A-128449.1 | UAUGCUGUAGUCUUGUUCCCA | 415 | 2828_2850 |
| AD-64341.1 | A-128401.2 | UCAUCUCCUUGUGUGGUUCUUA | 200 | A-128465.1 | UAAGAACCAACAAGAAGAUGAGG | 416 | 424_446 |
| AD-64342.1 | A-128415.2 | CUGCUGUAUGCCUCACUCUUA | 201 | A-128473.1 | UAAGAUGAGGCAUACAGCAGGA | 417 | 411_433 |
| AD-64343.1 | A-128427.2 | GUUGGAUGUCUGCGGCGUU | 202 | A-128479.1 | AACGCCCGCAGACACAUCCAACGA | 418 | 370_392 |
| AD-64344.1 | A-128441.2 | UUCAUCCUGCUGCUAUGCCUA | 203 | A-128487.1 | UAGGCAUAGCAGCAGGAUGAAGA | 419 | 405_427 |
| AD-64345.1 | A-128371.2 | UUCUUGUGACAAAAAUCCUA | 204 | A-128450.1 | UAGGAUUUUUGUCAACAAGAAAA | 420 | 210_232 |
| AD-64347.1 | A-123487.3 | GGAUGGUCUGCGCGCUUUUA | 205 | A-128466.1 | UAAAACGCCGCAGACACAUCCAG | 421 | 373_395 |
| AD-64348.1 | A-128417.2 | UAUAUGGAUGAUGGUAUUA | 206 | A-128474.1 | UAAUACCACAUCAUCCAUAUAAC | 422 | 734_756 |
| AD-64349.1 | A-128429.2 | UUCAUCCUGCUGCUAUGCCUC | 207 | A-128480.1 | GAGGCAUAGCAGCAGGAUGAAGA | 423 | 405_427 |
| AD-64350.1 | A-128443.2 | GUGCACUUCGCUUCACCUCUA | 208 | A-128488.1 | UAGAGGUGAAGCGAAGUGCACAC | 424 | 1577_1599 |
| AD-64351.1 | A-128373.2 | UUGACAAAAAUCCUCACAAUA | 209 | A-128451.1 | UAUUGUGAGGAUUUUUGUCAACA | 425 | 216_238 |
| AD-64352.1 | A-128389.2 | CCAAGUUUGCUGACGCAAAA | 210 | A-128459.1 | UUUUGCGUCAGCAAACACUUGGCA | 426 | 1174_1196 |
| AD-64353.1 | A-128389.2 | CCAAGUUUGCUGACGCAAA | 211 | A-128459.1 | UUUUGCGUCAGCAAACACUUGGCA | 427 | 1174_1196 |
| AD-64354.1 | A-128403.2 | AAGCCUCCAAGCUGUGCCUUA | 212 | A-128467.1 | UAAGGCACAGCUUGGAGGCUUGA | 428 | 1864_1886 |
| AD-64354.1 | A-128419.2 | CCCUUCAUCCUGCUGCUAUA | 213 | A-128475.1 | UAUAGCAGCAGGAUGAAGAGGAA | 429 | 401_423 |

TABLE 3-continued

Unmodified Sense and Antisense Strand Sequences of HBV dsRNAs

| Duple Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64355.1 | A-128431.2 | CCUGCUGCUAUGCCUCAUCUU | 214 | A-128481.1 | AAGAUGAGGCAUAGCAGCAGGAU | 430 | 410_432 |
| AD-64356.1 | A-128375.2 | CAUCUUCUUGUGUUCUUCU | 215 | A-128452.1 | AGAAGAACCACAAGAAGAUGAG | 431 | 425_447 |
| AD-64357.1 | A-128391.2 | CCGUCUGCCUUCUCUCAUCUA | 216 | A-128460.1 | UAGAUGAGAAGGCACAGACGGGG | 432 | 1547_1569 |
| AD-64358.1 | A-128405.2 | CCUCAUCUUCUUGUUGGUUCU | 217 | A-128468.1 | AGAACCAACAAGAAGAUGAGGCA | 433 | 422_444 |
| AD-64359.1 | A-128421.2 | CCACCAAAUGCCCCUAUCUUA | 218 | A-128476.1 | UAAGAUAGGGGCAUUUGGUGGUC | 434 | 2298_2320 |
| AD-64360.1 | A-128433.2 | GCUCCUCUGCCGAUCCAUACU | 219 | A-128482.1 | AGUAUGGAUCGGCAGAGGAGCCA | 435 | 1250_1272 |
| AD-64700.1 | A-129379.1 | ACUCGUGUGUACUUCUCUCA | 220 | A-127906.26 | UGAGAGAAGUACACCAGAGUCU | 436 | 250_272 |
| AD-64701.1 | A-127905.20 | ACUCGUGUGGACUUCUCUCA | 221 | A-129387.1 | UGAGAGAAGUCCACCACGAGUCU | 437 | 250_272 |
| AD-64702.1 | A-127905.28 | ACUCGUGUGGACUUCUCUCA | 222 | A-129395.1 | UGAGAGAAGUCCACCACGAGUCU | 438 | 250_272 |
| AD-64703.1 | A-129376.2 | ACUCGUGUGGACUUCACUCA | 223 | A-129385.5 | UGAGAGAAGUCCACCACGAGUCU | 439 | 250_272 |
| AD-64704.1 | A-129381.3 | ACUCGUGUGUACUUCACUCA | 224 | A-129389.6 | UGAGAGAAGUCCACCACGAGUCU | 440 | 250_272 |
| AD-64705.1 | A-129380.1 | ACUCGUGUGUACUUCACUCA | 225 | A-127906.27 | UGAGAGAAGUCCACCACGAGUCU | 441 | 250_272 |
| AD-64706.1 | A-127905.21 | ACUCGUGUGGACUUCUCUCA | 226 | A-129388.1 | UGAGAGAAGUCCACCACGAGUCU | 442 | 250_272 |
| AD-64707.1 | A-127905.29 | ACUCGUGUGGACUUCUCUCA | 227 | A-129396.1 | UGAGAGAAGUCCACCACGAGUCU | 443 | 250_272 |
| AD-64708.1 | A-129382.2 | ACUCGUGUGGACUUCUCUCA | 228 | A-129385.6 | UGAGAGAAGUCCACCACGAGUCU | 444 | 250_272 |
| AD-64709.1 | A-129373.4 | ACUCGUGUGGACUUCUCUCA | 229 | A-129391.2 | UGAGAGAAGUCCACCACGAGUCU | 445 | 250_272 |
| AD-64710.1 | A-129373.1 | ACUCGUGUGGACUUCUCUCA | 230 | A-127906.20 | UGAGAGAAGUCCACCACGAGUCU | 446 | 250_272 |
| AD-64711.1 | A-129381.1 | ACUCGUGUGUACUUCACUCA | 231 | A-127906.28 | UGAGAGAAGUCCACCACGAGUCU | 447 | 250_272 |
| AD-64712.1 | A-127905.22 | ACUCGUGUGGACUUCUCUCA | 232 | A-129389.1 | UGAGAGAAGUCCACCACGAGUCU | 448 | 250_272 |
| AD-64713.1 | A-127905.30 | ACUCGUGUGGACUUCUCUCA | 233 | A-129397.1 | UGAGAGAAGUCCACCACGAGUCU | 449 | 250_272 |
| AD-64714.1 | A-129384.2 | ACUCGUGUGGACUUCACUCA | 234 | A-129385.7 | UGAGAGAAGUCCACCACGAGUCU | 450 | 250_272 |
| AD-64715.1 | A-129373.2 | ACUCGUGUGGACUUCACUCA | 235 | A-129391.3 | UGAGAGAAGUCCACCACGAGUCU | 451 | 250_272 |
| AD-64716.1 | A-129376.4 | ACUCGUGUGGACUUCACUCA | 236 | A-127906.21 | UGAGAGAAGUCCACCACGAGUCU | 452 | 250_272 |
| AD-64717.1 | A-129382.1 | ACUCGUGUGGACUUCUCUCA | 237 | A-127906.29 | UGAGAGAAGUCCACCACGAGUCU | 453 | 250_272 |

TABLE 3-continued

Unmodified Sense and Antisense Strand Sequences of HBV dsRNAs

| Duple Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64718.1 | A-127905.23 | ACUCGUGUGGACUUCUCUCA | 238 | A-129390.1 | UGAGAGAAGUCCACCACGAGUCU | 454 | 250_272 |
| AD-64719.1 | A-127917.5 | ACUCGUGUGGACUUCUUCUCA | 239 | A-129385.2 | UGAGAGAAGUCCACCACGAGUCU | 455 | 250_272 |
| AD-64720.1 | A-129381.2 | ACUCGUGGUGUACUUCACUCA | 240 | A-129385.8 | UGAGAGAAGUCCACCACGAGUCU | 456 | 250_272 |
| AD-64721.1 | A-129382.4 | ACUCGUGGUGGACUUCUCUCA | 241 | A-129391.4 | UGAGAGAAGUCCACCACGAGUCU | 457 | 250_272 |
| AD-64722.1 | A-129375.1 | ACUCGUGUGGACUUCCCUCA | 242 | A-127906.22 | UGAGAGAAGUCCACCACGAGUCU | 458 | 250_272 |
| AD-64723.1 | A-129383.1 | ACUCGUGUGGACUUCUCUCA | 243 | A-127906.30 | UGAGAGAAGUCCACCACGAGUCU | 459 | 250_272 |
| AD-64725.1 | A-127917.6 | ACUCGUGUGGACUUCUCUCA | 244 | A-129398.1 | UGAGAGAAGUCCACCACGAGUCU | 460 | 250_272 |
| AD-64726.1 | A-129373.3 | ACUCGUGUGGACUUCUUCUCA | 245 | A-129389.2 | UGAGAGAAGUCCACCACGAGUCU | 461 | 250_272 |
| AD-64727.1 | A-129384.4 | ACUCGUGGUGGACUUCACUCA | 246 | A-129391.5 | UGAGAGAAGUCCACCACGAGUCU | 462 | 250_272 |
| AD-64728.1 | A-129376.1 | ACUCGUGGUGGACUUCACUCA | 247 | A-127906.23 | UGAGAGAAGUCCACCACGAGUCU | 463 | 250_272 |
| AD-64729.1 | A-129384.1 | ACUCGUGGUGGACUUCACUCA | 248 | A-127906.31 | UGAGAGAAGUCCACCACGAGUCU | 464 | 250_272 |
| AD-64730.1 | A-127905.25 | ACUCGUGUGGACUUCUCUCA | 249 | A-129392.1 | UGAGAGAAGUCCACCACGAGUCU | 465 | 250_272 |
| AD-64731.1 | A-129399.1 | ACUCGUGGUGUACUUCACUCA | 250 | A-129385.3 | UGAGAGAAGUCCACCACGAGUCU | 466 | 250_272 |
| AD-64732.1 | A-129376.3 | ACUCGUGGUGGACUUCACUCA | 251 | A-129391.6 | UGAGAGAAGUCCACCACGAGUCU | 467 | 250_272 |
| AD-64733.1 | A-129381.4 | ACUCGUGGUGUACUUCACUCA | 252 | A-127906.24 | UGAGAGAAGUCCACCACGAGUCU | 468 | 250_272 |
| AD-64734.1 | A-129377.1 | ACUCGUGUGGACUUCCCUCA | 253 | A-129385.1 | UGAGAGAAGUCCACCACGAGUCU | 469 | 250_272 |
| AD-64735.1 | A-127905.18 | ACUCGUGUGGACUUCUCUCA | 254 | A-129393.1 | UGAGAGAAGUCCACCACGAGUCU | 470 | 250_272 |
| AD-64736.1 | A-127905.26 | ACUCGUGUGGACUUCUCUCA | 255 | A-129398.2 | UGAGAGAAGUCCACCACGAGUCU | 471 | 250_272 |
| AD-64737.1 | A-129399.2 | ACUCGUGGUGGACUUCUCUCA | 256 | A-129389.4 | UGAGAGAAGUCCACCACGAGUCU | 472 | 250_272 |
| AD-64738.1 | A-129382.3 | ACUCGUGUGGACUUCUCUCA | 257 | A-127906.25 | UGAGAGAAGUCCACCACGAGUCU | 473 | 250_272 |
| AD-64739.1 | A-129378.1 | ACUCGUGGUGGACUUCGCUCA | 258 | A-129386.1 | UGAGAGAAGUCCACCACGAGUCU | 474 | 250_272 |
| AD-64740.1 | A-127905.19 | ACUCGUGUGGACUUCUCUCA | 259 | A-129394.1 | UGAGAGAAGUCCACCACGAGUCU | 475 | 250_272 |
| AD-64741.1 | A-127905.27 | ACUCGUGUGGACUUCUCUCA | 260 | | | 476 | 250_272 |

TABLE 3-continued

Unmodified Sense and Antisense Strand Sequences of HBV dsRNAs

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64742.1 | A-129373.2 | ACUCGUGGUGGACUUCUCUCA | 261 | A-129385.4 | UGAGAGAAGUCCACCACGAGUCU | 477 | 250_272 |
| AD-64743.1 | A-129384.3 | ACUCGUGGUGGACUUCACUCA | 262 | A-129389.5 | UGAGAGAAGUCCACCACGAGUCU | 478 | 250_272 |

TABLE 4

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-61522.2 | A-123463.2 | AfsgsUfuAfuAfugGfGfAfuGfaUfgUfgGfuAfL96 | 479 | A-123464.2 | usAfscCfaCfaUfcAfuccAfuAfuAfaCfusgsa | 694 |
| AD-61547.2 | A-123487.2 | GfsgsAfugGfuGfuCfUfGfgCfgGfgCfgUfuUfuAfL96 | 480 | A-123488.2 | usAfsaAfaCfgCfcGfcagAfcAfcAfuCfcsasg | 695 |
| AD-63938.2 | A-127896.1 | Y44ACUCGUGUGGACUUCUCUCA | 481 | A-127897.1 | UGAGAGAAGUCCACCACGAGUCU | 696 |
| AD-63939.2 | A-127909.1 | ascsucGfuGfgUfGfGfaCfuucUfcucaL96 | 482 | A-127906.3 | usGfsaGfaGfaAfgUfccaCfcAfcGfaGfuscsu | 697 |
| AD-63940.2 | A-127917.1 | ascsucguggugdGacuuc(Tgn)cucaL96 | 483 | A-127906.11 | usGfsaGfaGfaAfgUfccaCfcAfcGfaGfuscsu | 698 |
| AD-63941.2 | A-127905.8 | AfscsUfcGfuGfgUfGfGfaCfuUfcUfcUfcAfL96 | 484 | A-127925.1 | usGfsaGfaGfagaAfguccaCfcAfcgaGfusgsu | 699 |
| AD-63942.2 | A-127933.1 | uscsGfuGfgUfGfGfaCfuUfcUfcUfcUfcAfL96 | 485 | A-127934.1 | usGfsaGfaAfgAfgUfccaCfcAfcGfasgsu | 700 |
| AD-63943.2 | A-127944.2 | ascsucGfuGfguGfuGfGfaCfuuucucucaL96 | 486 | A-127942.2 | usGfsaAfgAfgAfaGfaCfcAfcGfaGfusgscsu | 701 |
| AD-63945.2 | A-127910.1 | ascsucguGfgUfGfGfaCfuucUfcucaL96 | 487 | A-127906.4 | usGfsaGfaGfaAfgUfccaCfcAfcGfaGfuscsu | 702 |
| AD-63946.2 | A-127918.1 | ascsucguGfuGfGfGfacuuCfucucaL96 | 488 | A-127906.12 | usGfsaGfaGfaAfgUfccaCfcAfcGfaGfuscsu | 703 |
| AD-63947.2 | A-127905.9 | AfscsUfcGfuGfgUfGfGfaCfuUfcUfcUfcAfL96 | 489 | A-127926.1 | usGfsaGfagaaGfUfccaCfcAfcgaGfuscsu | 704 |
| AD-63948.2 | A-127935.1 | gsusGfUfGfGfaCfuUfcUfcUfcAfL96 | 490 | A-127936.1 | usGfsaGfaGfaAfgUfccaCfcAfcsgsa | 705 |
| AD-63949.2 | A-127944.3 | ascsucGfuGfguGfuGfGfaCfuuucucucaL96 | 491 | A-127906.14 | usGfsaGfaGfaAfgUfccaCfcAfcGfaGfuscsu | 706 |
| AD-63950.2 | A-127900.1 | Y44UfcGfuGfgUfgUfGfGfaCfuUfcUfcUfcAfusuY44 | 492 | A-127901.1 | usGfsasGfaGfaAfgUfcCfacfcAfcGfausu | 707 |
| AD-63951.2 | A-127911.1 | ascsucguGfgUfGfGfaCfuUfcUfcUfcAfL96 | 493 | A-127906.5 | usGfsaGfaGfaAfgUfccaCfcAfcGfaGfuscsu | 708 |
| AD-63952.2 | A-127905.2 | AfscsUfcGfuGfgUfGfGfaCfuUfcUfcUfcAfL96 | 494 | A-127919.1 | usGfsaGfaGfaagUfccaCfcAfcGfaGfuscsu | 709 |
| AD-63953.10 | A-127905.10 | AfscsUfcGfuGfgUfGfGfaCfuUfcUfcUfcAfL96 | 495 | A-127927.1 | usGfsagaaAfgUfcccaCfcAfcgagucsu | 710 |
| AD-63955.2 | A-127945.1 | ascsucguggGfaCfuucucucaL96 | 496 | A-127940.3 | usGfsaAfgAfgAfaGfuccaCfcCfaCfcAfgAfgusscu | 711 |
| AD-63956.2 | A-127902.1 | Y44uscsGfuGfuGfGfaCfuUfcUfcUfcAfY44 | 497 | A-127903.1 | usGfsaGfaAfgAfgUfcCfaCfcAfcAfcasusu | 712 |
| AD-63957.2 | A-127912.1 | ascsucguGfuGfGfacuucucucaL96 | 498 | A-127906.6 | usGfsaGfaGfaAfgUfccaCfcAfcGfaGfuscsu | 713 |
| AD-63958.2 | A-127905.3 | AfscsUfcGfuGfgUfGfGfaCfuUfcUfcUfcAfL96 | 499 | A-127920.1 | usGfsagaaGfaAfgUfccaCfcAfcGfcgaGfuscsu | 714 |
| AD-63959.2 | A-127905.11 | AfscsUfcGfuGfgUfGfGfaCfuUfcUfcUfcAfL96 | 500 | A-127928.1 | usGfsaGfagaAfgucCfaCfcAfcgagucsu | 715 |
| AD-63960.2 | A-126619.2 | usasUfuUfCfCfuAfggGfuGfaCfaAfL96 | 501 | A-127938.1 | PusGfsaGfaAfgUfccaCfcAfcsgsa | 716 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-63961.2 | A-127945.2 | ascsucguggGfacuucucucaL96 | 502 | A-127942.3 | usGfsAfgaGfaAfgUfccaCfcAfcGfaguscsu | 717 |
| AD-63962.2 | A-127902.2 | Y44uscsGfuGfgUfgGfaCfuUfcUfcUfcAfY44 | 503 | A-127904.1 | PusGfsaGfaGfaAfgUfcCfaCfcAfcGfasusu | 718 |
| AD-63963.2 | A-127913.1 | ascsucguggUfgGfacuucucucaL96 | 504 | A-127906.7 | usGfsaGfaGfaAfgUfccaCfcAfcGfaGfuscsu | 719 |
| AD-63964.2 | A-127905.4 | AfscsUfcGfuGfgUfGfGfaCfuUfcUfcUfcAfL96 | 505 | A-127921.1 | usGfsagaGfaaGfuccaCfcAfcGfcgaguscsu | 720 |
| AD-63965.2 | A-127905.12 | AfscsUfcGfuGfgUfGfGfaCfuUfcUfcUfcAfL96 | 506 | A-127929.1 | usGfsAfgAfgAfaGfuccaCfcAfcCfgAfguscsu | 721 |
| AD-63966.2 | A-127939.1 | ascsUfcGfugguGfaCfuuCfucCfucaL96 | 507 | A-127940.1 | usGfsAfgAfgAfaGfuccaCfcAfcCfgAfguscsu | 722 |
| AD-63967.2 | A-127945.3 | ascsucguggGfacuucucucaL96 | 508 | A-127906.15 | usGfsaGfaGfaAfgUfccaCfcAfcGfaGfuscsu | 723 |
| AD-63968.2 | A-127905.1 | AfscsUfcGfuGfgUfGfGfaCfuUfcUfcUfcAfL96 | 509 | A-127906.1 | usGfsaGfaGfaAfgUfccaCfcAfcGfaGfuscsu | 724 |
| AD-63968.4 | A-127905.15 | AfscsUfcGfuGfgUfGfGfaCfuUfcUfcUfcAfL96 | 510 | A-127906.17 | usGfsaGfaGfaAfgUfccaCfcAfcGfaGfuscsu | 725 |
| AD-63968.5 | A-127905.17 | AfscsUfcGfuGfgUfGfGfaCfuUfcUfcUfcAfL96 | 511 | A-127906.18 | usGfsaGfaGfaAfgUfccaCfcAfcGfaGfuscsu | 726 |
| AD-63969.2 | A-127914.1 | ascsucguggGfacuucucucaL96 | 512 | A-127906.8 | usGfsaGfaGfaAfgUfccaCfcAfcGfaGfuscsu | 727 |
| AD-63970.2 | A-127905.5 | AfscsUfcGfuGfgUfGfGfaCfuUfcUfcUfcAfL96 | 513 | A-127922.1 | usGfsagaGfaagUfccaCfcAfcgaGfuscsu | 728 |
| AD-63971.2 | A-127905.13 | AfscsUfcGfuGfgUfGfGfaCfuUfcUfcUfcAfL96 | 514 | A-127930.1 | usGfsagaGfaaguccaCfcAfcgaguscsu | 729 |
| AD-63972.2 | A-127941.1 | ascsUfcGfuGfguGfaCfuuCfucCfucaL96 | 515 | A-127942.1 | usGfsAfgaGfaGfaAfgUfccaCfcAfcGfaguscsu | 730 |
| AD-63973.2 | A-127946.1 | ascsucguggduGfGfacuucucucaL96 | 516 | A-127947.1 | usdGsaGfaGfaAfgdTccadCfcAfcGfaGfuscsu | 731 |
| AD-63975.2 | A-127905.6 | AfscsUfcGfuGfgUfGfGfaCfuUfcUfcUfcAfL96 | 517 | A-127906.9 | usGfsagaGfaAfgUfccaCfcAfcGfcgaguscsu | 732 |
| AD-63976.2 | A-127917.2 | ascsucguggdGacuuc(Tgn)cucaL96 | 518 | A-127923.1 | usdGsagaGfaagUfccadCfcacgagusscsu | 733 |
| AD-63977.2 | A-127943.1 | ascsucguggdGacuuc(Tgn)cucaL96 | 519 | A-127931.1 | usdGsagagaaguccadCcacgagusscsu | 734 |
| AD-63978.2 | A-127915.1 | AfscsUfcGfuGfgUfGfGfaCfuUfcUfcUfcaL96 | 520 | A-127906.13 | usGfsaGfaGfaAfgUfccaCfcAfcGfaGfuscsu | 735 |
| AD-63979.2 | A-127908.1 | ascsucGfuGfgUfGfGfaCfuucUfcucAfL96 | 521 | A-127906.2 | usGfsaGfaGfaAfgUfccaCfcAfcGfaGfuscsu | 736 |
| AD-63980.2 | A-127916.1 | ascsucguggGfacuuc(Tgn)cucaL96 | 522 | A-127906.10 | usGfsaGfaGfaAfgUfccaCfcAfcGfaGfuscsu | 737 |
| AD-63981.2 | A-127905.7 | AfscsUfcGfuGfgUfGfGfaCfuUfcUfcUfcAfL96 | 523 | A-127924.1 | usGfsaGfagaAfgUfccaCfcAfcgaGfuscsu | 738 |
| AD-63982.2 | A-127917.3 | ascsucguggdGacuuc(Tgn)cucaL96 | 524 | A-127932.1 | PusGfsagagaaguccadCcacgagusscsu | 739 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-63983.2 | A-127944.1 | ascsucGfuGfguGfGfaCfuucucucaL96 | 525 | A-127940.2 | usGfsAfgAfgAfaGfuccaCfcCfaCfgAfguscsu | 740 |
| AD-63985.2 | A-127961.1 | gsusggugGfaCfUfUfcUfcucAfauuuL96 | 526 | A-127956.4 | asAfsaUfuGfaGfaGfaaGfUfcCfaCfcAfcsgsa | 741 |
| AD-63986.2 | A-127969.1 | gsusggugGfaCfUfUfcucuCfaauuuL96 | 527 | A-127956.12 | asAfsaUfuGfaGfaGfaagGfaaGfUfcCfaCfcAfcsgsa | 742 |
| AD-63987.2 | A-127955.9 | GfsusGfgUfgGfaCfUfUfcUfcUfcUfcAfaUfuUfL96 | 528 | A-127977.1 | asAfsaUfugagaGfaGfaGfaaGfUfcCfaccAfcsgsa | 743 |
| AD-63988.2 | A-127986.1 | usgsGfaCfUfUfcUfcUfcUfcAfaUfuUfL96 | 529 | A-127987.1 | asAfsaUfuGfaGfaGfaaGfUfcCfasc | 744 |
| AD-63989.2 | A-127996.1 | gsusgguggacUfUfcucucauuuL96 | 530 | A-127992.2 | asAfsAfUfuGfaGfaGfaaGfUfcCfaCfcacgsa | 745 |
| AD-63990.2 | A-127950.1 | Y44GfgUfggGfaCfUfUfcUfcUfcAfaUfuUfususuY44 | 531 | A-127951.1 | asAfsasUfuGfaGfaGfaAfgUfcCfaCfcusu | 746 |
| AD-63991.2 | A-127962.1 | gsusggugGfaCfUfUfcUfcUfcucaauuuL96 | 532 | A-127956.5 | asAfsaUfuGfaGfaGfaaGfUfcCfaCfcAfcsgsa | 747 |
| AD-63992.2 | A-127955.2 | GfsusGfgUfgGfaCfUfUfcUfcUfcUfcAfaUfuUfL96 | 533 | A-127956.6 | asAfsaUfuGfagaGfaGfaGfaaGfUfcCfaCfcAfcsgsa | 748 |
| AD-63993.2 | A-127955.10 | GfsusGfgUfgGfaCfUfUfcUfcUfcUlcUfcAfaUfuUfL96 | 534 | A-127970.1 | asAfsaUfuGfaGfaGfaGfaaGfUfcCfaccacsgsa | 749 |
| AD-63994.2 | A-127984.2 | gsgUfgGfaCfUfUfcUfcUfcUfcAfaUfuUfL96 | 535 | A-127978.1 | PasAfsaUfuGfaGfaGfaaGfUfcCfaCfcsasc | 750 |
| AD-63995.2 | A-127996.2 | gsusgguggacUfUfcucucauuuL96 | 536 | A-127993.2 | asAfsAfuuGfaGfaGfaGfaaGfUfcCfaCfcacgsa | 751 |
| AD-63996.2 | A-127952.1 | Y44gsgsUfgGfaCfUfUfcUfcUfcUfcAfaUfuUfY44 | 537 | A-127953.1 | asAfsAfUfuGfaGfaGfaGfaAfgUfcCfaCfcsusu | 752 |
| AD-63997.2 | A-127963.1 | gsusggugGfaCfuUfcucucaauuuL96 | 538 | A-127956.6 | asAfsaUfuGfaGfaGfaaGfUfcCfaCfcAfcsgsa | 753 |
| AD-63999.2 | A-127955.11 | GfsusGfgUfgGfaCfUfUfcUfcUfcUfcAfaUfuUfL96 | 539 | A-127979.1 | asAfsaUfugaGfagaagUfcCfaccacsgsa | 754 |
| AD-64000.2 | A-127986.2 | usgsGfaCfUfUfcUfcUfcUfcAfaUfuUfL96 | 540 | A-127989.1 | PasAfsaUfuGfaGfaGfaaGfUfcCfascc | 755 |
| AD-64001.2 | A-127996.3 | gsusgguggacUfUfcucucauuuL96 | 541 | A-127994.2 | asAfsAfUfuGfaGfaGfaaGfUfcCfcaCfcacgsa | 756 |
| AD-64002.2 | A-127952.2 | Y44gsgsUfgGfaCfUfUfcUfcUfcUfcAfaUfuUfY44 | 542 | A-127954.1 | PasAfsAfUfuGfaGfaGfaGfaAfgUfcCfaCfcsusu | 757 |
| AD-64003.2 | A-127964.1 | gsusggugGfaCfuUfcucucaauuuL96 | 543 | A-127956.7 | asAfsaUfuGfaGfaGfaaGfUfcCfaCfcAfcsgsa | 758 |
| AD-64004.2 | A-127955.4 | GfsusGfgUfgGfaCfUfUfcUfcUfcUfcAfaUfuUfL96 | 544 | A-127972.1 | asAfsaUfuGfaGfaGfaaGfUfcCfaccacsgsa | 759 |
| AD-64005.2 | A-127955.12 | GfsusGfgUfgGfaCfUfUfcUfcUfcUfcAfaUfuUfL96 | 545 | A-127980.1 | asAfsauuGfagAfgaagUfcCfaccacsgsa | 760 |
| AD-64006.2 | A-127990.1 | gsgsUfgguggacUfUfcUfcUfcUfcAfaUfuuL96 | 546 | A-127991.1 | asAfsaAfUfuGfaGfaGfaGfaaGfUfcCfaCfcacsgsa | 761 |
| AD-64007.2 | A-127996.4 | gsusgguggacUfUfcucucauuuL96 | 547 | A-127995.2 | asAfsaUfuGfaGfaGfaGfaaGfUfcCfaCfcacgsa | 762 |
| AD-64008.2 | A-127955.1 | GfsusGfgUfgGfaCfUfUfcUfcUfcUfcAfaUfuUfL96 | 548 | A-127956.1 | asAfsAfUfuGfaGfaGfaaGfUfcCfaCfcAfcsgsa | 763 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64008.4 | A-127955.15 | GfsusGfgUfgGfacUfUfUfcUfcUfcAfaUfuUfL96 | 549 | A-127956.14 | asAfsaUfuGfaGfaGfaagUfcCfaCfcAfcsgsa | 764 |
| AD-64009.2 | A-127965.1 | gsusgguggacuUfcucucaauuuL96 | 550 | A-127956.8 | asAfsaUfuGfaGfaGfaagUfcCfaCfcAfcsgsa | 765 |
| AD-64010.2 | A-127955.5 | GfsusGfgUfgGfacUfUfUfcUfcUfcAfaUfuUfL96 | 551 | A-127973.1 | asAfsauuGfagaGfaagUfcCfaccAfcsgsa | 766 |
| AD-64011.2 | A-127955.13 | GfsusGfgUfgGfacUfUfUfcUfcUfcAfcAfaUfuuL96 | 552 | A-127981.1 | asAfsauuGfagagaagUfcCfaccacgsa | 767 |
| AD-64012.2 | A-127990.2 | gsusGfguGfgUfgGfacUfUfUfcUfcUfcAfaUfuUfL96 | 553 | A-127992.1 | asAfsAfuUfuGfaGfaGfaagUfcCfaCfcacsgsa | 768 |
| AD-64013.2 | A-127997.1 | gsusgguggacdTdTcucucaauuuL96 | 554 | A-127998.1 | asdAsAfuugaGfaGfaGfaagTdCcaCfcacsgsa | 769 |
| AD-64014.2 | A-127957.1 | Y44GfsusGfgUfgGfacUfUfUfcUfcUfcAfaUfuUfL96 | 555 | A-127958.1 | PasAfsaUfuGfaGfaGfaagUfcCfaCfcAfcsgsa | 770 |
| AD-64015.2 | A-127966.1 | gsusgguggaCfuUfcucuc(Agn)auuuL96 | 556 | A-127956.9 | asAfsaUfuGfaGfaGfaagUfcCfaCfcAfcsgsa | 771 |
| AD-64016.2 | A-127955.6 | GfsusGfgUfgGfacUfUfUfcUfcUfcAfauUfL96 | 557 | A-127974.1 | asAfsauuGfagaGfaagUfcCfaccacgsa | 772 |
| AD-64017.2 | A-127968.2 | gsusgguggacudTcucuc(Agn)auuuL96 | 558 | A-127982.1 | asdAsauugagagaagdTccaccacgsa | 773 |
| AD-64018.2 | A-127990.3 | gsusGfguGfgUfgGfacUfUfUfcUfcUfcAfaUfuUfL96 | 559 | A-127993.1 | asAfsAfuuGfaGfaGfaagUfcCfaCfcAfcsgsa | 774 |
| AD-64019.2 | A-127959.1 | gsusgguggaUfgGfacUfUfUfcUfcucAfauuUfL96 | 560 | A-127956.2 | asAfsaUfuGfaGfaGfaagUfcCfaCfcAfcsgsa | 775 |
| AD-64020.2 | A-127967.1 | gsusgguggacuUfcucuc(Agn)auuuL96 | 561 | A-127956.10 | asAfsaUfuGfaGfaGfaagUfcCfaCfcAfcsgsa | 776 |
| AD-64021.2 | A-127955.7 | GfsusGfgUfgGfacUfUfUfcUfcUfcAfaUfuUfL96 | 562 | A-127975.1 | asAfsaUfugaGfaGfaagUfcCfaccAfcsgsa | 777 |
| AD-64022.2 | A-127968.3 | gsusgguggacudTcucuc(Agn)auuuL96 | 563 | A-127983.1 | PasdAsauugagagaagdTccaccacgsa | 778 |
| AD-64023.2 | A-127990.4 | gsusGfguGfgUfgGfacUfUfUfcUfcUfcAfaUfuUfL96 | 564 | A-127994.1 | asAfsAfuUfuGfaGfaGfaagUfcCfaCfcacsgsa | 779 |
| AD-64024.2 | A-127960.1 | gsusggUfgGfacUfUfUfcUfcucAfauuuL96 | 565 | A-127956.3 | asAfsaUfuGfaGfaGfaagUfcCfaCfcAfcsgsa | 780 |
| AD-64025.2 | A-127968.1 | gsusgguggacudTcucuc(Agn)auuuL96 | 566 | A-127956.11 | asAfsaUfuGfaGfaGfaagUfcCfaCfcAfcsgsa | 781 |
| AD-64026.2 | A-127955.8 | GfsusGfgUfgGfacUfUfUfcUfcUfcAfaUfuUfL96 | 567 | A-127976.1 | asAfsaUftugaGfagaagUfcCfaccAfcsgsa | 782 |
| AD-64027.2 | A-127984.1 | gsgUfgGfacUfUfUfcUfcUfcAfaUfuUfL96 | 568 | A-127985.1 | asAfsaUfuGfaGfaGfaagUfcCfaCfcsasc | 783 |
| AD-64028.2 | A-127990.5 | gsusggUfgGfacUfUfUfcUfcUfcAfauuuL96 | 569 | A-127995.1 | asAfsAfuUfugaGfaGfaagUfcCfaCfcacsgsa | 784 |
| AD-64272.2 | A-128001.2 | GfsusGfcAfcUfuCfGfcUfuUfcAfcCfcUfuGfL96 | 570 | A-128002.2 | csAfsgAfgGfuuGfaAfgcAfaGfuGfcAfcsasc | 785 |
| AD-64274.1 | A-128363.1 | GfsusUfgAfcAfaAfaAfucfcUfcAfcUfaUfL96 | 571 | A-128364.1 | asUfsuGfuGfaGfAfuuuUfgUfcaAfcsasa | 786 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64275.1 | A-128377.1 | UfsgsUfuGfaCfaAfAfaUfcCfucCfaCfaAfL96 | 572 | A-128378.1 | usUfsgUfgAfgGfaUfuuuUfgUfcAfaCfasasg | 787 |
| AD-64276.1 | A-128393.1 | GfsgsUfgGfaCfuUfCfUfcUfcAfaUfuAfL96 | 573 | A-128394.1 | usAfsaAfaUfuGfaGfagaAfgUfcCfaCfcsasc | 788 |
| AD-64277.1 | A-128407.1 | UfscsUfuUfgGfaAfgUfuGfgGfaUfuCfgAfL96 | 574 | A-128408.1 | usCfsgAfaUfcCfacuCfaAfaAfaGfascsa | 789 |
| AD-64277.1 | A-128407.1 | UfscsUfuUfgGfaAfgUfuGfgGfaUfuCfgAfL96 | 575 | A-128408.1 | usCfsgAfaUfcCfaCfacuCfaAfaAfaGfascsa | 790 |
| AD-64278.1 | A-128423.1 | AfscsUfgUfcCfaAfgCfcUfcCfaAfgCfuAfL96 | 576 | A-128424.1 | usAfsgCfuUfgGfaGfgcuUfgAfaCfaAfgsasc | 791 |
| AD-64279.1 | A-128435.1 | UfscsUfgCfcCfgAfUfcCfcaUfaCfuGfcGfgAfL96 | 577 | A-128436.1 | usCfscGfcAfgUfaUfggaUfcGfgCfaGfaagsg | 792 |
| AD-64280.1 | A-128379.1 | AfsgsUfgCfuCfugGfcCfgCfgUfuUfuAfuAfL96 | 578 | A-128380.1 | usAfsuAfaAfaCfgCfcgAfgCfAfcAfuscsc | 793 |
| AD-64281.1 | A-128395.1 | CfscsCfcGfucCfugUfgCfcUfcCfUfcAfuAfL96 | 579 | A-128396.1 | usAfsuGfaGfaAfgGfcacAfgGfaCfgGfgsasg | 794 |
| AD-64282.1 | A-128409.1 | GfscsUfaAfUfcAfUfCfgUfuGfgugGfuAfUfuL96 | 580 | A-128410.1 | asUfsgAfaCfaAfgAfgauGfaUfuAfgCfgsasg | 795 |
| AD-64283.1 | A-128425.1 | UfscsUfagGfaCffuCfGfUfgGfugGfaFfCfgGfaAfL96 | 581 | A-128426.1 | usUfscCfgAfuGffuAfuggAfuCfgGfcAfgsasg | 796 |
| AD-64284.1 | A-128437.1 | CfscsUfgGfaCfuCfCfgAfuCfAfuAfcAfuL96 | 582 | A-128438.1 | usAfsuUfuGfuUfcfaacAfaGfaAfaAfascsc | 797 |
| AD-64285.1 | A-128365.1 | UfscsUfuUfcUfuGfUfUfuGfaCfaAfaAfaFufcCfuAfL96 | 583 | A-128366.1 | usAfsgAfaAfgCfaAfcCfaaAfgAfaAfaAfascsc | 798 |
| AD-64286.1 | A-128381.1 | AfscsUfuUfcUfuGfUfUfgAfcAfaAfaFufcCfuAfL96 | 584 | A-128382.1 | asUfsuUfuGfuCfaAfacaAfgAfaAfaAfuugsa | 799 |
| AD-64289.1 | A-128367.1 | GfscsUfuUfuCfuUfgfGfUfUfgAfcCfaAfuCfuUfgFufuAfL96 | 585 | A-128368.1 | usAfscCfaAfgAfgAfugaUfuAfgGfcCfafgsasg | 800 |
| AD-64290.1 | A-128383.1 | CfscsCfuCfaCfaAfAfuAfUfCfCfuCfaGfaGfuAfUfL96 | 586 | A-128384.1 | usAfscUfCfuGfUfgGfuauUfgUfgAfgGfasusu | 801 |
| AD-64291.1 | A-128399.1 | UfscsCffuCfaCfaAfAfuAfuCfCfuCfUfaAfuL96 | 587 | A-128400.1 | usUfsgAfgGfaUfuUfugUfcAfaCfaAfgsasa | 802 |
| AD-64292.1 | A-128413.1 | CfscsUfuGfuCfaCfaAfCfAfaGfaFfgGfuUfgL96 | 588 | A-128414.1 | asGfsgCfaGfaGfgUfgaaAfaAfgUfuGfcsasu | 803 |
| AD-64293.1 | A-128439.1 | GfscsAfaCfaFfaGfaAfCfaGfcfcfUfcUfcCfuUfL96 | 589 | A-128440.1 | usAfsuGfcUfgUfagGfcucUffuUfcCfcsasa | 804 |
| AD-64294.1 | A-128369.1 | GfsgsUfgfuGfuAfCfaGfafCfuCfuCfaAfuUfL96 | 590 | A-128370.1 | asAfsuUfgAfgAfgGfAfaguCffcAfcCfaFgCfcsasg | 805 |
| AD-64295.1 | A-128385.1 | CfsgsUfgGfcUfaAfuGfCfCfuCfUfcfUfaAfuL96 | 591 | A-128386.1 | usAfsaGfaUfgAfgGfcauAfgCfaUfcAfgsgsa | 806 |
| AD-64297.1 | A-128415.1 | CfsgsGfcUfuAfUfgGfcUfCfUfcGfGfcUfcCfugL96 | 592 | A-128416.1 | asAfscGfcCfgCfaGfaccCfaUfcCfaAfcsgsa | 807 |
| AD-64298.1 | A-128427.1 | GfsgsGfaUfgGfuGfUfcUfcCfuGfcGfUfuUfL96 | 593 | A-128428.1 | asAfscGfcCfgCfaGfacCfaUfcCfaAfcsgsa | 808 |
| AD-64299.1 | A-128441.1 | UfsgsCfaUfcCfuGfUfGfcAfaAfaFfcCfuAfL96 | 594 | A-128442.1 | usAfsgGfcAfuAfgCfagcAfgGfaUfgAfasgsa | 809 |
| AD-64300.1 | A-128371.1 | UfsgsCfuUfgGfuGfAfcAfaAfaFfcCfuAfL96 | 595 | A-128372.1 | usAfsgGfaUfuUfugucAfaCfaAfgAfasasa | 810 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64302.1 | A-128417.1 | UfsasUfaUfgGfaUfGfaUfgUfgGfaUfuaUfL96 | 596 | A-128418.1 | usAfsaUfaCfcAfcAfucaUfcCfaUfaUfasasc | 811 |
| AD-64303.1 | A-128429.1 | UfsusCfaUfccCfuGfcUfUfgCfuAfuGfccCfuCfL96 | 597 | A-128430.1 | gsAfsgGfcAfuAfgCfagcAfgGfaUfgAfaagsa | 812 |
| AD-64304.1 | A-128443.1 | GfsusGfAfcCfUfuCfGfCfuUfcAfcCfuCfuAfL96 | 598 | A-128444.1 | usAfsgAfgGfuGfaAfgcAfaGfaGfuGfcAfcsasc | 813 |
| AD-64305.1 | A-128373.1 | UfsusGfaCfaAfaAfaUfccCfuCfaCfaAfuAfL96 | 599 | A-128374.1 | usAfsuUfgAfgGfauuUfuUfgUfcAfascsa | 814 |
| AD-64307.1 | A-128403.1 | AfsasGfcCfuCfaAfaGfcUfgUfgCfcUfuAfL96 | 600 | A-128404.1 | usAfsaGfgCfaCfaGfcuuGfgAfgGfcUfusgsa | 815 |
| AD-64308.1 | A-128419.1 | CfscsUfcUfcaUfcCfctuGfcUfgCfuAfuAfL96 | 601 | A-128420.1 | usAfsuAfgCfaGfcAfggaUfgAfaGfcUfgasa | 816 |
| AD-64309.1 | A-128431.1 | CfscsUfgCfugCfuEfAfugCfucUfcCfAfucUfuUfL96 | 602 | A-128432.1 | asAfsgAfuGfaGffCfauaGfcAfgCfaGfgsasu | 817 |
| AD-64310.1 | A-128375.1 | CfsasUfcUfuUfgUfuGfgUfcUfuufcCfuAfL96 | 603 | A-128376.1 | asGfsaAfgAfactcAfacaAfgAfaAfgaUfgsasg | 818 |
| AD-64311.1 | A-128391.1 | CfscsGfuGfuGfuCfuUfcUfuCfAfucUfuAfL96 | 604 | A-128392.1 | usAfsgAfuGfaGfaAfgcAfcAfgAfcGfgsgsg | 819 |
| AD-64312.1 | A-128405.1 | CfscsUfcAfuCfuUfCfuUfgGfnuUfcUfL96 | 605 | A-128406.1 | asGfsaAfccCfaAfcAfagaAfgAfuGfaGfgscsa | 820 |
| AD-64313.1 | A-128421.1 | CfscsAfccCfaAfaUfgCfccCfuGfaUfcCfaAfcUfL96 | 606 | A-128422.1 | usAfsaGfaUfaGfGfgcaUfufGfgUfgGfgsusc | 821 |
| AD-64314.1 | A-128433.1 | CfscsUfccCfuCfgAfucCfaAfcAfaUfL96 | 607 | A-128434.1 | asGfsuAfuGfgAfuCfggcAfgAfgGfaGfcscsa | 822 |
| AD-64315.1 | A-128363.2 | GfsusUfgCfafaAfAfaAfaUfcCftuCfacCfaAfL96 | 608 | A-128445.1 | PasUfsuGfuGfaGfgAfuuuUfgUfcAfcsasa | 823 |
| AD-64316.1 | A-128377.2 | UfsgsUfuGfaCfaAfcFfuUfcUfcUfaAfuUfuAfL96 | 609 | A-128453.1 | PusUfsgUfgAfgAfuagaAfgUfcCfaCfcsasg | 824 |
| AD-64317.1 | A-128393.2 | GfsgsUfgCfaCffuUfCfgAfgUfugUfgUfcGfuAfL96 | 610 | A-128461.1 | PusCfsgAfaUfcCfaCfacuCfcAfaAfaGfascsa | 825 |
| AD-64318.1 | A-128407.2 | UfscsUfuUftuGfauCfuAfaGfCfcUfcCfaAfgCfuAfL96 | 611 | A-128469.1 | PusAfsgCfuUfgGfaGfcuUfgAfaCfaAfgsasc | 826 |
| AD-64319.1 | A-128423.2 | AfscsUfgUfcAfaAfgCfcUfcUfgCfcUfaUfactuGfcGfL96 | 612 | A-128477.1 | PusCfsgCfaGfaUfaUfggaUfcGfgCfaGfgsasg | 827 |
| AD-64320.1 | A-128435.2 | UfscsUfgCfcCfGfaUfcUfcUfaUfactuGfcGfGfaAfL96 | 613 | A-128483.1 | PusCfscCfAfuAfuccAfuAfuAfaCfusgsg | 828 |
| AD-64321.1 | A-123463.3 | AfsgsUfuAfafuGfcGfaUfgAfaUfgUfgGfuAfuAfCfL96 | 614 | A-128446.1 | PusAfscCfaCfaUfcAfuccAfuAfcfCfusgsa | 829 |
| AD-64322.1 | A-128379.2 | AfsusGfuUfcCfuGfCfgtUfgCffuUfaAfuAfL96 | 615 | A-128454.1 | PusAfsuAfaAfaCfgCfcgcAfgAfcAfcAfuscsc | 830 |
| AD-64323.1 | A-128395.2 | CfscsCfcCfuGfuFgCfcCfuUfcUfcUfcAfL96 | 616 | A-128462.1 | PusAfsuGfaGfaAfgGfcacAfgAfcAfgGfgsasg | 831 |
| AD-64324.1 | A-128409.2 | GfscsCfuAfaUfcAfUfcFfuuCfuUfgGfuCfaUfL96 | 617 | A-128470.1 | PasUfsgAfaCfaAfgAfgauGfaUfuAfgCfgsasg | 832 |
| AD-64325.1 | A-128425.2 | UfscsUfaGfaCfuCfGfuGfgfuGfafcUfcUfL96 | 618 | A-128478.1 | PgsAfsgUfcCfaCfcAfacgAfgUfCfaGfascsu | 833 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64326.1 | A-128437.2 | CfsusGfcCfgafuCfCfAfuAfcUfgCfgGfaAfL96 | 619 | A-128484.1 | PusUfscCfgaGfuAfuggAfuCfgGfcAfgsasg | 834 |
| AD-64328.1 | A-128381.2 | AfsusCfuUfcUfuGfUfUfuGfuUfcUfuAfL96 | 620 | A-128455.1 | PusAfsgAfaGfaAfcCfaacAfaGfaAfgAfusgsa | 835 |
| AD-64330.1 | A-128411.2 | UfsusCfuCfucfaAfUfufuUfcUfaGfgGfgAfL96 | 621 | A-128471.1 | PusCfscCfcUfaGfaGfaAfaauUfgAfgAfgAfasgsu | 836 |
| AD-64331.1 | A-127905.16 | AfsusCfcGfuGfgUfgGfaCfuUfcUfcUfcAfL96 | 622 | A-127907.2 | PusGfsaGfaGfaAfgUfccaCfcAfcGfaGfuscsu | 837 |
| AD-64332.1 | A-128001.3 | GfsusGfcAfcUfucfgfcUfuAfcCfuCfuGfL96 | 623 | A-128485.1 | PcsAfsgAfgGfuGfaAfgcgAfaGfuGfcAfcsasc | 838 |
| AD-64333.1 | A-128367.2 | GfsusUfuUfcUfuEfGfUfuGfaCfaAfaAfaUfL96 | 624 | A-128448.1 | PasUfsuUfuUfgUfcAfacaAfgAfaAfaAfcscsc | 839 |
| AD-64334.1 | A-128383.2 | CfsusGfccUfuAfUfcAfafucfucfuUfgUfuAfL96 | 625 | A-128456.1 | PusAfsaCfaAfgAfgAfugaUfuAfgGfcAfgsasg | 840 |
| AD-64335.1 | A-128399.2 | UfscsCfuCfaCfaAfUfAfcCfacfaGfaGfuAfL96 | 626 | A-128464.1 | PusAfscUfcUfgUfgGfuauUfgUfgAfgGfasusu | 841 |
| AD-64336.1 | A-128413.2 | CfsusGfgUfgGfaCfAfAfAfaAfaUfcUfcUfcAfL96 | 627 | A-128472.1 | PasAfsaUfgAfgAfgAfaagUfcCfaCfcAfcsgsa | 842 |
| AD-64337.1 | A-127955.16 | GfsusGfgUfugGfaCfUfuUfuUfcAfcfcUfcUfL96 | 628 | A-127958.2 | PasGfsgCfaGfaGfgUfgaaAfaAfgUfuGfcsasu | 843 |
| AD-64338.1 | A-128439.2 | GfscsAfucCfuUfuUfcCfcUfaCfaGfcUfacAfL96 | 629 | A-128486.1 | PusAfsuGfcUfgUfaGfcucUfuGfuUfcCfcsasa | 844 |
| AD-64339.1 | A-128369.2 | GfsgsGfaAfcAfaGfAfGfcCfuCfaUfccUfcUfL96 | 630 | A-128449.1 | PusAfsaGfaAfcCfaAfcaaGfaAfgAfuGfasgsg | 845 |
| AD-64341.1 | A-128401.2 | UfscsAfucfuCfUfUfgUfCfUfgCfcCfuAfUfcCfuAfL96 | 631 | A-128465.1 | PusAfsaGfaUfgAfggCfcauAfgCfaGfcAfgsgsa | 846 |
| AD-64342.1 | A-128415.2 | CfsusGfcUfgGfuAfUfUfgCfgCfcUfuGfcGfuUfL96 | 632 | A-128473.1 | PasCfsGfcCfgaGfacaCfaUfccCfaAfcsgsa | 847 |
| AD-64343.1 | A-128427.2 | GfsusgGfaUfgGfaUfgfAfuGfuGfgGfuUfL96 | 633 | A-128479.1 | PusAfsgGfcAfuAfgCfagcAfgGfaUfgAfasgsa | 848 |
| AD-64344.1 | A-128441.2 | UfsusCfaUfccUfuGfuAfufuGfcCfcUfuAfL96 | 634 | A-128487.1 | PusAfsgGfcAfuAfgCfagcAfgGfaUfgAfasgsa | 849 |
| AD-64345.1 | A-128371.2 | UfsusCfuUfgUfuGfafcfaAfaAfaUfccUfuAfL96 | 635 | A-128450.1 | PusAfsgGfaUfuUfuUfgucAfaCfaAfgAfasasa | 850 |
| AD-64347.1 | A-123487.3 | GfsgsAfuGfuCfuCfUfGfcfgUfuUfuAfL96 | 636 | A-128466.1 | PusAfsaAfaCfgCfcgAfcAfcAfcAfuCfcsasg | 851 |
| AD-64348.1 | A-128417.2 | UfsasUfaUfgAfuGfAfUfGfaUfgGfuUfL96 | 637 | A-128474.1 | PusAfsaUfaCfcAfcAfucaUfccCfaUfaUfasasc | 852 |
| AD-64349.1 | A-128429.2 | UfsusCfaUfccUfgfCfUfufaUfgCfcUfcUfL96 | 638 | A-128480.1 | PgsAfsgGfcAfuAfgCfagcAfgGfaUfgAfasgsa | 853 |
| AD-64350.1 | A-128443.2 | GfscsAfcfaAfaAfufCfcUfaCfaAfaUfL96 | 639 | A-128488.1 | PusAfsgGfuGfaAfgcgAfaGfuGfcAfcsasc | 854 |
| AD-64351.1 | A-128373.2 | UfsusGfacfaAfaAfuGfuUfuGfcAfaAfuL96 | 640 | A-128451.1 | PusAfsuUfgUfgAfgGfauUfuUfgUfcAfascsa | 855 |
| AD-64352.1 | A-128389.2 | CfsfscsAfaGfuGfuUfuGfcUfgAfcGfcAfaAfL96 | 641 | A-128459.1 | PusUfsuGfcGfucfaGfcaaAfcAfcUfuGfscsa | 856 |
| AD-64352.1 | A-128389.2 | CfsfscsAfaGfuGfuUfuGfcfUfgAfcGfcAfaAfL96 | 642 | A-128459.1 | PusUfsuGfcGfucfaGfcaaAfcAfcUfuGfscsa | 857 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64353.1 | A-128403.2 | AfsasGfcCfuCfcAfAfgCfcUfgUfgCfcUfuAfL96 | 643 | A-128467.1 | PusAfsaGfgCfaCfaGfcuuGfgAfgGfcUfusgsa | 858 |
| AD-64354.1 | A-128419.2 | CfscsUfcUfucCfaUfcfcUfgCfcUfgCfuAfuAfL96 | 644 | A-128475.1 | PusAfsuAfgCfaGfcAfggaUfgAfaGfaGfgsasa | 859 |
| AD-64355.1 | A-128431.2 | CfscsUfgCfuGfcUfAfUfgCfcUfcAfucCfuUfL96 | 645 | A-128481.1 | PasAfsgAfuGfaGfgCfauaAfgCfAfgCfaGfgsasu | 860 |
| AD-64356.1 | A-128375.2 | CfsasUfcUfuCfuUfgUfuGfgUfuCfcAfucCfuUfL96 | 646 | A-128452.1 | PasGfsaAfgAfaCfcAfacaAfgAfaGfaUfgsasg | 861 |
| AD-64357.1 | A-128391.2 | CfscsGfuCfuGfuCfCfuUfcUfcAfucCfuAfL96 | 647 | A-128460.1 | PusAfsgAfuGfaGfaAfggcAfcAfgAfcGfgsgsg | 862 |
| AD-64358.1 | A-128405.2 | CfscsAfucCfuUfcCfuUfgGfuUfcCfuUfL96 | 648 | A-128468.1 | PasGfsaAfcCfaAfcAfagaAfgAfuGfaGfgscsa | 863 |
| AD-64359.1 | A-128421.2 | CfscsAfcCfaAfUfgCfcCfcUfaUfcUfuAfL96 | 649 | A-128476.1 | PusAfsaGfaUfaGfgGfgcaUfuUfgGfuGfgsusc | 864 |
| AD-64360.1 | A-128433.2 | GfscsUfccCfuGfCfCfgAfucUfcAfuAfcUfL96 | 650 | A-128482.1 | PasGfsuAfuGfAfuCfggcAfgAfgGfaGfcscsa | 865 |
| AD-64700.1 | A-129379.1 | ascsucguggdTacuu(Cgn)ucucaL96 | 651 | A-127906.26 | usGfsaGfaGfaAfgUfccaCfcAfcGfaGfuscsu | 866 |
| AD-64701.1 | A-127905.20 | AfscsUfcGfuGfgUfGfgUfaCfuUfcUfcUfcAfL96 | 652 | A-129387.1 | PusgsagaagdGaaguccaCcacgaguscsu | 867 |
| AD-64702.1 | A-127905.28 | AfscsUfcGfuGfgUfGfgUfaCfuUfcUfcUfcAfL96 | 653 | A-129395.1 | usGsagadGagaaguccadCcacgaguscsu | 868 |
| AD-64703.1 | A-129376.2 | ascsucguggdGacuucdAcucaL96 | 654 | A-129385.5 | usGsagadGaaguccadCcacgaguscsu | 869 |
| AD-64704.1 | A-129381.3 | ascsucguggdTgdGacuucdAcucaL96 | 655 | A-129389.6 | usGsagadGaaguccadCcacgaguscsu | 870 |
| AD-64705.1 | A-129380.1 | ascsucguggdTacuucdAcucaL96 | 656 | A-127906.27 | usGfsaGfaGfaAfgUfccaCfcAfcGfaGfuscsu | 871 |
| AD-64706.1 | A-127905.21 | AfscsUfcGfuGfgUfGfgUfaCfuUfcUfcUfcAfL96 | 657 | A-129388.1 | usdGsadGagaaguccadCcacgaguscsu | 872 |
| AD-64707.1 | A-127905.29 | AfscsUfcGfuGfgUfGfgUfaCfuUfcUfcUfcAfL96 | 658 | A-129396.1 | ussgsagadGaaguccadCcacgaguscsu | 873 |
| AD-64708.1 | A-129382.2 | ascsucguggdTgdGacuuc(Tgn)cucaL96 | 659 | A-129385.6 | usdGsagagaagdCcacgaguscsu | 874 |
| AD-64709.1 | A-129373.4 | ascsucguggdGacuu(Cgn)ucucaL96 | 660 | A-129391.2 | usdGsagadGaaudTccadCcacgaguscsu | 875 |
| AD-64710.1 | A-129373.1 | ascsucguggdGacuu(Cgn)ucucaL96 | 661 | A-127906.20 | usGfsaGfaGfaAfgUfccaCfcAfcGfaGfuscsu | 876 |
| AD-64711.1 | A-129381.1 | ascsucguggdTgdTacuucdAcucaL96 | 662 | A-127906.28 | usGfsaGfaGfaAfgUfccaCfcAfcGfaGfuscsu | 877 |
| AD-64712.1 | A-127905.22 | AfscsUfcGfuGfgUfGfgUfaCfuUfcUfcUfcAfL96 | 663 | A-129389.1 | usdGsagadGaaguccadCcacgaguscsu | 878 |
| AD-64713.1 | A-127905.30 | AfscsUfcGfuGfgUfGfgUfaCfuUfcUfcUfcAfL96 | 664 | A-129397.1 | PusgsagadGaaguccadCcacgaguscsu | 879 |
| AD-64714.1 | A-129384.2 | ascsucguggdTgdGacuucdAcucaL96 | 665 | A-129385.7 | usdGsagagaagdCcacgaguscsu | 880 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64715.1 | A-129376.4 | ascsucguggugGacuucdAcucaL96 | 666 | A-129391.3 | usdGsagadGaagdTccadCcacgaguscsu | 881 |
| AD-64716.1 | A-129374.1 | ascsucguggugGacuucu(Cgn)ucaL96 | 667 | A-127906.21 | usGfsaGfaGfaAfgUfccaCfcAfcGfaGfuscsu | 882 |
| AD-64717.1 | A-129382.1 | ascsucguggdTgdGacuuc(Tgn)cucaL96 | 668 | A-127906.29 | usGfsaGfaGfaAfgUfccaCfcAfcGfaGfuscsu | 883 |
| AD-64718.1 | A-127905.23 | AfscsUfcGfuGfgUfgUfgGfaCfuUfcUfcAfL96 | 669 | A-129390.1 | usdGsagagadAguccadCcacgaguscsu | 884 |
| AD-64719.1 | A-127917.5 | ascsucguggugGacuuc(Tgn)cucaL96 | 670 | A-129385.2 | usdGsagagaagdTccadCcacgaguscsu | 885 |
| AD-64720.1 | A-129381.2 | ascsucguggdTgdTacuucdAcucaL96 | 671 | A-129385.8 | usdGsagagaagdTccadCcacgaguscsu | 886 |
| AD-64721.1 | A-129382.4 | ascsucguggdTgdGacuuc(Tgn)cucaL96 | 672 | A-129391.4 | usdGsagadGaagdTccadCcacgaguscsu | 887 |
| AD-64722.1 | A-129375.1 | ascsucguggugGacuucY34cucaL96 | 673 | A-127906.22 | usGfsaGfaGfaAfgUfccaCfcAfcGfaGfuscsu | 888 |
| AD-64723.1 | A-129383.1 | ascsucguggdGdAcuuc(Tgn)cucaL96 | 674 | A-127906.30 | usGfsaGfaGfaAfgUfccaCfcAfcGfaGfuscsu | 889 |
| AD-64725.1 | A-127917.6 | ascsucguggugGacuuc(Tgn)cucaL96 | 675 | A-129398.1 | PusdGsagagaagdTccadCcacgaguscsu | 890 |
| AD-64726.1 | A-129373.3 | ascsucguggugGacuu(Cgn)ucucaL96 | 676 | A-129389.2 | usdGsagadGaaguccadCcacgaguscsu | 891 |
| AD-64727.1 | A-129384.4 | ascsucguggdTgdGacuucdAcucaL96 | 677 | A-129391.5 | usdGsagadGaagdTccadCcacgaguscsu | 892 |
| AD-64728.1 | A-129376.1 | ascsucguggugGacuucdAcucaL96 | 678 | A-127906.23 | usGfsaGfaGfaAfgUfccaCfcAfcGfaGfuscsu | 893 |
| AD-64729.1 | A-129384.1 | ascsucguggdTgdGacuucdAcucaL96 | 679 | A-127906.31 | usGfsaGfaGfaAfgUfccaCfcAfcGfaGfuscsu | 894 |
| AD-64730.1 | A-127905.25 | AfscsUfcGfuGfgUfgUfgGfaCfuUfcUfcAfL96 | 680 | A-129392.1 | usdGsagagaagdTccadCcacgaguscsu | 895 |
| AD-64731.1 | A-129399.1 | Y34ascsucguggugGacuuc(Tgn)cucaL96 | 681 | A-129385.3 | usdGsagagaagdTccadCcacgaguscsu | 896 |
| AD-64732.1 | A-129376.3 | ascsucguggugGacuucdAcucaL96 | 682 | A-129389.3 | usdGsagadGaaguccadCcacgaguscsu | 897 |
| AD-64733.1 | A-129381.4 | ascsucguggdTgdTacuucdAcucaL96 | 683 | A-127906.24 | usGfsaGfaGfaAfgUfccaCfcAfcGfaGfuscsu | 898 |
| AD-64734.1 | A-129377.1 | ascsucguggugGacuucdCcucaL96 | 684 | A-129385.1 | usdGsagagaagdTccadCcacgaguscsu | 899 |
| AD-64735.1 | A-127905.18 | AfscsUfcGfuGfgUfgUfgGfaCfuUfcUfcUfcAfL96 | 685 | A-129393.1 | usdGsagagaagdTccaCcacgaguscsu | 900 |
| AD-64736.1 | A-127905.26 | AfscsUfcGfuGfgUfgUfgGfaCfuUfcUfcUfcAfL96 | 686 | A-129398.2 | PusdGsagagaagdTccadCcacgaguscsu | 901 |
| AD-64737.1 | A-129399.2 | Y34ascsucguggugGacuuc(Tgn)cucaL96 | 687 | A-129389.4 | usdGsagadGaaguccadCcacgaguscsu | 902 |
| AD-64738.1 | A-129382.3 | ascsucguggdTgdGacuuc(Tgn)cucaL96 | 688 | A-127906.25 | usGfsaGfaGfaAfgUfccaCfcAfcGfaGfuscsu | 903 |
| AD-64739.1 | A-129378.1 | ascsucguggugGacuucdGcucaL96 | 689 | A-127906.25 | usGfsaGfaGfaAfgUfccaCfcAfcGfaGfuscsu | 904 |

TABLE 4-continued

Modified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64740.1 | A-127905.19 | AfscsUfcGfuGfgUfGfgfacfuUfcUfcUfcAfL96 | 690 | A-129386.1 | usgsagagaaagdTccadCcacgaguscsu | 905 |
| AD-64741.1 | A-127905.27 | AfscsUfcGfuGfgUfGfgfacfuUfcUfcUfcAfL96 | 691 | A-129394.1 | usGsagagaagdTccaCcacgaguscsu | 906 |
| AD-64742.1 | A-129373.2 | ascsucguggugdGacuu(Cgn)ucucaL96 | 692 | A-129385.4 | usdGsagagaagdTccadCcacgaguscsu | 907 |
| AD-64743.1 | A-129384.3 | ascsucguggdTgdGacuucdAcucaL96 | 693 | A-129389.5 | usdGsagadGaaguccadCcacgaguscsu | 908 |

TABLE 5

HBV single dose screen using Dual-Glo Luciferase ® Assay

| Duplex ID | 10 nM Avg | 0.1 nM Avg | 10 nM SD | 0.1 nM_SD |
|---|---|---|---|---|
| AD-63938.2 | 0.12 | ND | 0.01 | ND |
| AD-63950.2 | 0.38 | ND | 0.04 | ND |
| AD-63956.2 | 0.31 | ND | 0.02 | ND |
| AD-63962.2 | 0.16 | ND | 0.03 | ND |
| AD-63968.2 | 0.56 | ND | 0.10 | ND |
| AD-63968.2 | 0.79 | ND | 0.09 | ND |
| AD-63979.2 | 0.54 | ND | 0.02 | ND |
| AD-63939.2 | 0.51 | ND | 0.01 | ND |
| AD-63945.2 | 0.54 | ND | 0.08 | ND |
| AD-63951.2 | 0.60 | ND | 0.03 | ND |
| AD-63957.2 | 0.57 | ND | 0.02 | ND |
| AD-63963.2 | 0.91 | ND | 0.06 | ND |
| AD-63969.2 | 0.92 | ND | 0.02 | ND |
| AD-63975.2 | 0.83 | ND | 0.01 | ND |
| AD-63980.2 | 0.77 | ND | 0.01 | ND |
| AD-63940.2 | 0.77 | ND | 0.06 | ND |
| AD-63946.2 | 0.60 | ND | 0.10 | ND |
| AD-63952.2 | 0.48 | ND | 0.04 | ND |
| AD-63958.2 | 0.51 | ND | 0.01 | ND |
| AD-63964.2 | 0.58 | ND | 0.04 | ND |
| AD-63970.2 | 0.69 | ND | 0.07 | ND |
| AD-63976.2 | 0.63 | ND | 0.04 | ND |
| AD-63981.2 | 0.60 | ND | 0.04 | ND |
| AD-63941.2 | 0.56 | ND | 0.09 | ND |
| AD-63947.2 | 0.55 | ND | 0.08 | ND |
| AD-63953.2 | 0.56 | ND | 0.06 | ND |
| AD-63959.2 | 0.51 | ND | 0.03 | ND |
| AD-63965.2 | 0.55 | ND | 0.03 | ND |
| AD-63971.2 | 0.65 | ND | 0.02 | ND |
| AD-63977.2 | 0.88 | ND | 0.01 | ND |
| AD-63982.2 | 0.73 | ND | 0.07 | ND |
| AD-63942.2 | 0.32 | ND | 0.09 | ND |
| AD-63948.2 | 0.57 | ND | 0.09 | ND |
| AD-63960.2 | 0.92 | ND | 0.05 | ND |
| AD-63966.2 | 0.85 | ND | 0.06 | ND |
| AD-63972.2 | 0.82 | ND | 0.06 | ND |
| AD-63978.2 | 0.83 | ND | 0.02 | ND |
| AD-63983.2 | 0.89 | ND | 0.02 | ND |
| AD-63943.2 | 0.86 | ND | 0.04 | ND |
| AD-63949.2 | 0.76 | ND | 0.02 | ND |
| AD-63955.2 | 0.82 | ND | 0.02 | ND |
| AD-63961.2 | 0.83 | ND | 0.07 | ND |
| AD-63967.2 | 0.86 | ND | 0.03 | ND |
| AD-63973.2 | 0.86 | ND | 0.03 | ND |
| AD-63990.2 | 0.27 | ND | 0.07 | ND |
| AD-63996.2 | 0.29 | ND | 0.06 | ND |
| AD-64002.2 | 0.30 | ND | 0.11 | ND |
| AD-64008.2 | 0.28 | ND | 0.05 | ND |
| AD-64008.2 | 0.34 | ND | 0.07 | ND |
| AD-64014.2 | 0.30 | ND | 0.03 | ND |
| AD-64019.2 | 0.36 | ND | 0.04 | ND |
| AD-64024.2 | 0.27 | ND | 0.03 | ND |
| AD-63985.2 | 0.28 | ND | 0.06 | ND |
| AD-63991.2 | 0.33 | ND | 0.02 | ND |
| AD-63997.2 | 0.47 | ND | 0.07 | ND |
| AD-64003.2 | 0.69 | ND | 0.06 | ND |
| AD-64009.2 | 0.91 | ND | 0.03 | ND |
| AD-64015.2 | 0.69 | ND | 0.09 | ND |
| AD-64020.2 | 0.81 | ND | 0.06 | ND |
| AD-64025.2 | 0.77 | ND | 0.06 | ND |
| AD-63986.2 | 0.28 | ND | 0.05 | ND |
| AD-63992.2 | 0.44 | ND | 0.04 | ND |
| AD-64004.2 | 0.45 | ND | 0.04 | ND |
| AD-64010.2 | 0.37 | ND | 0.05 | ND |
| AD-64016.2 | 0.48 | ND | 0.05 | ND |
| AD-64021.2 | 0.39 | ND | 0.03 | ND |
| AD-64026.2 | 0.30 | ND | 0.02 | ND |
| AD-63987.2 | 0.20 | ND | 0.02 | ND |
| AD-63993.2 | 0.33 | ND | 0.02 | ND |
| AD-63999.2 | 0.36 | ND | 0.05 | ND |
| AD-64005.2 | 0.45 | ND | 0.11 | ND |
| AD-64011.2 | 0.39 | ND | 0.08 | ND |
| AD-64017.2 | 0.84 | ND | 0.06 | ND |
| AD-64022.2 | 0.81 | ND | 0.03 | ND |
| AD-64027.2 | 0.38 | ND | 0.05 | ND |
| AD-63988.2 | 0.37 | ND | 0.04 | ND |
| AD-63994.2 | 0.23 | ND | 0.01 | ND |
| AD-64000.2 | 0.29 | ND | 0.00 | ND |
| AD-64006.2 | 0.40 | ND | 0.04 | ND |
| AD-64012.2 | 0.45 | ND | 0.17 | ND |
| AD-64018.2 | 0.65 | ND | 0.07 | ND |
| AD-64023.2 | 0.53 | ND | 0.07 | ND |
| AD-64028.2 | 0.52 | ND | 0.07 | ND |
| AD-63989.2 | 0.47 | ND | 0.04 | ND |
| AD-63995.2 | 0.81 | ND | 0.03 | ND |
| AD-64001.2 | 0.83 | ND | 0.04 | ND |
| AD-64007.2 | 0.87 | ND | 0.04 | ND |
| AD-64013.2 | 0.88 | ND | 0.03 | ND |
| AD-64289.1 | 0.276 | ND | 0.009 | ND |
| AD-64333.1 | 0.208 | ND | 0.015 | ND |
| AD-64285.1 | 0.324 | ND | 0.034 | ND |
| AD-64300.1 | 0.225 | ND | 0.005 | ND |
| AD-64345.1 | 0.102 | ND | 0.090 | ND |
| AD-64292.1 | 0.288 | ND | 0.232 | ND |
| AD-64336.1 | 0.199 | ND | 0.056 | ND |
| AD-64275.1 | 0.287 | ND | 0.185 | ND |
| AD-64316.1 | 0.297 | ND | 0.024 | ND |
| AD-64274.1 | 0.209 | ND | 0.033 | ND |
| AD-64315.1 | 0.199 | ND | 0.002 | ND |
| AD-64305.1 | 0.360 | ND | 0.035 | ND |
| AD-64351.1 | 0.281 | ND | 0.014 | ND |
| AD-64291.1 | 0.725 | ND | 0.005 | ND |
| AD-64335.1 | 0.478 | ND | 0.020 | ND |
| AD-64283.1 | 0.917 | ND | 0.018 | ND |
| AD-64304.1 | 0.937 | ND | 0.050 | ND |
| AD-64325.1 | 0.446 | ND | 0.223 | ND |
| AD-64350.1 | 0.934 | ND | 0.055 | ND |
| AD-63968.4 | 0.748 | ND | 0.008 | ND |
| AD-64331.1 | 0.294 | ND | 0.038 | ND |
| AD-64008.4 | 0.416 | ND | 0.028 | ND |
| AD-64337.1 | 0.318 | ND | 0.049 | ND |
| AD-64295.1 | 0.415 | ND | 0.034 | ND |
| AD-64276.1 | 0.453 | ND | 0.073 | ND |
| AD-64317.1 | 0.203 | ND | 0.040 | ND |
| AD-64330.1 | 0.313 | ND | 0.030 | ND |
| AD-64298.1 | 0.797 | ND | 0.007 | ND |
| AD-64343.1 | 0.667 | ND | 0.020 | ND |
| AD-61547.2 | 0.637 | ND | 0.019 | ND |
| AD-64347.1 | 0.418 | ND | 0.066 | ND |
| AD-64280.1 | 0.754 | ND | 0.092 | ND |
| AD-64322.1 | 0.407 | ND | 0.013 | ND |
| AD-64308.1 | 0.720 | ND | 0.055 | ND |
| AD-64354.1 | 0.315 | ND | 0.034 | ND |
| AD-64303.1 | 0.815 | ND | 0.150 | ND |
| AD-64349.1 | 0.447 | ND | 0.030 | ND |
| AD-64299.1 | 0.831 | ND | 0.007 | ND |
| AD-64344.1 | 0.404 | ND | 0.009 | ND |
| AD-64309.1 | 0.856 | ND | 0.005 | ND |
| AD-64355.1 | 0.498 | ND | 0.040 | ND |
| AD-64297.1 | 0.895 | ND | 0.024 | ND |
| AD-64342.1 | 0.508 | ND | 0.006 | ND |
| AD-64312.1 | 0.590 | ND | 0.034 | ND |
| AD-64358.1 | 0.425 | ND | 0.044 | ND |
| AD-64341.1 | 0.223 | ND | 0.119 | ND |
| AD-64310.1 | 0.301 | ND | 0.064 | ND |
| AD-64356.1 | 0.336 | ND | 0.024 | ND |
| AD-64286.1 | 0.611 | ND | 0.012 | ND |
| AD-64328.1 | 0.317 | ND | 0.043 | ND |
| AD-61522.2 | 0.447 | ND | 0.008 | ND |
| AD-64321.1 | 0.237 | ND | 0.009 | ND |
| AD-64302.1 | 0.523 | ND | 0.020 | ND |
| AD-64348.1 | 0.208 | ND | 0.003 | ND |
| AD-64352.1 | 0.343 | ND | 0.224 | ND |
| AD-64352.1 | 0.567 | ND | 0.015 | ND |
| AD-64314.1 | 0.920 | ND | 0.044 | ND |
| AD-64360.1 | 0.778 | ND | 0.029 | ND |
| AD-64279.1 | 0.882 | ND | 0.034 | ND |
| AD-64320.1 | 0.589 | ND | 0.017 | ND |
| AD-64284.1 | 0.696 | ND | 0.119 | ND |
| AD-64326.1 | 0.552 | ND | 0.009 | ND |

TABLE 5-continued

HBV single dose screen using Dual-Glo Luciferase ® Assay

| Duplex ID | 10 nM Avg | 0.1 nM Avg | 10 nM SD | 0.1 nM_SD |
|---|---|---|---|---|
| AD-64281.1 | 0.921 | ND | 0.019 | ND |
| AD-64323.1 | 0.715 | ND | 0.097 | ND |
| AD-64311.1 | 0.815 | ND | 0.030 | ND |
| AD-64357.1 | 0.549 | ND | 0.001 | ND |
| AD-64272.2 | 0.965 | ND | 0.024 | ND |
| AD-64332.1 | 0.548 | ND | 0.013 | ND |
| AD-64293.1 | 0.837 | ND | 0.013 | ND |
| AD-64338.1 | 0.597 | ND | 0.031 | ND |
| AD-64290.1 | 0.489 | ND | 0.026 | ND |
| AD-64334.1 | 0.368 | ND | 0.003 | ND |
| AD-64282.1 | 0.767 | ND | 0.009 | ND |
| AD-64324.1 | 0.726 | ND | 0.077 | ND |
| AD-64278.1 | 0.951 | ND | 0.077 | ND |
| AD-64319.1 | 0.895 | ND | 0.029 | ND |
| AD-64307.1 | 0.890 | ND | 0.065 | ND |
| AD-64353.1 | 0.567 | ND | 0.500 | ND |
| AD-64277.1 | 0.416 | ND | 0.019 | ND |
| AD-64277.1 | 0.839 | ND | 0.058 | ND |
| AD-64318.1 | 0.613 | ND | 0.042 | ND |
| AD-64318.1 | 0.768 | ND | 0.042 | ND |
| AD-64313.1 | 0.698 | ND | 0.062 | ND |
| AD-64359.1 | 0.441 | ND | 0.081 | ND |
| AD-64294.1 | 0.563 | ND | 0.066 | ND |
| AD-64339.1 | 0.486 | ND | 0.044 | ND |
| AD-63968.5 | 0.57 | 0.72 | 0.07 | 0.03 |
| AD-63940.3 | 0.81 | 0.83 | 0.11 | 0.03 |
| AD-64710.1 | 0.79 | 0.85 | 0.12 | 0.04 |
| AD-64716.1 | 0.73 | 0.85 | 0.08 | 0.01 |
| AD-64722.1 | 0.67 | 0.80 | 0.06 | 0.02 |
| AD-64728.1 | 0.74 | 0.87 | 0.06 | 0.05 |
| AD-64734.1 | 0.78 | 0.83 | 0.08 | 0.05 |
| AD-64739.1 | 0.73 | 0.85 | 0.07 | 0.02 |
| AD-64700.1 | 0.54 | 0.75 | 0.13 | 0.02 |
| AD-64705.1 | 0.67 | 0.79 | 0.15 | 0.04 |
| AD-64711.1 | 0.57 | 0.83 | 0.13 | 0.04 |
| AD-64717.1 | 0.72 | 0.83 | 0.13 | 0.02 |
| AD-64723.1 | 0.83 | 0.87 | 0.12 | 0.01 |
| AD-64729.1 | 0.74 | 0.87 | 0.08 | 0.07 |
| AD-64735.1 | 0.73 | 0.89 | 0.05 | 0.04 |
| AD-64740.1 | 0.89 | 0.88 | 0.05 | 0.07 |
| AD-64701.1 | 0.88 | 0.84 | 0.07 | 0.05 |
| AD-64706.1 | 0.71 | 0.88 | 0.12 | 0.05 |
| AD-64712.1 | 0.81 | 0.86 | 0.13 | 0.07 |
| AD-64718.1 | 0.84 | 0.89 | 0.16 | 0.01 |
| AD-64730.1 | 0.88 | 0.89 | 0.02 | 0.04 |
| AD-64736.1 | 0.80 | 0.88 | 0.10 | 0.05 |
| AD-64741.1 | 0.85 | 0.83 | 0.06 | 0.05 |
| AD-64702.1 | 0.87 | 0.93 | 0.02 | 0.06 |
| AD-64707.1 | 0.95 | 0.88 | 0.05 | 0.08 |
| AD-64713.1 | 0.90 | 0.85 | 0.08 | 0.03 |
| AD-64719.1 | 0.80 | 0.89 | 0.09 | 0.09 |
| AD-64725.1 | 0.70 | 0.84 | 0.09 | 0.03 |
| AD-64731.1 | 0.82 | 0.87 | 0.04 | 0.08 |
| AD-64737.1 | 0.76 | 0.84 | 0.09 | 0.08 |
| AD-64742.1 | 0.76 | 0.85 | 0.09 | 0.03 |
| AD-64703.1 | 0.79 | 0.88 | 0.05 | 0.02 |
| AD-64708.1 | 0.83 | 0.82 | 0.08 | 0.06 |
| AD-64714.1 | 0.75 | 0.85 | 0.12 | 0.03 |
| AD-64720.1 | 0.61 | 0.81 | 0.17 | 0.04 |
| AD-64726.1 | 0.75 | 0.83 | 0.07 | 0.02 |
| AD-64732.1 | 0.86 | 0.84 | 0.14 | 0.10 |
| AD-64738.1 | 0.80 | 0.90 | 0.04 | 0.02 |
| AD-64743.1 | 0.75 | 0.85 | 0.12 | 0.04 |
| AD-64704.1 | 0.67 | 0.78 | 0.16 | 0.02 |
| AD-64709.1 | 0.83 | 0.86 | 0.16 | 0.03 |
| AD-64715.1 | 0.87 | 0.88 | 0.09 | 0.04 |
| AD-64721.1 | 0.77 | 0.82 | 0.12 | 0.06 |
| AD-64727.1 | 0.75 | 0.85 | 0.14 | 0.02 |
| AD-64733.1 | 0.67 | 0.81 | 0.14 | 0.03 |

Example 3. Synthesis and In Vitro Screening of Additional siRNA Duplexes

Additional iRNA molecules targeting the HBV genome were synthesized as described above. A detailed list of the additional unmodified HBV sense and antisense strand sequences is shown in Table 6 and a detailed list of the modified HBV sense and antisense strand sequences is shown in Table 7.

TABLE 6

Unmodified Sense and Antisense Strand Sequences of HBV dsRNAs

| Duplex ID | Sense Sequence (5' to 3') | SEQ ID NO: | Antisense Sequence (5' to 3') | SEQ ID NO: |
|---|---|---|---|---|
| AD-65369.1 | UCGUGGUGGACUUCUCUCA | 909 | UGAGAGAAGUCCACCACGAUU | 938 |
| AD-65381.1 | UCGUGGUGGACUUCUCUCA | 910 | UGAGAGAAGUCCACCACGAUU | 939 |
| AD-63962.1 | UCGUGGUGGACUUCUCUCA | 911 | UGAGAGAAGUCCACCACGAUU | 940 |
| AD-63938.1 | ACUCGUGGUGGACUUCUCUCA | 912 | UGAGAGAAGUCCACCACGAGUCU | 941 |
| AD-65561.1 | UCGUGGUGGACUUCUCUCA | 913 | UGAGAGAAGUCCACCACGAUU | 942 |
| AD-65566.1 | UCGUGGUGGACUUCUCUCA | 914 | UGAGAGAAGUCCACCACGAUU | 943 |
| AD-63944.1 | UCGUGGUGGACUUCUCUCAUU | 915 | UGAGAGAAGUCCACCACGAUU | 944 |
| AD-63968.1 | ACUCGUGGUGGACUUCUCUCA | 916 | UGAGAGAAGUCCACCACGAGUCU | 945 |
| AD-65406.1 | UCGUGGUGGACUUCUCUCA | 917 | UGAGAGAAGUCCACCACGAUU | 946 |
| AD-65396.1 | ACUCGUGGUGGACUUCUCUCA | 918 | UGAGAGAAGUCCACCACGAGUUU | 947 |
| AD-65427.1 | GUGCACUUCGCUUCACCUCUA | 919 | UAGAGGUGAAGCGAAGUGCACUU | 948 |
| AD-65573.1 | GUGCACUUCGCUUCACCUCUA | 920 | UAGAGGUGAAGCGAAGUGCACAC | 949 |

TABLE 6-continued

Unmodified Sense and Antisense Strand Sequences of HBV dsRNAs

| Duplex ID | Sense Sequence (5' to 3') | SEQ ID NO: | Antisense Sequence (5' to 3') | SEQ ID NO: |
|---|---|---|---|---|
| AD-65432.1 | GCACUUCGCUUCACCUCUA | 921 | UAGAGGUGAAGCGAAGUGCAC | 950 |
| AD-64332.1 | GUGCACUUCGCUUCACCUCUG | 922 | CAGAGGUGAAGCGAAGUGCACAC | 951 |
| AD-64322.1 | AUGUGUCUGCGGCGUUUUAUA | 923 | UAUAAAACGCCGCAGACACAUCC | 952 |
| AD-64272.1 | GUGCACUUCGCUUCACCUCUG | 924 | CAGAGGUGAAGCGAAGUGCACAC | 953 |
| AD-65583.1 | GCACUUCGCUUCACCUCUA | 925 | UAGAGGUGAAGCGAAGUGCUU | 954 |
| AD-63994.1 | GGUGGACUUCUCUCAAUUU | 926 | AAAUUGAGAGAAGUCCACCAC | 955 |
| AD-65370.1 | CGUGGUGGACUUCUCUCAAUU | 927 | AAUUGAGAGAAGUCCACCAGCAG | 956 |
| AD-65265.1 | GUGGUGGACUUCUCUCAAUUU | 928 | AAAUUGAGAGAAGUCCACCACGA | 957 |
| AD-65407.1 | CGUGGUGGACUUCUCUCAAUU | 929 | AAUUGAGAGAAGUCCACCAGCAG | 958 |
| AD-64027.1 | GGUGGACUUCUCUCAAUUU | 930 | AAAUUGAGAGAAGUCCACCAC | 959 |
| AD-65266.1 | GUGGUGGACUUCUCUCAAUUU | 931 | AAAUUGAGAGAAGUCCACCACGA | 960 |
| AD-65389.1 | UGGUGGUCUCUCUAAAUU | 932 | AAUUGAGAGAAGUCCACCAUU | 961 |
| AD-64008.1 | GUGGUGGACUUCUCUCAAUUU | 933 | AAAUUGAGAGAAGUCCACCACGA | 962 |
| AD-65377.1 | CGUGGUGGUCUCUCUAAAUU | 934 | AAUUGAGAGAAGUCCACCAGCUU | 963 |
| AD-65409.2 | GGUGGACUUCUCUCAAUUUA | 935 | UAAAAUUGAGAGAAGUCCACCAC | 964 |
| AD-65403.1 | GGUGGACUUCUCUCAAUUUA | 936 | UAAAAUUGAGAGAAGUCCACCAC | 965 |
| AD-65385.1 | UGGACUACUCUCAAAUUUA | 937 | UAAAAUUGAGAGAAGUCCAUU | 966 |

TABLE 7

Modified Sense and Antisense Strand Sequences of HBV dsRNAs

| DuplexID | Sense Sequence (5' to 3') | SEQ ID NO: | Antisense Sequence (5' to 3') | SEQ ID NO: |
|---|---|---|---|---|
| AD-65369 | uscsguGfgUfGfGfacuuCfUfcucaL96 | 967 | PusGfsagaGfaAfGfuccaCfcAfcgasusu | 996 |
| AD-65381 | uscsguGfgUfGfGfacuucucucaL96 | 968 | PusGfsagaGfaAfGfuccaCfcAfcgasusu | 997 |
| AD-63962 | Y44uscsGfuGfgUfgGfaCfuUfcUfcUfcAfY44 | 969 | PusGfsaGfaGfaAfgUfcCfaCfcAfcGfasusu | 998 |
| AD-63938 | Y44ACUCGUGGUGGACUUCUCUCA | 970 | UGAGAGAAGUCCACCACGAGUCU | 999 |
| AD-65561 | uscsguGfgUfGfGfacuuCfUfcucaL96 | 971 | UfsGfsagaGfaAfGfuccaCfcAfcgasusu | 1000 |
| AD-65566 | uscsguGfgUfGfGfacuucucucaL96 | 972 | UfsGfsagaGfaAfGfuccaCfcAfcgasusu | 1001 |
| AD-63944 | Y44ucGuGGuGGAcuucucucAusuY44 | 973 | UfGfagAfgAfAfGUfccaCfCAfcgAusu | 1002 |
| AD-63968 | AfscsUfcGfuGfgUfGfGfacCfuUfcUfcUfcAfL96 | 974 | usGfsaGfaGfaAfgUfccaCfcAfcGfaGfuscsu | 1003 |
| AD-65406 | uscsguGfgUfGfGfacuuCfUfcucaL96 | 975 | usGfsagaGfaAfGfuccaCfcAfcgasusu | 1004 |
| AD-65396 | ascsucguGfgUfGfGfacuucucucaL96 | 976 | usGfsagaGfaagucCfcAfcgagususu | 1005 |
| AD-65427 | gsusgcacUfuCfGfCfuucaccucuaL96 | 977 | PusAfsgagGfugaagcgAfaGfugcacsusu | 1006 |
| AD-65573 | gsusgcacUfuCfGfCfuucaCfCfucuaL96 | 978 | UfsAfsgagGfuGfAfagcgAfaGfugcacsasc | 1007 |
| AD-65432 | gscsacUfucGfCfuucacCfucuaL96 | 979 | PusAfsgagGfuGfAfagcgAfaGfugcsasc | 1008 |
| AD-64332 | GfsusGfcAfcUfuCfGfCfuUfcAfcCfuCfuGfL96 | 980 | PcsAfsgAfgGfuGfaAfgcgAfaGfuGfcAfcsasc | 1009 |
| AD-64322 | AfsusGfufuCfuGfCfGfgCfgUfuUfuAfuAfL96 | 981 | PusAfsuAfaAfaCfgCfgcAfgAfcAfcAfuscsc | 1010 |

TABLE 7-continued

Modified Sense and Antisense Strand Sequences of HBV dsRNAs

| DuplexID | Sense Sequence (5' to 3') | SEQ ID NO: | Antisense Sequence (5' to 3') | SEQ ID NO: |
|---|---|---|---|---|
| AD-64272 | GfsusGfcAfcUfuCfGfCfuUfcAfcCfuCfuGfL96 | 982 | csAfsgAfgGfuGfaAfgcgAfaGfuGfcAfcsasc | 1011 |
| AD-65583 | gscsacuucgdCuucac(Cgn)ucuaL96 | 983 | usdAsgagdGugaagcgdAagugcsusu | 1012 |
| AD-63994 | gsgsUfgGfaCfUfUfcUfcUfcAfaUfuUfL96 | 984 | PasAfsaUfuGfaGfaGfaagUfcCfaCfcsasc | 1013 |
| AD-65370 | csgsugguGfgAfCfUfucucUfCfaauuL96 | 985 | asAfsuugAfgAfGfaaguCfcAfccagcsasg | 1014 |
| AD-65265 | gsusggugGfaCfUfUfcUfcucaauuuL96 | 986 | asAfsaUfugagaGfaagUfcCfaccAfcsgsa | 1015 |
| AD-65407 | csgsugguGfgAfCfUfucucUfCfaauuL96 | 987 | asAfsuugAfgAfgAfaguCfcAfccagcsasg | 1016 |
| AD-64027 | gsgsUfgGfaCfUfUfcUfcUfcAfaUfuUfL96 | 988 | asAfsaUfuGfaGfaGfaagUfcCfaCfcsasc | 1017 |
| AD-65266 | gsusggugGfaCfUfUfUfcucuCfaauuuL96 | 989 | asAfsaUfugagaGfaagUfcCfaccAfcsgsa | 1018 |
| AD-65389 | usgsgudGgucdTucucuaaauuL96 | 990 | asdAsuugagagdAagudCcaccasusu | 1019 |
| AD-64008 | GfsusGfgUfgGfaCfUfUfcUfcUfcAfaUfuUfL96 | 991 | asAfsaUfuGfaGfaGfaagUfcCfaCfcAfcsgsa | 1020 |
| AD-65377 | csgsuggudGgucdTucucuaaauuL96 | 992 | asdAsuugagagdAagudCcaccagcsusu | 1021 |
| AD-65409 | gsgsuggaCfuUTCfUfcucaAfUfuuuaL96 | 993 | PusAfsaaaUfuGfAfgagaAfgUfccaccsasc | 1022 |
| AD-65403 | gsgsuggaCfuUTCfUfcucaAfUfuuuaL96 | 994 | usAfsaaaUfuGfAfgagaAfgUfccaccsasc | 1023 |
| AD-65385 | usgsgacuacdTcucaaauuuaL96 | 995 | usdAsaaauugadGagadAguccasusu | 1024 |

A single dose screen of these duplexes was performed in duplicate by transfecting the duplexes into HepG2.215 and Hep3B cells and measuring HBV viral RNA using primer/probe pairs to detect HBV P open reading frame (ORF) RNA (PORF-1_A and PORF-1_B) and/or primer sets to detect HBV S ORF RNA (SORF-2_A and SORF-2_B). The results of the assays in HepG2.2.15 cells are shown in Table 8 and the results of the assays in Hep3B cells are provided in Table 9.

TABLE 8

HBV single dose screen In HepG2.2.15 cells

| DuplexID | PORF-1 Primer/ Probe Set Experiment A | PORF-1 Primer/ Probe Set Duplicate Experiment B | SORF-2 Primer/ Probe Set Experiment A | SORF-2 Primer/ Probe Set Duplicate Experiment B |
|---|---|---|---|---|
| AD-65369 | 0.1875 | 0.042 | 0.0446 | 0.3018 |
| AD-65381 | 0.086 | 0.249 | 0.1008 | 0.553 |
| AD-63962 | 0.4838 | 0.3475 | 0.2237 | 0.5258 |
| AD-63938 | 0.3587 | 2.1213 | 0.0501 | 1.1434 |
| AD-65561 | 0.1076 | 0.3801 | 0.0718 | 0.6897 |
| AD-65566 | 0.4127 | 0.3211 | 0.185 | 11.1161 |
| AD-63944 | 0.9489 | 0.7098 | 0.393 | 0.2771 |
| AD-63968 | NoIC50 | NoIC50 | 1.8788 | NoIC50 |
| AD-65406 | 3.3749 | 18.8396 | 3.8204 | 2.2662 |
| AD-65396 | NoIC50 | 6.8758 | 3.7382 | 4.2157 |
| AD-65427 | 0.0089 | 0.0181 | 0.0066 | 0.015 |
| AD-65573 | 0.0174 | 0.0332 | 0.0029 | 0.0227 |
| AD-65432 | 0.0211 | 0.0593 | 0.0112 | 0.0366 |
| AD-64332 | 0.0268 | 0.0329 | 0.0624 | 0.0217 |
| AD-64322 | 0.0963 | 0.1077 | 0.0992 | 0.0963 |
| AD-64272 | 0.0773 | 0.1199 | 0.0763 | 0.093 |
| AD-65583 | 0.1624 | 0.2228 | 0.1568 | 0.1496 |
| AD-63994 | 0.7019 | 0.1467 | 0.0832 | 0.0385 |
| AD-65370 | 0.2404 | 0.7916 | 0.3952 | 0.1964 |
| AD-65265 | 0.2255 | 0.5008 | 0.2893 | 0.318 |
| AD-65407 | 0.9533 | 0.261 | 0.4254 | 0.1121 |
| AD-64027 | 0.7692 | 0.5887 | 0.5208 | 0.5697 |
| AD-65266 | 3.4109 | 0.5055 | 0.8532 | 0.3658 |
| AD-65389 | 0.9172 | 0.6514 | 0.4915 | 0.2872 |
| AD-64008 | 1.2738 | 0.7865 | 1.9519 | 0.808 |
| AD-65377 | 0.6052 | 1.6 | 24.9403 | 0.6065 |
| AD-65409 | 1.8304 | 1.6479 | 0.104 | 0.0557 |
| AD-65403 | 12.1516 | 0.667 | 1.006 | 0.233 |
| AD-65385 | NoIC50 | NoIC50 | NoIC50 | NoIC50 |

TABLE 9

HBV single dose screen In Hep3B cells

| DuplexID | PORF-1 Primer/ Probe Set Experiment A | PORF-1 Primer/ Probe Set Experiment B |
|---|---|---|
| AD-65369 | 0.0982 | 0.0508 |
| AD-65381 | 0.2392 | 0.1097 |
| AD-63962 | 0.0769 | 0.0706 |
| AD-63938 | 0.039 | 0.0111 |
| AD-65561 | 0.6316 | 0.6931 |
| AD-65566 | 0.2747 | 0.5331 |
| AD-63944 | 0.1317 | 0.0566 |
| AD-63968 | 0.4374 | 0.8811 |
| AD-65406 | 1.4961 | 1.2573 |
| AD-65396 | 1.9971 | 0.9952 |
| AD-65427 | 0.0234 | 0.006 |
| AD-65573 | 0.0346 | 0.0334 |

TABLE 9-continued

HBV single dose screen In Hep3B cells

| DuplexID | PORF-1 Primer/<br>Probe Set<br>Experiment A | PORF-1 Primer/<br>Probe Set<br>Experiment B |
|---|---|---|
| AD-65432 | 0.0352 | 0.2664 |
| AD-64332 | 0.0221 | 0.4541 |
| AD-64322 | 0.1743 | 0.1616 |
| AD-64272 | 0.1885 | 0.6699 |
| AD-65583 | 0.1241 | 8.1611 |
| AD-63994 | 3.3623 | 5.2897 |
| AD-65370 | 0.2281 | NoIC50 |
| AD-65265 | NoIC50 | 7.3426 |
| AD-65407 | 0.1404 | 1.3833 |
| AD-64027 | 27.1417 | 1.1832 |
| AD-65266 | NoIC50 | NoIC50 |
| AD-65389 | NoIC50 | NoIC50 |
| AD-64008 | NoIC50 | NoIC50 |
| AD-65377 | NoIC50 | NoIC50 |
| AD-65409 | 1.8065 | 3.436 |
| AD-65403 | 0.5113 | 18.0359 |
| AD-65385 | NoIC50 | NoIC50 |

A subset of these duplexes were also assayed for in vitro metabolic stability using two assays, a tritosome stability assay and a cytosol stability assay.

For the tritosome stability assays, rat liver tritosomes (Xenotech custom product PR14044) were thawed to room temperature and diluted to 0.5 units/mL Acid Phosphatase in 20 mM Sodium Citrate pH 5.0 Buffer. Twenty-four hour samples were prepared by mixing 100 μL of 0.5 units/mL Acid Phosphatase Tritosomes with 25 μL of 0.4 mg/mL siRNA sample in a microcentrifuge tube and incubating for twenty-four hours in an eppendorf Thermomixer set to 37° C. and 300 rpm. After twenty-four hours of incubation 300 μL of Phenomenex Lysis Loading Buffer (Cat.# ALO-8498) and 12.5 μL of a 0.4 mg/mL internal standard siRNA were added to each sample. Time 0 hour samples were prepared by mixing 100 μL of 0.5 units/mL Acid Phosphatase Tritosomes with 25 μL of 0.4 mg/mL siRNA sample, 300 μL of Phenomenex Lysis Loading Buffer, and 12.5 μL of a 0.4 mg/mL internal standard siRNA. siRNA was extracted from twenty-four hour samples and 0 hour samples using a Phenomenex Clarity OTX Starter Kit (Cat.# KSO-8494). After the samples were extracted they were transferred to a microcentrifuge tube and dried down using a Labconco CentriVap Concentrator (Cat.#7810010). The samples were then resuspended with 500 μL of nuclease free water. Fifty μL of each sample was run on an Agilent Technologies 1260 Infinity Binary LC with Agilent Technologies 6130 Quadrupole LC/MS. The Quaternary pump method was run for 12.20 minutes at 0.400 mL/min with the following timetable:

| Time Function | Parameter |
|---|---|
| 0.20 | 5% Buffer A(16 mM TEA 200 mM HFIP),<br>95% Buffer B (100% Methanol) |
| 2.50 | 5% Buffer A(16 mM TEA 200 mM HFIP),<br>95% Buffer B (100% Methanol) |
| 3.00 | 100% Buffer A(16 mM TEA 200 mM HFIP) |

The Binary Pump method was run for 12.20 min at 0.700 mL/min with the following timetable:

| Time Function | Parameter |
|---|---|
| 0.00 | 100% Buffer A(16 mM TEA 200 mM HFIP) |
| 0.40 | 100% Buffer A(16 mM TEA 200 mM HFIP) |
| 10.00 | 60% Buffer A(16 mM TEA 200 mM HFIP),<br>40% Buffer B (100% ACN) |
| 10.10 | 100% Buffer A(16 mM TEA 200 mM HFIP) |
| 12.20 | 100% Buffer A(16 mM TEA 200 mM HFIP) |

Both the left and right column was set at 75.00° C. The UV signal was measured at 260 nm wavelength. The percent remaining of each strand was calculated using the following equation:

$$\% \text{ Strand remaining} = 100 * (\text{Peak Area}_{strand\ 24h}/\text{Peak Area}_{strand\ 0h} * (\text{Peak Area}_{standard\ 24h}/\text{Peak Area}_{standard\ 0h})).$$

For the cytosol stability assay, female rat liver cytosol (Xenotech Cat. # R1500.C) were thawed to room temperature and diluted to 1 mg/mL in 50 mM Tris buffer: HCl pH 7.4, 5 mM MgCl2. 24 hour samples were prepared by mixing 100 uL of 1 mg/mL Cytosol with 25 uL of 0.4 mg/mL siRNA sample in a microcentrifuge tube and incubating for 24 hours in an eppendorf Thermomixer set to 37° C. and 300 rpm. After 24 hours of incubation 300 uL of Phenomenex Lysis Loading Buffer (Cat.# ALO-8498) and 12.5 uL of a 0.4 mg/mL internal standard siRNA were added to each sample. 0 hour samples were prepared by mixing 100 uL of 1 mg/mL Cytosol with 25 uL of 0.4 mg/mL siRNA sample, 300 uL of Phenomenex Lysis Loading Buffer, and 12.5 uL of a 0.4 mg/mL internal standard siRNA. siRNA was extracted from 24 hour samples and 0 hour samples using a Phenomenex Clarity OTX Starter Kit (Cat.# KSO-8494). After the samples were extracted they were transferred to a microcentrifuge tube and dried down using a Labconco CentriVap Concentrator (Cat. #7810010). The samples were then resuspended with 500 uL of nuclease free water. 50 uL of each sample was run on an Agilent Technologies 1260 Infinity Binary LC with Agilent Technologies 6130 Quadrupole LC/MS. The Quaternary pump method was run for 12.20 minutes at 0.400 mL/min with the following timetable:

| Time Function | Parameter |
|---|---|
| 0.20 | 5% Buffer A(16 mM TEA 200 mM HFIP),<br>95% Buffer B (100% Methanol) |
| 2.50 | 5% Buffer A(16 mM TEA 200 mM HFIP),<br>95% Buffer B (100% Methanol) |
| 3.00 | 100% Buffer A(16 mM TEA 200 mM HFIP) |

The Binary Pump method was run for 12.20 min at 0.700 mL/min with the following timetable:
Time Function Parameter

| Time Function | Parameter |
|---|---|
| 0.00 | 100% Buffer A(16 mM TEA 200 mM HFIP) |
| 0.40 | 100% Buffer A(16 mM TEA 200 mM HFIP) |
| 10.00 | 60% Buffer A(16 mM TEA 200 mM HFIP),<br>40% Buffer B (100% ACN) |
| 10.10 | 100% Buffer A(16 mM TEA 200 mM HFIP) |
| 12.20 | 100% Buffer A(16 mM TEA 200 mM HFIP) |

Both the left and right column was set at 75.00° C. The UV signal was measured at 260 nm wavelength. The percent remaining of each strand was calculated using the following equation:

% Strand remaining=100*(Peak Area$_{strand\ 24h}$/Peak Area$_{strand\ 0h}$*(Peak Area$_{standard\ 24h}$/Peak Area$_{standard\ 0h}$)).

The results of the twenty-four hour tritosome stability assays are provided in Table 10 and the results of the twenty-four hour cytosol stability assays are provided in Table 11.

TABLE 10

Twenty-four hour tritosome stability assays.

| % Antisense Remaining | % Sense Remaining | DuplexID |
|---|---|---|
| 87.59 | 72.43 | AD-65381 |
| 67.59 | 82.48 | AD-65566 |
| 30.52 | 34.98 | AD-63968 |
| 115.17 | 79.61 | AD-65427 |
| 43.00 | 76.84 | AD-65573 |
| 129.69 | 128.59 | AD-64272 |
| 100.30 | 119.85 | AD-65407 |
| 94.06 | 110.90 | AD-64008 |
| 98.63 | 127.48 | AD-65377 |
| 105.06 | 119.88 | AD-65409 |
| 117.55 | 104.30 | AD-65403 |

TABLE 11

Twenty-four hour cytosol stability assays.

| % Antisense Remaining | % Sense Remaining | DuplexID |
|---|---|---|
| 67.78 | 22.42 | AD-65381 |
| 55.89 | 15.26 | AD-65566 |
| 88.39 | 46.94 | AD-63968 |
| 89.50 | 66.35 | AD-65427 |
| 69.01 | 41.47 | AD-65573 |
| 96.77 | 78.00 | AD-64272 |
| 64.46 | 24.10 | AD-65407 |
| 35.39 | 26.39 | AD-64008 |
| 79.98 | 66.50 | AD-65377 |
| 86.24 | 74.25 | AD-65409 |
| 60.45 | 62.41 | AD-65403 |

Example 4. Synthesis and Screening of Additional siRNA Duplexes

Additional iRNA molecules targeting the HBV genome were designed and synthesized as described above. A detailed list of the additional unmodified HBV sense and antisense strand sequences is shown in Table 12 and a detailed list of the modified HBV sense and antisense strand sequences is shown in Table 13.

TABLE 12

Unmodified Sense and Antisense Strand Sequences of HBV dsRNAs

| Duplex ID | Sense ID | Sense Sequence Unmodified (5' to 3') | SEQ ID NO: | Antisense ID | Antisense Sequence Unmodified (5' to 3') | SEQ ID NO: |
|---|---|---|---|---|---|---|
| AD-65381 | A-130366.9 | UCGUGGUGGACUUCUCUCA | 1025 | A-131904.1 | UGAGAGAAGUCCACCACGAUU | 1036 |
| AD-66019 | A-130366.9 | UCGUGGUGGACUUCUCUCA | 1026 | A-131904.1 | UGAGAGAAGUCCACCACGAUU | 1037 |
| AD-65375 | A-130366.9 | UCGUGGUGGACUUCUCUCA | 1027 | A-130364.7 | UGAGAGAAGUCCACCACGAUU | 1038 |
| AD-65427 | A-130441.7 | GUGCACUUCGCUUCACCUCUA | 1028 | A-131905.1 | UAGAGGUGAAGCGAAGUGCACUU | 1039 |
| AD-66110 | A-130441.7 | GUGCACUUCGCUUCACCUCUA | 1029 | A-131905.1 | UAGAGGUGAAGCGAAGUGCACUU | 1040 |
| AD-65421 | A-130441.7 | GUGCACUUCGCUUCACCUCUA | 1030 | A-130442.6 | UAGAGGUGAAGCGAAGUGCACUU | 1041 |
| AD-65407 | A-130371.12 | CGUGGUGGACUUCUCUCAAUU | 1031 | A-130372.5 | AAUUGAGAGAAGUCCACCAGCAG | 1042 |
| AD-65377 | A-130384.4 | CGUGGUGGUCUUCUCUAAAUU | 1032 | A-130748.3 | AAUUGAGAGAAGUCCACCAGCUU | 1043 |
| AD-65409 | A-130388.15 | GGUGGACUUCUCUCAAUUUA | 1033 | A-131906.1 | UAAAAUUGAGAGAAGUCCACCAC | 1044 |
| AD-66111 | A-130388.15 | GGUGGACUUCUCUCAAUUUA | 1034 | A-131906.1 | UAAAAUUGAGAGAAGUCCACCAC | 1045 |
| AD-65403 | A-130388.15 | GGUGGACUUCUCUCAAUUUA | 1035 | A-130389.4 | UAAAAUUGAGAGAAGUCCACCAC | 1046 |

TABLE 13

Modified Sense and Antisense Strand Sequences of HBV dsRNAs

| Duplex ID | Sense ID | Sense Sequence (5' to 3') | SEQ ID NO: | Antisense ID | Antisense Sequence (5' to 3') | SEQ ID NO: |
|---|---|---|---|---|---|---|
| AD-65381 | A-130366.9 | uscsguGfgUfGfGfacuucucucaL96 | 1047 | A-131904.1 | PusGfsagaGfaAfGfuccaCfcAfcgasusu | 1058 |
| AD-66019 | A-130366.9 | uscsguGfgUfGfGfacuucucucaL96 | 1048 | A-131904.1 | VPusGfsagaGfaAfGfuccaCfcAfcgasusu | 1059 |

TABLE 13-continued

Modified Sense and Antisense Strand Sequences of HBV dsRNAs

| Duplex ID | Sense ID | Sense Sequence (5' to 3') | SEQ ID NO: | Antisense ID | Antisense Sequence (5' to 3') | SEQ ID NO: |
|---|---|---|---|---|---|---|
| AD-65375 | A-130366.9 | uscsguGfgUfGfGfacuucucucaL96 | 1049 | A-130364.7 | usGfsagaGfaAfGfuccaCfcAfcgasusu | 1060 |
| AD-65427 | A-130441.7 | gsusgcacUfuCfGfCfuucaccucuaL96 | 1050 | A-131905.1 | PusAfsgagGfugaagcgAfaGfugcacsusu | 1061 |
| AD-66110 | A-130441.7 | gsusgcacUfuCfGfCfuucaccucuaL96 | 1051 | A-131905.1 | VPusAfsgagGfugaagcgAfaGfugcacsusu | 1062 |
| AD-65421 | A-130441.7 | gsusgcacUfuCfGfCfuucaccucuaL96 | 1052 | A-130442.6 | usAfsgagGfugaagcgAfaGfugcacsusu | 1063 |
| AD-65407 | A-130371.12 | csgsugguGfgAfCfUfucucUfCfaauuL96 | 1053 | A-130372.5 | asAfsuugAfgAfgAfaguCfcAfccagcsasg | 1064 |
| AD-65377 | A-130384.4 | csgsuggudGgucdTucucuaaauuL96 | 1054 | A-130748.3 | asdAsuugagagdAagudCcaccagcsusu | 1065 |
| AD-65409 | A-130388.15 | gsgsuggaCfuUfCfUfcucaAfUfuuuaL96 | 1055 | A-131906.1 | PusAfsaaaUfuGfAfgagaAfgUfccaccsasc | 1066 |
| AD-66111 | A-130388.15 | gsgsuggaCfuUfCfUfcucaAfUfuuuaL96 | 1056 | A-131906.1 | VPusAfsaaaUfuGfAfgagaAfgUfccaccsasc | 1067 |
| AD-65403 | A-130388.15 | gsgsuggaCfuUfCfUfcucaAfUfuuuaL96 | 1057 | A-130389.4 | usAfsaaaUfuGfAfgagaAfgUfccaccsasc | 1068 |

A primary single dose screen of these iRNA duplexes was performed using the Dual-Glo® Luciferase assay, as described above. The results of this screen in Cos7 cells transfected with the indicated HBV iRNAs are shown in Table 14. Data are expressed as percent of mRNA remaining relative to negative control at 24 hours.

TABLE 14

HBV single dose primary screen In Cos7 cells using Dual-Glo Luciferase ® Assay

| | Dual luciferase primary screen | | | | |
|---|---|---|---|---|---|
| | % Message remaining at 24 hr | | | | DRC ED50 |
| Duplex ID | at 50 nM | STDEV | at 1 nM | STDEV | (nM) |
| AD-65381 | 9.3 | 0.24 | 15.6 | 0.77 | 0.019 |
| AD-66019 | ND | ND | ND | ND | ND |
| AD-65375 | 24.2 | 0.36 | 71.4 | 0.69 | No ED50 |
| AD-65427 | 28.8 | 1.60 | 41.0 | 1.73 | 0.117 |
| AD-66110 | ND | ND | ND | ND | ND |
| AD-65421 | 47.6 | 3.49 | 85.5 | 4.76 | No ED50 |
| AD-65407 | 14.3 | 0.52 | 25.3 | 2.11 | 0.038 |
| AD-65377 | 21.8 | 0.31 | 37.9 | 1.12 | 0.130 |
| AD-65409 | 9.5 | 0.41 | 13.2 | 0.71 | 0.013 |

TABLE 14-continued

HBV single dose primary screen In Cos7 cells using Dual-Glo Luciferase ® Assay

| | Dual luciferase primary screen | | | | |
|---|---|---|---|---|---|
| | % Message remaining at 24 hr | | | | DRC ED50 |
| Duplex ID | at 50 nM | STDEV | at 1 nM | STDEV | (nM) |
| AD-66111 | ND | ND | ND | ND | ND |
| AD-65403 | 12.6 | 0.50 | 37.2 | 2.31 | 0.069 |

ND—not done

These duplexes were also assayed for dose response for silencing viral RNA using the Dual-Glo® Luciferase assay, as described above. The doses of the duplexes used for these assays were 50 nM, 8.333333333 nM, 1.388888889 nM, 0.231481481 nM, 0.038580247 nM, 0.006430041 nM, 0.001071674 nM, 0.000178612 nM, $2.97687 \times 10^{-5}$ nM, $4.96145 \times 10^{6}$ nM, $8.26909 \times 10^{-7}$ nM, and $1.37818E \times 10^{-7}$ nM, which represent a 1 to 6 dilution of the duplexes starting at 50 nM over 12 doses. The results of this screen in Cos7 cells transfected with the indicated HBV iRNAs are shown in Table 15. Data are expressed as percent of mRNA remaining relative to negative control at 24 hours.

TABLE 15

Dose response screen In Cos7 cells using Dual-Glo Luciferase ® Assay
Dual luciferase HBV reporter cells
IC50 (nM) at 24 hr

| Duplex ID | Assay 1 | Assay 2 | Assay 3 | Assay 4 | Assay 5 | Assay 6 | Assay 7 | Average[1] | Stdev |
|---|---|---|---|---|---|---|---|---|---|
| AD-65381 | 0.019 | ND | ND | ND | ND | ND | ND | 0.019 | |
| AD-66019 | ND | 0.021 | 0.021 | 0.016 | 0.026 | 0.019 | 0.031 | 0.022 | 0.005 |
| AD-65375 | UD | 0.215 | 0.149 | 0.081 | 0.246 | 0.138 | 0.276 | 0.184 | 0.074 |

TABLE 15-continued

Dose response screen In Cos7 cells using Dual-Glo Luciferase ® Assay
Dual luciferase HBV reporter cells
IC50 (nM) at 24 hr

| Duplex ID | Assay 1 | Assay 2 | Assay 3 | Assay 4 | Assay 5 | Assay 6 | Assay 7 | Average[1] | Stdev |
|---|---|---|---|---|---|---|---|---|---|
| AD-65407 | 0.038 | 0.045 | 0.051 | 0.021 | 0.050 | 0.056 | 0.068 | 0.047 | 0.015 |
| AD-65377 | 0.130 | 0.029 | 0.046 | 0.087 | 0.096 | 0.146 | 0.090 | 0.089 | 0.042 |
| AD-65409 | 0.013 | ND | ND | ND | ND | ND | ND | 0.013 | |
| AD-66111 | ND | 0.018 | 0.013 | 0.012 | 0.018 | 0.021 | 0.033 | 0.019 | 0.007 |
| AD-65403 | 0.069 | 0.044 | 0.033 | 0.039 | 0.042 | 0.046 | 0.062 | 0.048 | 0.013 |
| AD-65427 | 0.017 | ND | ND | ND | ND | ND | ND | 0.117 | |
| AD-66110 | ND | 0.238 | 0.296 | 0.145 | 0.157 | 0.161 | ND | 0.199 | 0.065 |
| AD-65421 | UD | 1.219 | 1.385 | 2.254 | 0.799 | 2.906 | ND | 1.713 | 0.852 |

[1]Averages from 5-7 biological replicates run in triplicate
ND—not done

The in vitro efficacy and potency of these duplexes were also assayed. In particular, the dose response of the duplexes for silencing viral RNA in transfected HepG2.2.15 and Hep3B cell lysates and for silencing HBsAg in HepG2.2.15 cell supernatants were determined. Cells were transfected with 12 separate doses of the duplexes ranging from 50 nM to $1 \times 10^{-7}$ nM and at seventy-two hours after transfection, the level of viral RNA was determined using primer/probe pairs to detect the P ORF and/or the S ORF. The level of HBsAg was determined using an ELISA assay.

The results of the P ORF viral RNA silencing in HepG2.2.15 cells using the indicated duplexes are provided in Table 16. The results of the S ORF viral RNA silencing in HepG2.2.15 cells using the indicated duplexes are provided in Table 17. The results of HBsAg silencing in HepG2.2.15 cells are provided in Table 18.

The results of the P ORF viral RNA silencing in Hep3B cells using the indicated duplexes are provided in Table 19.

TABLE 16

Dose response screen In HepG2.2.15 cells
Viral RNA silencing in HepG2.2.15 cells
P-ORF primer/probe set
IC50 (nM) at 72 hr

| Duplex ID | Assay Development | | Optimized Assay | | |
|---|---|---|---|---|---|
| | | | Assay 1 | Assay 2 | Assay 3 |
| AD-65381 | 0.079 | 0.208 | ND | ND | ND | ND | ND |
| AD-66019 | ND | ND | 0.265 | 0.010 | 0.022 | 0.032 | 0.023 |
| AD-65375 | 12.3 | UD | UD | UD | 0.172 | 0.257 | 0.672 |
| AD-65407 | 0.247 | 1.0 | 0.365 | 0.109 | 0.069 | 0.103 | 0.095 |
| AD-65377 | 1.3 | UD | 4.9 | UD | 0.842 | 0.838 | 0.615 |
| AD-65409 | 0.436 | 1.0 | ND | ND | ND | ND | ND |
| AD-66111 | ND | ND | 0.456 | 0.030 | 50 | 0.294 | ND |
| AD-65403 | 9.2 | 10.4 | 3.4 | UD | 0.114 | 0.384 | 1.0 |
| AD-65427 | 0.007 | 0.018 | ND | ND | ND | ND | ND |
| AD-66110 | ND | ND | 0.012 | 0.053 | 0.016 | 0.010 | 0.021 |
| AD-65421 | 0.069 | 0.091 | 0.034 | 0.006 | 0.002 | 0.003 | 0.007 |

ND—not done

TABLE 17

Dose response screen In HepG2.2.15 cells
Viral RNA silencing in HepG2.2.15 cells
S-ORF primer/probe set
IC50 (nM) at 72 hr

| Duplex ID | Assay Development | | Optimized Assay | | |
|---|---|---|---|---|---|
| | | | Assay 1 | Assay 2 | Assay 3 |
| AD-65381 | 0.252 | 0.215 | ND | ND | ND | ND | ND |
| AD-66019 | ND | ND | 0.245 | 0.011 | 0.009 | 0.016 | 0.005 |
| AD-65375 | 45 | UD | UD | UD | 0.124 | 0.048 | 0.056 |
| AD-65407 | 0.232 | 0.645 | 0.577 | 0.015 | 0.021 | 0.023 | 0.016 |
| AD-65377 | 1.4 | 8.6 | UD | UD | 0.575 | 0.483 | 0.117 |
| AD-65409 | 0.433 | 0.242 | ND | ND | ND | ND | ND |
| AD-66111 | ND | ND | 2.1 | 0.455 | ND | 0.416 | ND |
| AD-65403 | 0.997 | 0.670 | 0.668 | UD | 0.074 | 0.270 | 1.1 |
| AD-65427 | 0.008 | 0.018 | ND | ND | ND | ND | ND |
| AD-66110 | ND | ND | 0.022 | 0.050 | 0.035 | 0.038 | 0.020 |
| AD-65421 | 0.083 | 0.097 | 0.046 | 0.003 | 0.003 | 0.005 | 0.001 |

ND—not done

TABLE 18

Dose response screen In HepG2.2.15 cells
HBsAg ELISA
IC50 (nM)

| Duplex ID | Assay 1 |
|---|---|
| AD-65381 | ND |
| AD-66019 | 0.105 |
| AD-65375 | 1.2 |
| AD-65407 | 0.102 |
| AD-65377 | 2.9 |
| AD-65409 | ND |
| AD-66111 | 0.018 |
| AD-65403 | 0.064 |
| AD-65427 | ND |
| AD-66110 | 0.002 |
| AD-65421 | 0.008 |

ND—not done

TABLE 19

Dose response screen In Hep3B cells

Hep3B cells screen DRC ED50 P-ORF primer/probe set

| Duplex ID | P-ORF run 1 | P-ORF run 2 | Combined |
|---|---|---|---|
| AD-65381 | 0.239 | 0.110 | 0.194 |
| AD-66019 | ND | ND | ND |
| AD-65375 | ND | ND | ND |
| AD-65427 | 0.023 | 0.006 | 0.018 |
| AD-66110 | ND | ND | ND |
| AD-65421 | ND | ND | ND |
| AD-65407 | 0.140 | 1.383 | 0.527 |
| AD-65377 | No ED50 | No ED50 | No ED50 |
| AD-65409 | 1.807 | 3.436 | 2.905 |
| AD-66111 | ND | ND | ND |
| AD-65403 | 0.511 | 18.036 | 5.013 |

ND—not done

These duplexes were also assayed for in vitro stability using two assays, a tritosome stability assay and a cytosol stability assay, as described above. The results of these assays are provided in Table 20.

TABLE 20

Twenty-four hour tritosome and cytosol stability assays.

In vitro metabolic stability
% parent remaining at 24 hr incubation

| Duplex ID | Endo-lysosome % AS | Endo-lysosome % SS | Cytosol % AS | Cytosol % SS |
|---|---|---|---|---|
| AD-65381 | 88 | 72 | 68 | 22 |
| AD-66019 | ND | ND | ND | ND |
| AD-65375 | ND | ND | ND | ND |
| AD-65407 | 100 | 120 | 64 | 24 |
| AD-65377 | 99 | 127 | 80 | 67 |
| AD-65409 | 105 | 120 | 86 | 74 |
| AD-66111 | ND | ND | ND | ND |
| AD-65403 | ND | ND | ND | ND |
| AD-65427 | 115 | 80 | 89 | 66 |
| AD-66110 | ND | ND | ND | ND |
| AD-65421 | ND | ND | ND | ND |

Dose response screens of various combinations of these duplexes were also performed in HepG2.215 cells. The doses of the duplexes used for these assays were 50 nM, 8.333333333 nM, 1.388888889 nM, 0.231481481 nM, 0.038580247 nM, 0.006430041 nM, 0.001071674 nM, 0.000178612 nM, $2.97687 \times 10^{-5}$ nM, $4.96145 \times 10^{-6}$ nM, $8.26909 \times 10^{-7}$ nM, and $1.37818E \times 10^{-7}$ nM, which represent a 1 to 6 dilution of the duplexes starting at 50 nM over 12 doses. At seventy-two hours after transfection of these duplexes, the level of viral RNA (P ORF and S ORF) and the level of secreted HBsAg were determined, as described above. The results of these assays are provided in Table 21.

TABLE 21

Seventy-two hour HBV single dose screen In HepG2.2.15 cells

| DuplexID | S-ORF2 IC50_A (nM) | S-ORF2 IC50_B (nM) | S-ORF2 IC50_Combine (nM) | P-ORF1 IC50_A (nM) | P-ORF1 IC50_B (nM) | P-ORF1 IC50_Combine (nM) | S Ag ELISA ED50 (nM) |
|---|---|---|---|---|---|---|---|
| AD-66019/AD-66110 | 0.0091 | 0.0017 | 0.0038 | 0.0213 | 0.002 | 0.0076 | 0.007482 |
| AD-66019/AD-65421 | 0.0438 | 0.2371 | 0.0131 | 0.0367 | 0.0106 | 0.0204 | 0.026398 |
| AD-65375/AD-66110 | 0.0832 | 1.0896 | 0.193 | 0.0377 | 0.2348 | 0.2022 | 0.004174 |
| AD-65375/AD-65421 | 0.084 | 0.0475 | 0.0708 | 0.0566 | 0.0388 | 0.0371 | 0.030822 |
| AD-65407/AD-66110 | 0.0387 | 0.001 | 0.0083 | 0.0402 | 0.0018 | 0.0116 | 0.010172 |
| AD-65407/AD-65421 | 0.0686 | 0.0062 | 0.0225 | 0.0711 | 0.0177 | 0.0396 | 0.066556 |
| AD-65377/AD-66110 | 0.0634 | 0.8267 | 0.6269 | 0.0477 | 0.073 | 0.0618 | 0.01435 |
| AD-65377/AD-65421 | 0.1461 | 0.0468 | 0.1372 | 0.1207 | 0.0088 | 0.0451 | 0.03419 |
| AD-66111/AD-66110 | 0.0382 | 0.0094 | 0.0161 | 0.0292 | 0.0027 | 0.0088 | 0.013155 |
| AD-66111/AD-65421 | 0.1628 | 0.0919 | 0.1579 | 0.1297 | 0.0396 | 0.0722 | 0.026889 |
| AD-65403/AD-66110 | 0.0499 | 0.0094 | 0.0444 | 0.0383 | 0.0164 | 0.0348 | 0.003783 |
| AD-65403/AD-65421 | 0.1011 | 0.0007 | 0.0208 | 0.1118 | 0.0031 | 0.0297 | 0.014569 |

Example 5. Synthesis and In Vitro Screening of Additional siRNA Duplexes

Additional iRNA molecules targeting the X ORF of the HBV genome were designed and synthesized as described above. A detailed list of the additional unmodified HBV sense and antisense strand sequences is shown in Table 22. A detailed list of the additional modified HBV sense and antisense strand sequences is shown in Table 23.

TABLE 22

Unmodified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-65776 | A-131859.1 | UGUGCACUUCGCUUCACCUCU | 1069 | A-131860.1 | AGAGGUGAAGCGAAGUGCACACG | 1115 |
| AD-65782 | A-131877.1 | UGCACUUCGCUUCACCUCUGA | 1070 | A-131878.1 | UCAGAGGUGAAGCGAAGUGCACA | 1116 |
| AD-65792 | A-131865.1 | GUGUGCACUUCGCUUCACCUA | 1071 | A-131866.1 | UAGGUGAAGCGAAGUGCACACGG | 1117 |
| AD-65781 | A-131861.1 | CGUGUGCACUUCGCUUCACCU | 1072 | A-131862.1 | AGGUGAAGCGAAGUGCACACGGU | 1118 |
| AD-64304 | A-128443.6 | GUGCACUUCGCUUCACCUCUA | 1073 | A-128444.5 | UAGAGGUGAAGCGAAGUGCACAC | 1119 |
| AD-65771 | A-131857.1 | CCGUGUGCACUUCGCUUCACA | 1074 | A-131858.1 | UGUGAAGCGAAGUGCACACGGUC | 1120 |
| AD-65758 | A-131867.1 | CACUUCGCUUCACCUCUGCAA | 1075 | A-131868.1 | UUGCAGAGGUGAAGCGAAGUGCA | 1121 |
| AD-65777 | A-131875.1 | ACUUCGCUUCACCUCUGCACA | 1076 | A-131876.1 | UGUGCAGAGGUGAAGCGAAGUGC | 1122 |
| AD-61567 | A-123525.2 | GGCUGUAGGCAUAAAUUGGUA | 1077 | A-123526.2 | UACCAAUUUAUGCCUACAGCCUC | 1123 |
| AD-65772 | A-131873.1 | UUCGCUUCACCUCUGCACGUA | 1078 | A-131874.1 | UACGUGCAGAGGUGAAGCGAAGU | 1124 |
| AD-65767 | A-131871.1 | UCGCUUCACCUCUGCACGUCA | 1079 | A-131872.1 | UGACGUGCAGAGGUGAAGCGAAG | 1125 |
| AD-65763 | A-131869.1 | CUUCGCUUCACCUCUGCACGU | 1080 | A-131870.1 | ACGUGCAGAGGUGAAGCGAAGUG | 1126 |
| AD-64281 | A-128395.3 | CCCCGUCUGUGCCUUCUCAUA | 1081 | A-128396.2 | UAUGAGAAGGCACAGACGGGGAG | 1127 |
| AD-64311 | A-128391.3 | CCGUCUGUGCCUUCUCAUCUA | 1082 | A-128392.2 | UAGAUGAGAAGGCACAGACGGGG | 1128 |
| AD-65790 | A-131837.1 | CCAGCACCAUGCAACUUUUUA | 1083 | A-131838.1 | UAAAAAGUUGCAUGGUGCUGGUG | 1129 |
| AD-65761 | A-131841.1 | CACCAGCACCAUGCAACUUUU | 1084 | A-131842.1 | AAAAGUUGCAUGGUGCUGGUGCG | 1130 |
| AD-65786 | A-131849.1 | CACCAUGCAACUUUUUCACCU | 1085 | A-131850.1 | AGGUGAAAAGUUGCAUGGUGCU | 1131 |
| AD-65785 | A-131835.1 | CAAUGUCAACGACCGACCUUA | 1086 | A-131836.1 | UAAGGUCGGUCGUUGACAUUGCA | 1132 |
| AD-65787 | A-131863.1 | CGCUUCACCUCUGCACGUCGA | 1087 | A-131864.1 | UCGACGUGCAGAGGUGAAGCGAA | 1133 |
| AD-65770 | A-131845.1 | ACCUUGAGGCAUACUUCAAAG | 1088 | A-131846.1 | CUUUGAAGUAUGCCUCAAGGUCG | 1134 |
| AD-65766 | A-131843.1 | CCGACCUUGAGGCAUACUUCA | 1089 | A-131844.1 | UGAAGUAUGCCUCAAGGUCGGUC | 1135 |
| AD-61555 | A-123521.2 | GACCUUGAGGCAUACUUCAAA | 1090 | A-123522.2 | UUUGAAGUAUGCCUCAAGGUCGG | 1136 |
| AD-65762 | A-131855.1 | ACCGACCUUGAGGCAUACUUA | 1091 | A-131856.1 | UAAGUAUGCCUCAAGGUCGGUCG | 1137 |
| AD-65755 | A-131827.1 | UCGCAUGGAGACCACCGUGAA | 1092 | A-131828.1 | UUCACGGUGGUCUCCAUGCGACG | 1138 |
| AD-65788 | A-131811.1 | UUACAUAAGAGGACUCUUGGA | 1093 | A-131812.1 | UCCAAGAGUCCUCUUAUGUAAGA | 1139 |
| AD-65768 | A-131803.1 | UCUUACAUAAGAGGACUCUUA | 1094 | A-131804.1 | UAAGAGUCCUCUUAUGUAAGACC | 1140 |
| AD-61561 | A-123523.2 | ACUUCAAAGACUGUUUGUUUA | 1095 | A-123524.2 | UAAACAAACAGUCUUUGAAGUAU | 1141 |
| AD-65764 | A-131801.1 | UACUUCAAAGACUGUUUGUUU | 1096 | A-131802.1 | AAACAAACAGUCUUUGAAGUAUG | 1142 |
| AD-65753 | A-131799.1 | AUACUUCAAAGACUGUUUGUU | 1097 | A-131800.1 | AACAAACAGUCUUUGAAGUAUGC | 1143 |
| AD-65765 | A-131817.1 | UUGUUUAAAGACUGGGAGGAA | 1098 | A-131818.1 | UUCCUCCCAGUCUUUAAACAAAC | 1144 |
| AD-65769 | A-131819.1 | GCAUACUUCAAAGACUGUUUA | 1099 | A-131820.1 | UAAACAGUCUUUGAAGUAUGCCU | 1145 |
| AD-65759 | A-131815.1 | CAAAGACUGUUUGUUUAAAGA | 1100 | A-131816.1 | UCUUUAAACAAACAGUCUUUGAA | 1146 |
| AD-65774 | A-131831.1 | AGACUGUUUGUUUAAAGACUA | 1101 | A-131832.1 | UAGUCUUUAAACAAACAGUCUUU | 1147 |
| AD-65778 | A-131807.1 | GUUUGUUUAAAGACUGGGAGA | 1102 | A-131808.1 | UCUCCCAGUCUUUAAACAAACAG | 1148 |

TABLE 22-continued

Unmodified Sense and Antisense Strand Sequences of HBV dsRNAs

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-65773 | A-131805.1 | GGGGGAGGAGAUUAGAUUAAA | 1103 | A-131806.1 | UUUAAUCUAAUCUCCUCCCCAA | 1149 |
| AD-65789 | A-131825.1 | GGGGAGGAGAUUAGAUUAAAG | 1104 | A-131826.1 | CUUUAAUCUAAUCUCCUCCCCA | 1150 |
| AD-65783 | A-131809.1 | GUUGGGGAGGAGAUUAGAUU | 1105 | A-131810.1 | AAUCUAAUCUCCUCCCCAACUC | 1151 |
| AD-65754 | A-131813.1 | UUGGGGGAGGAGAUUAGAUUA | 1106 | A-131814.1 | UAAUCUAAUCUCCUCCCCAACU | 1152 |
| AD-65779 | A-131821.1 | GGGAGGAGAUUAGAUUAAAGA | 1107 | A-131822.1 | UCUUUAAUCUAAUCUCCUCCCC | 1153 |
| AD-65791 | A-131851.1 | UUAGAUUAAAGGUCUUUGUAA | 1108 | A-131852.1 | UUACAAAGACCUUUAAUCUAAUC | 1154 |
| AD-65760 | A-131829.1 | UAGAUUAAAGGUCUUUGUACU | 1109 | A-131830.1 | AGUACAAAGACCUUUAAUCUAAU | 1155 |
| AD-65784 | A-131823.1 | AUUAGAUUAAAGGUCUUUGUA | 1110 | A-131824.1 | UACAAAGACCUUUAAUCUAAUCU | 1156 |
| AD-65757 | A-131853.1 | GAGGAGAUUAGAUUAAAGGUA | 1111 | A-131854.1 | UACCUUUAAUCUAAUCUCCUCCC | 1157 |
| AD-65775 | A-131847.1 | GGACUCUUGGACUCUCUGCAA | 1112 | A-131848.1 | UUGCAGAGAGUCCAAGAGUCCUC | 1158 |
| AD-65780 | A-131833.1 | ACUCUUGGACUCUCUGCAAUA | 1113 | A-131834.1 | UAUUGCAGAGAGUCCAAGAGUCC | 1159 |
| AD-65756 | A-131839.1 | AGAUUAAAGGUCUUUGUACUA | 1114 | A-131840.1 | UAGUACAAAGACCUUUAAUCUAA | 1160 |

TABLE 23

Unmodified Sense and Antisense Strand Sequences of HBV dsRNAs

| Duplex ID | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-65776 | A-131859.1 | UfsgsUfgCfaCfuUfCfGfcUfuCfaCfcUfcUfL96 | 1161 | A-131860.1 | asGfsaGfgUfgAfaGfcgaAfgUfgCfaCfascsg | 1207 |
| AD-65782 | A-131877.1 | UfsgsCfaCfuUfcGfCfUfuCfaCfcUfcUfgAfL96 | 1162 | A-131878.1 | usCfsaGfaGfgUfgAfagcGfaAfgUfgCfascsa | 1208 |
| AD-65792 | A-131865.1 | GfsusGfuGfcAfcUfUfCfgCfuUfcAfcCfuAfL96 | 1163 | A-131866.1 | usAfsgGfuGfaAfgCfgaaGfuGfcAfcAfcsgsg | 1209 |
| AD-65781 | A-131861.1 | CfsgsUfgUfgCfaCfUfUfcGfcUfuCfaCfcUfL96 | 1164 | A-131862.1 | asGfsgUfgAfaGfcGfaagUfgCfaCfaCfgsgsu | 1210 |
| AD-64304 | A-128443.6 | GfsusGfcAfcUfuCfGfCfuUfcAfcCfuCfuAfL96 | 1165 | A-128444.5 | usAfsgAfgGfuGfaAfgcgAfaGfuGfcAfcsasc | 1211 |
| AD-65771 | A-131857.1 | CfscsGfuGfuGfcAfCfUfuCfgCfuUfcAfcAfL96 | 1166 | A-131858.1 | usGfsuGfaAfgCfgAfaguGfcAfcAfcGfgsusc | 1212 |
| AD-65758 | A-131867.1 | CfsasCfuUfcGfcUtUfCfaCfcUfcUfgCfaAfL96 | 1167 | A-131868.1 | usUfsgCfaGfaGfgUfgaaGfcGfaAfgUfgscsa | 1213 |
| AD-65777 | A-131875.1 | AfscsUfuCfgCfuUfCfAfcCfuCfuGfcAfcAfL96 | 1168 | A-131876.1 | usGfsuGfcAfgAfgGfugaAfgCfgAfaGfusgsc | 1214 |
| AD-61567 | A-123525.2 | GfsgsCfuGfuAfgGfCfAfuAfaAfuUfgGfuAfL96 | 1169 | A-123526.2 | usAfscCfaAfuUfuAfugcCfuAfcAfgCfcsusc | 1215 |
| AD-65772 | A-131873.1 | UfsusCfgCfuUfcAfCfCfuCfuGfcAfcGfuAfL96 | 1170 | A-131874.1 | usAfscGfuGfcAfgAfgguGfaAfgCfgAfasgsu | 1216 |
| AD-65767 | A-131871.1 | UfscsGfcUfuCfaCfCfUfcUfgCfaCfgUfcAfL96 | 1171 | A-131872.1 | usGfsaCfgUfgCfaGfaggUfgAfaGfcGfasasg | 1217 |
| AD-65763 | A-131869.1 | CfsusUfcGfcUfuCfAfCfcUfcUfgCfaCfgUfL96 | 1172 | A-131870.1 | asCfsgUfgCfaGfaGfgugAfaGfcGfaAfgsusg | 1218 |
| AD-64281 | A-128395.3 | CfscsCfcGfuCfuGfUfGfcCfuUfcUfcAfuAfL96 | 1173 | A-128396.2 | usAfsuGfaGfaAfgGfcacAfgAfcGfgGfgsasg | 1219 |
| AD-64311 | A-128391.3 | CfscsGfuCfuGfuGfCfCfuUfcUfcAfuCfuAfL96 | 1174 | A-128392.2 | usAfsgAfuGfaGfaAfggcAfcAfgAfcGfgsgsg | 1220 |
| AD-65790 | A-131837.1 | CfscsAfgCfaCfcAfUfGfcAfaCfuUfuUfuAfL96 | 1175 | A-131838.1 | usAfsaAfaAfgUfuGfcauGfgUfgCfuGfgsusg | 1221 |
| AD-65761 | A-131841.1 | CfsasCfcAfgCfaCfCfAfuGfcAfaCfuUfuUfL96 | 1176 | A-131842.1 | asAfsaAfgUfuGfcAfuggUfgCfuGfgUfgscsg | 1222 |
| AD-65786 | A-131849.1 | CfsasCfcAfuGfcAfAfCfuUfuUfuCfaCfcUfL96 | 1177 | A-131850.1 | asGfsgUfgAfaAfaAfguuGfcAfuGfgUfgscsu | 1223 |
| AD-65785 | A-131835.1 | CfsasAfuGfuCfaAfCfGfaCfcGfaCfcUfuAfL96 | 1178 | A-131836.1 | usAfsaGfgUfcGfgUfcguUfgAfcAfuUfgscsa | 1224 |
| AD-65787 | A-131863.1 | CfsgsCfuUfcAfcCtUfCfuGfcAfcGfuCfgAfL96 | 1179 | A-131864.1 | usCfsgAfcGfuGfcAfgagGfuGfaAfgCfgsasa | 1225 |
| AD-65770 | A-131845.1 | AfscsCfuUfgAfgGfCfAfuAfcUfuCfaAfaGfL96 | 1180 | A-131846.1 | csUfsuUfgAfaGfuAfugcCfuCfaAfgGfuscsg | 1226 |
| AD-65766 | A-131843.1 | CfscsGfaCfcUfuGfAfGfgCfaUfaCfuUfcAfL96 | 1181 | A-131844.1 | usGfsaAfgUfaUfgCfcucAfaGfgUfcGfgsusc | 1227 |
| AD-61555 | A-123521.2 | GfsasCfcUfuGfaGfGfCfaUfaCfuUfcAfaAfL96 | 1182 | A-123522.2 | usUfsuGfaAfgUfaUfgccUfcAfaGfgUfcsgsg | 1228 |
| AD-65762 | A-131855.1 | AfscsCfgAfcCfuUfGfAfgGfcAfuAfcUfuAfL96 | 1183 | A-131856.1 | usAfsaGfuAfuGfcCfucaAfgGfuCfgGfuscsg | 1229 |

TABLE 23-continued

| Unmodified Sense and Antisense Strand Sequences of HBV dsRNAs | | | | | | |
|---|---|---|---|---|---|---|
| Duplex ID | Sense Oligo Name | Sense Sequence (5' to 3') | SEQ ID NO: | Antisense Oligo Name | Antisense Sequence (5' to 3') | SEQ ID NO: |
| AD-65755 | A-131827.1 | UfscsGfcAfuGfgAfGfAfcCfaCfcGfuGfaAfL96 | 1184 | A-131828.1 | usUfscAfcGfgUfgGfucuCfcAfuGfcGfascsg | 1230 |
| AD-65788 | A-131811.1 | UfsusAfcAfuAfaGfAfGfgAfcUfcUfuGfgAfL96 | 1185 | A-131812.1 | usCfscAfaGfaGfuCfcucUfuAfuGfuAfasgsa | 1231 |
| AD-65768 | A-131803.1 | UfscsUfuAfcAfuAfAfGfaGfgAfcUfcUfuAfL96 | 1186 | A-131804.1 | usAfsaGfaGfuCfcUfcuuAfuGfuAfaGfascsc | 1232 |
| AD-61561 | A-123523.2 | AfscsUfuCfaAfaGfAfCfuGfuUfuGfuUfuAfL96 | 1187 | A-123524.2 | usAfsaAfcAfaAfcAfgucUfuUfgAfaGfusasu | 1233 |
| AD-65764 | A-131801.1 | UfsasCfuUfcAfaAfGfAfcUfgUfuUfgUfuUfL96 | 1188 | A-131802.1 | asAfsaCfaAfaCfaGfucuUfuGfaAfgUfasusg | 1234 |
| AD-65753 | A-131799.1 | AfsusAfcUfuCfaAfAfGfaCfuGfuUfuGfuUfL96 | 1189 | A-131800.1 | asAfscAfaAfcAfgUfcuuUfgAfaGfuAfusgsc | 1235 |
| AD-65765 | A-131817.1 | UfsusGfuUfuAfaAfGfAfcUfgGfgAfgGfaAfL96 | 1190 | A-131818.1 | usUfscCfuCfcCfaGfucuUfuAfaAfcAfasasc | 1236 |
| AD-65769 | A-131819.1 | GfscsAfuAfcUfuCfAfAfaGfaCfuGfuUfuAfL96 | 1191 | A-131820.1 | usAfsaAfcAfgUfcUfuugAfaGfuAfuGfcscsu | 1237 |
| AD-65759 | A-131815.1 | CfsasAfaGfaCfuGfUfUfuGfuUfuAfaAfgAfL96 | 1192 | A-131816.1 | usCfsuUfuAfaAfcAfaacAfgUfcUfuUfgsasa | 1238 |
| AD-65774 | A-131831.1 | AfsgsAfcUfgUfuUfGfUfuUfaAfaGfaCfuAfL96 | 1193 | A-131832.1 | usAfsgUfcUfuUfaAfacaAfaCfaGfuCfususu | 1239 |
| AD-65778 | A-131807.1 | GfsusUfuGfuUfuAfAfAfgAfcUfgGfgAfgAfL96 | 1194 | A-131808.1 | usCfsuCfcCfaGfuCfuuuAfaAfcAfaAfcsasg | 1240 |
| AD-65773 | A-131805.1 | GfsgsGfgGfaGfgAfGfAfuUfaGfaUfuAfaAfL96 | 1195 | A-131806.1 | usUfsuAfaUfcUfaAfucuCfcUfcCfcCfcsasa | 1241 |
| AD-65789 | A-131825.1 | GfsgsGfgAfgGfaGfAfUfuAfgAfuUfaAfaGfL96 | 1196 | A-131826.1 | csUfsuUfaAfuCfuAfaucUfcCfuCfcCfcscsa | 1242 |
| AD-65783 | A-131809.1 | GfsusUfgGfgGfgAfGfGfaGfaUfuAfgAfuUfL96 | 1197 | A-131810.1 | asAfsuCfuAfaUfcUfccuCfcCfcCfaAfcsusc | 1243 |
| AD-65754 | A-131813.1 | UfsusGfgGfgGfaGfGfAfgAfuUfaGfaUfuAfL96 | 1198 | A-131814.1 | usAfsaUfcUfaAfuCfuccUfcCfcCfcAfascsu | 1244 |
| AD-65779 | A-131821.1 | GfsgsGfaGfgAfgAfUfUfaGfaUfuAfaAfgAfL96 | 1199 | A-131822.1 | usCfsuUfuAfaUfcUfaauCfuCfcUfcCfcscsc | 1245 |
| AD-65791 | A-131851.1 | UfsusAfgAfuUfaAfAfGfgUfcUfuUfgUfaAfL96 | 1200 | A-131852.1 | usUfsaCfaAfaGfaCfcuuUfaAfuCfuAfasusc | 1246 |
| AD-65760 | A-131829.1 | UfsasGfaUfuAfaAfGfGfuCfuUfuGfuAfcUfL96 | 1201 | A-131830.1 | asGfsuAfcAfaAfgAfccuUfuAfaUfcUfasasu | 1247 |
| AD-65784 | A-131823.1 | AfsusUfaGfaUfuAfAfAfgGfuCfuUfuGfuAfL96 | 1202 | A-131824.1 | usAfscAfaAfgAfcCfuuuAfaUfcUfaAfuscsu | 1248 |
| AD-65757 | A-131853.1 | GfsasGfgAfgAfuUfAfGfaUfuAfaAfgGfuAfL96 | 1203 | A-131854.1 | usAfscCfuUfuAfaUfcuaAfuCfuCfcUfcscsc | 1249 |
| AD-65775 | A-131847.1 | GfsgsAfcUfcUfuGfGfAfcUfcUfcUfgCfaAfL96 | 1204 | A-131848.1 | usUfsgCfaGfaGfaGfuccAfaGfaGfuCfcsusc | 1250 |
| AD-65780 | A-131833.1 | AfscsUfcUfuGfgAfCfUfcUfcUfgCfaAfuAfL96 | 1205 | A-131834.1 | usAfsuUfgCfaGfaGfaguCfcAfaGfaGfuscsc | 1251 |
| AD-65756 | A-131839.1 | AfsgsAfuUfaAfaGfGfUfcUfuUfgUfaCfuAfL96 | 1206 | A-131840.1 | usAfsgUfaCfaAfaGfaccUfuUfaAfuCfusasa | 1252 |

A single dose screen of these duplexes was performed in Cos7 cells at 1 nm and 50 nm using the Dual-Glo® Luciferase assay described above. The results of the assays are provided in Table 24.

TABLE 24

HBV single dose screen using Dual-Glo Luciferase ® Assay

| DuplexID | 50 nM | STDEV | 1 nM | STDEV |
|---|---|---|---|---|
| AD-65776 | 20.11 | 4.21 | 40.79 | 1.89 |
| AD-65782 | 26.31 | 3.10 | 61.07 | 9.16 |
| AD-65792 | 43.31 | 5.24 | 61.09 | 6.02 |
| AD-65781 | 25.77 | 3.66 | 39.63 | 2.87 |
| AD-64304 | 18.87 | 1.26 | 29.72 | 3.37 |
| AD-65771 | 17.16 | 1.78 | 37.55 | 2.20 |
| AD-65758 | 31.74 | 8.26 | 65.77 | 11.05 |
| AD-65777 | 59.76 | 11.15 | 77.63 | 5.14 |
| AD-61567 | 17.69 | 5.29 | 26.45 | 5.66 |
| AD-65772 | 58.07 | 9.67 | 75.66 | 4.92 |
| AD-65767 | 29.65 | 1.60 | 39.64 | 4.36 |
| AD-65763 | 25.10 | 5.77 | 47.78 | 9.99 |
| AD-64281 | 39.07 | 6.80 | 51.46 | 4.19 |
| AD-64311 | 20.51 | 1.96 | 37.80 | 3.53 |
| AD-65790 | 50.41 | 7.00 | 70.30 | 1.95 |
| AD-65761 | 13.30 | 4.38 | 21.14 | 3.49 |
| AD-65786 | 12.45 | 3.51 | 22.62 | 0.33 |
| AD-65785 | 36.87 | 6.04 | 51.49 | 4.18 |
| AD-65787 | 27.97 | 5.73 | 48.18 | 7.65 |
| AD-65770 | 22.67 | 5.39 | 41.48 | 8.52 |
| AD-65766 | 31.44 | 3.35 | 50.25 | 0.45 |
| AD-61555 | 18.43 | 10.83 | 22.61 | 0.57 |
| AD-65762 | 18.87 | 4.86 | 34.94 | 4.81 |
| AD-65755 | 47.03 | 9.38 | 83.19 | 9.68 |
| AD-65788 | 35.85 | 10.13 | 58.07 | 4.78 |
| AD-65768 | 24.02 | 2.49 | 28.55 | 2.53 |
| AD-61561 | 8.11 | 1.29 | 14.26 | 2.27 |
| AD-65764 | 16.89 | 3.99 | 29.10 | 1.03 |
| AD-65753 | 19.10 | 2.87 | 29.79 | 5.26 |
| AD-65765 | 55.40 | 10.72 | 76.93 | 8.79 |
| AD-65769 | 19.24 | 4.47 | 23.18 | 2.54 |
| AD-65759 | 48.86 | 4.81 | 87.31 | 13.75 |
| AD-65774 | 102.27 | 12.33 | 100.79 | 3.24 |
| AD-65778 | 64.39 | 2.60 | 80.67 | 2.59 |
| AD-65773 | 72.64 | 7.87 | 80.80 | 4.83 |
| AD-65789 | 73.59 | 4.35 | 94.72 | 3.32 |
| AD-65783 | 54.41 | 7.15 | 84.46 | 4.32 |
| AD-65754 | 62.51 | 4.12 | 102.63 | 21.42 |
| AD-65779 | 47.40 | 7.51 | 76.20 | 2.05 |

TABLE 24-continued

HBV single dose screen using Dual-Glo Luciferase ® Assay

| DuplexID | 50 nM | STDEV | 1 nM | STDEV |
|---|---|---|---|---|
| AD-65791 | 12.09 | 0.70 | 19.19 | 3.46 |
| AD-65760 | 13.50 | 4.84 | 25.37 | 2.09 |
| AD-65784 | 19.84 | 1.27 | 31.04 | 3.49 |
| AD-65757 | 22.66 | 3.97 | 24.50 | 5.81 |
| AD-65775 | 47.78 | 3.30 | 58.81 | 3.05 |
| AD-65780 | 29.10 | 2.87 | 42.85 | 2.73 |
| AD-65756 | 10.49 | 1.62 | 19.95 | 2.58 |

Based on these assays, RNAi agents targeting five sites in the HBV X ORF (nucleotides 1551, 1577, 1580, 1806, and 1812 of GenBank Accession No. NC_003977.1 were selected for lead optimization and additional agents were designed and synthesized. These additional agents are evaluated in in vitro assays as described above. A detailed list of the additional unmodified sense and antisense strand sequences targeting the HBV X ORF is shown in Table 25. A detailed list of the additional modified sense and antisense strand sequences targeting the HBV X ORF is shown in Table 26.

These iRNA agents were also assessed for in vivo efficacy using an AAV-HBV mouse model (see, e.g., Yang, et al. (2014) *Cell and Mol Immunol* 11:71). This mouse model exhibits sustained HBV viremia after infection with a recombinant adeno-associated virus (AAV) carrying a replicable HBV genome. Liver expression of the HBV gene in these mice mimics HBV infection in humans and these mice exhibit significant liver inflammation and liver damage, manifested by increased ALT levels, fibrosis and steatosis.

Figure 2:
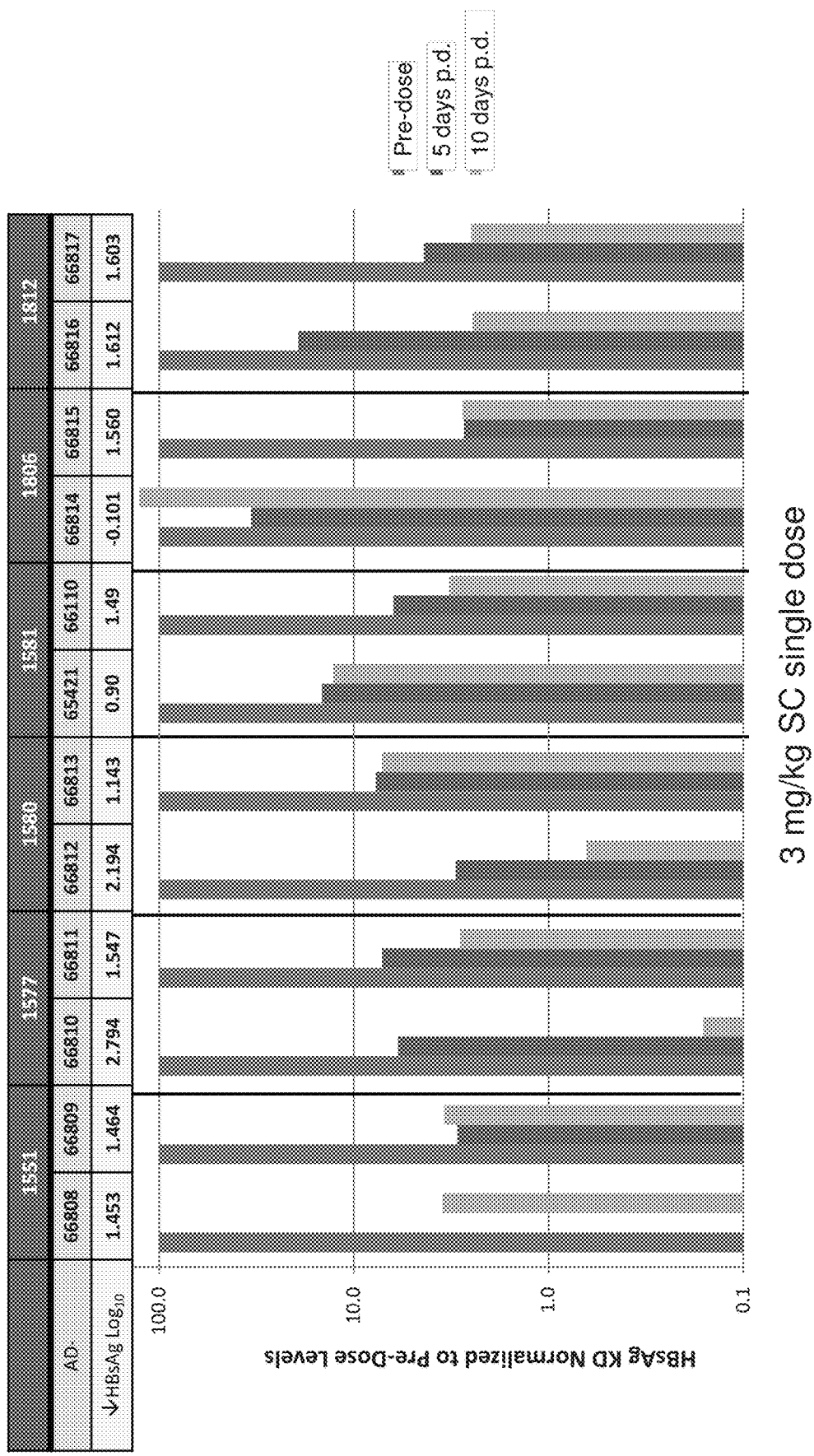
FIG. 2 is a graph depicting the log decrease of HBsAg serum levels normalized to pre-dose HBsAg serum levels following administration of a single 3 mg/kg dose of the indicated iRNA agents.
Figure 3:
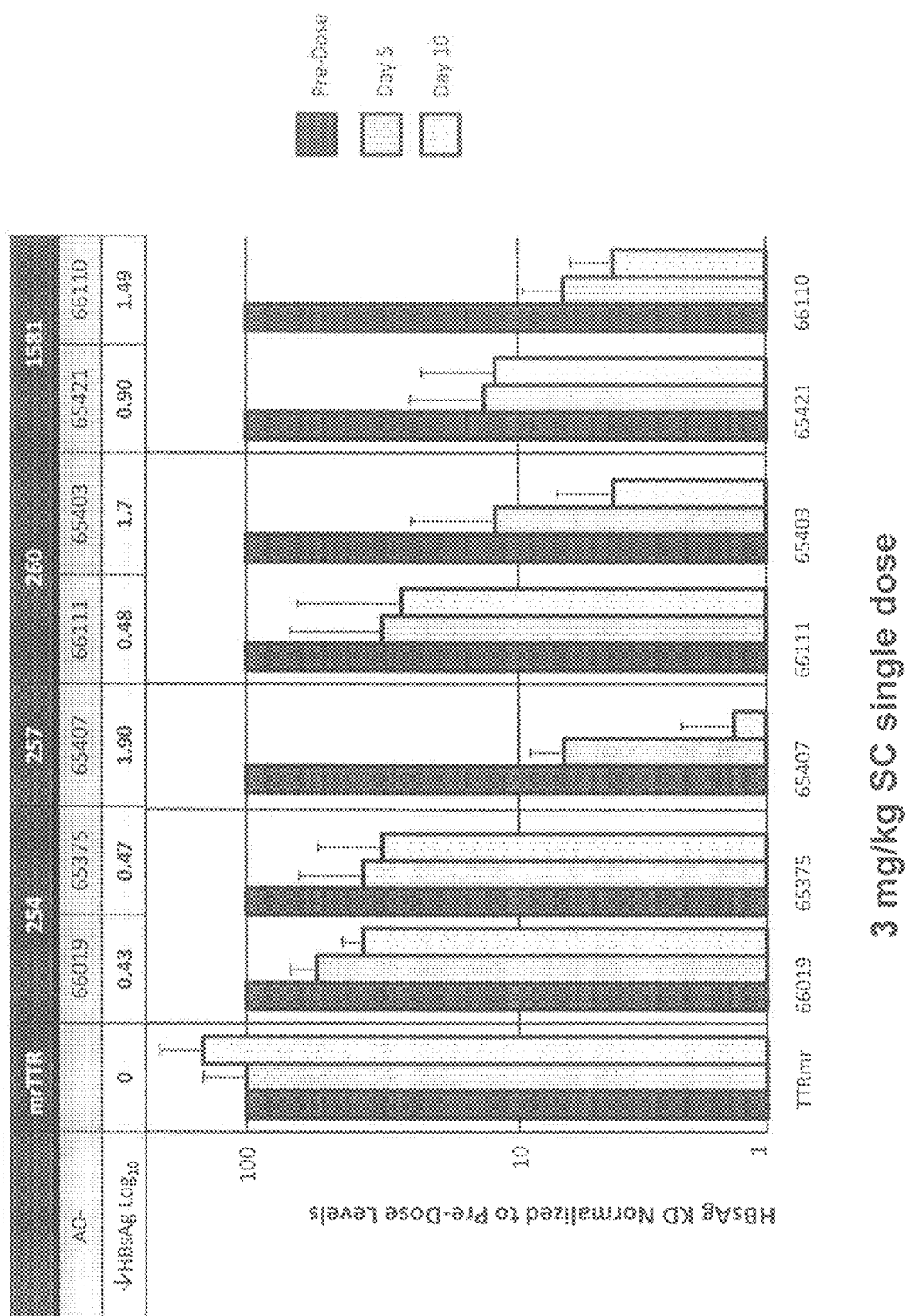
FIG. 3 is a graph depicting the log decrease of HBsAg serum levels normalized to pre-dose HBsAg serum levels following administration of a single 3 mg/kg dose of the indicated iRNA agents.
Figure 4:
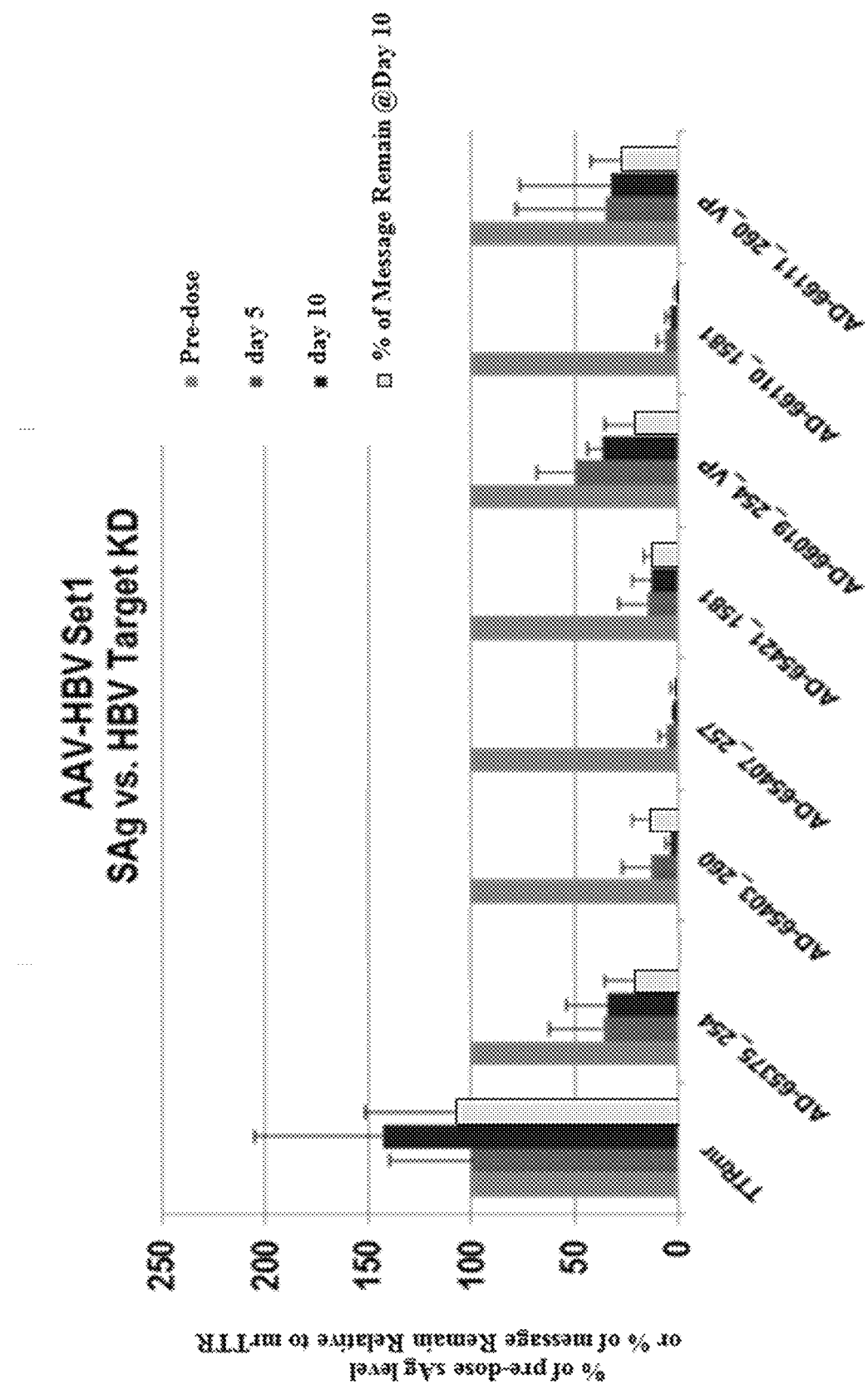
FIG. 4 is a graph depicting the percent of pre-dose HBsAg remaining at days 5 and 10 following administration of a single 3 mg/kg dose of the indicated iRNA agents.
Figure 5:
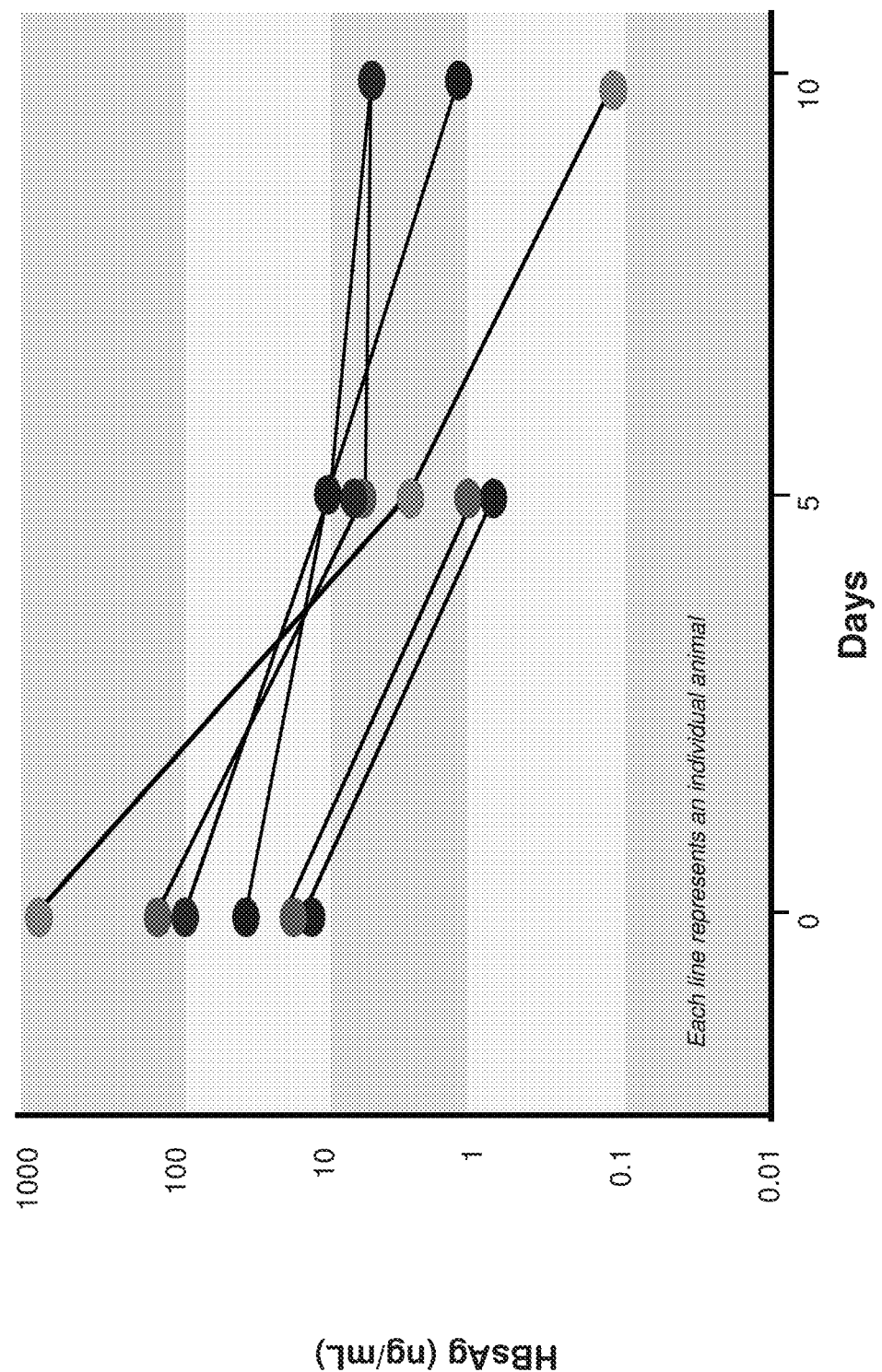
FIG. 5 is a graph depicting the log decrease of HBsAg serum levels normalized to pre-dose HBsAg serum levels following administration of a single 3 mg/kg dose of AD-65403.
Figure 6A:
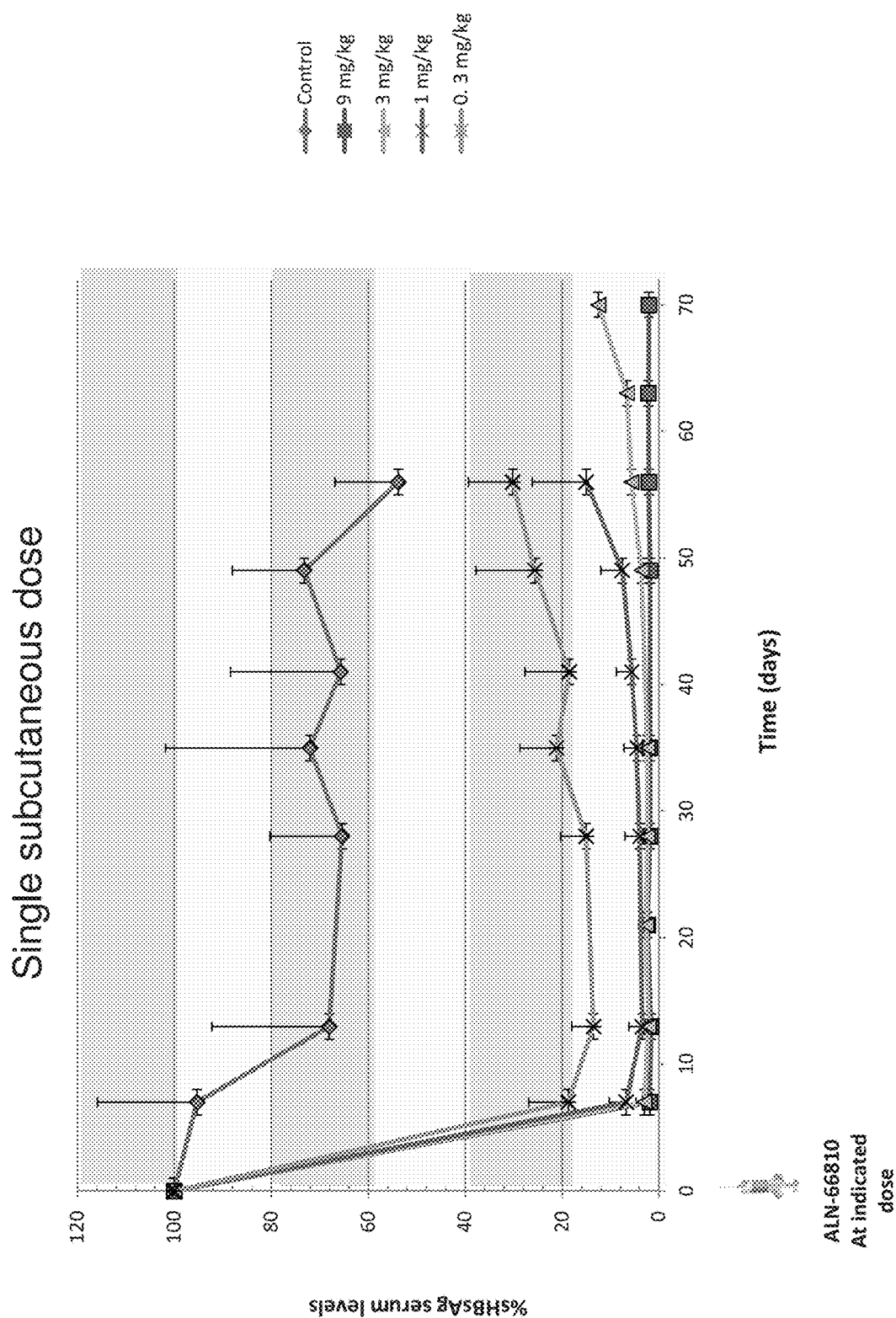
FIG. 6A is a graph depicting the decrease of HBsAg serum levels normalized to pre-dose HBsAg serum levels on a standard linear scale following administration of a single subcutaneous 0.3 mg/kg, 1 mg/kg, 3 mg/kg, or 9 mg/kg dose of AD-66810.
Figure 6B:
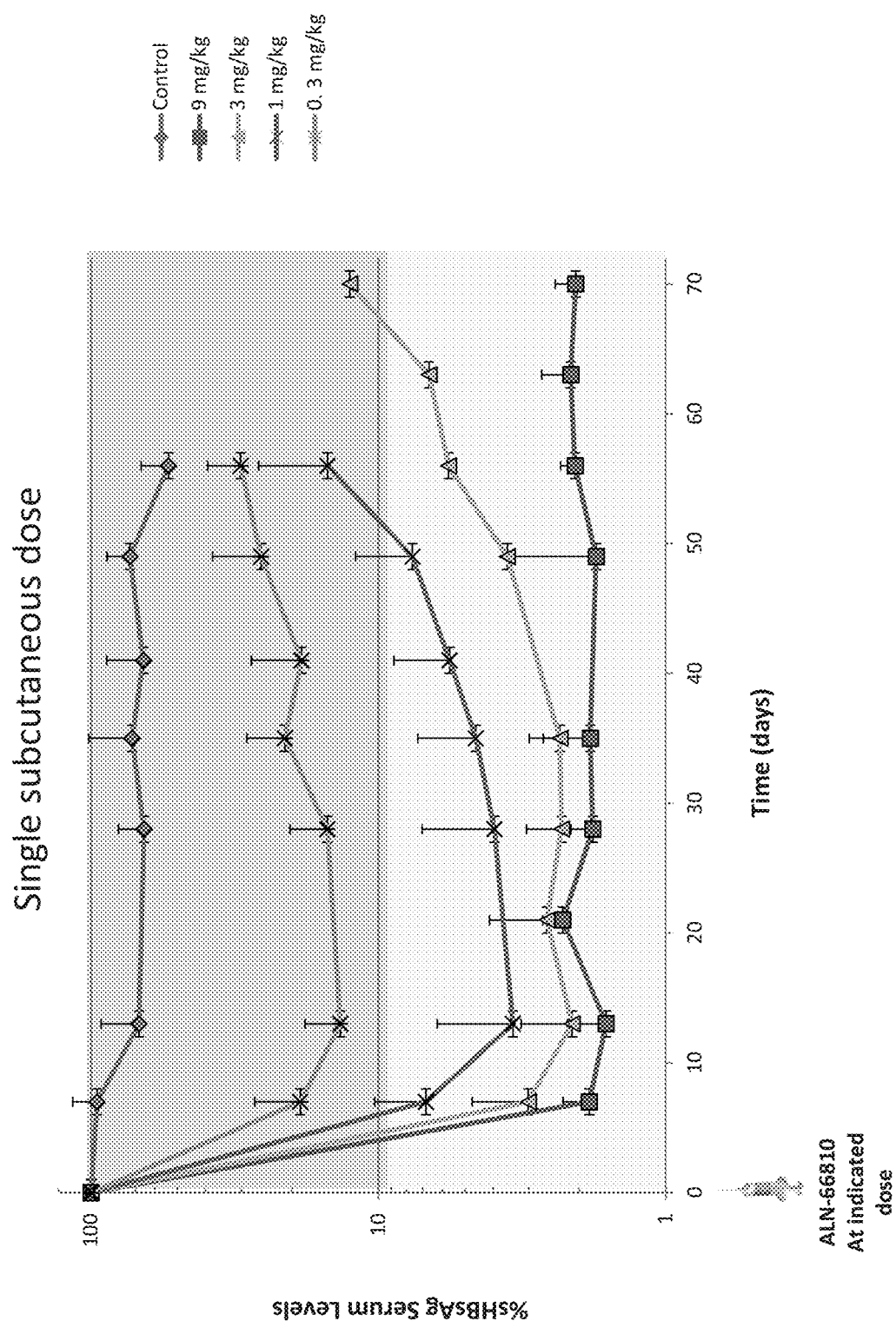
FIG. 6B is a graph depicting the decrease of HBsAg serum levels normalized to pre-dose HBsAg serum levels on a $\log_{10}$ scale following administration of a single subcutaneous 0.3 mg/kg, 1 mg/kg, 3 mg/kg, or 9 mg/kg dose of AD-66810.
Figure 7:
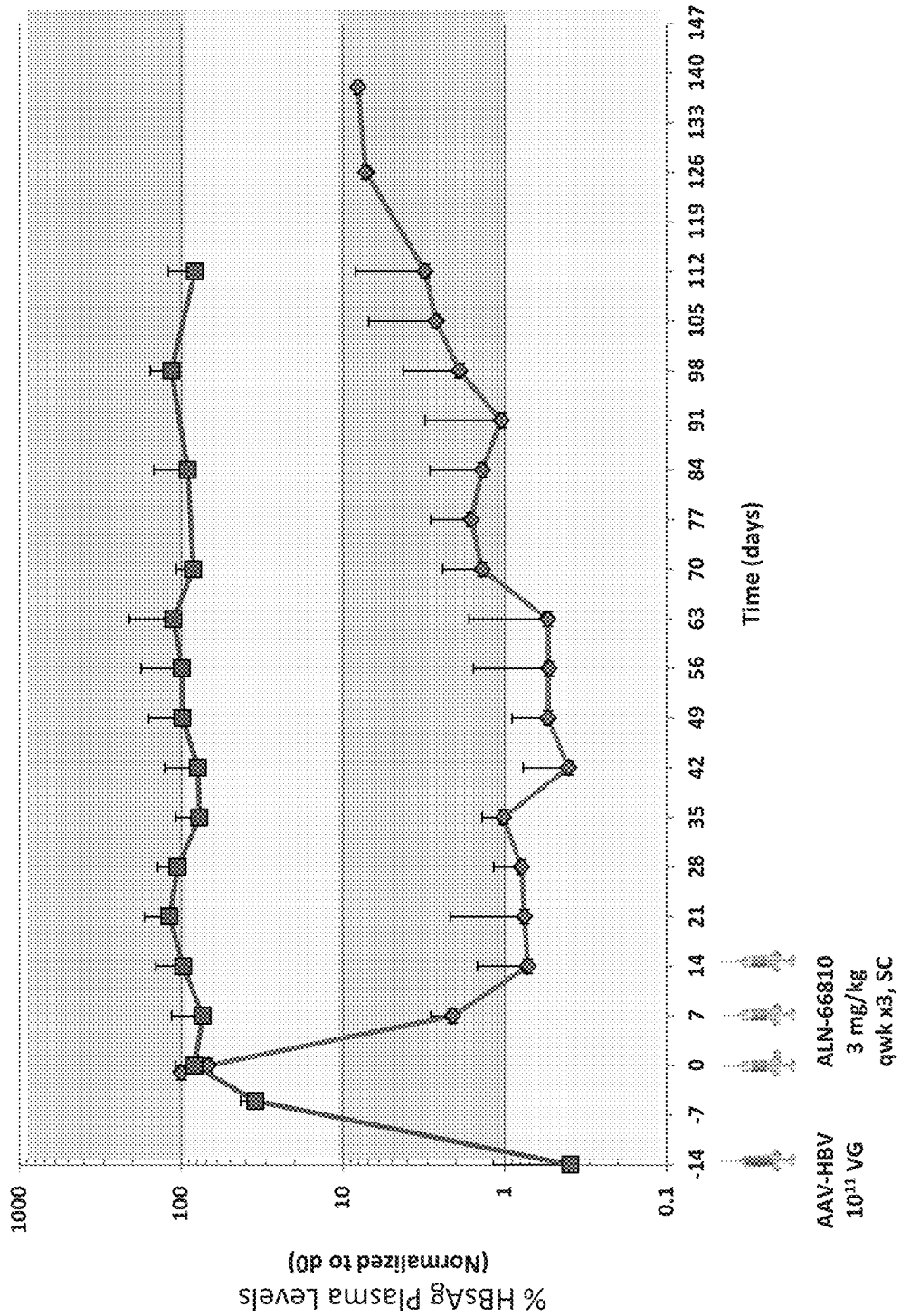
FIG. 7 is a graph depicting the decrease of HBsAg plasma levels normalized to pre-dose HBsAg plasma levels on a $\log_{10}$ scale following administration of three weekly subcutaneous 3 mg/kg doses of AD-66810.

These AAV-HBV mice were subcutaneously administered a single 3 mg/kg dose of AD-66808, AD-66809, AD-66810, AD-66811, AD-66812, AD-66813, AD-66814, AD-66815, AD-66816, and AD-66817 and the level of HBsAg was determined in the serum of the animals pre-dose, and at day 14/15 post-dose. The results of these experiments are provided in FIG. 2 and Table 27 and demonstrate that serum levels of HBsAg are decrease following a single administration of these agents. Table 27 also provides the results of a single dose screen in Cos7 cells transfected with the indicated HBV iRNAs using the Dual-Glo® Luciferase assay, as described above, for the same RNAi agents. Data are expressed as percent of mRNA remaining relative to negative control at 24 hours.

TABLE 25

Unmodified HBV X ORF Sense and Antisense Sequences.

| DuplexID | Sense Sequence Unmodified (5' to 3') | SEQ ID NO: | Antisense Sequence Umodified (5' to 3') | SEQ ID NO: |
|---|---|---|---|---|
| AD-66808 | GUCUGUGCCUUCUCAUCUA | 1253 | UAGAUGAGAAGGCACAGACUU | 1263 |
| AD-66809 | GUCUGUGCCUUCUCAUCUA | 1254 | UAGAUGAGAAGGCACAGACUU | 1264 |
| AD-66810 | GUGUGCACUUCGCUUCACA | 1255 | UGUGAAGCGAAGUGCACACUU | 1265 |
| AD-66811 | GUGUGCACUUCGCUUCACA | 1256 | UGUGAAGCGAAGUGCACACUU | 1266 |
| AD-66812 | UGUGCACUUCGCUUCACCUCU | 1257 | AGAGGUGAAGCGAAGUGCACAUU | 1267 |
| AD-66813 | UGUGCACUUCGCUUCACCUCU | 1258 | AGAGGUGAAGCGAAGUGCACAUU | 1268 |
| AD-66814 | CACCAGCACCAUGCAACUUUU | 1259 | AAAAGUUGCAUGGUGCUGGUGUU | 1269 |
| AD-66815 | CACCAGCACCAUGCAACUUUU | 1260 | AAAAGUUGCAUGGUGCUGGUGUU | 1270 |
| AD-66816 | CACCAUGCAACUUUUUCACCU | 1261 | AGGUGAAAAGUUGCAUGGUGUU | 1271 |
| AD-66817 | CACCAUGCAACUUUUUCACCU | 1262 | AGGUGAAAAGUUGCAUGGUGUU | 1272 |

TABLE 26

Modified HBV X ORF Sense and Antisense Sequences.

| DuplexID | Sense Sequence Unmodified (5' to 3') | SEQ ID NO: | Antisense Sequence Umodified (5' to 3') | SEQ ID NO: |
|---|---|---|---|---|
| AD-66808 | gsuscuGfuGfCfCfuucucaucuaL96 | 1273 | usAfsgauGfaGfAfaggcAfcAfgacsusu | 1283 |
| AD-66809 | gsuscuGfuGfCfCfuucucaucuaL96 | 1274 | UfsAfsgauGfaGfAfaggcAfcAfgacsusu | 1284 |
| AD-66810 | gsusguGfcAfCfCfucgcuucacaL96 | 1275 | usGfsugaAfgCfGfaaguGfcAfcacsusu | 1285 |
| AD-66811 | gsusguGfcAfCfCfucgcuucacaL96 | 1276 | UfsGfsugaAfgCfGfaaguGfcAfcacsusu | 1286 |
| AD-66812 | usgsugcaCfuUfCfGfcuucaccucuL96 | 1277 | asGfsaggUfgAfAfgcgaAfgUfgcacasusu | 1287 |
| AD-66813 | usgsugcaCfuUfCfGfcuucaccucuL96 | 1278 | AfsGfsaggUfgAfAfgcgaAfgUfgcacasusu | 1288 |
| AD-66814 | csasccagCfaCfCfAfugcaacuuuuL96 | 1279 | asAfsaagUfuGfCfauggUfgCfuggugsusu | 1289 |
| AD-66815 | csasccagCfaCfCfAfugcaacuuuuL96 | 1280 | AfsAfsaagUfuGfCfauggUfgCfuggugsusu | 1290 |
| AD-66816 | csasccauGfcAfAfCfuuuuucaccuL96 | 1281 | asGfsgugAfaAfAfaguuGfcAfuggugsusu | 1291 |
| AD-66817 | csasccauGfcAfAfCfuuuuucaccuL96 | 1282 | AfsGfsgugAfaAfAfaguuGfcAfuggugsusu | 1292 |

TABLE 27

| Site (# vRNA[1]) | Duplex ID | In vitro $IC_{50}$ Luc HBV (nM) | $Log_{10}$ HBsAg KD In Vivo @ 3 mg/kg |
|---|---|---|---|
| 1551 | AD-66808 | 0.187 | 2.4 |
| (4) | AD-66809 | 0.014 | 1.46 |
| 1577 | AD-66810 | 0.290 | 1.7 |
| (4) | AD-66811 | 0.029 | 1.3 |
| 1580 | AD-66812 | 0.795 | 2.19 |
| (4) | AD-66813 | 0.074 | >>1.14 |
| 1806 | AD-66814 | 0.0002 | 1.5 |
| e.g., every five days post-dose until the HBsAg level returns to baseline for all animals. Administration of AD-65403, AD-66810, or a combination of AD-65403 and AD-66810 results in sustained and specific knockdown of serum HBsAg.

Example 8. Treatment of HDV Infection with iRNA Agents Targeting Hepatitis B Virus Hepatitis Delta virus (HDV) is a defective RNA virus which requires the help of HBV for its replication and assembly of new virions. Therefore, HDV is only infectious in the presence of active HBV infection. The HDV genome contains only one actively transcribed open reading frame which encodes two isoforms of hepatitis delta antigen. Post-translational modifications of small and large delta antigens (S-HDAg and L-HDAg) involving phosphorylation and isoprenylation respectively confer these antigens their specific properties. Effective treatment of HBV will also ameliorate HDV infection.

A chimpanzee model of HDV is known. A subset of iRNA agents of the invention are assessed for in vivo efficacy using the chimpanzee HDV model or other appropriate model of HDV. HDV infected chimpanzees are administered one or more doses of AD-65403 and AD-66810, either alone or in combination with each other. Exemplary dosing regimens include a single 3 mg/kg total iRNA agent dose of AD-65403, AD-66810, or a combination of AD-65403 and AD-66810 (i.e., 1.5 mg/kg of each iRNA agent for a total of 3 mg/kg of iRNA agent administered as an admixture or as two separate doses); or a single dose of 0.3 mg/kg, 1 mg/kg, 3 mg/kg, or 9 mg/kg total iRNA agent dose of AD-65403, AD-66810, or a combination of AD-65403 and AD-66810. Exemplary multi-dose regimens include, for example, three weekly doses, one per week using any of the dosage levels provided in the exemplary single dose regimens. An appropriate control iRNA is also administered as a control as is routine in the art.

The level of one or more of S-HDAg, L-HDAg, and HDV RNA, optionally in combination with HBsAg, is determined in the serum of the animals pre-dose and at predetermined intervals post-dose, e.g., every five days to monitor antigen or RNA levels. Administration of AD-65403, AD-66810, or a combination of AD-65403 and AD-66810 results in sustained and specific knockdown of serum HBsAg resulting in amelioration of HDV as demonstrated by, for example, a statistically significant decrease in one or more of S-HDAg, L-HDAg, and HDV RNA. These results demonstrate that administration of one or both of AD-65403 and AD-66810 is effective in the treatment of HDV.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A double stranded RNAi agent for inhibiting expression of hepatitis B virus (HBV) in a cell, wherein said double stranded RNAi agent comprises a sense strand and an antisense strand forming a double-stranded region,
    wherein said sense strand comprises 5'-GUGUGCAC-UUCGCUUCACA-3' (SEQ IDNO:39) and said antisense strand comprises 5'-UGUGAAGCGAAGUG-CACACUU-3' (SEQ ID NO:40),
        wherein substantially all of the nucleotides of said sense strand and substantially all of the nucleotides of said antisense strand are modified nucleotides,
        wherein said sense strand is conjugated to a ligand attached at the 3'-terminus, and
    wherein the ligand is one or more GalNAc derivatives and it is attached to the 3' terminus of said sense strand through a bivalent or trivalent branched linker.

2. The double stranded RNAi agent of claim 1, wherein all of the nucleotides of said sense strand and all of the nucleotides of said antisense strand are modified nucleotides.

3. The double stranded RNAi agent of claim 1, wherein at least one of said modified nucleotides is selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

4. The double stranded RNAi agent of claim 1, wherein at least one strand comprises a 3' overhang of at least 1 nucleotide; or at least one strand comprises a 3' overhang of at least 2 nucleotides.

5. The double stranded RNAi agent of claim 1, wherein each strand has 19-30 nucleotides.

6. The double stranded RNAi agent of claim 1, wherein the ligand is

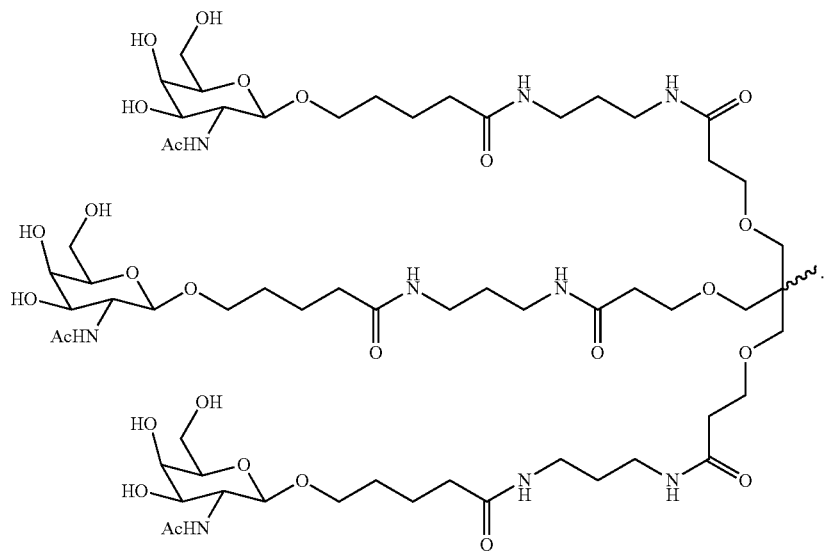 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

7. The double stranded RNAi agent of claim 1, wherein the ligand attached through a bivalent or trivalent branched linker is

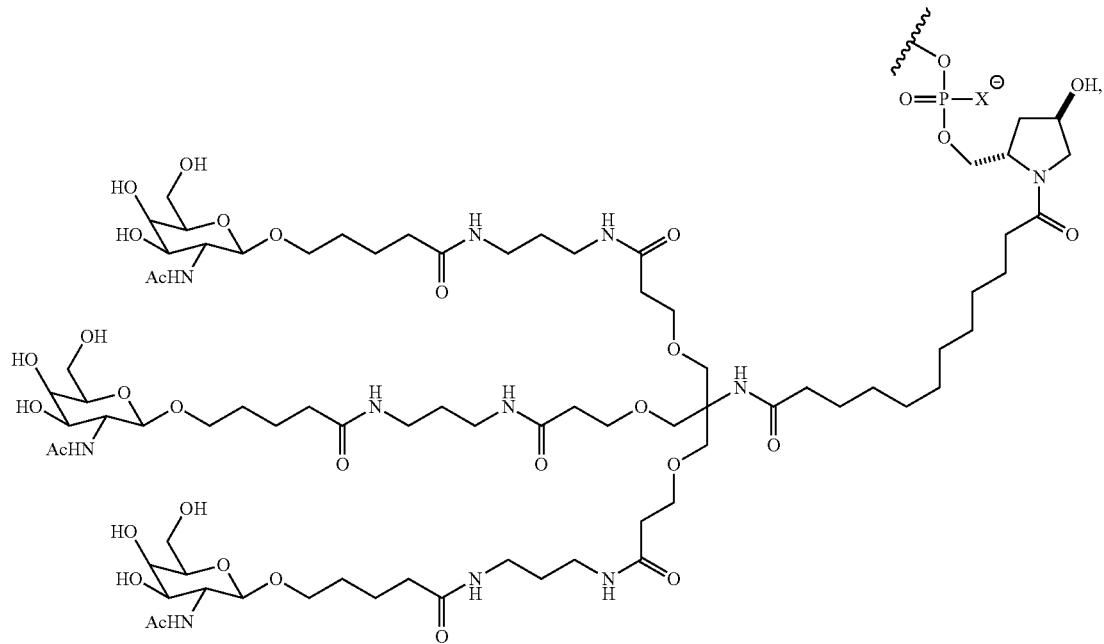

wherein X is O or S.

8. The double stranded RNAi agent of claim 1, wherein at least one of said modified nucleotides is selected from the group consisting of a 2'-O-methyl modified nucleotide, a 2'-fluoro modified nucleotide, and a nucleotide comprising a phosphorothioate group.

9. The double stranded RNAi agent of claim 1, wherein the sense strand comprises the nucleotide sequence of 5'-gsusguGfcAfCfUfucgcuucaca-3' (SEQ ID NO:41) and the antisense strand comprises the nucleotide sequence of 5'-usGfsugaAfgCfGfaaguGfcAfcacsusu-3' (SEQ ID NO:42), wherein a, g, c, and u are 2'-O-methyl (2'-OMe) A, 2'-OMe G, 2'-OMe C, and 2'-OMe U, respectively; Af, Cf, Gf, and Uf are 2'-fluoro A, 2'-fluoro C, 2'-fluoro G, and 2'-fluoro U, respectively; and s is a phosphorothioate linkage.

10. The double stranded RNAi agent of claim 9, wherein the ligand is

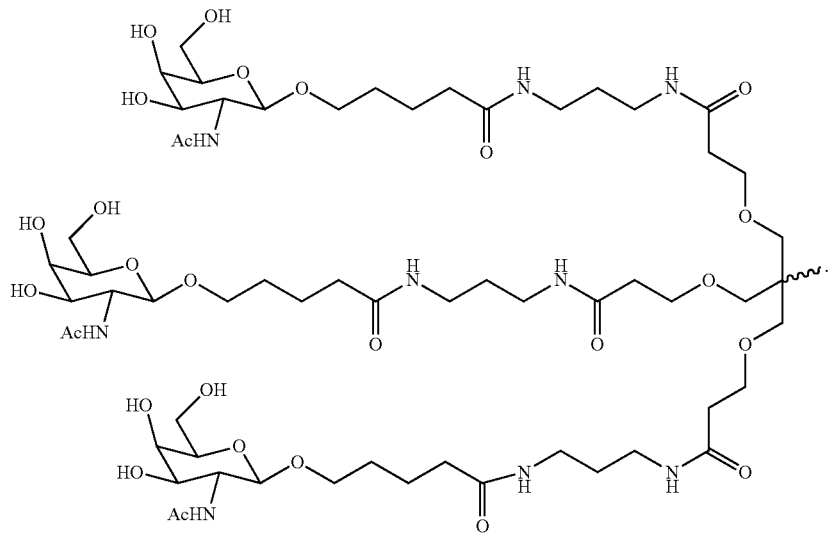 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

11. The double stranded RNAi agent of claim 10, wherein the RNAi agent ligand attached through a bivalent or trivalent branched linker is

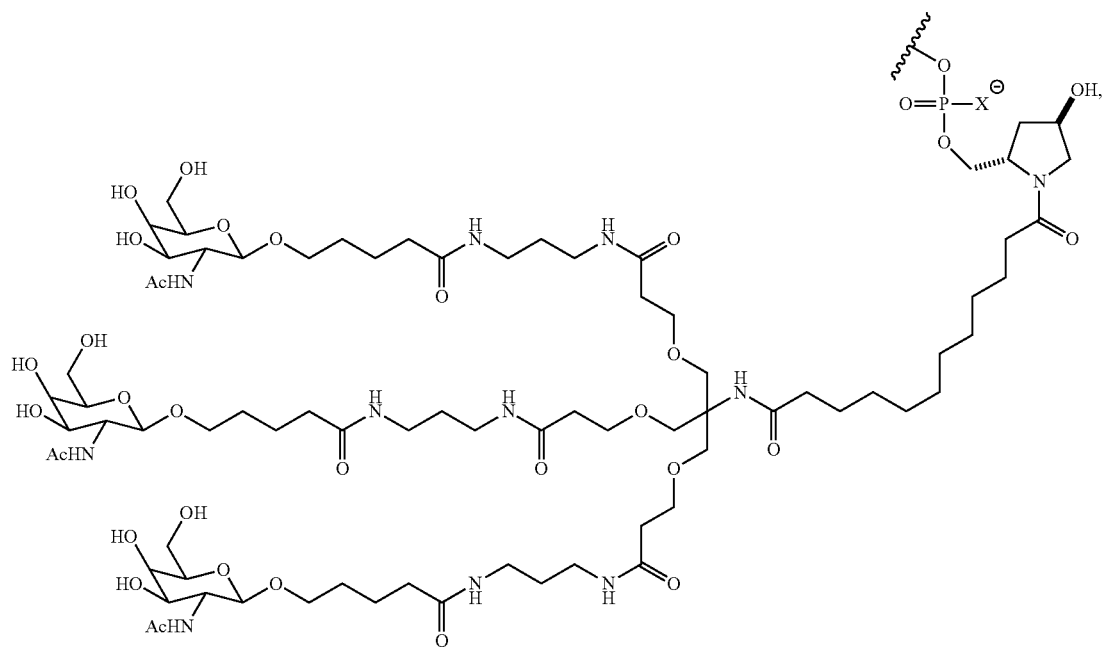

wherein X is O or S.

12. A pharmaceutical composition comprising the double stranded RNAi agent of claim 1 or 9 and a pharmaceutically acceptable carrier.

13. A method of inhibiting Hepatitis B virus (HBV) gene expression and/or replication of HBV in a cell, the method comprising:
   (a) contacting the cell with the double stranded RNAi agent of claim 1 or 9; and (b) maintaining the cell produced in step (a) for a time sufficient to obtain degradation of the mRNA transcript of an HBV gene, thereby inhibiting expression of the HBV gene and/or replication of the HBV in the cell.

14. The method of claim 13, wherein the HBV gene expression is inhibited by at least about 30%, about 40%, about 50%, about 60%, about 70%, about 80%, about 90%, about 95%, about 98% or about 100%.

15. A method of reducing the viral load of Hepatitis B virus (HBV) in a subject infected with HBV, comprising administering to the subject a therapeutically effective amount of the double stranded RNAi agent of claim 1 or 9, thereby reducing the viral load of HBV in the subject.

16. A method of treating a subject having a Hepatitis 13 virus (HBV) infection, comprising administering to the subject a therapeutically effective amount of the double stranded RNAi agent of claim 1 or 9, thereby treating said subject.

17. The method of claim 16, wherein the double stranded RNAi agent is administered to the subject at a weight based dose of about 0.01 mg/kg to about 10 mg/kg or about 0.5 mg/kg to about 50 mg/kg; a weight based dose of about 10 mg/kg to about 30 mg/kg; a weight based dose of about 3 mg/kg; a weight based dose of about 10 mg/kg; or a fixed dose of about 50 mg to 200 mg.

18. The method of claim 16, wherein the double stranded RNAi agent is administered subcutaneously; or intravenously.

19. The method of claim 16, further comprising administering to the subject an additional therapeutic agent.

20. The method of claim 19, wherein the additional therapeutic agent is selected from the group consisting of an antiviral agent, a reverse transcriptase inhibitor, an immune stimulator, a therapeutic vaccine, a viral entry inhibitor, an oligonucleotide that inhibits the secretion or release of HbsAg, a capsid inhibitor, a covalently closed circular (ccc) HBV DNA inhibitor, and a combination of any of the foregoing.

21. A method of reducing the level of a Hepatitis D virus (HDV) antigen in a subject infected with HDV, comprising administering to the subject a therapeutically effective amount of the double stranded RNAi agent of claim 1 or 11, thereby reducing the level of the HDV antigen in the subject.

22. A pharmaceutical composition comprising the double stranded RNAi agent of claim 10 or 11 and a pharmaceutically acceptable carrier.

23. A method of treating a subject having an HBV infection, comprising administering to the subject a therapeutically effective amount of the double stranded RNAi agent of claim 10 or 11, thereby treating said subject.

24. A method of treating a subject having an HBV infection, comprising administering to the subject a therapeutically effective amount of the pharmaceutical composition of claim 22, thereby treating said subject.

* * * * *

SEQUENCE LISTING

```
<160> NUMBER OF SEQ ID NOS: 1292

<210> SEQ ID NO 1
<211> LENGTH: 3215
<212> TYPE: DNA
<213> ORGANISM: Hepatitis B virus

<400> SEQUENCE: 1
ctccacaaca ttccaccaag ctctgctaga tcccagagtg aggggcctat attttcctgc     60
tggtggctcc agttccggaa cagtaaaccc tgttccgact actgcctcac ccatatcgtc    120
aatcttctcg aggactgggg accctgcacc gaacatggag agcacaacat caggattcct    180
aggacccctg ctcgtgttac aggcggggtt tttcttgttg acaagaatcc tcacaatacc    240
acagagtcta gactcgtggt ggacttctct caattttcta gggggagcac ccacgtgtcc    300
tggccaaaat tcgcagtccc caacctccaa tcactcacca acctcttgtc ctccaacttg    360
tcctggctat cgctggatgt gtctgcggcg ttttatcata ttcctcttca tcctgctgct    420
atgcctcatc ttcttgttgg ttcttctgga ctaccaaggt atgttgcccg tttgtcctct    480
acttccagga acatcaacta ccagcacggg accatgcaga acctgcacga ttcctgctca    540
aggaacctct atgtttccct cttgttgctg tacaaaacct tcggacggaa actgcacttg    600
tattcccatc ccatcatcct gggctttcgc aagattccta tgggagtggg cctcagtccg    660
tttctcctgg ctcagtttac tagtgccatt tgttcagtgg ttcgtagggc tttcccccac    720
tgtttggctt tcagctatat ggatgatgtg gtattggggg ccaagtctgt acaacatctt    780
gagtcccttt ttacctctat taccaatttt cttttgtctt tgggtataca tttgaaccct    840
aataaaacca aacgttgggg ctactccctt aacttcatgg gatatgtaat tggaagttgg    900
ggtactttac cgcaggaaca tattgtacaa aaactcaagc aatgttttcg aaaattgcct    960
```

```
gtaaatagac ctattgattg gaaagtatgt caaagaattg tgggtctttt gggctttgct      1020 gccccttta cacaatgtgg ctatcctgcc ttgatgcctt tatatgcatg tatacaatct       1080
aagcaggctt tcactttctc gccaacttac aaggcctttc tgtgtaaaca atatctaaac      1140
ctttaccccg ttgcccggca acggtcaggt ctctgccaag tgtttgctga cgcaaccccc      1200
acgggttggg gcttggccat aggccatcgg cgcatgcgtg gaacctttgt ggctcctctg      1260
ccgatccata ctgcggaact cctagcagct tgttttgctc gcagccggtc tggagcgaaa      1320
cttatcggaa ccgacaactc agttgtcctc tctcggaaat acacctcctt tccatggctg      1380
ctaggctgtg ctgccaactg gatcctgcgc gggacgtcct ttgtctacgt cccgtcggcg      1440
ctgaatcccg cggacgaccc gtctcggggc cgtttgggcc tctaccgtcc ccttcttcat      1500
ctgccgttcc ggccgaccac ggggcgcacc tctctttacg cggtctcccc gtctgtgcct      1560
tctcatctgc cggaccgtgt gcacttcgct tcacctctgc acgtagcatg gagaccaccg      1620
tgaacgccca ccaggtcttg cccaaggtct tacacaagag gactcttgga ctctcagcaa      1680
tgtcaacgac cgaccttgag gcatacttca aagactgttt gtttaaagac tgggaggagt      1740
tgggggagga gattaggtta aaggtctttg tactaggagg ctgtaggcat aaattggtct      1800
gttcaccagc accatgcaac ttttccccct ctgcctaatc atctcatgtt catgtcctac      1860
tgttcaagcc tccaagctgt gccttgggtg gctttgggc atggacattg acccgtataa       1920
agaatttgga gcttctgtgg agttactctc ttttttgcct tctgacttct ttccttctat      1980
tcgagatctc ctcgacaccg cctctgctct gtatcgggag gccttagagt ctccggaaca      2040
ttgttcacct caccatacag cactcaggca agctattctg tgttggggtg agttgatgaa      2100
tctggccacc tgggtgggaa gtaatttgga agacccagca tccagggaat tagtagtcag      2160
ctatgtcaat gttaatatgg gcctaaaaat tagacaacta ttgtggtttc acatttcctg      2220
ccttactttt ggaagagaaa ctgtccttga gtatttggtg tcttttggag tgtggattcg      2280
cactcctccc gcttacagac caccaaatgc ccctatctta tcaacacttc cggaaactac      2340
tgttgttaga cgacgaggca ggtcccctag aagaagaact ccctcgcctc gcagacgaag      2400
gtctcaatcg ccgcgtcgca gaagatctca atctcgggaa tctcaatgtt agtatccctt      2460
ggactcataa ggtgggaaac tttactgggc tttattcttc tactgtacct gtctttaatc      2520
ctgattggaa aactccctcc tttcctcaca ttcatttaca ggaggacatt attaatagat      2580
gtcaacaata tgtgggccct ctgacagtta atgaaaaaag gagattaaaa ttaattatgc      2640
ctgctaggtt ctatcctaac cttaccaaat atttgcccct ggacaaaggc attaaaccgt      2700
attatcctga atatgcagtt aatcattact tcaaaactag gcattattta catactctgt      2760
ggaaggctgg cattctatat aagagagaaa ctacacgcag cgcctcattt tgtgggtcac      2820
catattcttg ggaacaagag ctacagcatg ggaggttggt cttccaaacc tcgacaaggc      2880
atggggacga atctttctgt tcccaatcct ctgggattct ttcccgatca ccagttggac      2940
cctgcgttcg gagccaactc aaacaatcca gattgggact caaccccaa caaggatcac       3000 tggccagagg caaatcaggt aggagcggga gcatttggtc cagggttcac cccaccacac      3060
ggaggccttt tggggtggag ccctcaggct caggcatat tgacaacact gccagcagca       3120
cctcctcctg cctccaccaa tcggcagtca ggaagacagc ctactcccat ctctccacct      3180
ctaagagaca gtcatcctca ggccatgcag tggaa                                 3215
```

<210> SEQ ID NO 2
<211> LENGTH: 3215

```
<212> TYPE: DNA
<213> ORGANISM: Hepatitis B virus

<400> SEQUENCE: 2
ttccactgca tggcctgagg atgactgtct cttagaggtg gagagatggg agtaggctgt      60
cttcctgact gccgattggt ggaggcagga ggaggtgctg ctggcagtgt tgtcaatatg     120
ccctgagcct gagggctcca ccccaaaagg cctccgtgtg gtggggtgaa ccctggacca     180
aatgctcccg ctcctacctg atttgcctct ggccagtgat ccttgttggg gttgaagtcc     240
caatctggat tgtttgagtt ggctccgaac gcagggtcca actggtgatc gggaaagaat     300
cccagaggat tgggaacaga aagattcgtc cccatgcctt gtcgaggttt ggaagaccaa     360
cctcccatgc tgtagctctt gttcccaaga atatggtgac ccacaaaatg aggcgctgcg     420
tgtagtttct ctcttatata gaatgccagc cttccacaga gtatgtaaat aatgcctagt     480
tttgaagtaa tgattaactg catattcagg ataatacggt ttaatgcctt gtccaaggg      540
caaatatttg gtaaggttag gatagaacct agcaggcata attaatttta atctccttt     600
ttcattaact gtcagagggc ccacatattg ttgacatcta ttaataatgt cctcctgtaa     660
atgaatgtga ggaaaggagg gagttttcca atcaggatta aagacaggta cagtagaaga     720
ataaagccca gtaaagtttc ccaccttatg agtccaaggg atactaacat tgagattccc     780
gagattgaga tcttctgcga cgcggcgatt gagaccttcg tctgcgaggc gagggagttc     840
ttcttctagg ggacctgcct cgtcgtctaa caacagtagt ttccggaagt gttgataaga     900
taggggcatt tggtggtctg taagcgggag gagtgcgaat ccacactcca aaagacacca     960
aatactcaag gacagtttct cttccaaaag taaggcagga aatgtgaaac cacaatagtt    1020
gtctaatttt taggcccata ttaacattga catagctgac tactaattcc ctggatgctg    1080
ggtcttccaa attacttccc acccaggtgg ccagattcat caactcaccc caacacagaa    1140
tagcttgcct gagtgctgta tggtgaggtg aacaatgttc cggagactct aaggcctccc    1200
gatacagagc agaggcggtg tcgaggagat ctcgaataga aggaaagaag tcagaaggca    1260
aaaaagagag taactccaca gaagctccaa attctttata cgggtcaatg tccatgcccc    1320
aaagccaccc aaggcacagc ttggaggctt gaacagtagg acatgaacat gagatgatta    1380
ggcagagggg aaaaagttgc atggtgctgg tgaacagacc aatttatgcc tacagcctcc    1440
tagtacaaag acctttaacc taatctcctc ccccaactcc tcccagtctt aaacaaaca     1500
gtctttgaag tatgcctcaa ggtcggtcgt tgacattgct gagagtccaa gagtcctctt    1560
gtgtaagacc ttgggcaaga cctggtgggc gttcacggtg gtctccatgc tacgtgcaga    1620
ggtgaagcga agtgcacacg gtccggcaga tgagaaggca cagacgggga gaccgcgtaa    1680
agagaggtgc gccccgtggt cggccggaac ggcagatgaa gaaggggacg gtagaggccc    1740
aaacggcccc gagacgggtc gtccgcggga ttcagcgccg acgggacgta gacaaaggac    1800
gtcccgcgca ggatccagtt ggcagcacag cctagcagcc atggaaagga ggtgtatttc    1860
cgagagagga caactgagtt gtcggttccg ataagtttcg ctccagaccg gctgcgagca    1920
aaacaagctg ctaggagttc cgcagtatgg atcggcagag gagccacaaa ggttccacgc    1980
atgcgccgat ggcctatggc caagcccaa cccgtggggg ttgcgtcagc aaacacttgg     2040
cagagacctg accgttgccg ggcaacgggg taaaggttta gatattgttt acacagaaag    2100
gccttgtaag ttggcgagaa agtgaaagcc tgcttagatt gtatacatgc atataaaggc    2160
atcaaggcag gatagccaca ttgtgtaaaa ggggcagcaa agcccaaaag acccacaatt    2220
```

```
ctttgacata ctttccaatc aataggtcta tttacaggca attttcgaaa acattgcttg      2280 agttttttgta caatatgttc ctgcggtaaa gtaccccaac ttccaattac atatcccatg    2340
aagttaaggg agtagcccca acgtttggtt ttattagggt tcaaatgtat acccaaagac    2400
aaaagaaaat tggtaataga ggtaaaaagg gactcaagat gttgtacaga cttggccccc    2460
aataccacat catccatata gctgaaagcc aaacagtggg ggaaagccct acgaaccact    2520
gaacaaatgg cactagtaaa ctgagccagg agaaacggac tgaggcccac tcccatagga    2580
atcttgcgaa agcccaggat gatgggatgg gaatacaagt gcagtttccg tccgaaggtt    2640
ttgtacagca acaagaggga aacatagagg ttccttgagc aggaatcgtg caggttctgc    2700
atggtcccgt gctggtagtt gatgttcctg gaagtagagg acaaacgggc aacataccct    2760
ggtagtccag aagaaccaac aagaagatga ggcatagcag caggatgaag aggaatatga    2820
taaaacgccg cagacacatc cagcgatagc caggacaagt tggaggacaa gaggttggtg    2880
agtgattgga ggttggggac tgcgaatttt ggccaggaca cgtgggtgct ccccctagaa    2940
aattgagaga agtccaccac gagtctagac tctgtggtat tgtgaggatt cttgtcaaca    3000
agaaaaaccc cgcctgtaac acgagcaggg gtcctaggaa tcctgatgtt gtgctctcca    3060
tgttcggtgc agggtcccca gtcctcgaga agattgacga tatgggtgag gcagtagtcg    3120
gaacagggtt tactgttccg gaactggagc caccagcagg aaaatatagg cccctcactc    3180
tgggatctag cagagcttgg tggaatgttg tggag                               3215
```

<210> SEQ ID NO 3
<211> LENGTH: 3215
<212> TYPE: DNA
<213> ORGANISM: Hepatitis B virus
<220> FEATURE:
<221> NAME/KEY: modified_base
<222> LOCATION: (2768)..(2768)
<223> OTHER INFORMATION: a, c, t, g, unknown or other

<400> SEQUENCE: 3

```
ctccaccaca ttccaccaag ctctgctaca ccccagagta aggggcctat actttcctgc      60
tggtggctcc agttccggaa cagtaaaccc tgttccgact actgcctctc ccatatcgtc    120
aatcttctcg aggactgggg accctgcacc gaacatggag aacacaacat caggattcct    180 aggaccctg ctcgtgttac aggcggggtt tttcttgttg acaagaatcc tcacaatacc    240
acagagtcta gactcgtggt ggacttctct caattttcta gggggagcac ccacgtgtcc    300
tggccaaaat tcgcagtccc caacctccaa tcactcacca acctcttgtc ctccaatttg    360
tcctggctat cgctggatgt gtctgcggcg ttttatcata ttcctcttca tcctgctgct    420
atgcctcatc ttcttgttgg ttcttctgga ctaccaaggt atgttgcccg tttgtcctct    480
acttccagga acatcaacta ccagcacggg accatgcaag acctgcacga ttcctgctca    540
aggcacctct atgtttccct cttgttgctg tacaaaacct tcggacggaa actgcacttg    600
tattcccatc ccatcatcct gggctttcgc aagattccta tgggagtggg cctcagtccg    660
tttctcctgg ctcagtttac tagtgccatt tgttcagtgg ttcgtagggc tttcccccac    720
tgtttggctt tcagttatat ggatgatgtg gtattggggg ccaagtctgt acaacatctt    780
gagtcccttt ttaccgctgt taccaatttt cttttgtctt gggtataca tttgaaccct    840 aataaaacca aacgttgggg ttactccctt aacttcatgg gatatgtaat tggaagttgg    900
ggtactttac cgcaagacca tattgtacta aaaatcaagc aatgttttcg aaaactgcct    960
gtaaatagac ctattgattg gaaagtatgt cagagaattg tgggtctttt gggctttgct   1020
```

```
gccccttttta cacaatgtgg ctatcctgcc ttaatgcctt tatatgcatg tatacaatct    1080
aagcaggctt tcactttctc gccaacttac aaggcctttc tgtgtaaaca atatctgaac    1140
ctttaccccg ttgcccggca acggtcaggt ctctgccaag tgtttgctga cgcaaccccc    1200
actgatgggg gcttggctat tggccatcgc cgcatgcgtg gaacctttgt ggctcctctg    1260
ccgatccata ctgcggaact cctagcagct tgttttgctc gcagccggtc tggagcgaaa    1320
ctgatcggaa cggacaactc tgttgttctc tctcggaaat acacctcctt ccatggctg    1380 ctagggtgtg ctgccaactg gatcctgcgc gggacgtcct ttgtttacgt cccgtcggcg    1440
ctgaatcccg cggacgaccc atctcggggc cgtttgggtc tctaccgtcc ccttcttcat    1500
ctgccgttcc ggccgaccac ggggcgcacc tctctttacg cggtctcccc gtctgtgcct    1560
tctcatctgc cggaccgtgt gcacttcgct tcacctctgc acgtcgcatg gagaccaccg    1620
tgaacgccca ccaggtcttg cccaaggtct tatataagag gactcttgga ctctcagcaa    1680
tgtcaacgac cgaccttgag gcatacttca aagactgttt gtttaaggac tgggaggagt    1740
tgggggagga gattaggtta atgatctttg tactaggagg ctgtaggcat aaattggtct    1800
gttcaccagc accatgcaac ttttttcacct ctgcctaatc atctcatgtt catgtcctac    1860
tgttcaagcc tccaagctgt gccttgggtg gctttaggac atggacattg acccatataa    1920
agaatttgga gcttctgtgg agttactctc ttttttgcct tctgactttt ttccttctat    1980
tcgagatctc ctcgacaccg cctctgctct gtatcgggag gccttagagt ctccggaaca    2040
ttgttcacct caccatacag cactcagaca agccattctg tgttggggtg agttgatgaa    2100
tctggccacc tgggtgggaa gtaatttgga agacccagca tccagggaat tagtagtcag    2160
ctatgtcaat gttaatatgg gcctaaaaat cagacaacta ctgtggtttc acatttcctg    2220
tcttactttt ggaagagaaa ctgttcttga gtatttggtg tcttttggag tgtggattcg    2280
cactcctcct gcttacagac catcaaatgc ccctatctta tcaacacttc cggaaactac    2340
tgttgttaga cgacgaggca ggtcccctag aagaagaact ccctcgcctc gcagacgaag    2400
gtctcaatcg ccgcgtcgca gaagatctca atctcgggaa cctcaatgtt agtatcccctt   2460 ggactcataa ggtgggaaac tttactgggc tttattcttc tactgtacct gtctttaatc    2520
ctgagtggca aactccctct tttcctcata ttcatttgca ggaggacatt attaatagat    2580
gtcaacaata tgtgggccct cttacagtta atgaaaaaag gagattaaaa ttaattatgc    2640
ctgctaggtt ctatcctaac cttaccaaat atttgccctt ggacaaaggc attaaaccat    2700
attatccgga acatgcagtt aatcattact tcaaaactag gcattattta catactctgt    2760
ggaaggcngg cattctatat aagagagaaa ctacacgcag cgcctcattt tgtgggtcac    2820
catattcttg ggaacaagag ctacagcatg ggaggttggt cttccaaacc tcgacaaggc    2880
atggggacaa atctttctgt tcccaatcct ctgggattct ttcccgatca ccagttggac    2940
cctgcgttcg gagccaactc aaacaatcca gattgggact tcaacccaa caaggatcac    3000 tggccagagg caaatcaggt aggagcggga gcattcgggc cagggttcac cccaccacac    3060
ggcggtcttt tggggtggag ccctcaggct caggcacat tgacaacagt gccagtagca    3120
cctcctcctg cctccaccaa tcggcagtca ggaagacagc ctactcccat ctctccacct    3180
ctaagagaca gtcatcctca ggccatgcag tggaa                              3215
```

<210> SEQ ID NO 4
<211> LENGTH: 3215
<212> TYPE: DNA

<213> ORGANISM: Hepatitis B virus
<220> FEATURE:
<221> NAME/KEY: modified_base
<222> LOCATION: (448)..(448)
<223> OTHER INFORMATION: a, c, t, g, unknown or other

<400> SEQUENCE: 4

```
ttccactgca tggcctgagg atgactgtct cttagaggtg gagagatggg agtaggctgt      60
cttcctgact gccgattggt ggaggcagga ggaggtgcta ctggcactgt tgtcaatgtg     120
ccctgagcct gagggctcca ccccaaaaga ccgccgtgtg gtggggtgaa ccctggcccg     180
aatgctcccg ctcctacctg atttgcctct ggccagtgat ccttgttggg gttgaagtcc     240
caatctggat tgtttgagtt ggctccgaac gcagggtcca actggtgatc gggaaagaat     300
cccagaggat tgggaacaga aagatttgtc cccatgcctt gtcgaggttt ggaagaccaa     360
cctcccatgc tgtagctctt gttcccaaga atatggtgac ccacaaaatg aggcgctgcg     420
tgtagtttct ctcttatata gaatgccngc cttccacaga gtatgtaaat aatgcctagt     480
tttgaagtaa tgattaactg catgttccgg ataatatggt ttaatgcctt tgtccaaggg     540
caaatatttg gtaaggttag gatagaacct agcaggcata attaattta atctcctttt     600
ttcattaact gtaagagggc ccacatattg ttgacatcta ttaataatgt cctcctgcaa     660
atgaatatga ggaaaagagg gagtttgcca ctcaggatta agacaggta cagtagaaga     720
ataaagccca gtaaagtttc ccaccttatg agtccaaggg atactaacat tgaggttccc     780
gagattgaga tcttctgcga cgcggcgatt gagaccttcg tctgcgaggc gagggagttc     840
ttcttctagg ggacctgcct cgtcgtctaa caacagtagt ttccggaagt gttgataaga     900
taggggcatt tgatggtctg taagcaggag gagtgcgaat ccacactcca aaagacacca     960
aatactcaag aacagtttct cttccaaaag taagacagga aatgtgaaac cacagtagtt    1020
gtctgatttt taggcccata ttaacattga catagctgac tactaattcc ctggatgctg    1080
ggtcttccaa attacttccc acccaggtgg ccagattcat caactcaccc caacacagaa    1140
tggcttgtct gagtgctgta tggtgaggtg aacaatgttc cggagactct aaggcctccc    1200
gatacagagc agaggcggtg tcgaggagat ctcgaataga aggaaaaaag tcagaaggca    1260
aaaaagagag taactccaca gaagctccaa attctttata tgggtcaatg tccatgtcct    1320
aaagccaccc aaggcacagc ttggaggctt gaacagtagg acatgaacat gagatgatta    1380
ggcagaggtg aaaaagttgc atggtgctgg tgaacagacc aatttatgcc tacagcctcc    1440
tagtacaaag atcattaacc taatctcctc ccccaactcc tcccagtcct aaacaaaca    1500
gtctttgaag tatgcctcaa ggtcggtcgt tgacattgct gagagtccaa gagtcctctt    1560
atataagacc ttgggcaaga cctggtgggc gttcacggtg gtctccatgc gacgtgcaga    1620
ggtgaagcga agtgcacacg gtccggcaga tgagaaggca cagacgggga gaccgcgtaa    1680
agagaggtgc gccccgtggt cggccggaac ggcagatgaa gaaggggacg gtagagaccc    1740
aaacggcccc gagatgggtc gtccgcggga ttcagcgccg acgggacgta aacaaaggac    1800
gtcccgcgca ggatccagtt ggcagcacac cctagcagcc atggaaagga ggtgtatttc    1860
cgagagagaa caacagagtt gtccgttccg atcagtttcg ctccagaccg gctgcgagca    1920
aaacaagctg ctaggagttc gcagtatgg atcggcagag gagccacaaa ggttccacgc    1980
atgcggcgat ggccaatagc caagccccat ccagtggggg ttgcgtcagc aaacacttgg    2040
cagagacctg accgttgccg ggcaacgggg taaaggttca gatattgttt acacagaaag    2100
gccttgtaag ttggcgagaa agtgaaagcc tgcttagatt gtatacatgc atataaaggc    2160
```

```
attaaggcag gatagccaca ttgtgtaaaa ggggcagcaa agcccaaaag acccacaatt    2220
ctctgacata ctttccaatc aataggtcta tttacaggca gttttcgaaa acattgcttg    2280 attttttagta caatatggtc ttgcggtaaa gtaccccaac ttccaattac atatcccatg   2340
aagttaaggg agtaacccca acgtttggtt ttattagggt tcaaatgtat acccaaagac    2400
aaaagaaaat tggtaacagc ggtaaaaagg gactcaagat gttgtacaga cttggccccc    2460
aataccacat catccatata actgaaagcc aaacagtggg ggaaagccct acgaaccact    2520
gaacaaatgg cactagtaaa ctgagccagg agaaacggac tgaggcccac tcccatagga    2580
atcttgcgaa agcccaggat gatgggatgg gaatacaagt gcagtttccg tccgaaggtt    2640
ttgtacagca acaagaggga aacatagagg tgccttgagc aggaatcgtg caggtcttgc    2700
atggtcccgt gctggtagtt gatgttcctg gaagtagagg acaaacgggc aacataccct    2760
ggtagtccag aagaaccaac aagaagatga ggcatagcag caggatgaag aggaatatga    2820
taaaacgccg cagacacatc cagcgatagc caggacaaat tggaggacaa gaggttggtg    2880
agtgattgga ggttggggac tgcgaatttt ggccaggaca cgtgggtgct ccccctagaa    2940
aattgagaga agtccaccac gagtctagac tctgtggtat tgtgaggatt cttgtcaaca    3000
agaaaaaccc cgcctgtaac acgagcaggg gtcctaggaa tcctgatgtt gtgttctcca    3060
tgttcggtgc agggtcccca gtcctcgaga agattgacga tatgggagag gcagtagtcg    3120
gaacagggtt tactgttccg gaactggagc caccagcagg aaagtatagg ccccttactc    3180
tggggtgtag cagagcttgg tggaatgtgg tggag                               3215

<210> SEQ ID NO 5
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ucguggugga cuucucuca                                                 19

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ugagagaagu ccaccacgau u                                              21

<210> SEQ ID NO 7
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gugcacuucg cuucaccucu a                                              21
```

```
<210> SEQ ID NO 8
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
uagaggugaa gcgaagugca cuu                                              23

<210> SEQ ID NO 9
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgugguggac uucucucaau u                                                21

<210> SEQ ID NO 10
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aauugagaga aguccaccag cag                                              23

<210> SEQ ID NO 11
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gguggacuuc ucucaauuuu a                                                21

<210> SEQ ID NO 12
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
uaaaauugag agaaguccac cac                                              23

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 13
ucguggugga cuucucuca                                          19

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ugagagaagu ccaccacgau u                                       21

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ucguggugga cuucucuca                                          19

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ugagagaagu ccaccacgau u                                       21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gugcacuucg cuucaccucu a                                       21

<210> SEQ ID NO 18
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
uagaggugaa gcgaagugca cuu                                     23

<210> SEQ ID NO 19
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gugcacuucg cuucaccucu a                                              21

<210> SEQ ID NO 20
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
uagaggugaa gcgaagugca cuu                                            23

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cgugguggac uucucucaau u                                              21

<210> SEQ ID NO 22
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
aauugagaga aguccaccag cag                                            23

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
cgugguggac uucucucaau u                                              21

<210> SEQ ID NO 24
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aauugagaga aguccaccag cag                                            23
```

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gguggacuuc ucucaauuuu a                                              21

<210> SEQ ID NO 26
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uaaaauugag agaaguccac cac                                            23

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gguggacuuc ucucaauuuu a                                              21

<210> SEQ ID NO 28
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
uaaaauugag agaaguccac cac                                            23

<210> SEQ ID NO 29
<211> LENGTH: 1553
<212> TYPE: DNA
<213> ORGANISM: Homo sapiens

<400> SEQUENCE: 29
cgaggctccg caccagccgc gcttctgtcc gcctgcaggg cattccagaa agatgaggat     60
atttgctgtc tttatattca tgacctactg gcatttgctg aacgcattta ctgtcacggt    120
tcccaaggac ctatatgtgg tagagtatgg tagcaatatg acaattgaat gcaaattccc    180
agtagaaaaa caattagacc tggctgcact aattgtctat tgggaaatgg aggataagaa    240
cattattcaa tttgtgcatg gagaggaaga cctgaaggtt cagcatagta gctacagaca    300
gagggcccgg ctgttgaagg accagctctc cctgggaaat gctgcacttc agatcacaga    360
tgtgaaattg caggatgcag gggtgtaccg ctgcatgatc agctatggtg gtgccgacta    420

| | |
|---|---|
| caagcgaatt actgtgaaag tcaatgcccc atacaacaaa atcaaccaaa gaattttggt | 480 |
| tgtggatcca gtcacctctg aacatgaact gacatgtcag gctgagggct accccaaggc | 540 |
| cgaagtcatc tggacaagca gtgaccatca agtcctgagt ggtaagacca ccaccaccaa | 600 |
| ttccaagaga gaggagaagc ttttcaatgt gaccagcaca ctgagaatca acacaacaac | 660 |
| taatgagatt ttctactgca cttttaggag attagatcct gaggaaaacc atacagctga | 720 |
| attggtcatc ccagaactac ctctggcaca tcctccaaat gaaaggactc acttggtaat | 780 |
| tctgggagcc atcttattat gccttggtgt agcactgaca ttcatcttcc gtttaagaaa | 840 |
| agggagaatg atggatgtga aaaaatgtgg catccaagat acaaactcaa agaagcaaag | 900 |
| tgatacacat ttggaggaga cgtaatccag cattggaact tctgatcttc aagcagggat | 960 |
| tctcaacctg tggtttaggg gttcatcggg gctgagcgtg acaagaggaa ggaatgggcc | 1020 |
| cgtgggatgc aggcaatgtg ggacttaaaa ggcccaagca ctgaaaatgg aacctggcga | 1080 |
| aagcagagga ggagaatgaa gaaagatgga gtcaaacagg gagcctggag ggagaccttg | 1140 |
| atactttcaa atgcctgagg ggctcatcga cgcctgtgac agggagaaag gatacttctg | 1200 |
| aacaaggagc ctccaagcaa atcatccatt gctcatccta ggaagacggg ttgagaatcc | 1260 |
| ctaatttgag ggtcagttcc tgcagaagtg ccctttgcct ccactcaatg cctcaatttg | 1320 |
| ttttctgcat gactgagagt ctcagtgttg aacgggaca gtatttatgt atgagttttt | 1380 |
| cctatttatt ttgagtctgt gaggtcttct tgtcatgtga gtgtggttgt gaatgatttc | 1440 |
| ttttgaagat atattgtagt agatgttaca attttgtcgc caaactaaac ttgctgctta | 1500 |
| atgatttgct cacatctagt aaaacatgga gtatttgtaa aaaaaaaaaa aaa | 1553 |

<210> SEQ ID NO 30
<211> LENGTH: 1553
<212> TYPE: DNA
<213> ORGANISM: Homo sapiens

<400> SEQUENCE: 30

| | |
|---|---|
| tttttttttt ttttttacaaa tactccatgt tttactagat gtgagcaaat cattaagcag | 60 |
| caagtttagt ttggcgacaa aattgtaaca tctactacaa tatatcttca aaagaaatca | 120 |
| ttcacaacca cactcacatg acaagaagac ctcacagact caaaataaat aggaaaaact | 180 |
| catacataaa tactgtcccg ttccaacact gagactctca gtcatgcaga aaacaaattg | 240 |
| aggcattgag tggaggcaaa gggcacttct gcaggaactg accctcaaat tagggattct | 300 |
| caacccgtct tcctaggatg agcaatggat gatttgcttg gaggctcctt gttcagaagt | 360 |
| atcctttctc cctgtcacag gcgtcgatga gcccctcagg catttgaaag tatcaaggtc | 420 |
| tccctccagg ctccctgttt gactccatct ttcttcattc tcctcctctg ctttcgccag | 480 |
| gttccatttt cagtgcttgg gccttttaag tcccacattg cctgcatccc acgggcccat | 540 |
| tccttcctct tgtcacgctc agcccgatg aaccoctaaa ccacaggttg agaatccctg | 600 |
| cttgaagatc agaagttcca atgctggatt acgtctcctc caaatgtgta tcactttgct | 660 |
| tctttgagtt tgtatcttgg atgccacatt ttttcacatc catcattctc ccttttctta | 720 |
| aacggaagat gaatgtcagt gctacaccaa ggcataataa gatggctccc agaattacca | 780 |
| agtgagtcct ttcatttgga ggatgtgcca gaggtagttc tgggatgacc aattcagctg | 840 |
| tatggttttc ctcaggatct aatctcctaa aagtgcagta gaaaatctca ttagttgttg | 900 |
| tgttgattct cagtgtgctg gtcacattga aaagcttctc ctctctcttg gaattggtgg | 960 |
| tggtggtctt accactcagg acttgatggt cactgcttgt ccagatgact tcggccttgg | 1020 |

```
ggtagccctc agcctgacat gtcagttcat gttcagaggt gactggatcc acaaccaaaa    1080
ttctttggtt gattttgttg tatggggcat tgactttcac agtaattcgc ttgtagtcgg    1140
caccaccata gctgatcatg cagcggtaca cccctgcatc ctgcaatttc acatctgtga    1200
tctgaagtgc agcatttccc agggagagct ggtccttcaa cagccgggcc ctctgtctgt    1260
agctactatg ctgaaccttc aggtcttcct ctccatgcac aaattgaata atgttcttat    1320
cctccatttc ccaatagaca attagtgcag ccaggtctaa ttgttttttct actgggaatt    1380 tgcattcaat tgtcatattg ctaccatact ctaccacata taggtccttg ggaaccgtga    1440
cagtaaatgc gttcagcaaa tgccagtagg tcatgaatat aaagacagca aatatcctca    1500
tctttctgga atgccctgca ggcggacaga agcgcggctg gtgcggagcc tcg           1553

<210> SEQ ID NO 31
<211> LENGTH: 3653
<212> TYPE: DNA
<213> ORGANISM: Mus musculus

<400> SEQUENCE: 31
gaaatcgtgg tccccaagcc tcatgccagg ctgcacttgc acgtcgcggg ccagtctcct      60
cgcctgcaga tagttcccaa acatgagga tatttgctgg cattatattc acagcctgct     120
gtcacttgct acgggcgttt actatcacgg ctccaaagga cttgtacgtg gtggagtatg     180
gcagcaacgt cacgatggag tgcagattcc ctgtagaacg ggagctggac ctgcttgcgt     240
tagtggtgta ctgggaaaag gaagatgagc aagtgattca gtttgtggca ggagaggagg     300
accttaagcc tcagcacagc aacttcaggg ggagagcctc gctgccaaag gaccagcttt     360
tgaagggaaa tgctgccctt cagatcacag acgtcaagct gcaggacgca ggcgtttact     420
gctgcataat cagctacggt ggtgcggact acaagcgaat cacgctgaaa gtcaatgccc     480
cataccgcaa aatcaaccag agaatttccg tggatccagc cacttctgag catgaactaa     540
tatgtcaggc cgagggttat ccagaagctg aggtaatctg acaaacagt gaccaccaac     600 ccgtgagtgg gaagagaagt gtcaccactt cccggacaga ggggatgctt ctcaatgtga     660
ccagcagtct gagggtcaac gccacagcga atgatgtttt ctactgtacg ttttggagat     720
cacagccagg gcaaaaccac acagcggagc tgatcatccc agaactgcct gcaacacatc     780
ctccacagaa caggactcac tgggtgcttc tgggatccat cctgttgttc ctcattgtag     840
tgtccacggt cctcctcttc ttgagaaaac aagtgagaat gctagatgtg gagaaatgtg     900
gcgttgaaga tacaagctca aaaaaccgaa atgatacaca attcgaggag acgtaagcag     960
tgttgaaccc tctgatcgtc gattggcagc ttgtggtctg tgaaagaaag ggcccatggg    1020
acatgagtcc aaagactcaa gatggaacct gaggagaga accaagaaag tgttgggaga    1080
ggagcctgga acaacggaca tttttttccag ggagacactg ctaagcaagt tgcccatcag    1140
tcgtcttggg aaatggattg agggttcctg gcttagcagc tggtccttgc acagtgacct    1200
tttcctctgc tcagtgccgg gatgagagat ggagtcatga gtgttgaaga ataagtgcct    1260
tctatttatt ttgagtctgt gtgttctcac tttgggcatg taattatgac tggtgaattc    1320
tgacgacatg atagatctta agatgtagtc accaaactca actgctgctt agcatcctcc    1380
gtaactactg atacaagcag ggaacacaga ggtcacctgc ttggtttgac aggctcttgc    1440
tgtctgactc aaataatctt tatttttcag tcctcaaggc tcttcgatag cagttgttct    1500
gtatcagcct tataggtgtc aggtatagca ctcaacatct catctcatta caatagcaac    1560
```

```
cctcatcacc atagcaacag ctaacctctg ttatcctcac ttcatagcca ggaagctgag    1620
cgactaagtc acttgcccac agagtatcag ctctcagatt tctgttcttc agccactgtc    1680 cttcaggat agaatttgtc gttaagaaat taatttaaaa actgattatt gagtagcatt     1740
gtatatcaat cacaacatgc cttgtgcact gtgctggcct ctgagcataa agatgtacgc    1800
cggagtaccg gtcggacatg tttatgtgtg ttaaatactc agagaaatgt tcattaacaa    1860
ggagcttgca ttttagagac actggaaagt aactccagtt cattgtctag cattacattt    1920
acctcatttg ctatccttgc catacagtct cttgttctcc atgaagtgtc atgaatcttg    1980
ttgaatagtt cttttatttt ttaaatgttt ctatttaaat gatattgaca tctgaggcga    2040
tagctcagtt ggtaaaaccc tttcctcaca agtgtgaaac cctgagtctt atccctagaa    2100
cccacataaa aaacagttgc gtatgtttgt gcatgctttt gatcccagca ctagggaggc    2160
agaggcaggc agatcctgag ctctcattga ccacccagcc tagcctacat ggttagctcc    2220
aggcctacag gagctggcag agcctgaaaa acgatgccta gacacacaca cacacacaca    2280
cacacacaca cacacacaca cacaccatgt actcatagac ctaagtgcac cctcctacac    2340
atgcacacac atacaattca aacacaaatc aacagggaat tgtctcagaa tggtccccaa    2400
gacaaagaag aagaaaaaca ccaaaccagc tctattccct cagcctatcc tctctactcc    2460
ttcctagaag caactactat tgttttttgta tataaattta cccaacgaca gttaatatgt    2520
agaatatata ttaaagtgtc tgtcaatata tattatctct ttcttcttt cttcttttct     2580 ttctttcttt ctttctttct ttctttcttt ctttctttct ttcttccttc cttccttcct    2640
tccttccttc cttccttcct ttctttcttt ctttcttttt ttctgtctat ctgtacctaa    2700
atggttgctc actatgcatt ttctgtgctc ttcgcccttt ttatttaatg tatggatatt    2760
tatgctgctt ccagaatgga tctaaagctc tttgtttcta ggttttctcc cccatccttc    2820
taggcatctc tcacactgtc taggccagac accatgtctg ctgcctgaat ctgtagacac    2880
catttataaa gcacgtactc accgagtttg tatttggctt gttctgtgtc tgattaaagg    2940
gagaccatga gtccccaggg tacactgagt taccccagta ccaaggggga gccttgtttg    3000
tgtctccatg gcagaagcag gcctggagcc attttggttt cttccttgac ttctctcaaa    3060
cacagacgcc tcacttgctc attacaggtt ctcctttggg aatgtcagca ttgctccttg    3120
actgctggct gccctggaag gagcccatta gctctgtgtg agcccttgac agctactgcc    3180
tctccttacc acaggggcct ctaagatact gttacctaga ggtcttgagg atctgtgttc    3240
tctgggggga ggaaaggagg aggaacccag aactttctta cagttttcct tgttctgtca    3300
catgtcaaga ctgaaggaac aggctgggct acgtagtgag atcctgtctc aaaggaaaga    3360
cgagcatagc cgaaccccccg gtggaacccc ctctgttacc tgttcacaca agcttattga    3420
tgagtctcat gttaatgtct tgtttgtatg aagtttaaga aaatatcggg ttgggcaaca    3480 cattctatt attcatttta tttgaaatct taatgccatc tcatggtgtt ggattggtgt    3540
ggcactttat tcttttgtgt tgtgtataac cataaatttt attttgcatc agattgtcaa    3600
tgtattgcat taatttaata aatatttttta tttattaaaa aaaaaaaaaa aaa          3653
```

<210> SEQ ID NO 32
<211> LENGTH: 3653
<212> TYPE: DNA
<213> ORGANISM: Mus musculus

<400> SEQUENCE: 32

```
tttttttttt ttttttttaat aaataaaaat atttattaaa ttaatgcaat acattgacaa      60
```

```
tctgatgcaa aataaaattt atggttatac acaacacaaa agaataaagt gccacaccaa      120
tccaacacca tgagatggca ttaagatttc aaataaaatg aataaataga atgtgttgcc      180
caacccgata ttttcttaaa cttcatacaa acaagacatt aacatgagac tcatcaataa      240
gcttgtgtga acaggtaaca gagggggttc caccgggggt tcggctatgc tcgtctttcc      300
tttgagacag gatctcacta cgtagcccag cctgttcctt cagtcttgac atgtgacaga      360
acaaggaaaa ctgtaagaaa gttctgggtt cctcctcctt tcctccccccc agagaacaca      420 gatcctcaag acctctaggt aacagtatct tagaggcccc tgtggtaagg agaggcagta      480
gctgtcaagg gctcacacag agctaatggg ctccttccag ggcagccagc agtcaaggag      540
caatgctgac attcccaaag gagaacctgt aatgagcaag tgaggcgtct gtgtttgaga      600
gaagtcaagg aagaaaccaa aatggctcca ggcctgcttc tgccatggag acacaaacaa      660 ggctcccccct tggtactggg gtaactcagt gtaccctggg gactcatggt ctcccttttaa      720 tcagacacag aacaagccaa atacaaactc ggtgagtacg tgctttataa atggtgtcta      780
cagattcagg cagcagacat ggtgtctggc ctagacagtg tgagagatgc ctagaaggat      840
gggggagaaa acctagaaac aaagagcttt agatccattc tggaagcagc ataaatatcc      900
atacattaaa taaaagggc gaagagcaca gaaaatgcat agtgagcaac catttaggta      960
cagatagaca gaaaaaaga aagaaagaaa gaaggaagg aaggaaggaa ggaaggaagg     1020
aaggaaggaa gaaagaaaga aagaaagaaa gaaagaaaga agaaagaaa gaaagaaagg     1080 aagaaagaaa gaaagagata atatatattg acagacactt taatatatat tctacatatt     1140
aactgtcgtt gggtaaattt atatacaaaa acaatagtag ttgcttctag gaaggagtag     1200
agaggatagg ctgagggaat agagctggtt tggtgttttt cttcttcttt gtcttgggga     1260
ccattctgag acaattccct gttgatttgt gtttgaattg tatgtgtgtg catgtgtagg     1320
agggtgcact taggtctatg agtacatggt gtgtgtgtgt gtgtgtgtgt gtgtgtgtgt     1380
gtgtgtgtgt gtctaggcat cgttttttcag gctctgccag ctcctgtagg cctggagcta     1440
accatgtagg ctaggctggg tggtcaatga gagctcagga tctgcctgcc tctgcctccc     1500
tagtgctggg atcaaaagca tgcacaaaca tacgcaactg ttttttatgt gggttctagg     1560
gataagactc agggtttcac acttgtgagg aaagggtttt accaactgag ctatcgcctc     1620
agatgtcaat atcatttaaa tagaaacatt taaaaataa aagaactatt caacaagatt     1680
catgacactt catggagaac aagagactgt atggcaagga tagcaaatga ggtaaatgta     1740
atgctagaca atgaactgga gttactttcc agtgtctcta aaatgcaagc tccttgttaa     1800
tgaacatttc tctgagtatt taacacacat aaacatgtcc gaccggtact ccggcgtaca     1860
tctttatgct cagaggccag cacagtgcac aaggcatgtt gtgattgata tacaatgcta     1920
ctcaataatc agttttttaaa ttaatttctt aacgacaaat tctatcctga aaggacagtg     1980
gctgaagaac agaaatctga gagctgatac tctgtgggca agtgacttag tcgctcagct     2040
tcctggctat gaagtgagga taacagaggt tagctgttgc tatggtgatg agggttgcta     2100
ttgtaatgag atgagatgtt gagtgctata cctgacacct ataaggctga tacagaacaa     2160
ctgctatcga agagccttga ggactgaaaa ataaagatta tttgagtcag acagcaagag     2220
cctgtcaaac caagcaggtg acctctgtgt tccctgcttg tatcagtagt tacggaggat     2280
gctaagcagc agttgagttt ggtgactaca tcttaagatc tatcatgtcg tcagaattca     2340
ccagtcataa ttacatgccc aaagtgagaa cacacagact caaaataaat agaaggcact     2400
```

```
tattcttcaa cactcatgac tccatctctc atcccggcac tgagcagagg aaaaggtcac    2460
tgtgcaagga ccagctgcta agccaggaac cctcaatcca tttcccaaga cgactgatgg    2520
gcaacttgct tagcagtgtc tccctggaaa aaatgtccgt tgttccaggc tcctctccca    2580
acactttctt ggttctctcc ctcaggttcc atcttgagtc tttggactca tgtcccatgg    2640
gccctttctt tcacagacca caagctgcca atcgacgatc agagggttca acactgctta    2700
cgtctcctcg aattgtgtat catttcggtt ttttgagctt gtatcttcaa cgccacattt    2760
ctccacatct agcattctca cttgtttttct caagaagagg aggaccgtgg acactacaat    2820
gaggaacaac aggatggatc ccagaagcac ccagtgagtc ctgttctgtg gaggatgtgt    2880
tgcaggcagt tctgggatga tcagctccgc tgtgtggttt tgccctggct gtgatctcca    2940
aaacgtacag tagaaaacat cattcgctgt ggcgttgacc ctcagactgc tggtcacatt    3000
gagaagcatc ccctctgtcc gggaagtggt gacacttctc ttcccactca cgggttggtg    3060
gtcactgttt gtccagatta cctcagcttc tggataaccc tcggcctgac atattagttc    3120
atgctcagaa gtggctggat ccacggaaat tctctggttg attttgcggt atggggcatt    3180
gactttcagc gtgattcgct tgtagtccgc accaccgtag ctgattatgc agcagtaaac    3240
gcctgcgtcc tgcagcttga cgtctgtgat ctgaagggca gcatttccct tcaaaagctg    3300
gtcctttggc agcgaggctc tcccctgaa gttgctgtgc tgaggcttaa ggtcctcctc    3360
tcctgccaca aactgaatca cttgctcatc ttccttttcc cagtacacca ctaacgcaag    3420
caggtccagc tcccgttcta cagggaatct gcactccatc gtgacgttgc tgccatactc    3480
caccacgtac aagtcctttg gagccgtgat agtaaacgcc cgtagcaagt gacagcaggc    3540
tgtgaatata tgccagcaa atatcctcat gttttgggaa ctatctgcag gcgaggagac    3600
tggcccgcga cgtgcaagtg cagcctggca tgaggcttgg ggaccacgat ttc           3653

<210> SEQ ID NO 33
<211> LENGTH: 1080
<212> TYPE: DNA
<213> ORGANISM: Rattus norvegicus

<400> SEQUENCE: 33
atgaggatat ttgctgtcct tatagtcaca gcctgcagtc acgtgctagc ggcatttacc     60
atcacagctc caaggacct gtacgtggtg gagtatggca gcaatgtcac gatggaatgc    120
agattcccag tagaacagaa attggacctg cttgccttag tggtgtactg ggaaaaggaa    180
gacaaggaag ttattcagtt tgtggaggga gaggaggacc tgaagcctca acacagcagc    240
ttcaggggga gagccttctt gccaaaggac cagcttttga aggggaacgc ggtgcttcag    300
atcacagatg tcaagctgca ggacgcaggt gtctactgct gcatgatcag ctatggtgga    360
gcggactaca gcgaatcac attgaaagtc aacgctccat accgcaaaat caaccaaaga    420
atttccatgg atccagccac ttctgagcat gaactaatgt gccaggctga gggttaccca    480
gaagccgaag tgatctggac aaacagtgac caccagtccc tgagtgggga aacaactgtc    540
accacttccc agactgagga gaagcttctc aacgtgacca gcgttctgag ggtcaacgca    600
acagctaatg atgttttcca ctgtacgttc tggagagtac actcagggga gaaccacacg    660
gctgaactga tcatcccaga actgcctgta ccacgtctcc cacataacag gacacactgg    720
gtactcctgg gatccgtcct tttgttcctc atcgtggggt tcaccgtctt cttctgcttg    780
agaaaacaag tgagaatgct agatgtgaaa aatgcggct cgaagatag aaattcaaag    840 aaccgaaatg ttcgaggaga cgtaagcagt gttgaaccct ctgagcctcg aggcgggatt    900
```

```
ggcagcttgt ggtctgtgaa agaaagggcc cgtgggacat gggtccaggg actcaaaaat      960
ggaaccggag aggagaagag aacaaagaaa gtgttggaag aggagcctgg gacgaaagac     1020
atttctacag gagacactgc taagcaagtt acccatcagt catctcgggc aataagttga     1080
```

<210> SEQ ID NO 34
<211> LENGTH: 1080
<212> TYPE: DNA
<213> ORGANISM: Rattus norvegicus

<400> SEQUENCE: 34

```
tcaacttatt gcccgagatg actgatgggt aacttgctta gcagtgtctc ctgtagaaat       60
gtctttcgtc ccaggctcct cttccaacac tttctttgtt ctcttctcct ctccggttcc      120 attttgagt ccctggaccc atgtcccacg ggccctttct ttcacagacc acaagctgcc       180
aatcccgcct cgaggctcag agggttcaac actgcttacg tctcctcgaa catttcggtt      240 cttttgaattt ctatcttcga agccgcattt ttccacatct agcattctca cttgttttct     300
caagcagaag aagacggtga accccacgat gaggaacaaa aggacggatc ccaggagtac      360
ccagtgtgtc ctgttatgtg ggagacgtgg tacaggcagt tctgggatga tcagttcagc      420
cgtgtggttc tccctgagt gtactctcca gaacgtacag tggaaaacat cattagctgt       480
tgcgttgacc ctcagaacgc tggtcacgtt gagaagcttc cctcagtct gggaagtggt       540 gacagttgtt tccccactca gggactggtg gtcactgttt gtccagatca cttcggcttc      600
tgggtaaccc tcagcctggc acattagttc atgctcagaa gtggctggat ccatggaaat      660
tctttggttg attttgcggt atggagcgtt gactttcaat gtgattcgct tgtagtccgc      720
tccaccatag ctgatcatgc agcagtagac acctgcgtcc tgcagcttga catctgtgat      780
ctgaagcacc gcgttcccct tcaaaagctg gtcctttggc aagaaggctc tccccctgaa      840
gctgctgtgt tgaggcttca ggtcctcctc tccctccaca aactgaataa cttccttgtc      900
ttccttttcc cagtacacca ctaaggcaag caggtccaat ttctgttcta ctgggaatct      960
gcattccatc gtgacattgc tgccatactc caccacgtac aggtcctttg gagctgtgat     1020
ggtaaatgcc gctagcacgt gactgcaggc tgtgactata aggacagcaa atatcctcat     1080
```

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 35

```
cguggugguc tucucuaaau u                                                 21
```

<210> SEQ ID NO 36
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

```
<221> NAME/KEY: source
<223> OTHER INFORMATION: /note="Description of Combined DNA/RNA
      Molecule: Synthetic oligonucleotide"

<400> SEQUENCE: 36
aauugagaga aguccaccag cuu                                              23

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
cguggugguc uucucucaau u                                                21

<210> SEQ ID NO 38
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
aauugagaga aguccaccag cuu                                              23

<210> SEQ ID NO 39
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gugugcacuu cgcuucaca                                                   19

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
ugugaagcga agugcacacu u                                                21

<210> SEQ ID NO 41
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
gugugcacuu cgcuucaca                                                   19
```

-continued

```
<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ugugaagcga agugcacacu u                                              21

<210> SEQ ID NO 43
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      RFGF peptide"

<400> SEQUENCE: 43

Ala Ala Val Ala Leu Leu Pro Ala Val Leu Leu Ala Leu Leu Ala Pro
1               5                   10                  15

<210> SEQ ID NO 44
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 44

Ala Ala Leu Leu Pro Val Leu Leu Ala Ala Pro
1               5                   10

<210> SEQ ID NO 45
<211> LENGTH: 13
<212> TYPE: PRT
<213> ORGANISM: Human immunodeficiency virus

<400> SEQUENCE: 45

Gly Arg Lys Lys Arg Arg Gln Arg Arg Pro Pro Gln
1               5                   10

<210> SEQ ID NO 46
<211> LENGTH: 16
<212> TYPE: PRT
<213> ORGANISM: Drosophila sp.

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
aguuauaugg augauguggu a                                              21
```

```
<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ggaugugucu gcggcguuuu a                                                  21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
acucguggug gacuucucuc a                                                  21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
acucguggug gacuucucuc a                                                  21

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 51
acucguggug gacuuctcuc a                                                  21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
acucguggug gacuucucuc a                                                  21

<210> SEQ ID NO 53
<211> LENGTH: 19
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 53
ucguggugga cuucucuca                                                    19

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
acucguggug gacuucucuc a                                                 21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
acucguggug gacuucucuc a                                                 21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
acucguggug gacuucucuc a                                                 21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
acucguggug gacuucucuc a                                                 21

<210> SEQ ID NO 58
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gugguggacu ucucuca                                                      17
```

```
<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
acucguggug gacuucucuc a                                              21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ucguggugga cuucucucau u                                              21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
acucguggug gacuucucuc a                                              21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
acucguggug gacuucucuc a                                              21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
acucguggug gacuucucuc a                                              21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 64
acucguggug gacuucucuc a          21

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
ucguggugga cuucucuca          19

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
acucguggug gacuucucuc a          21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
acucguggug gacuucucuc a          21

<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
acucguggug gacuucucuc a          21

<210> SEQ ID NO 69
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
uauuuccuag gguacaa          17

<210> SEQ ID NO 70
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acucguggug gacuucucuc a                                              21

<210> SEQ ID NO 71
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ucguggugga cuucucuca                                                 19

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
acucguggug gacuucucuc a                                              21

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
acucguggug gacuucucuc a                                              21

<210> SEQ ID NO 74
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
acucguggug gacuucucuc a                                              21

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
acucguggug gacuucucuc a                                              21
```

-continued

```
<210> SEQ ID NO 76
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
acucguggug gacuucucuc a                                              21

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
acucguggug gacuucucuc a                                              21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
acucguggug gacuucucuc a                                              21

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
acucguggug gacuucucuc a                                              21

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
acucguggug gacuucucuc a                                              21

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 81
acucguggug gacuucucuc a                                              21

<210> SEQ ID NO 82
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
acucguggug gacuucucuc a                                              21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
acucguggug gacuucucuc a                                              21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic  oligonucleotide"

<400> SEQUENCE: 84
acucguggug gacuucucuc a                                              21

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 85
acucguggug gacuuctcuc a                                              21

<210> SEQ ID NO 86
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
acucguggug gacuucucuc a                                              21

```
<210> SEQ ID NO 87
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 87
acucguggug gacuuctcuc a                                              21

<210> SEQ ID NO 88
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
acucguggug gacuucucuc a                                              21

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
acucguggug gacuucucuc a                                              21

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 90
acucguggug gacuuctcuc a                                              21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
acucguggug gacuucucuc a                                              21
```

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 92
acucguggug gacuuctcuc a                                              21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
acucguggug gacuucucuc a                                              21

<210> SEQ ID NO 94
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gugguggacu ucucucaauu u                                              21

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gugguggacu ucucucaauu u                                              21

<210> SEQ ID NO 96
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gugguggacu ucucucaauu u                                              21

<210> SEQ ID NO 97
<211> LENGTH: 17
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 97
uggacuucuc ucaauuu                                                    17

<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gugguggacu ucucucaauu u                                               21

<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gguggacuuc ucucaauuuu u                                               21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gugguggacu ucucucaauu u                                               21

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gugguggacu ucucucaauu u                                               21

<210> SEQ ID NO 102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gugguggacu ucucucaauu u                                               21
```

<210> SEQ ID NO 103
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
gguggacuuc ucucaauuu                                                19

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
gugguggacu ucucucaauu u                                             21

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gguggacuuc ucucaauuu                                                19

<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
gugguggacu ucucucaauu u                                             21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
gugguggacu ucucucaauu u                                             21

<210> SEQ ID NO 108
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 108
uggacuucuc ucaauuu                                          17

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gugguggacu ucucucaauu u                                     21

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gguggacuuc ucucaauuu                                        19

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gugguggacu ucucucaauu u                                     21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gugguggacu ucucucaauu u                                     21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
gugguggacu ucucucaauu u                                     21

<210> SEQ ID NO 114
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gugguggacu ucucucaauu u                                              21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
gugguggacu ucucucaauu u                                              21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gugguggacu ucucucaauu u                                              21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
gugguggacu ucucucaauu u                                              21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
gugguggacu ucucucaauu u                                              21

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
gugguggacu ucucucaauu u                                              21
```

<210> SEQ ID NO 120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gugguggacu ucucucaauu u                                              21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
gugguggacu ucucucaauu u                                              21

<210> SEQ ID NO 122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 122
gugguggact tcucucaauu u                                              21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
gugguggacu ucucucaauu u                                              21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
gugguggacu ucucucaauu u                                              21

<210> SEQ ID NO 125
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
gugguggacu ucucucaauu u                                           21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 126
gugguggacu tcucucaauu u                                           21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gugguggacu ucucucaauu u                                           21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gugguggacu ucucucaauu u                                           21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gugguggacu ucucucaauu u                                           21

<210> SEQ ID NO 130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 130
gugguggacu ucucucaauu u                                              21

<210> SEQ ID NO 131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 131
gugguggacu tcucucaauu u                                              21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gugguggacu ucucucaauu u                                              21

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
gugguggacu ucucucaauu u                                              21

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 134
gugguggacu tcucucaauu u                                              21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 135
gugguggacu ucucucaauu u                                              21

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gguggacuuc ucucaauuu                                                 19

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gugguggacu ucucucaauu u                                              21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gugcacuucg cuucaccucu g                                              21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
guugacaaaa auccucacaa u                                              21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
uguugacaaa aauccucaca a                                              21

<210> SEQ ID NO 141
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 141
gguggacuuc ucucaauuuu a                                              21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ucuuuuggag uguggauucg a                                              21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ucuuuuggag uguggauucg a                                              21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
acuguucaag ccuccaagcu a                                              21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ucugccgauc cauacugcgg a                                              21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
augugucugc ggcguuuuau a                                              21
```

```
<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ccccgucugu gccuucucau a                                          21

<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gccuaaucau cucuuguuca u                                          21

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
ucuagacucg ugguggacuu c                                          21

<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
cugccgaucc auacugcgga a                                          21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
uuuuucuugu ugacaaaaau a                                          21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 152
aucuucuugu ugguucuucu a                                          21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
guuuuucuug uugacaaaaa u                                          21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
cugccuaauc aucucuuguu a                                          21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
uccucacaau accacagagu a                                          21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cuuguugaca aaaauccuca a                                          21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
gcaacuuuuu caccucugcc u                                          21

<210> SEQ ID NO 158
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
gggaacaaga gcuacagcau a                                              21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cgugguggac uucucucaau u                                              21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
cugcugcuau gccucaucuu a                                              21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
guuggaugug ucugcggcgu u                                              21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
uucauccugc ugcuaugccu a                                              21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
uucuuguuga caaaaauccu a                                              21
```

```
<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
uauauggaug augugguauu a                                              21

<210> SEQ ID NO 165
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
uucauccugc ugcuaugccu c                                              21

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gugcacuucg cuucaccucu a                                              21

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
uugacaaaaa uccucacaau a                                              21

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
aagccuccaa gcugugccuu a                                              21

<210> SEQ ID NO 169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 169
ccucuucauc cugcugcuau a                                              21

<210> SEQ ID NO 170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
ccugcugcua ugccucaucu u                                              21

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
caucuucuug uugguucuuc u                                              21

<210> SEQ ID NO 172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
ccgucugugc cuucucaucu a                                              21

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
ccucaucuuc uuguugguuc u                                              21

<210> SEQ ID NO 174
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
ccaccaaaug ccccuaucuu a                                              21

<210> SEQ ID NO 175
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gcuccucugc cgauccauac u                                          21

<210> SEQ ID NO 176
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
guugacaaaa auccucacaa u                                          21

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
uguugacaaa aauccucaca a                                          21

<210> SEQ ID NO 178
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gguggacuuc ucucaauuuu a                                          21

<210> SEQ ID NO 179
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
ucuuuuggag uguggauucg a                                          21

<210> SEQ ID NO 180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
```
ucuuuuggag uguggauucg a       21

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
acuguucaag ccuccaagcu a       21

<210> SEQ ID NO 182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
ucugccgauc cauacugcgg a       21

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
aguuauaugg augauguggu a       21

<210> SEQ ID NO 184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
augugucugc ggcguuuuau a       21

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
ccccgucugu gccuucucau a       21

<210> SEQ ID NO 186
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 186
gccuaaucau cucuuguuca u                                              21

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
ucuagacucg ugguggacuu c                                              21

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
cugccgaucc auacugcgga a                                              21

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aucuucuugu ugguucuucu a                                              21

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
uucucucaau uuucuagggg a                                              21

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
acucguggug gacuucucuc a                                              21

<210> SEQ ID NO 192
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gugcacuucg cuucaccucu g                                              21

<210> SEQ ID NO 193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
guuuuucuug uugacaaaaa u                                              21

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
cugccuaauc aucucuuguu a                                              21

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
uccucacaau accacagagu a                                              21

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
cuuguugaca aaauccuca a                                               21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
```
gugguggacu ucucucaauu u         21

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
gcaacuuuuu caccucugcc u         21

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gggaacaaga gcuacagcau a         21

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
ucaucuucuu guugguucuu a         21

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
cugcugcuau gccucaucuu a         21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
guuggaugug ucugcggcgu u         21

<210> SEQ ID NO 203
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 203
uucauccugc ugcuaugccu a                                              21

<210> SEQ ID NO 204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
uucuuguuga caaaaauccu a                                              21

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ggaugugucu gcggcguuuu a                                              21

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
uauauggaug augugguauu a                                              21

<210> SEQ ID NO 207
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
uucauccugc ugcuaugccu c                                              21

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
gugcacuucg cuucaccucu a                                              21
```

```
<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
uugacaaaaa uccucacaau a                                              21

<210> SEQ ID NO 210
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ccaaguguuu gcugacgcaa a                                              21

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ccaaguguuu gcugacgcaa a                                              21

<210> SEQ ID NO 212
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aagccuccaa gcugugccuu a                                              21

<210> SEQ ID NO 213
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
ccucuucauc cugcugcuau a                                              21

<210> SEQ ID NO 214
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 214
ccugcugcua ugccucaucu u                                                  21

<210> SEQ ID NO 215
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
caucuucuug uugguucuuc u                                                  21

<210> SEQ ID NO 216
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
ccgucugugc cuucucaucu a                                                  21

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
ccucaucuuc uuguuggduuc u                                                 21

<210> SEQ ID NO 218
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ccaccaaaug ccccuaucuu a                                                  21

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gcuccucugc cgauccauac u                                                  21

<210> SEQ ID NO 220
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 220
acucguggug tacuucucuc a                                              21

<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
acucguggug gacuucucuc a                                              21

<210> SEQ ID NO 222
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
acucguggug gacuucucuc a                                              21

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
acucguggug gacuucacuc a                                              21

<210> SEQ ID NO 224
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 224
acucguggtg tacuucacuc a                                              21

<210> SEQ ID NO 225
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 225
acucguggug tacuucacuc a                                               21

<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
acucguggug gacuucucuc a                                               21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
acucguggug gacuucucuc a                                               21

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 228
acucguggtg gacuuctcuc a                                               21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
acucguggug gacuucucuc a                                               21

<210> SEQ ID NO 230
<211> LENGTH: 21
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 230
acucguggug gacuucucuc a                                              21

<210> SEQ ID NO 231
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 231
acucguggtg tacuucacuc a                                              21

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
acucguggug gacuucucuc a                                              21

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
acucguggug gacuucucuc a                                              21

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 234
acucguggtg gacuucacuc a                                              21

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 235
acucguggug gacuucacuc a                                              21

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
acucguggug gacuucucuc a                                              21

<210> SEQ ID NO 237
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 237
acucguggtg gacuuctcuc a                                              21

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
acucguggug gacuucucuc a                                              21

<210> SEQ ID NO 239
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 239
acucguggug gacuuctcuc a                                              21

<210> SEQ ID NO 240
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 240
acucguggtg tacuucacuc a                                              21

<210> SEQ ID NO 241
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 241
acucguggtg gacuuctcuc a                                              21

<210> SEQ ID NO 242
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
acucguggug gacuuccuca                                                20

<210> SEQ ID NO 243
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 243
acucguggug gacuuctcuc a                                              21

<210> SEQ ID NO 244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 244
acucguggug gacuuctcuc a                                              21

<210> SEQ ID NO 245
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
acucguggug gacuucucuc a                                              21

<210> SEQ ID NO 246
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 246
acucguggtg gacuucacuc a                                              21

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
acucguggug gacuucacuc a                                              21

<210> SEQ ID NO 248
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 248
acucguggtg gacuucacuc a                                              21

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
acucguggug gacuucucuc a                                              21

<210> SEQ ID NO 250
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 250
acucguggug gacuuctcuc a                                              21

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
acucguggug gacuucacuc a                                              21

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 252
acucguggtg tacuucacuc a                                              21

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
acucguggug gacuucccuc a                                              21

<210> SEQ ID NO 254
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
acucguggug gacuucucuc a                                              21

<210> SEQ ID NO 255
<211> LENGTH: 21
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
acucguggug gacuucucuc a                                              21

<210> SEQ ID NO 256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 256
acucguggug gacuuctcuc a                                              21

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 257
acucguggtg gacuuctcuc a                                              21

<210> SEQ ID NO 258
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
acucguggug gacuucgcuc a                                              21

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
acucguggug gacuucucuc a                                              21

<210> SEQ ID NO 260
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 260
acucguggug gacuucucuc a                                              21

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
acucguggug gacuucucuc a                                              21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 262
acucguggtg gacuucacuc a                                              21

<210> SEQ ID NO 263
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
uaccacauca uccauauaac uga                                            23

<210> SEQ ID NO 264
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
uaaaacgccg cagacacauc cag                                            23

<210> SEQ ID NO 265
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 265
ugagagaagu ccaccacgag ucu                                              23

<210> SEQ ID NO 266
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
ugagagaagu ccaccacgag ucu                                              23

<210> SEQ ID NO 267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
ugagagaagu ccaccacgag ucu                                              23

<210> SEQ ID NO 268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ugagagaagu ccaccacgag ucu                                              23

<210> SEQ ID NO 269
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
ugagagaagu ccaccacgag u                                                21

<210> SEQ ID NO 270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
ugagagaagu ccaccacgag ucu                                              23

<210> SEQ ID NO 271
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 271
ugagagaagu ccaccacgag ucu                                              23

<210> SEQ ID NO 272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
ugagagaagu ccaccacgag ucu                                              23

<210> SEQ ID NO 273
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
ugagagaagu ccaccacgag ucu                                              23

<210> SEQ ID NO 274
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
ugagagaagu ccaccacga                                                   19

<210> SEQ ID NO 275
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
ugagagaagu ccaccacgag ucu                                              23

<210> SEQ ID NO 276
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
ugagagaagu ccaccacgau u                                                21
```

<210> SEQ ID NO 277
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
ugagagaagu ccaccacgag ucu                                              23

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
ugagagaagu ccaccacgag ucu                                              23

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
ugagagaagu ccaccacgag ucu                                              23

<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
ugagagaagu ccaccacgag ucu                                              23

<210> SEQ ID NO 281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ugagagaagu ccaccacgau u                                                21

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 282
ugagagaagu ccaccacgag ucu                                              23

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
ugagagaagu ccaccacgag ucu                                              23

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
ugagagaagu ccaccacgag ucu                                              23

<210> SEQ ID NO 285
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
ugagagaagu ccaccacga                                                   19

<210> SEQ ID NO 286
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
ugagagaagu ccaccacgag ucu                                              23

<210> SEQ ID NO 287
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ugagagaagu ccaccacgau u                                                21

<210> SEQ ID NO 288
<211> LENGTH: 23
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
ugagagaagu ccaccacgag ucu                                         23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
ugagagaagu ccaccacgag ucu                                         23

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
ugagagaagu ccaccacgag ucu                                         23

<210> SEQ ID NO 291
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
ugagagaagu ccaccacgag ucu                                         23

<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ugagagaagu ccaccacgag ucu                                         23

<210> SEQ ID NO 293
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
ugagagaagu ccaccacgag ucu                                         23
```

<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
ugagagaagu ccaccacgag ucu                                              23

<210> SEQ ID NO 295
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
ugagagaagu ccaccacgag ucu                                              23

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
ugagagaagu ccaccacgag ucu                                              23

<210> SEQ ID NO 297
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
ugagagaagu ccaccacgag ucu                                              23

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
ugagagaagu ccaccacgag ucu                                              23

<210> SEQ ID NO 299
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 299
ugagagaagu ccaccacgag ucu                                              23

<210> SEQ ID NO 300
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 300
ugagagaagt ccaccacgag ucu                                              23

<210> SEQ ID NO 301
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
ugagagaagu ccaccacgag ucu                                              23

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
ugagagaagu ccaccacgag ucu                                              23

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
ugagagaagu ccaccacgag ucu                                              23

<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
ugagagaagu ccaccacgag ucu                                              23

```
<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
ugagagaagu ccaccacgag ucu                                           23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
ugagagaagu ccaccacgag ucu                                           23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
ugagagaagu ccaccacgag ucu                                           23

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
ugagagaagu ccaccacgag ucu                                           23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
ugagagaagu ccaccacgag ucu                                           23

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 310
aaauugagag aaguccacca cga          23

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
aaauugagag aaguccacca cga          23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
aaauugagag aaguccacca cga          23

<210> SEQ ID NO 313
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
aaauugagag aaguccacc          19

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
aaauugagag aaguccacca cga          23

<210> SEQ ID NO 315
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
aaauugagag aaguccaccu u          21

<210> SEQ ID NO 316
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
aaauugagag aaguccacca cga                                         23

<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
aaauugagag aaguccacca cga                                         23

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
aaauugagag aaguccacca cga                                         23

<210> SEQ ID NO 319
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
aaauugagag aaguccacca c                                           21

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
aaauugagag aaguccacca cga                                         23

<210> SEQ ID NO 321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
```
aaauugagag aaguccaccu u                                                  21

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
aaauugagag aaguccacca cga                                                23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
aaauugagag aaguccacca cga                                                23

<210> SEQ ID NO 324
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
aaauugagag aaguccacc                                                     19

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
aaauugagag aaguccacca cga                                                23

<210> SEQ ID NO 326
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
aaauugagag aaguccaccu u                                                  21

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 327
aaauugagag aaguccacca cga					23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 328
aaauugagag aaguccacca cga					23

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 329
aaauugagag aaguccacca cga					23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 330
aaauugagag aaguccacca cga					23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 331
aaauugagag aaguccacca cga					23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 332
aaauugagag aaguccacca cga					23

<210> SEQ ID NO 333

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
aaauugagag aaguccacca cga                                            23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
aaauugagag aaguccacca cga                                            23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
aaauugagag aaguccacca cga                                            23

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
aaauugagag aaguccacca cga                                            23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
aaauugagag aaguccacca cga                                            23

<210> SEQ ID NO 338
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

<223> OTHER INFORMATION: /note="Description of Combined DNA/RNA
Molecule: Synthetic oligonucleotide"

<400> SEQUENCE: 338
aaauugagag aagtccacca cga                                             23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 339
aaauugagag aaguccacca cga                                             23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 340
aaauugagag aaguccacca cga                                             23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 341
aaauugagag aaguccacca cga                                             23

<210> SEQ ID NO 342
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 342
aaauugagag aagtccacca cga                                             23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 343
aaauugagag aaguccacca cga 23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 344
aaauugagag aaguccacca cga 23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 345
aaauugagag aaguccacca cga 23

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 346
aaauugagag aaguccacca cga 23

<210> SEQ ID NO 347
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 347
aaauugagag aagtccacca cga 23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 348
aaauugagag aaguccacca cga 23

<210> SEQ ID NO 349
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
aaauugagag aaguccacca cga                                           23

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
aaauugagag aaguccacca cga                                           23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
aaauugagag aaguccacca cga                                           23

<210> SEQ ID NO 352
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
aaauugagag aaguccacca c                                             21

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
aaauugagag aaguccacca cga                                           23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
```

```
cagaggugaa gcgaagugca cac                                          23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
auugugagga uuuuugucaa caa                                          23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
uugugaggau uuuugucaac aag                                          23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
uaaaauugag agaaguccac cac                                          23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
ucgaauccac acuccaaaag aca                                          23

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
ucgaauccac acuccaaaag aca                                          23

<210> SEQ ID NO 360
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 360
uagcuuggag gcuugaacaa gac                                              23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
uccgcaguau ggaucggcag agg                                              23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
uauaaaacgc cgcagacaca ucc                                              23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
uaugagaagg cacagacggg gag                                              23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
augaacaaga gaugauuagc gag                                              23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
gaaguccacc acgagucuag acu                                              23

<210> SEQ ID NO 366
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
uuccgcagua uggaucggca gag                                           23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367 uauuuuguc aacaagaaaa acc                                            23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
uagaagaacc aacaagaaga uga                                           23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
auuuuuguca acaagaaaaa ccc                                           23

<210> SEQ ID NO 370
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
uaacaagaga ugauuaggca gag                                           23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
```
uacucugugg uauugugagg auu                                          23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
uugaggauuu uugucaacaa gaa                                          23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
aggcagaggu gaaaaaguug cau                                          23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
uaugcuguag cucuuguucc caa                                          23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
aauugagaga aguccaccag cag                                          23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
uaagaugagg cauagcagca gga                                          23

<210> SEQ ID NO 377
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 377
aacgccgcag acacauccaa cga                                            23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
uaggcauagc agcaggauga aga                                            23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
uaggauuuuu gucaacaaga aaa                                            23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
uaauaccaca ucauccauau aac                                            23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
gaggcauagc agcaggauga aga                                            23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
uagaggugaa gcgaagugca cac                                            23
```

```
<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
uauugugagg auuuuuguca aca                                          23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
uaaggcacag cuuggaggcu uga                                          23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
uauagcagca ggaugaagag gaa                                          23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
aagaugaggc auagcagcag gau                                          23

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
agaagaacca acaagaagau gag                                          23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 388
uagaugagaa ggcacagacg ggg                                           23

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
agaaccaaca agaagaugag gca                                           23

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
uaagauaggg gcauuuggug guc                                           23

<210> SEQ ID NO 391
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
aguauggauc ggcagaggag cca                                           23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
auugugagga uuuuugucaa caa                                           23

<210> SEQ ID NO 393
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
uugugaggau uuuugucaac aag                                           23

<210> SEQ ID NO 394
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 394
uaaaauugag agaaguccac cac                                              23

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
ucgaauccac acuccaaaag aca                                              23

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
ucgaauccac acuccaaaag aca                                              23

<210> SEQ ID NO 397
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
uagcuuggag gcuugaacaa gac                                              23

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
uccgcaguau ggaucggcag agg                                              23

<210> SEQ ID NO 399
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
uaccacauca uccauauaac uga                                              23
```

<210> SEQ ID NO 400
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
uauaaaacgc cgcagacaca ucc                                              23

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
uaugagaagg cacagacggg gag                                              23

<210> SEQ ID NO 402
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
augaacaaga gaugauuagc gag                                              23

<210> SEQ ID NO 403
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
gaaguccacc acgagucuag acu                                              23

<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
uuccgcagua uggaucggca gag                                              23

<210> SEQ ID NO 405
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 405
uagaagaacc aacaagaaga uga                                        23

<210> SEQ ID NO 406
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
uccccuagaa aauugagaga agu                                        23

<210> SEQ ID NO 407
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
ugagagaagu ccaccacgag ucu                                        23

<210> SEQ ID NO 408
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
cagaggugaa gcgaagugca cac                                        23

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
auuuuuguca acaagaaaaa ccc                                        23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
uaacaagaga ugauuaggca gag                                        23

<210> SEQ ID NO 411
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
uacucugugg uauugugagg auu                                              23

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
uugaggauuu uugucaacaa gaa                                              23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
aaauugagag aaguccacca cga                                              23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
aggcagaggu gaaaaaguug cau                                              23

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
uaugcuguag cucuuguucc caa                                              23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
uaagaaccaa caagaagaug agg                                              23
```

```
<210> SEQ ID NO 417
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
uaagaugagg cauagcagca gga                                              23

<210> SEQ ID NO 418
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
aacgccgcag acacauccaa cga                                              23

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
uaggcauagc agcaggauga aga                                              23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
uaggauuuuu gucaacaaga aaa                                              23

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
uaaaacgccg cagacacauc cag                                              23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 422
uaauaccaca ucauccauau aac                                      23

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
gaggcauagc agcaggauga aga                                      23

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
uagaggugaa gcgaagugca cac                                      23

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
uauugugagg auuuuuguca aca                                      23

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
uuugcgucag caaacacuug gca                                      23

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
uuugcgucag caaacacuug gca                                      23

<210> SEQ ID NO 428
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
uaaggcacag cuuggaggcu uga                                            23

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
uauagcagca ggaugaagag gaa                                            23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
aagaugaggc auagcagcag gau                                            23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
agaagaacca acaagaagau gag                                            23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
uagaugagaa ggcacagacg ggg                                            23

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
```
agaaccaaca agaagaugag gca        23

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
uaagauaggg gcauuggug guc        23

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
aguauggauc ggcagaggag cca        23

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
ugagagaagu ccaccacgag ucu        23

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 437
ugagagaagt ccaccacgag ucu        23

<210> SEQ ID NO 438
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
ugagagaagu ccaccacgag ucu        23

<210> SEQ ID NO 439
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 439
ugagagaagt ccaccacgag ucu                                              23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
ugagagaagu ccaccacgag ucu                                              23

<210> SEQ ID NO 441
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
ugagagaagu ccaccacgag ucu                                              23

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
ugagagaagu ccaccacgag ucu                                              23

<210> SEQ ID NO 443
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 443
ugagagaagt ccaccacgag ucu                                              23

<210> SEQ ID NO 444
<211> LENGTH: 23
<212> TYPE: DNA
```

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 444
ugagagaagt ccaccacgag ucu                                              23

<210> SEQ ID NO 445
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 445
ugagagaagt ccaccacgag ucu                                              23

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
ugagagaagu ccaccacgag ucu                                              23

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
ugagagaagu ccaccacgag ucu                                              23

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
ugagagaagu ccaccacgag ucu                                              23

<210> SEQ ID NO 449
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 449
ugagagaagt ccaccacgag ucu                                              23

<210> SEQ ID NO 450
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 450
ugagagaagt ccaccacgag ucu                                              23

<210> SEQ ID NO 451
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 451
ugagagaagt ccaccacgag ucu                                              23

<210> SEQ ID NO 452
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
ugagagaagu ccaccacgag ucu                                              23

<210> SEQ ID NO 453
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
ugagagaagu ccaccacgag ucu                                              23

<210> SEQ ID NO 454
```

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 454
ugagagaagu ccaccacgag ucu                                          23

<210> SEQ ID NO 455
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 455
ugagagaagt ccaccacgag ucu                                          23

<210> SEQ ID NO 456
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 456
ugagagaagt ccaccacgag ucu                                          23

<210> SEQ ID NO 457
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 457
ugagagaagt ccaccacgag ucu                                          23

<210> SEQ ID NO 458
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 458
ugagagaagu ccaccacgag ucu                                          23

```
<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
ugagagaagu ccaccacgag ucu                                              23

<210> SEQ ID NO 460
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 460
ugagagaagt ccaccacgag ucu                                              23

<210> SEQ ID NO 461
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
ugagagaagu ccaccacgag ucu                                              23

<210> SEQ ID NO 462
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 462
ugagagaagt ccaccacgag ucu                                              23

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
ugagagaagu ccaccacgag ucu                                              23
```

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
ugagagaagu ccaccacgag ucu                                              23

<210> SEQ ID NO 465
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 465
ugagagaagt ccaccacgag ucu                                              23

<210> SEQ ID NO 466
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 466
ugagagaagt ccaccacgag ucu                                              23

<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ugagagaagu ccaccacgag ucu                                              23

<210> SEQ ID NO 468
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 468
ugagagaagt ccaccacgag ucu                                          23

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
ugagagaagu ccaccacgag ucu                                          23

<210> SEQ ID NO 470
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 470
ugagagaagt ccaccacgag ucu                                          23

<210> SEQ ID NO 471
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 471
ugagagaagt ccaccacgag ucu                                          23

<210> SEQ ID NO 472
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 472
ugagagaagt ccaccacgag ucu                                          23

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
                    Synthetic oligonucleotide"

<400> SEQUENCE: 473
ugagagaagu ccaccacgag ucu                                             23

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
ugagagaagu ccaccacgag ucu                                             23

<210> SEQ ID NO 475
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 475
ugagagaagt ccaccacgag ucu                                             23

<210> SEQ ID NO 476
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 476
ugagagaagt ccaccacgag ucu                                             23

<210> SEQ ID NO 477
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 477
ugagagaagt ccaccacgag ucu                                             23

<210> SEQ ID NO 478
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 478
ugagagaagu ccaccacgag ucu                                              23

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
aguuauaugg augauguggu a                                                21

<210> SEQ ID NO 480
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
ggaugugucu gcggcguuuu a                                                21

<210> SEQ ID NO 481
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 481
nacucguggu ggacuucucu ca                                               22

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
acucguggug gacuucucuc a                                                21

<210> SEQ ID NO 483
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 483
acucguggug gacuuctcuc a                                              21

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
acucguggug gacuucucuc a                                              21

<210> SEQ ID NO 485
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
ucguggugga cuucucuca                                                 19

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
acucguggug gacuucucuc a                                              21

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
acucguggug gacuucucuc a                                              21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
acucguggug gacuucucuc a                                              21
```

```
<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
acucguggug gacuucucuc a                                              21

<210> SEQ ID NO 490
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
gugguggacu ucucuca                                                   17

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
acucguggug gacuucucuc a                                              21

<210> SEQ ID NO 492
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 492
nucguggugg acuucucuca uun                                            23

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
acucguggug gacuucucuc a                                              21

<210> SEQ ID NO 494
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
acucguggug gacuucucuc a                                              21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
acucguggug gacuucucuc a                                              21

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
acucguggug gacuucucuc a                                              21

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 497
nucguggugg acuucucuca n                                              21

<210> SEQ ID NO 498
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
acucguggug gacuucucuc a                                              21

<210> SEQ ID NO 499
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
acucguggug gacuucucuc a                                              21

<210> SEQ ID NO 500
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
acucguggug gacuucucuc a                                              21

<210> SEQ ID NO 501
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
uauuuccuag gguacaa                                                   17

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
acucguggug gacuucucuc a                                              21

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 503
nucguggugg acuucucuca n                                              21

<210> SEQ ID NO 504
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
acucguggug gacuucucuc a                                              21

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
acucguggug gacuucucuc a                                              21

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
acucguggug gacuucucuc a                                              21

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
acucguggug gacuucucuc a                                              21

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
acucguggug gacuucucuc a                                              21

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
acucguggug gacuucucuc a                                              21
```

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
acucguggug gacuucucuc a                                              21

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
acucguggug gacuucucuc a                                              21

<210> SEQ ID NO 512
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
acucguggug gacuucucuc a                                              21

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
acucguggug gacuucucuc a                                              21

<210> SEQ ID NO 514
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
acucguggug gacuucucuc a                                              21

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 515
acucguggug gacuucucuc a                                              21

<210> SEQ ID NO 516
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 516
acucguggug gacuucucuc a                                              21

<210> SEQ ID NO 517
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 517
acucguggug gacuuctcuc a                                              21

<210> SEQ ID NO 518
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
acucguggug gacuucucuc a                                              21

<210> SEQ ID NO 519
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 519
acucguggug gacuuctcuc a                                              21

<210> SEQ ID NO 520
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 520
acucguggug gacuucucuc a                                              21

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
acucguggug gacuucucuc a                                              21

<210> SEQ ID NO 522
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 522
acucguggug gacuuctcuc a                                              21

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
acucguggug gacuucucuc a                                              21

<210> SEQ ID NO 524
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 524
acucguggug gacuuctcuc a                                              21

<210> SEQ ID NO 525
<211> LENGTH: 21
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 525
acucguggug gacuucucuc a                                              21

<210> SEQ ID NO 526
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
gugguggacu cucucaauu u                                               21

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
gugguggacu cucucaauu u                                               21

<210> SEQ ID NO 528
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
gugguggacu cucucaauu u                                               21

<210> SEQ ID NO 529
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
uggacuucuc ucaauuu                                                   17

<210> SEQ ID NO 530
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
gugguggacu cucucaauu u                                               21

```
<210> SEQ ID NO 531
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 531
ngguggacuu cucucaauuu uun                                            23

<210> SEQ ID NO 532
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
gugguggacu ucucucaauu u                                              21

<210> SEQ ID NO 533
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
gugguggacu ucucucaauu u                                              21

<210> SEQ ID NO 534
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
gugguggacu ucucucaauu u                                              21

<210> SEQ ID NO 535
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
gguggacuuc ucucaauuu                                                 19

<210> SEQ ID NO 536
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
gugguggacu ucucucaauu u                                              21

<210> SEQ ID NO 537
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 537
ngguggacuu cucucaauuu n                                              21

<210> SEQ ID NO 538
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
gugguggacu ucucucaauu u                                              21

<210> SEQ ID NO 539
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
gugguggacu ucucucaauu u                                              21

<210> SEQ ID NO 540
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
uggacuucuc ucaauuu                                                   17

<210> SEQ ID NO 541
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
gugguggacu ucucucaauu u                                              21

<210> SEQ ID NO 542
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 542
ngguggacuu cucucaauuu n                                              21

<210> SEQ ID NO 543
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
gugguggacu ucucucaauu u                                              21

<210> SEQ ID NO 544
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
gugguggacu ucucucaauu u                                              21

<210> SEQ ID NO 545
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
gugguggacu ucucucaauu u                                              21

<210> SEQ ID NO 546
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
gugguggacu ucucucaauu u                                              21

<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
gugguggacu ucucucaauu u                                              21

<210> SEQ ID NO 548
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
gugguggacu ucucucaauu u                                              21

<210> SEQ ID NO 549
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
gugguggacu ucucucaauu u                                              21

<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
gugguggacu ucucucaauu u                                              21

<210> SEQ ID NO 551
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
gugguggacu ucucucaauu u                                              21
```

```
<210> SEQ ID NO 552
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
gugguggacu ucucucaauu u                                              21

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
gugguggacu ucucucaauu u                                              21

<210> SEQ ID NO 554
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 554
gugguggact tcucucaauu u                                              21

<210> SEQ ID NO 555
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 555
ngugguggac uucucucaau uu                                             22

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
gugguggacu ucucucaauu u                                              21
```

-continued

<210> SEQ ID NO 557
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
gugguggacu ucucucaauu u                                              21

<210> SEQ ID NO 558
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 558
gugguggacu tcucucaauu u                                              21

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
gugguggacu ucucucaauu u                                              21

<210> SEQ ID NO 560
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
gugguggacu ucucucaauu u                                              21

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
gugguggacu ucucucaauu u                                              21

<210> SEQ ID NO 562
<211> LENGTH: 21
<212> TYPE: RNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 562
gugguggacu ucucucaauu u                                              21

<210> SEQ ID NO 563
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 563
gugguggacu tcucucaauu u                                              21

<210> SEQ ID NO 564
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
gugguggacu ucucucaauu u                                              21

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
gugguggacu ucucucaauu u                                              21

<210> SEQ ID NO 566
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 566
gugguggacu tcucucaauu u                                              21

<210> SEQ ID NO 567
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 567
gugguggacu ucucucaauu u                                              21

<210> SEQ ID NO 568
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568 ggugganucuuc ucucaauuu                                                19

<210> SEQ ID NO 569
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
gugguggacu ucucucaauu u                                              21

<210> SEQ ID NO 570
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
gugcacuucg cuucaccucu g                                              21

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
guugacaaaa auccucacaa u                                              21

<210> SEQ ID NO 572
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
uguugacaaa aauccucaca a                                              21
```

-continued

```
<210> SEQ ID NO 573
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
gguggacuuc ucucaauuuu a                                              21

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
ucuuuuggag uguggauucg a                                              21

<210> SEQ ID NO 575
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
ucuuuuggag uguggauucg a                                              21

<210> SEQ ID NO 576
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
acuguucaag ccuccaagcu a                                              21

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
ucugccgauc cauacugcgg a                                              21

<210> SEQ ID NO 578
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 578
augugucugc ggcguuuuau a                                              21

<210> SEQ ID NO 579
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
ccccgucugu gccuucucau a                                              21

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
gccuaaucau cucuuguuca u                                              21

<210> SEQ ID NO 581
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
ucuagacucg ugguggacuu c                                              21

<210> SEQ ID NO 582
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
cugccgaucc auacugcgga a                                              21

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
uuuuucuugu ugacaaaaau a                                              21

<210> SEQ ID NO 584
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 584
aucuucuugu ugguucuucu a                                              21

<210> SEQ ID NO 585
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585 guuuucuug uugacaaaaa u                                               21

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
cugccuaauc aucucuuguu a                                              21

<210> SEQ ID NO 587
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
uccucacaau accacagagu a                                              21

<210> SEQ ID NO 588
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
cuuguugaca aaauccuca a                                               21

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
gcaacuuuuu caccucugcc u                                              21
```

-continued

```
<210> SEQ ID NO 590
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
gggaacaaga gcuacagcau a                                              21

<210> SEQ ID NO 591
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
cgugguggac uucucucaau u                                              21

<210> SEQ ID NO 592
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
cugcugcuau gccucaucuu a                                              21

<210> SEQ ID NO 593
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
guuggaugug ucugcggcgu u                                              21

<210> SEQ ID NO 594
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uucauccugc ugcuaugccu a                                              21

<210> SEQ ID NO 595
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 595
uucuuguuga caaaaauccu a                                              21

<210> SEQ ID NO 596
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
uauauggaug augugguauu a                                              21

<210> SEQ ID NO 597
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
uucauccugc ugcuaugccu c                                              21

<210> SEQ ID NO 598
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
gugcacuucg cuucaccucu a                                              21

<210> SEQ ID NO 599
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uugacaaaaa uccucacaau a                                              21

<210> SEQ ID NO 600
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
aagccuccaa gcugugccuu a                                              21

<210> SEQ ID NO 601
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
ccucuucauc cugcugcuau a                                              21

<210> SEQ ID NO 602
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
ccugcugcua ugccucaucu u                                              21

<210> SEQ ID NO 603
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
caucuucuug uugguucuuc u                                              21

<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
ccgucugugc cuucucaucu a                                              21

<210> SEQ ID NO 605
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
ccucaucuuc uuguugguuc u                                              21

<210> SEQ ID NO 606
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
ccaccaaaug ccccuaucuu a                                              21
```

```
<210> SEQ ID NO 607
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gcuccucugc cgauccauac u                                              21

<210> SEQ ID NO 608
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
guugacaaaa auccucacaa u                                              21

<210> SEQ ID NO 609
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uguugacaaa aauccucaca a                                              21

<210> SEQ ID NO 610
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610 ggugggacuuc ucucaauuuu a                                             21

<210> SEQ ID NO 611
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
ucuuuuggag uguggauucg a                                              21

<210> SEQ ID NO 612
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 612
acuguucaag ccuccaagcu a                                          21

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
ucugccgauc cauacugcgg a                                          21

<210> SEQ ID NO 614
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
aguuauaugg augauguggu a                                          21

<210> SEQ ID NO 615
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
augugucugc ggcguuuuau a                                          21

<210> SEQ ID NO 616
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
ccccgucugu gccuucucau a                                          21

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
gccuaaucau cucuuguuca u                                          21

<210> SEQ ID NO 618
<211> LENGTH: 21

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
ucuagacucg ugguggacuu c                                             21

<210> SEQ ID NO 619
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
cugccgaucc auacugcgga a                                             21

<210> SEQ ID NO 620
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
aucuucuugu ugguucuucu a                                             21

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
uucucucaau uuucuagggg a                                             21

<210> SEQ ID NO 622
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
acucguggug gacuucucuc a                                             21

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
```
gugcacuucg cuucaccucu g                                    21

<210> SEQ ID NO 624
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
guuuuucuug uugacaaaaa u                                    21

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
cugccuaauc aucucuuguu a                                    21

<210> SEQ ID NO 626
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
uccucacaau accacagagu a                                    21

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
cuuguugaca aaauccuca a                                     21

<210> SEQ ID NO 628
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
gugguggacu ucucucaauu u                                    21

<210> SEQ ID NO 629
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 629
gcaacuuuuu caccucugcc u                                              21

<210> SEQ ID NO 630
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
gggaacaaga gcuacagcau a                                              21

<210> SEQ ID NO 631
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
ucaucuucuu guugguucuu a                                              21

<210> SEQ ID NO 632
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
cugcugcuau gccucaucuu a                                              21

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
guuggaugug ucugcggcgu u                                              21

<210> SEQ ID NO 634
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
uucauccugc ugcuaugccu a                                              21

<210> SEQ ID NO 635
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
uucuuguuga caaaaauccu a                                              21

<210> SEQ ID NO 636
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
ggaugugucu gcggcguuuu a                                              21

<210> SEQ ID NO 637
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
uauauggaug auguggauau a                                              21

<210> SEQ ID NO 638
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
uucauccugc ugcuaugccu c                                              21

<210> SEQ ID NO 639
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
gugcacuucg cuucaccucu a                                              21

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
```

```
uugacaaaaa uccucacaau a                                              21

<210> SEQ ID NO 641
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
ccaaguguuu gcugacgcaa a                                              21

<210> SEQ ID NO 642
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
ccaaguguuu gcugacgcaa a                                              21

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
aagccuccaa gcugugccuu a                                              21

<210> SEQ ID NO 644
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
ccucuucauc cugcugcuau a                                              21

<210> SEQ ID NO 645
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
ccugcugcua ugccucaucu u                                              21

<210> SEQ ID NO 646
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 646
caucuucuug uugguucuuc u                                              21

<210> SEQ ID NO 647
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
ccgucugugc cuucucaucu a                                              21

<210> SEQ ID NO 648
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
ccucaucuuc uuguugguuc u                                              21

<210> SEQ ID NO 649
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
ccaccaaaug ccccuaucuu a                                              21

<210> SEQ ID NO 650
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
gcuccucugc cgauccauac u                                              21

<210> SEQ ID NO 651
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 651
```
acucguggug tacuucucuc a                                           21

<210> SEQ ID NO 652
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
acucguggug gacuucucuc a                                           21

<210> SEQ ID NO 653
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
acucguggug gacuucucuc a                                           21

<210> SEQ ID NO 654
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 654
acucguggug gacuucacuc a                                           21

<210> SEQ ID NO 655
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 655
acucguggtg tacuucacuc a                                           21

<210> SEQ ID NO 656
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 656
acucguggug tacuucacuc a                                              21

<210> SEQ ID NO 657
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
acucguggug gacuucucuc a                                              21

<210> SEQ ID NO 658
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
acucguggug gacuucucuc a                                              21

<210> SEQ ID NO 659
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 659
acucguggtg gacuuctcuc a                                              21

<210> SEQ ID NO 660
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 660
acucguggug gacuucucuc a                                              21

<210> SEQ ID NO 661
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 661
acucguggug gacuucucuc a                                              21

<210> SEQ ID NO 662
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 662
acucguggtg tacuucacuc a                                              21

<210> SEQ ID NO 663
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
acucguggug gacuucucuc a                                              21

<210> SEQ ID NO 664
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
acucguggug gacuucucuc a                                              21

<210> SEQ ID NO 665
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 665
acucguggtg gacuucacuc a                                              21

<210> SEQ ID NO 666
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 666
acucguggug gacuucacuc a                                              21

<210> SEQ ID NO 667
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 667
acucguggug gacuucucuc a                                              21

<210> SEQ ID NO 668
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 668
acucguggtg gacuuctcuc a                                              21

<210> SEQ ID NO 669
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
acucguggug gacuucucuc a                                              21

<210> SEQ ID NO 670
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 670
acucguggug gacuuctcuc a                                              21
```

```
<210> SEQ ID NO 671
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 671
acucguggtg tacuucacuc a                                           21

<210> SEQ ID NO 672
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 672
acucguggtg gacuuctcuc a                                           21

<210> SEQ ID NO 673
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose)

<400> SEQUENCE: 673
acucguggug gacuucncuc a                                           21

<210> SEQ ID NO 674
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 674
acucguggug gacuuctcuc a                                           21
```

```
<210> SEQ ID NO 675
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 675
acucguggug gacuuctcuc a                                              21

<210> SEQ ID NO 676
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 676
acucguggug gacuucucuc a                                              21

<210> SEQ ID NO 677
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 677
acucguggtg gacuucacuc a                                              21

<210> SEQ ID NO 678
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 678
acucguggug gacuucacuc a                                              21

<210> SEQ ID NO 679
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

```
          Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 679
acucguggtg gacuucacuc a                                             21

<210> SEQ ID NO 680
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
acucguggug gacuucucuc a                                             21

<210> SEQ ID NO 681
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-4-methoxy-3-
      phosphate (abasic 2'-OMe furanose)

<400> SEQUENCE: 681
nacucguggu ggacuuctcu ca                                            22

<210> SEQ ID NO 682
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 682
acucguggug gacuucacuc a                                             21

<210> SEQ ID NO 683
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 683
acucguggtg tacuucacuc a                                             21

<210> SEQ ID NO 684
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 684
acucguggug gacuucccuc a                                             21

<210> SEQ ID NO 685
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
acucguggug gacuucucuc a                                             21

<210> SEQ ID NO 686
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
acucguggug gacuucucuc a                                             21

<210> SEQ ID NO 687
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-4-methoxy-3-
      phosphate (abasic 2'-OMe furanose)

<400> SEQUENCE: 687
nacucguggu ggacuuctcu ca                                            22

<210> SEQ ID NO 688
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 688
acucguggtg gacuuctcuc a                                              21

<210> SEQ ID NO 689
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 689
acucguggug gacuucgcuc a                                              21

<210> SEQ ID NO 690
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
acucguggug gacuucucuc a                                              21

<210> SEQ ID NO 691
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
acucguggug gacuucucuc a                                              21

<210> SEQ ID NO 692
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 692
acucguggug gacuucucuc a                                              21

<210> SEQ ID NO 693
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 693
acucguggtg gacuucacuc a                                              21

<210> SEQ ID NO 694
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
uaccacauca uccauauaac uga                                            23

<210> SEQ ID NO 695
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
uaaaacgccg cagacacauc cag                                            23

<210> SEQ ID NO 696
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
ugagagaagu ccaccacgag ucu                                            23

<210> SEQ ID NO 697
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
ugagagaagu ccaccacgag ucu                                            23

<210> SEQ ID NO 698
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 698
ugagagaagu ccaccacgag ucu                                              23

<210> SEQ ID NO 699
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
ugagagaagu ccaccacgag ucu                                              23

<210> SEQ ID NO 700
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
ugagagaagu ccaccacgag u                                                21

<210> SEQ ID NO 701
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
ugagagaagu ccaccacgag ucu                                              23

<210> SEQ ID NO 702
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
ugagagaagu ccaccacgag ucu                                              23

<210> SEQ ID NO 703
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
ugagagaagu ccaccacgag ucu                                              23

<210> SEQ ID NO 704
<211> LENGTH: 23

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
ugagagaagu ccaccacgag ucu                                        23

<210> SEQ ID NO 705
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
ugagagaagu ccaccacga                                             19

<210> SEQ ID NO 706
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
ugagagaagu ccaccacgag ucu                                        23

<210> SEQ ID NO 707
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
ugagagaagu ccaccacgau u                                          21

<210> SEQ ID NO 708
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
ugagagaagu ccaccacgag ucu                                        23

<210> SEQ ID NO 709
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
```
ugagagaagu ccaccacgag ucu                                            23

<210> SEQ ID NO 710
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
ugagagaagu ccaccacgag ucu                                            23

<210> SEQ ID NO 711
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
ugagagaagu ccaccacgag ucu                                            23

<210> SEQ ID NO 712
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
ugagagaagu ccaccacgau u                                              21

<210> SEQ ID NO 713
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
ugagagaagu ccaccacgag ucu                                            23

<210> SEQ ID NO 714
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
ugagagaagu ccaccacgag ucu                                            23

<210> SEQ ID NO 715
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 715
ugagagaagu ccaccacgag ucu                                              23

<210> SEQ ID NO 716
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
ugagagaagu ccaccacga                                                   19

<210> SEQ ID NO 717
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
ugagagaagu ccaccacgag ucu                                              23

<210> SEQ ID NO 718
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
ugagagaagu ccaccacgau u                                                21

<210> SEQ ID NO 719
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
ugagagaagu ccaccacgag ucu                                              23

<210> SEQ ID NO 720
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
ugagagaagu ccaccacgag ucu                                              23

<210> SEQ ID NO 721
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
ugagagaagu ccaccacgag ucu                                                 23

<210> SEQ ID NO 722
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
ugagagaagu ccaccacgag ucu                                                 23

<210> SEQ ID NO 723
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
ugagagaagu ccaccacgag ucu                                                 23

<210> SEQ ID NO 724
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
ugagagaagu ccaccacgag ucu                                                 23

<210> SEQ ID NO 725
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
ugagagaagu ccaccacgag ucu                                                 23

<210> SEQ ID NO 726
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
```
ugagagaagu ccaccacgag ucu 23

<210> SEQ ID NO 727
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
ugagagaagu ccaccacgag ucu 23

<210> SEQ ID NO 728
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
ugagagaagu ccaccacgag ucu 23

<210> SEQ ID NO 729
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
ugagagaagu ccaccacgag ucu 23

<210> SEQ ID NO 730
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
ugagagaagu ccaccacgag ucu 23

<210> SEQ ID NO 731
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 731
ugagagaagt ccaccacgag ucu 23

<210> SEQ ID NO 732

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
ugagagaagu ccaccacgag ucu                                              23

<210> SEQ ID NO 733
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
ugagagaagu ccaccacgag ucu                                              23

<210> SEQ ID NO 734
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 734
ugagagaagu ccaccacgag ucu                                              23

<210> SEQ ID NO 735
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
ugagagaagu ccaccacgag ucu                                              23

<210> SEQ ID NO 736
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
ugagagaagu ccaccacgag ucu                                              23

<210> SEQ ID NO 737
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 737
ugagagaagu ccaccacgag ucu                                           23

<210> SEQ ID NO 738
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
ugagagaagu ccaccacgag ucu                                           23

<210> SEQ ID NO 739
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 739
ugagagaagu ccaccacgag ucu                                           23

<210> SEQ ID NO 740
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
ugagagaagu ccaccacgag ucu                                           23

<210> SEQ ID NO 741
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
aaauugagag aaguccacca cga                                           23

<210> SEQ ID NO 742
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
```
aaauugagag aaguccacca cga                                      23

<210> SEQ ID NO 743
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
aaauugagag aaguccacca cga                                      23

<210> SEQ ID NO 744
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
aaauugagag aaguccacc                                           19

<210> SEQ ID NO 745
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
aaauugagag aaguccacca cga                                      23

<210> SEQ ID NO 746
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
aaauugagag aaguccaccu u                                        21

<210> SEQ ID NO 747
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
aaauugagag aaguccacca cga                                      23

<210> SEQ ID NO 748
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
aaauugagag aaguccacca cga                                              23

<210> SEQ ID NO 749
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
aaauugagag aaguccacca cga                                              23

<210> SEQ ID NO 750
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
aaauugagag aaguccacca c                                                21

<210> SEQ ID NO 751
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
aaauugagag aaguccacca cga                                              23

<210> SEQ ID NO 752
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
aaauugagag aaguccaccu u                                                21

<210> SEQ ID NO 753
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
aaauugagag aaguccacca cga                                              23

<210> SEQ ID NO 754

-continued

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
aaauugagag aaguccacca cga                                          23

<210> SEQ ID NO 755
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
aaauugagag aaguccacc                                               19

<210> SEQ ID NO 756
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
aaauugagag aaguccacca cga                                          23

<210> SEQ ID NO 757
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
aaauugagag aaguccaccu u                                            21

<210> SEQ ID NO 758
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
aaauugagag aaguccacca cga                                          23

<210> SEQ ID NO 759
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
```
aaauugagag aaguccacca cga                                                  23

<210> SEQ ID NO 760
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
aaauugagag aaguccacca cga                                                  23

<210> SEQ ID NO 761
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
aaauugagag aaguccacca cga                                                  23

<210> SEQ ID NO 762
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
aaauugagag aaguccacca cga                                                  23

<210> SEQ ID NO 763
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
aaauugagag aaguccacca cga                                                  23

<210> SEQ ID NO 764
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
aaauugagag aaguccacca cga                                                  23

<210> SEQ ID NO 765
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 765
aaauugagag aaguccacca cga                                        23

<210> SEQ ID NO 766
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
aaauugagag aaguccacca cga                                        23

<210> SEQ ID NO 767
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
aaauugagag aaguccacca cga                                        23

<210> SEQ ID NO 768
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
aaauugagag aaguccacca cga                                        23

<210> SEQ ID NO 769
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 769
aaauugagag aagtccacca cga                                        23

<210> SEQ ID NO 770
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
```
aaauugagag aaguccacca cga                                                    23

<210> SEQ ID NO 771
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
aaauugagag aaguccacca cga                                                    23

<210> SEQ ID NO 772
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
aaauugagag aaguccacca cga                                                    23

<210> SEQ ID NO 773
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 773
aaauugagag aagtccacca cga                                                    23

<210> SEQ ID NO 774
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
aaauugagag aaguccacca cga                                                    23

<210> SEQ ID NO 775
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
aaauugagag aaguccacca cga                                                    23

<210> SEQ ID NO 776

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
aaauugagag aaguccacca cga                                               23

<210> SEQ ID NO 777
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
aaauugagag aaguccacca cga                                               23

<210> SEQ ID NO 778
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 778
aaauugagag aagtccacca cga                                               23

<210> SEQ ID NO 779
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
aaauugagag aaguccacca cga                                               23

<210> SEQ ID NO 780
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
aaauugagag aaguccacca cga                                               23

<210> SEQ ID NO 781
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 781
aaauugagag aaguccacca cga                                                 23

<210> SEQ ID NO 782
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
aaauugagag aaguccacca cga                                                 23

<210> SEQ ID NO 783
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
aaauugagag aaguccacca c                                                   21

<210> SEQ ID NO 784
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
aaauugagag aaguccacca cga                                                 23

<210> SEQ ID NO 785
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
cagaggugaa gcgaagugca cac                                                 23

<210> SEQ ID NO 786
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
auugugagga uuuuugucaa caa                                                 23

<210> SEQ ID NO 787
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
uugugaggau uuuugucaac aag                                          23

<210> SEQ ID NO 788
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
uaaaauugag agaaguccac cac                                          23

<210> SEQ ID NO 789
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
ucgaauccac acuccaaaag aca                                          23

<210> SEQ ID NO 790
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
ucgaauccac acuccaaaag aca                                          23

<210> SEQ ID NO 791
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
uagcuuggag gcuugaacaa gac                                          23

<210> SEQ ID NO 792
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
```
uccgcaguau ggaucggcag agg                                               23

<210> SEQ ID NO 793
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
uauaaaacgc cgcagacaca ucc                                               23

<210> SEQ ID NO 794
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
uaugagaagg cacagacggg gag                                               23

<210> SEQ ID NO 795
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
augaacaaga gaugauuagc gag                                               23

<210> SEQ ID NO 796
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
gaaguccacc acgagucuag acu                                               23

<210> SEQ ID NO 797
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
uuccgcagua uggaucggca gag                                               23

<210> SEQ ID NO 798
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 798 uauuuuguc aacaagaaaa acc                                              23

<210> SEQ ID NO 799
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
uagaagaacc aacaagaaga uga                                             23

<210> SEQ ID NO 800
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800 auuuuguca acaagaaaaa ccc                                              23

<210> SEQ ID NO 801
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
uaacaagaga ugauuaggca gag                                             23

<210> SEQ ID NO 802
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
uacucugugg uauugugagg auu                                             23

<210> SEQ ID NO 803
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
uugaggauuu uugucaacaa gaa                                             23
```

```
<210> SEQ ID NO 804
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
aggcagaggu gaaaaaguug cau                                          23

<210> SEQ ID NO 805
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
uaugcuguag cucuuguucc caa                                          23

<210> SEQ ID NO 806
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
aauugagaga aguccaccag cag                                          23

<210> SEQ ID NO 807
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
uaagaugagg cauagcagca gga                                          23

<210> SEQ ID NO 808
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
aacgccgcag acacauccaa cga                                          23

<210> SEQ ID NO 809
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 809
uaggcauagc agcaggauga aga                                          23

<210> SEQ ID NO 810
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
uaggauuuuu gucaacaaga aaa                                          23

<210> SEQ ID NO 811
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
uaauaccaca ucauccauau aac                                          23

<210> SEQ ID NO 812
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
gaggcauagc agcaggauga aga                                          23

<210> SEQ ID NO 813
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
uagaggugaa gcgaagugca cac                                          23

<210> SEQ ID NO 814
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
uauugugagg auuuuuguca aca                                          23

<210> SEQ ID NO 815
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 815
uaaggcacag cuuggaggcu uga                                            23

<210> SEQ ID NO 816
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
uauagcagca ggaugaagag gaa                                            23

<210> SEQ ID NO 817
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
aagaugaggc auagcagcag gau                                            23

<210> SEQ ID NO 818
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
agaagaacca acaagaagau gag                                            23

<210> SEQ ID NO 819
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
uagaugagaa ggcacagacg ggg                                            23

<210> SEQ ID NO 820
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
agaaccaaca agaagaugag gca                                            23
```

```
<210> SEQ ID NO 821
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
uaagauaggg gcauuuggug guc                                              23

<210> SEQ ID NO 822
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
aguauggauc ggcagaggag cca                                              23

<210> SEQ ID NO 823
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
auugugagga uuuuugucaa caa                                              23

<210> SEQ ID NO 824
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
uugugaggau uuuugucaac aag                                              23

<210> SEQ ID NO 825
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
uaaaauugag agaaguccac cac                                              23

<210> SEQ ID NO 826
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 826
ucgaauccac acuccaaaag aca                                          23

<210> SEQ ID NO 827
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
uagcuuggag gcuugaacaa gac                                          23

<210> SEQ ID NO 828
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
uccgcaguau ggaucggcag agg                                          23

<210> SEQ ID NO 829
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
uaccacauca uccauauaac uga                                          23

<210> SEQ ID NO 830
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
uauaaaacgc cgcagacaca ucc                                          23

<210> SEQ ID NO 831
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
uaugagaagg cacagacggg gag                                          23

<210> SEQ ID NO 832
<211> LENGTH: 23
<212> TYPE: RNA

<210> SEQ ID NO 832
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 832
augaacaaga gaugauuagc gag                                              23

<210> SEQ ID NO 833
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 833
gaaguccacc acgagucuag acu                                              23

<210> SEQ ID NO 834
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 834
uuccgcagua uggaucggca gag                                              23

<210> SEQ ID NO 835
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 835
uagaagaacc aacaagaaga uga                                              23

<210> SEQ ID NO 836
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 836
uccccuagaa aauugagaga agu                                              23

<210> SEQ ID NO 837
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 837
ugagagaagu ccaccacgag ucu                                              23

<210> SEQ ID NO 838
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
cagaggugaa gcgaagugca cac                                              23

<210> SEQ ID NO 839
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
auuuuuguca acaagaaaaa ccc                                              23

<210> SEQ ID NO 840
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
uaacaagaga ugauuaggca gag                                              23

<210> SEQ ID NO 841
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
uacucugugg uauugugagg auu                                              23

<210> SEQ ID NO 842
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
uugaggauuu uugucaacaa gaa                                              23

<210> SEQ ID NO 843
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
                              Synthetic oligonucleotide"

<400> SEQUENCE: 843
aaauugagag aaguccacca cga                                          23

<210> SEQ ID NO 844
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
aggcagaggu gaaaaaguug cau                                          23

<210> SEQ ID NO 845
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
uaugcuguag cucuuguucc caa                                          23

<210> SEQ ID NO 846
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
uaagaaccaa caagaagaug agg                                          23

<210> SEQ ID NO 847
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
uaagaugagg cauagcagca gga                                          23

<210> SEQ ID NO 848
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
aacgccgcag acacauccaa cga                                          23

<210> SEQ ID NO 849
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
uaggcauagc agcaggauga aga                                              23

<210> SEQ ID NO 850
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
uaggauuuuu gucaacaaga aaa                                              23

<210> SEQ ID NO 851
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
uaaaacgccg cagacacauc cag                                              23

<210> SEQ ID NO 852
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
uaauaccaca ucauccauau aac                                              23

<210> SEQ ID NO 853
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
gaggcauagc agcaggauga aga                                              23

<210> SEQ ID NO 854
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
```
uagaggugaa gcgaagugca cac                                           23

<210> SEQ ID NO 855
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
uauugugagg auuuuuguca aca                                           23

<210> SEQ ID NO 856
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
uuugcgucag caaacacuug gca                                           23

<210> SEQ ID NO 857
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
uuugcgucag caaacacuug gca                                           23

<210> SEQ ID NO 858
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
uaaggcacag cuuggaggcu uga                                           23

<210> SEQ ID NO 859
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
uauagcagca ggaugaagag gaa                                           23

<210> SEQ ID NO 860
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 860
aagaugaggc auagcagcag gau                                              23

<210> SEQ ID NO 861
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
agaagaacca acaagaagau gag                                              23

<210> SEQ ID NO 862
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
uagaugagaa ggcacagacg ggg                                              23

<210> SEQ ID NO 863
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
agaaccaaca agaagaugag gca                                              23

<210> SEQ ID NO 864
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
uaagauaggg gcauuuggug guc                                              23

<210> SEQ ID NO 865
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
aguauggauc ggcagaggag cca                                              23

<210> SEQ ID NO 866
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
ugagagaagu ccaccacgag ucu                                            23

<210> SEQ ID NO 867
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 867
ugagagaagt ccaccacgag ucu                                            23

<210> SEQ ID NO 868
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 868
ugagagaagu ccaccacgag ucu                                            23

<210> SEQ ID NO 869
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 869
ugagagaagt ccaccacgag ucu                                            23

<210> SEQ ID NO 870
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 870
ugagagaagu ccaccacgag ucu                                              23

<210> SEQ ID NO 871
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
ugagagaagu ccaccacgag ucu                                              23

<210> SEQ ID NO 872
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 872
ugagagaagu ccaccacgag ucu                                              23

<210> SEQ ID NO 873
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 873
ugagagaagt ccaccacgag ucu                                              23

<210> SEQ ID NO 874
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 874
ugagagaagt ccaccacgag ucu                                              23

<210> SEQ ID NO 875
<211> LENGTH: 23
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 875
ugagagaagt ccaccacgag ucu                                              23

<210> SEQ ID NO 876
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
ugagagaagu ccaccacgag ucu                                              23

<210> SEQ ID NO 877
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
ugagagaagu ccaccacgag ucu                                              23

<210> SEQ ID NO 878
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 878
ugagagaagu ccaccacgag ucu                                              23

<210> SEQ ID NO 879
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 879
ugagagaagt ccaccacgag ucu                                              23

<210> SEQ ID NO 880
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 880
ugagagaagt ccaccacgag ucu                                        23

<210> SEQ ID NO 881
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 881
ugagagaagt ccaccacgag ucu                                        23

<210> SEQ ID NO 882
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
ugagagaagu ccaccacgag ucu                                        23

<210> SEQ ID NO 883
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
ugagagaagu ccaccacgag ucu                                        23

<210> SEQ ID NO 884
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 884
ugagagaagu ccaccacgag ucu                                        23
```

```
<210> SEQ ID NO 885
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 885
ugagagaagt ccaccacgag ucu                                              23

<210> SEQ ID NO 886
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 886
ugagagaagt ccaccacgag ucu                                              23

<210> SEQ ID NO 887
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 887
ugagagaagt ccaccacgag ucu                                              23

<210> SEQ ID NO 888
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
ugagagaagu ccaccacgag ucu                                              23

<210> SEQ ID NO 889
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
```

```
ugagagaagu ccaccacgag ucu                                            23
```

<210> SEQ ID NO 890
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 890

```
ugagagaagt ccaccacgag ucu                                            23
```

<210> SEQ ID NO 891
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 891

```
ugagagaagu ccaccacgag ucu                                            23
```

<210> SEQ ID NO 892
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 892

```
ugagagaagt ccaccacgag ucu                                            23
```

<210> SEQ ID NO 893
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893

```
ugagagaagu ccaccacgag ucu                                            23
```

<210> SEQ ID NO 894
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"

<400> SEQUENCE: 894
ugagagaagu ccaccacgag ucu                                              23

<210> SEQ ID NO 895
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 895
ugagagaagt ccaccacgag ucu                                              23

<210> SEQ ID NO 896
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 896
ugagagaagt ccaccacgag ucu                                              23

<210> SEQ ID NO 897
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 897
ugagagaagu ccaccacgag ucu                                              23

<210> SEQ ID NO 898
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 898
ugagagaagt ccaccacgag ucu                                              23
```

```
<210> SEQ ID NO 899
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
ugagagaagu ccaccacgag ucu                                        23

<210> SEQ ID NO 900
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 900
ugagagaagt ccaccacgag ucu                                        23

<210> SEQ ID NO 901
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 901
ugagagaagt ccaccacgag ucu                                        23

<210> SEQ ID NO 902
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 902
ugagagaagt ccaccacgag ucu                                        23

<210> SEQ ID NO 903
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 903
ugagagaagu ccaccacgag ucu                                           23

<210> SEQ ID NO 904
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
ugagagaagu ccaccacgag ucu                                           23

<210> SEQ ID NO 905
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 905
ugagagaagt ccaccacgag ucu                                           23

<210> SEQ ID NO 906
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 906
ugagagaagt ccaccacgag ucu                                           23

<210> SEQ ID NO 907
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 907
ugagagaagt ccaccacgag ucu                                           23

<210> SEQ ID NO 908
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 908
ugagagaagu ccaccacgag ucu                                            23

<210> SEQ ID NO 909
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
ucguggugga cuucucuca                                                 19

<210> SEQ ID NO 910
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
ucguggugga cuucucuca                                                 19

<210> SEQ ID NO 911
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
ucguggugga cuucucuca                                                 19

<210> SEQ ID NO 912
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
acucguggug gacuucucuc a                                              21

<210> SEQ ID NO 913
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 913
ucguggugga cuucucuca                                                    19

<210> SEQ ID NO 914
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
ucguggugga cuucucuca                                                    19

<210> SEQ ID NO 915
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
ucguggugga cuucucucau u                                                 21

<210> SEQ ID NO 916
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
acucguggug gacuucucuc a                                                 21

<210> SEQ ID NO 917
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
ucguggugga cuucucuca                                                    19

<210> SEQ ID NO 918
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
acucguggug gacuucucuc a                                                 21

<210> SEQ ID NO 919
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 919
gugcacuucg cuucaccucu a                                              21

<210> SEQ ID NO 920
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
gugcacuucg cuucaccucu a                                              21

<210> SEQ ID NO 921
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
gcacuucgcu ucaccucua                                                 19

<210> SEQ ID NO 922
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
gugcacuucg cuucaccucu g                                              21

<210> SEQ ID NO 923
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
augugucugc ggcguuuuau a                                              21

<210> SEQ ID NO 924
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
gugcacuucg cuucaccucu g                                              21
```

-continued

```
<210> SEQ ID NO 925
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
gcacuucgcu ucaccucua                                                  19

<210> SEQ ID NO 926
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
gguggacuuc ucucaauuu                                                  19

<210> SEQ ID NO 927
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
cgugguggac uucucucaau u                                               21

<210> SEQ ID NO 928
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
gugguggacu ucucucaauu u                                               21

<210> SEQ ID NO 929
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
cgugguggac uucucucaau u                                               21

<210> SEQ ID NO 930
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 930
gguggacuuc ucucaauuu                                                    19

<210> SEQ ID NO 931
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
gugguggacu ucucucaauu u                                                 21

<210> SEQ ID NO 932
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 932
uggugguctu cucuaaauu                                                    19

<210> SEQ ID NO 933
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
gugguggacu ucucucaauu u                                                 21

<210> SEQ ID NO 934
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 934
cguggugguc tucucuaaau u                                                 21

<210> SEQ ID NO 935
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 935
gguggacuuc ucucaauuuu a    21

<210> SEQ ID NO 936
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
gguggacuuc ucucaauuuu a    21

<210> SEQ ID NO 937
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 937
uggacuactc ucaaauuua    19

<210> SEQ ID NO 938
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
ugagagaagu ccaccacgau u    21

<210> SEQ ID NO 939
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
ugagagaagu ccaccacgau u    21

<210> SEQ ID NO 940
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
ugagagaagu ccaccacgau u    21

```
<210> SEQ ID NO 941
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
ugagagaagu ccaccacgag ucu                                              23

<210> SEQ ID NO 942
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
ugagagaagu ccaccacgau u                                                21

<210> SEQ ID NO 943
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
ugagagaagu ccaccacgau u                                                21

<210> SEQ ID NO 944
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
ugagagaagu ccaccacgau u                                                21

<210> SEQ ID NO 945
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
ugagagaagu ccaccacgag ucu                                              23

<210> SEQ ID NO 946
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 946
ugagagaagu ccaccacgau u                                              21

<210> SEQ ID NO 947
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
ugagagaagu ccaccacgag uuu                                            23

<210> SEQ ID NO 948
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
uagaggugaa gcgaagugca cuu                                            23

<210> SEQ ID NO 949
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949
uagaggugaa gcgaagugca cac                                            23

<210> SEQ ID NO 950
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
uagaggugaa gcgaagugca c                                              21

<210> SEQ ID NO 951
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 951
cagaggugaa gcgaagugca cac                                            23

<210> SEQ ID NO 952
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 952
uauaaaacgc cgcagacaca ucc                                              23

<210> SEQ ID NO 953
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
cagaggugaa gcgaagugca cac                                              23

<210> SEQ ID NO 954
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
uagaggugaa gcgaagugcu u                                                21

<210> SEQ ID NO 955
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
aaauugagag aaguccacca c                                                21

<210> SEQ ID NO 956
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
aauugagaga aguccaccag cag                                              23

<210> SEQ ID NO 957
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
aaauugagag aaguccacca cga                                              23
```

<210> SEQ ID NO 958
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 958
aauugagaga aguccaccag cag                                              23

<210> SEQ ID NO 959
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 959
aaauugagag aaguccacca c                                                21

<210> SEQ ID NO 960
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 960
aaauugagag aaguccacca cga                                              23

<210> SEQ ID NO 961
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 961
aauugagaga aguccaccau u                                                21

<210> SEQ ID NO 962
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 962
aaauugagag aaguccacca cga                                              23

<210> SEQ ID NO 963
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 963
aauugagaga aguccaccag cuu                                          23

<210> SEQ ID NO 964
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
uaaaauugag agaaguccac cac                                          23

<210> SEQ ID NO 965
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
uaaaauugag agaaguccac cac                                          23

<210> SEQ ID NO 966
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
uaaaauugag agaaguccau u                                            21

<210> SEQ ID NO 967
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
ucguggugga cuucucuca                                               19

<210> SEQ ID NO 968
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
ucguggugga cuucucuca                                               19

<210> SEQ ID NO 969
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 969
nucguggugg acuucucuca n                                              21

<210> SEQ ID NO 970
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 970
nacucguggu ggacuucucu ca                                             22

<210> SEQ ID NO 971
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
ucguggugga cuucucuca                                                 19

<210> SEQ ID NO 972
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
ucguggugga cuucucuca                                                 19

<210> SEQ ID NO 973
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
```

-continued

```
<222> LOCATION: (23)..(23)
<223> OTHER INFORMATION: 2-hydroxymethyl-tetrahydrofurane-5-phosphate

<400> SEQUENCE: 973
nucguggugg acuucucuca uun                                           23

<210> SEQ ID NO 974
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 974
acucguggug gacuucucuc a                                             21

<210> SEQ ID NO 975
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
ucguggugga cuucucuca                                                19

<210> SEQ ID NO 976
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
acucguggug gacuucucuc a                                             21

<210> SEQ ID NO 977
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
gugcacuucg cuucaccucu a                                             21

<210> SEQ ID NO 978
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
gugcacuucg cuucaccucu a                                             21

<210> SEQ ID NO 979
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
gcacuucgcu ucaccucua                                                  19

<210> SEQ ID NO 980
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
gugcacuucg cuucaccucu g                                               21

<210> SEQ ID NO 981
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
augugucugc ggcguuuuau a                                               21

<210> SEQ ID NO 982
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
gugcacuucg cuucaccucu g                                               21

<210> SEQ ID NO 983
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 983
gcacuucgcu ucaccucua                                                  19

<210> SEQ ID NO 984
<211> LENGTH: 19
<212> TYPE: RNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 984
gguggacuuc ucucaauuu                                              19

<210> SEQ ID NO 985
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
cgugguggac uucucucaau u                                           21

<210> SEQ ID NO 986
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
gugguggacu ucucucaauu u                                           21

<210> SEQ ID NO 987
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
cgugguggac uucucucaau u                                           21

<210> SEQ ID NO 988
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
gguggacuuc ucucaauuu                                              19

<210> SEQ ID NO 989
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
gugguggacu ucucucaauu u                                           21

<210> SEQ ID NO 990
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 990
uggugguctu cucuaaauu                                                     19

<210> SEQ ID NO 991
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 991
gugguggacu ucucucaauu u                                                  21

<210> SEQ ID NO 992
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 992
cguggugguc tucucuaaau u                                                  21

<210> SEQ ID NO 993
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
gguggacuuc ucucaauuuu a                                                  21

<210> SEQ ID NO 994
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
gguggacuuc ucucaauuuu a                                                  21

<210> SEQ ID NO 995
<211> LENGTH: 19
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 995
uggacuacuc ucaaauuua                                                19

<210> SEQ ID NO 996
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
ugagagaagu ccaccacgau u                                             21

<210> SEQ ID NO 997
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
ugagagaagu ccaccacgau u                                             21

<210> SEQ ID NO 998
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
ugagagaagu ccaccacgau u                                             21

<210> SEQ ID NO 999
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
ugagagaagu ccaccacgag ucu                                           23

<210> SEQ ID NO 1000
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1000
ugagagaagu ccaccacgau u                                    21

<210> SEQ ID NO 1001
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
ugagagaagu ccaccacgau u                                    21

<210> SEQ ID NO 1002
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
ugagagaagu ccaccacgau u                                    21

<210> SEQ ID NO 1003
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
ugagagaagu ccaccacgag ucu                                  23

<210> SEQ ID NO 1004
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
ugagagaagu ccaccacgau u                                    21

<210> SEQ ID NO 1005
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
ugagagaagu ccaccacgag uuu                                  23

<210> SEQ ID NO 1006
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
uagaggugaa gcgaagugca cuu                                             23

<210> SEQ ID NO 1007
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
uagaggugaa gcgaagugca cac                                             23

<210> SEQ ID NO 1008
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1008
uagaggugaa gcgaagugca c                                               21

<210> SEQ ID NO 1009
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
cagaggugaa gcgaagugca cac                                             23

<210> SEQ ID NO 1010
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
uauaaaacgc cgcagacaca ucc                                             23

<210> SEQ ID NO 1011
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
```
cagaggugaa gcgaagugca cac                                            23

<210> SEQ ID NO 1012
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1012
uagaggugaa gcgaagugcu u                                              21

<210> SEQ ID NO 1013
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1013
aaauugagag aaguccacca c                                              21

<210> SEQ ID NO 1014
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
aauugagaga aguccaccag cag                                            23

<210> SEQ ID NO 1015
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
aaauugagag aaguccacca cga                                            23

<210> SEQ ID NO 1016
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
aauugagaga aguccaccag cag                                            23

<210> SEQ ID NO 1017
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
aaauugagag aaguccacca c                                              21

<210> SEQ ID NO 1018
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
aaauugagag aaguccacca cga                                            23

<210> SEQ ID NO 1019
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1019
aauugagaga aguccaccau u                                              21

<210> SEQ ID NO 1020
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
aaauugagag aaguccacca cga                                            23

<210> SEQ ID NO 1021
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1021
aauugagaga aguccaccag cuu                                            23

<210> SEQ ID NO 1022
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
uaaaauugag agaaguccac cac                                              23

<210> SEQ ID NO 1023
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
uaaaauugag agaaguccac cac                                              23

<210> SEQ ID NO 1024
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1024
uaaaauugag agaaguccau u                                                21

<210> SEQ ID NO 1025
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
ucguggugga cuucucuca                                                   19

<210> SEQ ID NO 1026
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
ucguggugga cuucucuca                                                   19

<210> SEQ ID NO 1027
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1027
ucguggugga cuucucuca                                              19

<210> SEQ ID NO 1028
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
gugcacuucg cuucaccucu a                                           21

<210> SEQ ID NO 1029
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
gugcacuucg cuucaccucu a                                           21

<210> SEQ ID NO 1030
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1030
gugcacuucg cuucaccucu a                                           21

<210> SEQ ID NO 1031
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1031
cgugguggac uucucucaau u                                           21

<210> SEQ ID NO 1032
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1032
cguggugguc tucucuaaau u                                           21
```

<210> SEQ ID NO 1033
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1033
gguggacuuc ucucaauuuu a                                              21

<210> SEQ ID NO 1034
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1034
gguggacuuc ucucaauuuu a                                              21

<210> SEQ ID NO 1035
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1035
gguggacuuc ucucaauuuu a                                              21

<210> SEQ ID NO 1036
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1036
ugagagaagu ccaccacgau u                                              21

<210> SEQ ID NO 1037
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
ugagagaagu ccaccacgau u                                              21

<210> SEQ ID NO 1038
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1038
ugagagaagu ccaccacgau u                                              21

<210> SEQ ID NO 1039
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
uagaggugaa gcgaagugca cuu                                            23

<210> SEQ ID NO 1040
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
uagaggugaa gcgaagugca cuu                                            23

<210> SEQ ID NO 1041
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
uagaggugaa gcgaagugca cuu                                            23

<210> SEQ ID NO 1042
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
aauugagaga aguccaccag cag                                            23

<210> SEQ ID NO 1043
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
aauugagaga aguccaccag cuu                                            23

<210> SEQ ID NO 1044
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
uaaaauugag agaaguccac cac                                          23

<210> SEQ ID NO 1045
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
uaaaauugag agaaguccac cac                                          23

<210> SEQ ID NO 1046
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046
uaaaauugag agaaguccac cac                                          23

<210> SEQ ID NO 1047
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1047
ucguggugga cuucucuca                                               19

<210> SEQ ID NO 1048
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
ucguggugga cuucucuca                                               19

<210> SEQ ID NO 1049
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1049
ucguggugga cuucucuca                                               19
```

```
<210> SEQ ID NO 1050
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050
gugcacuucg cuucaccucu a                                              21

<210> SEQ ID NO 1051
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1051
gugcacuucg cuucaccucu a                                              21

<210> SEQ ID NO 1052
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1052
gugcacuucg cuucaccucu a                                              21

<210> SEQ ID NO 1053
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1053
cgugguggac uucucucaau u                                              21

<210> SEQ ID NO 1054
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1054
cguggugguc tucucuaaau u                                              21

<210> SEQ ID NO 1055
<211> LENGTH: 21
<212> TYPE: RNA
```

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1055
gguggacuuc ucucaauuuu a                                                 21

<210> SEQ ID NO 1056
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1056
gguggacuuc ucucaauuuu a                                                 21

<210> SEQ ID NO 1057
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1057
gguggacuuc ucucaauuuu a                                                 21

<210> SEQ ID NO 1058
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1058
ugagagaagu ccaccacgau u                                                 21

<210> SEQ ID NO 1059
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1059
ugagagaagu ccaccacgau u                                                 21

<210> SEQ ID NO 1060
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1060
ugagagaagu ccaccacgau u                                                 21

-continued

```
<210> SEQ ID NO 1061
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1061
uagaggugaa gcgaagugca cuu                                            23

<210> SEQ ID NO 1062
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1062
uagaggugaa gcgaagugca cuu                                            23

<210> SEQ ID NO 1063
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1063
uagaggugaa gcgaagugca cuu                                            23

<210> SEQ ID NO 1064
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1064
aauugagaga aguccaccag cag                                            23

<210> SEQ ID NO 1065
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1065
aauugagaga aguccaccag cuu                                            23

<210> SEQ ID NO 1066
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1066
uaaaauugag agaaguccac cac                                             23

<210> SEQ ID NO 1067
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1067
uaaaauugag agaaguccac cac                                             23

<210> SEQ ID NO 1068
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1068
uaaaauugag agaaguccac cac                                             23

<210> SEQ ID NO 1069
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1069
ugugcacuuc gcuucaccuc u                                               21

<210> SEQ ID NO 1070
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1070
ugcacuucgc uucaccucug a                                               21

<210> SEQ ID NO 1071
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1071
gugugcacuu cgcuucaccu a                                               21
```

<210> SEQ ID NO 1072
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1072
cgugugcacu ucgcuucacc u    21

<210> SEQ ID NO 1073
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1073
gugcacuucg cuucaccucu a    21

<210> SEQ ID NO 1074
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1074
ccgugugcac uucgcuucac a    21

<210> SEQ ID NO 1075
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1075
cacuucgcuu caccucugca a    21

<210> SEQ ID NO 1076
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1076
acuucgcuuc accucugcac a    21

<210> SEQ ID NO 1077
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 1077
ggcuguaggc auaaauuggu a                                             21

<210> SEQ ID NO 1078
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1078
uucgcuucac cucugcacgu a                                             21

<210> SEQ ID NO 1079
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1079
ucgcuucacc ucugcacguc a                                             21

<210> SEQ ID NO 1080
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1080
cuucgcuuca ccucugcacg u                                             21

<210> SEQ ID NO 1081
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1081
ccccgucugu gccuucucau a                                             21

<210> SEQ ID NO 1082
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1082
ccgucugugc cuucucaucu a                                             21

<210> SEQ ID NO 1083
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1083
ccagcaccau gcaacuuuuu a                                          21

<210> SEQ ID NO 1084
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1084
caccagcacc augcaacuuu u                                          21

<210> SEQ ID NO 1085
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1085
caccaugcaa cuuuuucacc u                                          21

<210> SEQ ID NO 1086
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1086
caaugucaac gaccgaccuu a                                          21

<210> SEQ ID NO 1087
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1087
cgcuucaccu cugcacgucg a                                          21

<210> SEQ ID NO 1088
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1088
```
accuugaggc auacuucaaa g					21

<210> SEQ ID NO 1089
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1089
ccgaccuuga ggcauacuuc a					21

<210> SEQ ID NO 1090
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1090
gaccuugagg cauacuucaa a					21

<210> SEQ ID NO 1091
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1091
accgaccuug aggcauacuu a					21

<210> SEQ ID NO 1092
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1092
ucgcauggag accaccguga a					21

<210> SEQ ID NO 1093
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1093
uuacauaaga ggacucuugg a					21

<210> SEQ ID NO 1094
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1094
ucuuacauaa gaggacucuu a                                              21

<210> SEQ ID NO 1095
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1095
acuucaaaga cuguuuguuu a                                              21

<210> SEQ ID NO 1096
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1096
uacuucaaag acuguuuguu u                                              21

<210> SEQ ID NO 1097
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1097
auacuucaaa gacuguuugu u                                              21

<210> SEQ ID NO 1098
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1098
uuguuuaaag acugggagga a                                              21

<210> SEQ ID NO 1099
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1099
gcauacuuca aagacuguuu a                                              21

<210> SEQ ID NO 1100
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1100
caaagacugu uuguuaaag a                                              21

<210> SEQ ID NO 1101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1101
agacuguuug uuuaaagacu a                                             21

<210> SEQ ID NO 1102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1102
guuuguuuaa agacugggag a                                             21

<210> SEQ ID NO 1103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligoncleotide"

<400> SEQUENCE: 1103
gggggaggag auuagauuaa a                                             21

<210> SEQ ID NO 1104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1104
ggggaggaga uuagauuaaa g                                             21

<210> SEQ ID NO 1105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1105
``` guuggggag gagauuagau u					21

<210> SEQ ID NO 1106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1106 uuggggagg agauuagauu a					21

<210> SEQ ID NO 1107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1107
gggaggagau uagauuaaag a					21

<210> SEQ ID NO 1108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1108
uuagauuaaa ggucuuugua a					21

<210> SEQ ID NO 1109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1109
uagauuaaag gucuuuguac u					21

<210> SEQ ID NO 1110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1110
auuagauuaa aggucuuugu a					21

<210> SEQ ID NO 1111
<211> LENGTH: 21
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 1111
gaggagauua gauuaaaggu a                                                  21

<210> SEQ ID NO 1112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1112
ggacucuugg acucucugca a                                                  21

<210> SEQ ID NO 1113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1113
acucuuggac ucucugcaau a                                                  21

<210> SEQ ID NO 1114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1114
agauuaaagg ucuuuguacu a                                                  21

<210> SEQ ID NO 1115
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1115
agaggugaag cgaagugcac acg                                                23

<210> SEQ ID NO 1116
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1116
ucagagguga agcgaagugc aca                                                23
```

```
<210> SEQ ID NO 1117
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1117
uaggugaagc gaagugcaca cgg                                              23

<210> SEQ ID NO 1118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1118
aggugaagcg aagugcacac ggu                                              23

<210> SEQ ID NO 1119
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1119
uagaggugaa gcgaagugca cac                                              23

<210> SEQ ID NO 1120
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1120
ugugaagcga agugcacacg guc                                              23

<210> SEQ ID NO 1121
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1121
uugcagaggu gaagcgaagu gca                                              23

<210> SEQ ID NO 1122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1122
ugugcagagg ugaagcgaag ugc                                              23

<210> SEQ ID NO 1123
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1123
uaccaauuua ugccuacagc cuc                                              23

<210> SEQ ID NO 1124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1124
uacgugcaga ggugaagcga agu                                              23

<210> SEQ ID NO 1125
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1125
ugacgugcag aggugaagcg aag                                              23

<210> SEQ ID NO 1126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1126
acgugcagag gugaagcgaa gug                                              23

<210> SEQ ID NO 1127
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1127
uaugagaagg cacagacggg gag                                              23

<210> SEQ ID NO 1128
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1128
uagaugagaa ggcacagacg ggg                                           23

<210> SEQ ID NO 1129
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1129
uaaaaaguug cauggugcug gug                                           23

<210> SEQ ID NO 1130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1130
aaaaguugca uggugcuggu gcg                                           23

<210> SEQ ID NO 1131
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1131
aggugaaaaa guugcauggu gcu                                           23

<210> SEQ ID NO 1132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1132
uaaggucggu cguugacauu gca                                           23

<210> SEQ ID NO 1133
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1133
ucgacgugca gaggugaagc gaa                                           23
```

<210> SEQ ID NO 1134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1134
cuuugaagua ugccucaagg ucg     23

<210> SEQ ID NO 1135
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1135
ugaaguaugc cucaaggucg guc     23

<210> SEQ ID NO 1136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1136
uuugaaguau gccucaaggu cgg     23

<210> SEQ ID NO 1137
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1137
uaaguaugcc ucaaggucgg ucg     23

<210> SEQ ID NO 1138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1138
uucacggugg ucuccaugcg acg     23

<210> SEQ ID NO 1139
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 1139
uccaagaguc cucuuaugua aga                                              23

<210> SEQ ID NO 1140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1140
uaagaguccu cuuauguaag acc                                              23

<210> SEQ ID NO 1141
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1141
uaaacaaaca gucuuugaag uau                                              23

<210> SEQ ID NO 1142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1142
aaacaaacag ucuuugaagu aug                                              23

<210> SEQ ID NO 1143
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1143
aacaaacagu cuuugaagua ugc                                              23

<210> SEQ ID NO 1144
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1144
uuccucccag ucuuuaaaca aac                                              23

<210> SEQ ID NO 1145
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1145
uaaacagucu uugaaguaug ccu                                             23

<210> SEQ ID NO 1146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1146
ucuuuaaaca aacagucuuu gaa                                             23

<210> SEQ ID NO 1147
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1147
uagucuuuaa acaaacaguc uuu                                             23

<210> SEQ ID NO 1148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1148
ucucccaguc uuuaaacaaa cag                                             23

<210> SEQ ID NO 1149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1149
uuuaaucuaa ucuccucccc caa                                             23

<210> SEQ ID NO 1150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1150
cuuuaaucua aucuccuccc cca                                             23
```

```
<210> SEQ ID NO 1151
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1151
aaucuaaucu ccuccccaa cuc                                              23

<210> SEQ ID NO 1152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1152
uaaucuaauc uccucccca acu                                              23

<210> SEQ ID NO 1153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1153
ucuuuaaucu aaucuccucc ccc                                             23

<210> SEQ ID NO 1154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1154
uuacaaagac cuuuaaucua auc                                             23

<210> SEQ ID NO 1155
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1155
aguacaaaga ccuuuaaucu aau                                             23

<210> SEQ ID NO 1156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 1156
uacaaagacc uuuaaucuaa ucu                                        23

<210> SEQ ID NO 1157
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1157
uaccuuuaau cuaaucuccu ccc                                        23

<210> SEQ ID NO 1158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1158
uugcagagag uccaagaguc cuc                                        23

<210> SEQ ID NO 1159
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1159
uauugcagag aguccaagag ucc                                        23

<210> SEQ ID NO 1160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1160
uaguacaaag accuuuaauc uaa                                        23

<210> SEQ ID NO 1161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1161
ugugcacuuc gcuucaccuc u                                          21

<210> SEQ ID NO 1162
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1162
ugcacuucgc uucaccucug a                                              21

<210> SEQ ID NO 1163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1163
gugugcacuu cgcuucaccu a                                              21

<210> SEQ ID NO 1164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1164
cgugugcacu ucgcuucacc u                                              21

<210> SEQ ID NO 1165
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1165
gugcacuucg cuucaccucu a                                              21

<210> SEQ ID NO 1166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1166
ccgugugcac uucgcuucac a                                              21

<210> SEQ ID NO 1167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1167
```

-continued cacuucgcuu caccucugca a            21

<210> SEQ ID NO 1168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1168
acuucgcuuc accucugcac a            21

<210> SEQ ID NO 1169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1169
ggcuguaggc auaaauuggu a            21

<210> SEQ ID NO 1170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1170
uucgcuucac cucugcacgu a            21

<210> SEQ ID NO 1171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1171
ucgcuucacc ucugcacguc a            21

<210> SEQ ID NO 1172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1172
cuucgcuuca ccucugcacg u            21

<210> SEQ ID NO 1173
<211> LENGTH: 21
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 1173
ccccgucugu gccuucucau a                                           21

<210> SEQ ID NO 1174
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1174
ccgucugugc cuucucaucu a                                           21

<210> SEQ ID NO 1175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1175
ccagcaccau gcaacuuuuu a                                           21

<210> SEQ ID NO 1176
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1176
caccagcacc augcaacuuu u                                           21

<210> SEQ ID NO 1177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1177
caccaugcaa cuuuuucacc u                                           21

<210> SEQ ID NO 1178
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1178
caaugucaac gaccgaccuu a                                           21

<210> SEQ ID NO 1179

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1179
cgcuucaccu cugcacgucg a                                              21

<210> SEQ ID NO 1180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1180
accuugaggc auacuucaaa g                                              21

<210> SEQ ID NO 1181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1181
ccgaccuuga ggcauacuuc a                                              21

<210> SEQ ID NO 1182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1182
gaccuugagg cauacuucaa a                                              21

<210> SEQ ID NO 1183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1183
accgaccuug aggcauacuu a                                              21

<210> SEQ ID NO 1184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1184
```
ucgcauggag accaccguga a                                              21

<210> SEQ ID NO 1185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1185
uuacauaaga ggacucuugg a                                              21

<210> SEQ ID NO 1186
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1186
ucuuacauaa gaggacucuu a                                              21

<210> SEQ ID NO 1187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1187
acuucaaaga cuguuuguuu a                                              21

<210> SEQ ID NO 1188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1188
uacuucaaag acuguuuguu u                                              21

<210> SEQ ID NO 1189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1189
auacuucaaa gacuguuugu u                                              21

<210> SEQ ID NO 1190
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1190
uuguuuaaag acugggagga a                                              21

<210> SEQ ID NO 1191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1191
gcauacuuca aagacuguuu a                                              21

<210> SEQ ID NO 1192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1192
caaagacugu uuguuuaaag a                                              21

<210> SEQ ID NO 1193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1193
agacuguuug uuuaaagacu a                                              21

<210> SEQ ID NO 1194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1194
guuuguuuaa agacugggag a                                              21

<210> SEQ ID NO 1195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1195
gggggaggag auuagauuaa a                                              21
```

```
<210> SEQ ID NO 1196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1196
ggggaggaga uuagauuaaa g                                              21

<210> SEQ ID NO 1197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1197 guuggggag gagauuagau u                                               21

<210> SEQ ID NO 1198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1198 uuggggagg agauuagauu a                                               21

<210> SEQ ID NO 1199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1199
gggaggagau uagauuaaag a                                              21

<210> SEQ ID NO 1200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1200
uuagauuaaa ggucuuugua a                                              21

<210> SEQ ID NO 1201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1201
uagauuaaag gcuuuguac u                                                   21

<210> SEQ ID NO 1202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1202
auuagauuaa aggucuuugu a                                                  21

<210> SEQ ID NO 1203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1203
gaggagauua gauuaaaggu a                                                  21

<210> SEQ ID NO 1204
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1204
ggacucuugg acucucugca a                                                  21

<210> SEQ ID NO 1205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1205
acucuuggac ucucugcaau a                                                  21

<210> SEQ ID NO 1206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1206
agauuaaagg ucuuuguacu a                                                  21

<210> SEQ ID NO 1207
<211> LENGTH: 23
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 1207
agaggugaag cgaagugcac acg                                           23

<210> SEQ ID NO 1208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1208
ucagagguga agcgaagugc aca                                           23

<210> SEQ ID NO 1209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1209
uaggugaagc gaagugcaca cgg                                           23

<210> SEQ ID NO 1210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1210
aggugaagcg aagugcacac ggu                                           23

<210> SEQ ID NO 1211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1211
uagaggugaa gcgaagugca cac                                           23

<210> SEQ ID NO 1212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1212
ugugaagcga agugcacacg guc                                           23
```

<210> SEQ ID NO 1213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1213
uugcagaggu gaagcgaagu gca    23

<210> SEQ ID NO 1214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1214
ugugcagagg ugaagcgaag ugc    23

<210> SEQ ID NO 1215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1215
uaccaauuua ugccuacagc cuc    23

<210> SEQ ID NO 1216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1216
uacgugcaga ggugaagcga agu    23

<210> SEQ ID NO 1217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1217
ugacgugcag aggugaagcg aag    23

<210> SEQ ID NO 1218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 1218
acgugcagag gugaagcgaa gug                                          23

<210> SEQ ID NO 1219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1219
uaugagaagg cacagacggg gag                                          23

<210> SEQ ID NO 1220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1220
uagaugagaa ggcacagacg ggg                                          23

<210> SEQ ID NO 1221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1221
uaaaaaguug cauggugcug gug                                          23

<210> SEQ ID NO 1222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1222
aaaaguugca uggugcuggu gcg                                          23

<210> SEQ ID NO 1223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1223
aggugaaaaa guugcauggu gcu                                          23

<210> SEQ ID NO 1224
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1224
uaaggucggu cguugacauu gca                                           23

<210> SEQ ID NO 1225
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1225
ucgacgugca gaggugaagc gaa                                           23

<210> SEQ ID NO 1226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1226
cuuugaagua ugccucaagg ucg                                           23

<210> SEQ ID NO 1227
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1227
ugaaguaugc cucaaggucg guc                                           23

<210> SEQ ID NO 1228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1228
uuugaaguau gccucaaggu cgg                                           23

<210> SEQ ID NO 1229
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1229
uaaguaugcc ucaaggucgg ucg                                           23
```

```
<210> SEQ ID NO 1230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1230
uucacggugg ucuccaugcg acg                                            23

<210> SEQ ID NO 1231
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1231
uccaagaguc cucuuaugua aga                                            23

<210> SEQ ID NO 1232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1232
uaagaguccu cuuauguaag acc                                            23

<210> SEQ ID NO 1233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1233
uaaacaaaca gucuuugaag uau                                            23

<210> SEQ ID NO 1234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1234
aaacaaacag ucuuugaagu aug                                            23

<210> SEQ ID NO 1235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1235
aacaaacagu cuuugaagua ugc                                    23

<210> SEQ ID NO 1236
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1236
uuccucccag ucuuuaaaca aac                                    23

<210> SEQ ID NO 1237
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1237
uaaacagucu uugaaguaug ccu                                    23

<210> SEQ ID NO 1238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1238
ucuuuaaaca aacagucuuu gaa                                    23

<210> SEQ ID NO 1239
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1239
uagucuuuaa acaaacaguc uuu                                    23

<210> SEQ ID NO 1240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1240
ucucccaguc uuuaaacaaa cag                                    23

<210> SEQ ID NO 1241
<211> LENGTH: 23

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1241
uuuaaucuaa ucuccuccccc caa                                              23

<210> SEQ ID NO 1242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1242
cuuuaaucua aucuccuccc cca                                               23

<210> SEQ ID NO 1243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1243
aaucuaaucu ccuccccaa cuc                                                23

<210> SEQ ID NO 1244
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1244
uaaucuaauc uccucccca acu                                                23

<210> SEQ ID NO 1245
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1245
ucuuuaaucu aaucuccucc ccc                                               23

<210> SEQ ID NO 1246
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1246
```
uuacaaagac cuuuaaucua auc                                    23

<210> SEQ ID NO 1247
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1247
aguacaaaga ccuuuaaucu aau                                    23

<210> SEQ ID NO 1248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1248
uacaaagacc uuuaaucuaa ucu                                    23

<210> SEQ ID NO 1249
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1249
uaccuuuaau cuaaucuccu ccc                                    23

<210> SEQ ID NO 1250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1250
uugcagagag uccaagaguc cuc                                    23

<210> SEQ ID NO 1251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1251
uauugcagag aguccaagag ucc                                    23

<210> SEQ ID NO 1252
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1252
uaguacaaag accuuuaauc uaa                                           23

<210> SEQ ID NO 1253
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1253
gucugugccu ucucaucua                                                19

<210> SEQ ID NO 1254
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1254
gucugugccu ucucaucua                                                19

<210> SEQ ID NO 1255
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1255
gugugcacuu cgcuucaca                                                19

<210> SEQ ID NO 1256
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1256
gugugcacuu cgcuucaca                                                19

<210> SEQ ID NO 1257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1257
ugugcacuuc gcuucaccuc u                                             21

<210> SEQ ID NO 1258
```

-continued

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1258
ugugcacuuc gcuucaccuc u                                              21

<210> SEQ ID NO 1259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1259
caccagcacc augcaacuuu u                                              21

<210> SEQ ID NO 1260
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1260
caccagcacc augcaacuuu u                                              21

<210> SEQ ID NO 1261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1261
caccaugcaa cuuuuucacc u                                              21

<210> SEQ ID NO 1262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1262
caccaugcaa cuuuuucacc u                                              21

<210> SEQ ID NO 1263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1263
```

-continued uagaugagaa ggcacagacu u                                               21

<210> SEQ ID NO 1264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1264
uagaugagaa ggcacagacu u                                               21

<210> SEQ ID NO 1265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1265
ugugaagcga agugcacacu u                                               21

<210> SEQ ID NO 1266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1266
ugugaagcga agugcacacu u                                               21

<210> SEQ ID NO 1267
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1267
agaggugaag cgaagugcac auu                                             23

<210> SEQ ID NO 1268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1268
agaggugaag cgaagugcac auu                                             23

<210> SEQ ID NO 1269
<211> LENGTH: 23
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 1269
aaaaguugca uggugcuggu guu                                          23

<210> SEQ ID NO 1270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1270
aaaaguugca uggugcuggu guu                                          23

<210> SEQ ID NO 1271
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1271
aggugaaaaa guugcauggu guu                                          23

<210> SEQ ID NO 1272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1272
aggugaaaaa guugcauggu guu                                          23

<210> SEQ ID NO 1273
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1273
gucugugccu ucucaucua                                               19

<210> SEQ ID NO 1274
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1274
gucugugccu ucucaucua                                               19
```

```
<210> SEQ ID NO 1275
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1275
gugugcacuu cgcuucaca                                                  19

<210> SEQ ID NO 1276
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1276
gugugcacuu cgcuucaca                                                  19

<210> SEQ ID NO 1277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1277
ugugcacuuc gcuucaccuc u                                               21

<210> SEQ ID NO 1278
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1278
ugugcacuuc gcuucaccuc u                                               21

<210> SEQ ID NO 1279
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1279
caccagcacc augcaacuuu u                                               21

<210> SEQ ID NO 1280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1280
caccagcacc augcaacuuu u                                              21

<210> SEQ ID NO 1281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1281
caccaugcaa cuuuuucacc u                                              21

<210> SEQ ID NO 1282
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1282
caccaugcaa cuuuuucacc u                                              21

<210> SEQ ID NO 1283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1283
uagaugagaa ggcacagacu u                                              21

<210> SEQ ID NO 1284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1284
uagaugagaa ggcacagacu u                                              21

<210> SEQ ID NO 1285
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1285
ugugaagcga agugcacacu u                                              21

<210> SEQ ID NO 1286
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1286
ugugaagcga agugcacacu u                                          21

<210> SEQ ID NO 1287
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1287
agaggugaag cgaagugcac auu                                        23

<210> SEQ ID NO 1288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1288
agaggugaag cgaagugcac auu                                        23

<210> SEQ ID NO 1289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1289
aaaaguugca uggugcuggu guu                                        23

<210> SEQ ID NO 1290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1290
aaaaguugca uggugcuggu guu                                        23

<210> SEQ ID NO 1291
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1291
aggugaaaaa guugcauggu guu                                        23
```

```
<210> SEQ ID NO 1292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1292
aggugaaaaa guugcauggu guu                                              23
```

UNITED STATES PATENT AND TRADEMARK OFFICE
CERTIFICATE OF CORRECTION

PATENT NO. : 10,513,703 B2
APPLICATION NO. : 15/591532
DATED : December 24, 2019
INVENTOR(S) : Gregory Hinkle et al.

Page 1 of 1

It is certified that error appears in the above-identified patent and that said Letters Patent is hereby corrected as shown below:

On the Title Page

Item (56), References Cited, Other Publications:
"Choi et al., "Targeting Cancer Cells with Basic Structural and Functional Features of Small Interfering RNA," Cell Cycle 4(5):669-671, 2005." should read, --Choi et al., "Targeting Cancer Cells with DNA-Assembled Dendrimers," Cell Cycle 4(5):669-671, 2005.--.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*